United States Patent
Pauza et al.

(10) Patent No.: US 12,410,446 B2
(45) Date of Patent: *Sep. 9, 2025

(54) METHODS AND COMPOSITIONS FOR THE ACTIVATION OF GAMMA-DELTA T-CELLS

(71) Applicant: American Gene Technologies International Inc., Rockville, MD (US)

(72) Inventors: Charles David Pauza, Rockville, MD (US); Haishan Li, Rockville, MD (US); Tyler Lahusen, Rockville, MD (US); Mei-Ling Liou, Rockville, MD (US)

(73) Assignee: AMERICAN GENE TECHNOLOGIES INTERNATIONAL INC., Rockville, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/051,821

(22) Filed: Nov. 1, 2022

(65) Prior Publication Data

US 2023/0340531 A1  Oct. 26, 2023

Related U.S. Application Data

(60) Division of application No. 16/563,738, filed on Sep. 6, 2019, now Pat. No. 11,519,006, which is a continuation of application No. 16/182,443, filed on Nov. 6, 2018, now Pat. No. 10,428,350, which is a continuation of application No. 16/008,991, filed on Jun. 14, 2018, now Pat. No. 10,472,649, which is a continuation of application No. 15/850,937, filed on Dec. 21, 2017, now Pat. No. 10,023,880, which is a continuation of application No. 15/652,080, filed on Jul. 17, 2017, now Pat. No. 9,914,938, which is a continuation of application No. PCT/US2017/013399, filed on Jan. 13, 2017.

(60) Provisional application No. 62/279,474, filed on Jan. 15, 2016.

(51) Int. Cl.
| | |
|---|---|
| C12N 15/86 | (2006.01) |
| A61K 31/675 | (2006.01) |
| A61K 31/7105 | (2006.01) |
| A61K 38/16 | (2006.01) |
| C12N 5/0783 | (2010.01) |
| C12N 15/113 | (2010.01) |
| A61K 39/00 | (2006.01) |
| A61K 48/00 | (2006.01) |
| C12N 5/00 | (2006.01) |
| C12Q 1/68 | (2018.01) |

(52) U.S. Cl.
CPC .......... *C12N 15/86* (2013.01); *A61K 31/675* (2013.01); *A61K 31/7105* (2013.01); *A61K 38/16* (2013.01); *C12N 5/0636* (2013.01); *C12N 15/113* (2013.01); *A61K 2039/5158* (2013.01); *A61K 48/00* (2013.01); *C12N 5/00* (2013.01); *C12N 2310/14* (2013.01); *C12N 2310/141* (2013.01); *C12N 2310/531* (2013.01)

(58) Field of Classification Search
None
See application file for complete search history.

(56) References Cited

U.S. PATENT DOCUMENTS

| | | | |
|---|---|---|---|
| 5,654,195 A | 8/1997 | Sodroski et al. | |
| 5,668,255 A | 9/1997 | Murphy | |
| 5,674,703 A | 10/1997 | Woo et al. | |
| 6,156,514 A | 12/2000 | Acevedo et al. | |
| 6,399,383 B1 | 6/2002 | Apt et al. | |
| 6,635,472 B1 | 10/2003 | Lauermann | |
| 7,371,542 B2 | 5/2008 | Ivanova et al. | |
| 8,124,752 B2 | 2/2012 | Bumcrot et al. | |
| 8,287,857 B2 | 10/2012 | Dudley et al. | |
| 8,993,532 B2 | 3/2015 | Hannon et al. | |
| 9,522,176 B2 | 12/2016 | DeRosa et al. | |
| 9,527,904 B2 | 12/2016 | Balazs et al. | |
| 9,834,790 B1 | 12/2017 | Pauza et al. | |
| 9,834,791 B2 | 12/2017 | Zhang et al. | |
| 9,914,938 B2 | 3/2018 | Pauza et al. | |
| 10,023,880 B2 | 7/2018 | Pauza et al. | |
| 10,036,038 B2 | 7/2018 | Pauza et al. | |
| 10,036,040 B2 | 7/2018 | Pauza et al. | |
| 10,137,144 B2 | 11/2018 | Pauza et al. | |
| 10,208,295 B2 | 2/2019 | DeRosa et al. | |
| 10,233,464 B2 | 3/2019 | Pauza et al. | |
| 10,420,789 B2 | 9/2019 | Pauza et al. | |
| 10,428,350 B2 | 10/2019 | Pauza et al. | |
| 10,472,649 B2 | 11/2019 | Pauza et al. | |
| 10,767,183 B2 | 9/2020 | Lahusen et al. | |
| 10,772,905 B2 | 9/2020 | Pauza et al. | |

(Continued)

FOREIGN PATENT DOCUMENTS

| | | |
|---|---|---|
| BR | 2515 | 3/2019 |
| CN | 101516365 A | 8/2009 |

(Continued)

OTHER PUBLICATIONS

Nielson et al., Molecular therapy vol. 15, Suppl 1:S270, May 2007.*

(Continued)

*Primary Examiner* — Sean McGarry
(74) *Attorney, Agent, or Firm* — COOLEY LLP

(57) ABSTRACT

The present invention relates generally to methods and compositions for gene therapy and immunotherapy that activate gamma delta T-cells, and in particular, can be used in the treatment of various cancers and infectious diseases.

13 Claims, 15 Drawing Sheets

Specification includes a Sequence Listing.

(56) References Cited

U.S. PATENT DOCUMENTS

| | | |
|---|---|---|
| 2002/0168345 A1 | 11/2002 | Dong |
| 2003/0013196 A1 | 1/2003 | Engelman et al. |
| 2003/0096787 A1 | 5/2003 | Perricaudet et al. |
| 2003/0119770 A1 | 6/2003 | Lai et al. |
| 2003/0138444 A1 | 7/2003 | Zavitz et al. |
| 2004/0142416 A1 | 7/2004 | Laipis et al. |
| 2004/0161412 A1 | 8/2004 | Penn et al. |
| 2004/0180847 A1 | 9/2004 | Dobie et al. |
| 2004/0192629 A1 | 9/2004 | Xu et al. |
| 2004/0214158 A1 | 10/2004 | Sethi et al. |
| 2004/0248296 A1 | 12/2004 | Beresford et al. |
| 2004/0265306 A1 | 12/2004 | Arthos et al. |
| 2005/0019927 A1 | 1/2005 | Hildinger et al. |
| 2005/0138677 A1 | 6/2005 | Pfister et al. |
| 2006/0057553 A1 | 3/2006 | Aguilar-Cordova |
| 2006/0073576 A1 | 4/2006 | Barnett et al. |
| 2006/0183230 A1 | 8/2006 | Silla et al. |
| 2006/0246520 A1 | 11/2006 | Champagne et al. |
| 2007/0026521 A1 | 2/2007 | Colosi |
| 2007/0141679 A1 | 6/2007 | Sodroski et al. |
| 2007/0203333 A1 | 8/2007 | McSwiggen et al. |
| 2008/0003225 A1 | 1/2008 | Vie et al. |
| 2008/0003682 A1 | 1/2008 | Lois-Caballe et al. |
| 2008/0039413 A1 | 2/2008 | Morris et al. |
| 2008/0131940 A1 | 6/2008 | Chiu et al. |
| 2008/0153737 A1 | 6/2008 | Lieberman et al. |
| 2008/0199961 A1 | 8/2008 | Rasko et al. |
| 2008/0227736 A1 | 9/2008 | Chen et al. |
| 2008/0293142 A1 | 11/2008 | Liu et al. |
| 2009/0148936 A1 | 6/2009 | Stout et al. |
| 2009/0304688 A1 | 12/2009 | Fournie et al. |
| 2010/0017911 A1 | 1/2010 | Dawson et al. |
| 2010/0069372 A1 | 3/2010 | Kazantsev |
| 2010/0119511 A1 | 5/2010 | Wang et al. |
| 2010/0120155 A1 | 5/2010 | Brennan et al. |
| 2010/0286166 A1 | 11/2010 | Pey Rodríguez et al. |
| 2010/0316676 A1 | 12/2010 | Sanders et al. |
| 2011/0008803 A1 | 1/2011 | Stockwell |
| 2011/0177155 A1 | 7/2011 | Peer et al. |
| 2011/0207226 A1 | 8/2011 | Ni et al. |
| 2012/0027725 A1 | 2/2012 | Galvin et al. |
| 2012/0034197 A1 | 2/2012 | Young |
| 2012/0053223 A1 | 3/2012 | Benkirane et al. |
| 2012/0114607 A1 | 5/2012 | Lai et al. |
| 2012/0201794 A1 | 8/2012 | Chen et al. |
| 2013/0078276 A1 | 3/2013 | Robinson et al. |
| 2013/0090371 A1 | 4/2013 | Lu |
| 2013/0122380 A1 | 5/2013 | Visco et al. |
| 2013/0142766 A1 | 6/2013 | Dodo et al. |
| 2013/0211380 A1 | 8/2013 | Cabrera Aquino et al. |
| 2014/0155468 A1 | 6/2014 | Gregory et al. |
| 2014/0162894 A1 | 6/2014 | Hatchwell et al. |
| 2014/0178340 A1 | 6/2014 | Robbins et al. |
| 2014/0234958 A1 | 8/2014 | Kasahara et al. |
| 2014/0248277 A1 | 9/2014 | Hoffman et al. |
| 2014/0336245 A1 | 11/2014 | Mingozzi et al. |
| 2014/0348794 A1 | 11/2014 | Chiorini et al. |
| 2015/0010578 A1 | 1/2015 | Balazs et al. |
| 2015/0018539 A1 | 1/2015 | Fellmann |
| 2015/0126580 A1 | 5/2015 | DePinho et al. |
| 2015/0132255 A1 | 5/2015 | Sorensen et al. |
| 2015/0176006 A1 | 6/2015 | Krause et al. |
| 2016/0060707 A1 | 3/2016 | Goldenberg et al. |
| 2016/0243169 A1 | 8/2016 | Chen et al. |
| 2016/0287635 A1 | 10/2016 | Hariri et al. |
| 2016/0289681 A1 | 10/2016 | Rossi et al. |
| 2017/0015976 A1 | 1/2017 | Nelson |
| 2017/0028036 A1 | 2/2017 | Mingozzi et al. |
| 2017/0037369 A1 | 2/2017 | Ramsborg et al. |
| 2017/0335344 A1 | 11/2017 | Pauza et al. |
| 2018/0010147 A1 | 1/2018 | Pauza et al. |
| 2018/0142257 A1 | 5/2018 | Pauza et al. |
| 2018/0142258 A1 | 5/2018 | Pauza et al. |
| 2018/0161455 A1 | 6/2018 | Pauza et al. |
| 2018/0177866 A1 | 6/2018 | Pauza |
| 2018/0195046 A1 | 7/2018 | Deng et al. |
| 2018/0195050 A1 | 7/2018 | Szalay et al. |
| 2018/0256624 A1 | 9/2018 | Pauza et al. |
| 2018/0305716 A1 | 10/2018 | Pauza et al. |
| 2018/0355032 A1 | 12/2018 | Roberts et al. |
| 2019/0046633 A1 | 2/2019 | Pauza et al. |
| 2019/0062786 A1 | 2/2019 | Pauza et al. |
| 2019/0078096 A1 | 3/2019 | Lahusen et al. |
| 2019/0083523 A1 | 3/2019 | Pauza et al. |
| 2019/0218573 A1 | 7/2019 | Pauza et al. |
| 2019/0388456 A1 | 12/2019 | Pauza et al. |
| 2020/0017570 A1 | 1/2020 | Walcheck et al. |
| 2020/0063161 A1 | 2/2020 | Pauza et al. |
| 2020/0087682 A1 | 3/2020 | Lahusen et al. |
| 2020/0109417 A1 | 4/2020 | Pauza et al. |
| 2020/0155590 A1 | 5/2020 | Lai et al. |
| 2020/0181645 A1 | 6/2020 | Pauza et al. |
| 2020/0318081 A1 | 10/2020 | Lahusen et al. |
| 2020/0354679 A1 | 11/2020 | Niazi |
| 2021/0047644 A1 | 2/2021 | Lahusen et al. |

FOREIGN PATENT DOCUMENTS

| | | |
|---|---|---|
| CN | 101679466 A | 3/2010 |
| CN | 101805750 A | 8/2010 |
| CN | 103184224 A | 7/2013 |
| CN | 105112370 A | 12/2015 |
| CN | 108883100 A | 11/2018 |
| EP | 1647595 A1 | 4/2006 |
| EP | 3402483 A1 | 11/2018 |
| EP | 3413926 A1 | 12/2018 |
| EP | 3426777 A2 | 1/2019 |
| EP | 3468617 A1 | 4/2019 |
| EP | 3468618 A2 | 4/2019 |
| EP | 3481418 A1 | 5/2019 |
| EP | 3481435 A1 | 5/2019 |
| IN | 201947000153 | 2/2019 |
| JP | 2002506652 A | 3/2002 |
| JP | 2007527240 A | 9/2007 |
| JP | 2008518591 A | 6/2008 |
| JP | 2008538174 A | 10/2008 |
| JP | 2012508591 A | 4/2012 |
| JP | 2012523243 A | 10/2012 |
| JP | 2013530152 A | 7/2013 |
| JP | 2013544600 A | 12/2013 |
| JP | 2015518838 A | 7/2015 |
| JP | 2016502404 A | 1/2016 |
| JP | 2019509029 A | 4/2019 |
| WO | WO-9947691 A1 | 9/1999 |
| WO | WO-0220554 A2 | 3/2002 |
| WO | WO-03093436 A2 | 11/2003 |
| WO | WO-2004053137 A2 | 6/2004 |
| WO | WO-2005028634 A2 | 3/2005 |
| WO | WO-2005033282 A2 | 4/2005 |
| WO | WO-2006039721 A2 | 4/2006 |
| WO | WO-2006048215 A1 | 5/2006 |
| WO | WO-2006089001 A2 | 8/2006 |
| WO | WO-2007000668 A2 | 1/2007 |
| WO | WO-2007015122 A1 | 2/2007 |
| WO | WO-2007132292 A2 | 11/2007 |
| WO | WO-2007133674 A2 | 11/2007 |
| WO | WO-2008025025 A2 | 2/2008 |
| WO | WO-2008090185 A1 | 7/2008 |
| WO | WO-2009001224 A2 | 12/2008 |
| WO | WO-2009100928 A1 | 8/2009 |
| WO | WO-2009147445 A1 | 12/2009 |
| WO | WO-2010051521 A1 | 5/2010 |
| WO | WO-2010111522 A2 | 9/2010 |
| WO | WO-2010117974 A2 | 10/2010 |
| WO | WO-2010119039 A1 | 10/2010 |
| WO | WO-2010127166 A2 | 11/2010 |
| WO | WO-2011008348 A2 | 1/2011 |
| WO | WO-2011071476 A2 | 6/2011 |
| WO | WO-2011119942 A1 | 9/2011 |
| WO | WO-2011148194 A1 | 12/2011 |
| WO | WO-2012048303 A2 | 4/2012 |
| WO | WO-2012061075 A2 | 5/2012 |
| WO | WO-2012071559 A2 | 5/2012 |
| WO | WO-2012145624 A2 | 10/2012 |

(56) References Cited

FOREIGN PATENT DOCUMENTS

| WO | WO-2013056148 A2 | 4/2013 |
| --- | --- | --- |
| WO | WO-2013096455 A1 | 6/2013 |
| WO | WO-2014016817 A2 | 1/2014 |
| WO | WO-2014117050 A2 | 7/2014 |
| WO | WO-2014187881 A1 | 11/2014 |
| WO | WO-2014195159 A1 | 12/2014 |
| WO | WO-2015017755 A1 | 2/2015 |
| WO | WO-2015042308 A2 | 3/2015 |
| WO | WO-2015061491 A1 | 4/2015 |
| WO | WO-2015078999 A1 | 6/2015 |
| WO | WO-2015086854 A1 | 6/2015 |
| WO | WO-2015164759 A2 | 10/2015 |
| WO | WO-2016046234 A2 | 3/2016 |
| WO | WO-2016061232 A2 | 4/2016 |
| WO | WO-2016069716 A1 | 5/2016 |
| WO | WO-2016189159 A1 | 12/2016 |
| WO | WO-2016200997 A1 | 12/2016 |
| WO | WO-2017007994 A1 | 1/2017 |
| WO | WO-2017068077 A1 | 4/2017 |
| WO | WO-2017100551 A1 | 6/2017 |
| WO | WO-2017123918 A1 | 7/2017 |
| WO | WO-2017139065 A1 | 8/2017 |
| WO | WO-2017156311 A2 | 9/2017 |
| WO | WO-2017165641 A1 | 9/2017 |
| WO | WO-2017173453 A1 | 10/2017 |
| WO | WO-2017213697 A1 | 12/2017 |
| WO | WO-2017214327 A2 | 12/2017 |
| WO | WO-2018009246 A1 | 1/2018 |
| WO | WO-2018009847 A1 | 1/2018 |
| WO | WO-2018017882 A1 | 1/2018 |
| WO | WO-2018126112 A1 | 7/2018 |
| WO | WO-2018129540 A1 | 7/2018 |
| WO | WO-2018148443 A1 | 8/2018 |
| WO | WO-2018187231 A2 | 10/2018 |
| WO | WO-2018232359 A1 | 12/2018 |
| WO | WO-2019070674 A2 | 4/2019 |
| WO | WO-2020011247 A1 | 1/2020 |
| WO | WO-2020097049 A1 | 5/2020 |
| WO | WO-2020243717 A1 | 12/2020 |
| WO | WO-2021178571 A1 | 9/2021 |

OTHER PUBLICATIONS

Altschul S.F., et al., "Basic Local Alignment Search Tool," Journal Molecular Biology, 1990, vol. 215, pp. 403-410.

Ausubel F.M., et al., "Short Protocols in Molecular Biology: A Compendium of Methods from Current Protocols in Molecular Biology," Wiley, John & Sons, Inc., 1995, 1 Page.

Office Action for European Patent Application No. 17739028.3, mailed May 22, 2023, 125 pages.

US; Restriction Requirement issued in U.S. Appl. No. 17/570,313 on Nov. 15, 2023.

CN; Office Action issued in Application No. 201880039828.4 on Nov. 30, 2023.

IL; Notice of Allowance issued in Application No. 297238 on Dec. 11, 2023.

Advisory Action for U.S. Appl. No. 13/333,882, mailed Nov. 16, 2018, 3 Pages.

Advisory Action for U.S. Appl. No. 15/736,284, mailed Jul. 23, 2019, 3 Pages.

Akinsheye I., et al., "Fetal Hemoglobin in Sickle Cell Anemia," Blood, Jul. 7, 2011, vol. 118, No. 1, pp. 19-27.

Altschul S.F., et al., "Gapped Blast and PSI-Blast: A New Generation of Protein Database Search Programs," Nucleic Acids Research, Jul. 1997, vol. 25, No. 17, pp. 3389-3402.

Anderson J.S., et al., "Preintegration HIV-1 Inhibition by a Combination Lentiviral Vector Containing a Chimeric TRIM5a Protein, a CCR5 shRNA, and TAR Decoy," Molecular Therapy, Dec. 2009, vol. 17, No. 12, pp. 2103-2114.

Bartholome K., "Genetics and Biochemistry of the Phenylketonuria-Present State," Human Genetics, 1979, vol. 51, No. 03, pp. 241-245.

Benyamine A., et al., "BTN3A Molecules Considerably Improve Vγ9Vδ2T Cells-based Immunotherapy in Acute Myeloid Leukemia," OncoImmunology, Oct. 2, 2016, vol. 5, No. 10, 10 Pages, the whole document.

Berge S.M., et al., "Pharmaceutical Salts," Journal of Pharmaceutical Sciences, Jan. 1977, vol. 66, No. 1, pp. 1-19.

Bergvall M., et al. "The E1 Proteins," Virology, 2013, vol. 445, pp. 35-56.

Blau N., et al., "Phenylketonuria," The Lancet, Oct. 23, 2010, vol. 376(9750), pp. 1417-1427.

Blick G., et al., "Cyclophosphamide Enhances SB-728-T Engraftment to Levels Associated with HIV-RNA Control," CROI Conference on Retroviruses and Opportunistic Infections, Mar. 3-6, 2014, 3 Pages.

Bourguignon P., et al., "Processing of Blood Samples Influences PBMC Viability and Outcome of Cell-mediated Immune Responses in Antiretroviral Therapy-naïve HIV-1-infected Patients," Journal of Immunological Methods, Dec. 1, 2014, vol. 414, pp. 1-10.

Brites C., et al., "Infection by HTLV-1 is Associated with High Levels of Proinflammatory Cytokines in HIV-HCV-Coinfected Patients," Journal of Acquired Immune Deficiency Syndromes, Feb. 1, 2018, vol. 77, No. 2, pp. 230-234.

Briz V., et al., "Validation of Generation 4 Phosphorus-Containing Polycationic Dendrimer for Gene Delivery Against HIV-1," Current Medical Chemistry, 2012, vol. 19, No. 29, pp. 5044-5051.

Cannon J.R., et al., "Pseudotype-Dependent Lentiviral Transduction of Astrocytes or Neurons in the Rat Substantia Nigra," Experimental Neurology, Mar. 2011, vol. 228, No. 1, pp. 41-52, DOI:10.1016/J.expneurol.2010.10.016.

Capietto A-H., et al., "Stimulated Yδ T Cells Increase the in Vivo Efficacy of Trastuzumab in HER-2+ Breast Cancer," Journal of Immunology, 2011, vol. 187(2), pp. 1031-1038.

Cell Host Microbe, 2007, vol. 2, pp. 96-105, ISSN 0004294204.

Chandler R.J., et al., "Vector Design Influences Hepatic Genotoxicity After Adeno-Associated Virus Gene Therapy," Journal of Clinical Investigation, Feb. 2015, vol. 125, No. 2, pp. 870-880.

Charron C.E., et al., "Dominant-Negative Interference in the Pahenu2 Mouse Model of PKU: Effectiveness of Vectors Expressing Either Modified Forms of Phenylalanine Hydroxylase (PAH) or Ribozymes Plus a Hardened PAH mRNA," Molecular Therapy, 2005, vol. 11, pp. S163-S164.

Charron C.E., "Gene Therapy for Phenylketonuria: Dominant-Negative Interference in a Recessive Disease," Dissertation, University of Florida, 2005, 89 pages, [Retrieved on Jul. 26, 2018] Retrieved from URL: http://etd.fcla.edu/UF/UFE0011392/charron_c.pdf.

Chen H.C., et al., "An Unconventional Trail to Cancer Therapy," European Journal of Immunology, 2013, vol. 43, No. 12, pp. 3159-3162, DOI: 10.1002/eji.201344105, ISSN 0004789814, XP071226184.

Chen Z., et al., "CD16+ Gammadelta T Cells Mediate Antibody Dependent Cellular Cytotoxicity: Potential Mechanism in The Pathogenesis of Multiple Sclerosis," Clinical Immunology, 2008, vol. 128(2), pp. 219-227.

Cheng M., et al., "Establishment, Characterization, and Successful Adaptive Therapy Against Human Tumors of NKG Cell, a New Human NK Cell Line", Cell Transplantation, Jun. 2011, vol. 20, pp. 1731-1746.

Chiang C-M., et al., "Viral E1 and E2 Proteins Support Replication of Homologous and Heterologous Papillomaviral Origins," Proceedings of the National Academy of Sciences of the United States of America, Jul. 1, 1992, vol. 89, pp. 5799-5803.

Choi J-G., et al., "Multiplexing Seven miRNA-Based shRNAs to Suppress HIV Replication," Molecular Therapy : The Journal of the American Society of Gene Therapy, Feb. 2015, vol. 23, No. 02, pp. 310-320, DOI: 10.1038/mt.2014.205, ISSN 1525-0016, XP055432740.

Christophersen E.B., et al., "A Technique of Transumbilical Portal Vein Catheterization in Adults," The Archives of Surgery, 1967, vol. 95(6), pp. 960-963, (Abstract Only).

Coligan, et al., "Short Protocols in Protein Science," Wiley, John & Sons, Inc, 2003.

Coligan J.E., et al., "Current Protocols in Protein Science," Short Protocols in Protein Science, 1996, vol. 24, No. 409, 1 Page.

(56) References Cited

OTHER PUBLICATIONS

Condiotti R., et al., "Prolonged Liver-Specific Transgene Expression by a Non-Primate Lentiviral Vector," Biochemical and Biophysical Research Communications, Jul. 30, 2004, vol. 320, No. 3, pp. 998-1006.
Corrected Notice of Allowance for U.S. Appl. No. 16/563,738, mailed Aug. 31, 2022, 5 Pages.
Corrected Notice of Allowance for U.S. Appl. No. 16/687,525, mailed Mar. 3, 2021, 2 Pages.
Couzi L., et al., "Antibody-Dependent Anti-Cytomegalovirus Activity of Human Gammadelta T Cells Expressing CD16 (FcgammaRIIIa)," Blood, 2012, vol. 119(6), pp. 1418-1427.
Craenenbroeck K.V., et al., "Episomal Vectors for Gene Expression in Mammalian Cells," European Journal Biochemistry, Jul. 14, 2000, vol. 267, pp. 5665-5678.
Cronin J., et al., "Altering The Tropism of Lentiviral Vectors Through Pseudotyping," Current Gene Therapy, Aug. 2005, vol. 5, No. 4, pp. 387-398.
Davis-Gardner M.E., et al., "eCD4-Ig promotes ADCC activity of sera from HIV-1-infected patients", Department of Immunology and Microbiology, The Scripps Research Institute, PLOS Pathogen, Dec. 18, 2017, 19 Pages, Retrieved from URL: https://doi.org/10.1371/journal.ppat.1006786.
Deveraux J., et al., "A Comprehensive Set of Sequence Analysis Programs for the VAX," Nucleic Acids Research, 1984, vol. 12, No. 1, pp. 387-395.
Dickler H.B., et al., "Lymphocyte Binding of Aggregated IgG and Surface Ig Staining in Chronic Lymphocytic Leukaemia," Clinical and Experimental Immunology, 1973, vol. 14, No. 01, pp. 97-106.
Dieli F., et al., "Targeting Human γδ T Cells with Zoledronate and Interleukin-2 for Immunotherapy of Hormone-Refractory Prostate Cancer," Europe PMC Funders Group, Cancer Research, Aug. 1, 2007, vol. 67, No. 15, pp. 7450-7457.
Ding Z., et al., "Administration-Route and Gender-Independent Longterm Therapeutic Correction of Phenylketonuria (PKU) in a Mouse Model by Recombinant Adeno-Associated Virus 8 Pseudotyped Vector-Mediated Gene Transfer," Gene Therapy, Dec. 1, 2005, vol. 13, pp. 587-593.
Ding Z., et al., "Liver-Directed, AAV-and Lentivirus-Mediated Gene Therapy in the Phenylketonuria Mouse Model Pah-enu2," Molecular Therapy, May 2005, vol. 11, Supplement. 1, p. S348, XP055751452.
Donsante A., et al., "AAV Vector Integration Sites in Mouse Hepatocellular Carcinoma," Science, Jul. 27, 2007, vol. 317, No. 5837, p. 477.
Douek D.C., et al., "HIV Preferentially Infects HIV-Specific CD4+ T Cells," Nature, May 2, 2002, vol. 417, No. 6884, pp. 95-98.
Eguchi K., et al., "Primary Sjogren's Syndrome with Antibodies to HTLV-I: Clinical and Laboratory Features," Annals of the Rheumatic Diseases, 1992, vol. 51, No. 6, pp. 769-776.
Eisensmith R.C., et al., "Multiple Origins for Phenylketonuria in Europe," American Journal of Human Genetics, 1992, vol. 51, No. 6, pp. 1355-1365.
Extended European Search Report for European Application No. 17750547.6, mailed Sep. 6, 2019, 6 Pages.
Extended European Search Report for European Application No. 17764128.9, mailed Aug. 12, 2019, 8 Pages.
Extended European Search Report for European Application No. 17810976.5, mailed Dec. 19, 2019, 8 Pages.
Extended European Search Report for European Application No. 17824652.6, mailed Feb. 6, 2020, 8 Pages.
Extended European Search Report for European Application No. 17825011.4, mailed Feb. 6, 2020, 8 Pages.
Extended European Search Report for European Application No. 17831904.2, mailed Mar. 11, 2020, 9 Pages.
Extended European Search Report for European Application No. 18736295.9, mailed Aug. 20, 2020, 12 Pages.
Extended European Search Report for European Application No. 18781288.8, mailed Dec. 8, 2020, 11 Pages.
Extended European Search Report for European Application No. 19883230.5, mailed Jul. 21, 2022, 9 Pages.
Extended European Search Report for European Application No. 17739028.3, mailed Jun. 6, 2019, 8 Pages.
Extended European Search Report for European Application No. 13731655.0, mailed Feb. 24, 2014, 5 Pages.
Extended European Search Report for European Application No. 16904834.5, mailed Dec. 19, 2019, 8 Pages.
Extended European Search Report for European Application No. 18817253.0, mailed Feb. 10, 2021, 8 Pages.
Extended European Search Report for European Application No. 22154806.8, mailed Jul. 4, 2022, 8 Pages.
Extended European Search Report for European Application No. 16808223.8, mailed Dec. 13, 2018, 9 Pages.
Extended European Search Report for European Application No. 16822021.8, mailed Dec. 11, 2018, 8 Pages.
Final Office Action for U.S. Appl. No. 13/333,882, mailed Aug. 27, 2018, 11 Pages.
Final Office Action for U.S. Appl. No. 15/580,661, mailed Jun. 2, 2020, 16 Pages.
Final Office Action for U.S. Appl. No. 15/736,284, mailed May 2, 2019, 22 Pages.
Final Office Action for U.S. Appl. No. 16/076,655, mailed Jul. 27, 2020, 17 Pages.
Final Office Action for U.S. Appl. No. 16/132,247, mailed Jul. 1, 2019, 7 Pages.
Final Office Action for U.S. Appl. No. 16/182,443, mailed May 2, 2019, 07 Pages.
Final Office Action for U.S. Appl. No. 16/312,056, mailed Feb. 26, 2021, 22 Pages.
Final Office Action for U.S. Appl. No. 16/614,682, mailed Aug. 2, 2022, 34 Pages.
First Office Action in the CN Application No. 201780017712.6, mailed May 8, 2020, 10 Pages.
Fisher D.B., et al., "The Inhibition of Phenylalanine and Tyrosine Hydroxylases by High Oxygen Levels," Journal of Neurochemistry, May 1972, vol. 19, No. 5, pp. 1359-1365, (Abstract Only).
Fisher J.P.H., et al., "Effective Combination Treatment of GD2-Expressing Neuroblastoma and Ewing's Sarcoma Using Anti-GD2 ch14.18/CHO Antibody with Vγ9Vδ2+ γT Cells," OncoImmunology, 2016, vol. 5, Issue No. 1, e1025194, 32 Pages.
Fujiwara Y., et al., "A Nucleolar Stress-Specific p53-miR-101 Molecular Circuit Functions as an Intrinsic Tumor-Suppressor Network," EBiomedicine, NL, Jul. 7, 2018, vol. 33, pp. 33-48, DOI: 10.1016/j.ebiom.2018.06.031, ISSN: 2352-3964, XP055939874, Retrieved from URL: https://www.sciencedirect.com/science/article/pii/S235239641830238X?via%3Dihub.
Fusetti F., et al., "Structure of Tetrameric Human Phenylalanine Hydroxylase and Its Implications for Phenylketonuria," Journal of Biological Chemistry, Jul. 3, 1998, vol. 273, No. 27, pp. 16962-16967, DOI: 10.1074/jbc.273.27.16962, XP055559179.
Futsch N., et al., "HTLV-1, the Other Pathogenic Yet Neglected Human Retrovirus: From Transmission to Therapeutic Treatment," Viruses, 2018, vol. 10, No. 01, 25 Pages, DOI:10.3390/Y10010001.
Gagniuc P., et al., "Eukaryotic Genomes May Exhibit up to 10 Generic Classes of Gene Promoters," BMC Genomics, 2012, vol. 13, 17 Pages, DOI:10.1186/1471-2164-13-512, XP021134695.
GenBank Accession No. JG619773, "MNESC1NG-T3-001_L15_6FEB2009_054 MNESC1NG Cell Culture from Mahonia Nervosa Berberis Nervosa cDNA, mRNA Sequence," Feb. 13, 2014, 1 Page, Entire document, [Retrieved on Dec. 5, 2017], Retrieved from URL: https://www.ncbi.nlm.nih.gov/nucest/JG619773.
Genbank: "(long Control Region) [Human Papillomavirus, Type 16, Genomic, 860 nt]" GenBank Accession No. S60559, May 7, 1993, entire DNA sequence, pp. 1, [Located online Nov. 21, 2017] Retrieved from URL: https://ncbi.nlm.nih.gov/nuccore/S60559.
Gennaro A.R., "Remington's Pharmaceutical Sciences," 17th edition, Mack Publishing Company, Easton, Pa., Oct. 1985, vol. 74, No. 10, pp. 1143-1144.
Gertner-Dardenne J., et al., "Bromohydrin Pyrophosphate Enhances Antibody-Dependent Cell-Mediated Cytotoxicity Induced by Therapeutic Antibodies," Blood, 2009, vol. 113(20), pp. 4875-4884.

(56) References Cited

OTHER PUBLICATIONS

Gessain A., et al., "Antibodies to Human T-Lymphotropic Virus Type-I in Patients with Tropical Spastic Paraparesis," The Lancet, Aug. 24, 1985, vol. 02, No. 8452, pp. 407-410.
Gessain A., et al., "Epidemiological Aspects and World Distribution of HTLV-1 Infection," Frontiers in Microbiology, Nov. 2012, vol. 03, Article 388, 23 Pages.
Gober H-J., et al., "Human T Cell Receptor γδ Cells Recognize Endogenous Mevalonate Metabolites in Tumor Cells," Journal of Experimental Medicine, Jan. 20, 2003, vol. 197, No. 2, pp. 163-168.
Goepfert P.A., et al., "Specificity and 6-Month Durability of Immune Responses Induced by DNA and Recombinant Modified Vaccinia Ankara Vaccines Expressing HIV-1 Virus-Like Particles," The Journal of Infectious Diseases, Jul. 1, 2014, vol. 210, pp. 99-110, XP055410056.
Goncalves D.U., et al., "Epidemiology, Treatment, and Prevention of Human T-Cell Leukemia Virus Type 1-Associated Diseases," Clinical Microbiology Reviews, Jul. 2010, vol. 23, No. 03, pp. 577-589.
Gorziglia M.I., et al., "Elimination of Both E1 and E2A from Adenovirus Vectors Further Improves Prospects for In Vivo Human gene Therapy," Journal of Virology, Jun. 1996, vol. 70, No. 6, pp. 4173-4178.
Grisch-Chan H.M., et al., "Low-Dose Gene Therapy for Murine PKU Using Episomal Naked DNA Vectors Expressing PAH from Its Endogenous Liver Promoter," Molecular Therapy Nucleic Acids, 2017, vol. 7, pp. 339-349.
Guldberg P., et al., "Aberrant Phenylalanine Metabolismin Phenylketonuria Heterozygotes," Journal of Inherited Metabolic Disease, 1998, vol. 21, No. 4, pp. 365-372.
Hafid A.Z., et al., "Phenylketonuria: A Review of Current and Future Treatments," Translational Pediatrics, 2015, vol. 4, No. 4 pp. 304-317.
Harlow E., et al., "Antibodies: A Laboratory Manual," Cold Spring Harbor Laboratory Press, 1988, 1 Page.
Harly C., et al., "Key Implication of CD277/butyrophilin-3 (BTN3A) in Cellular Stress Sensing by a Major Human T-cell Subset," Blood, Sep. 13, 2012, vol. 120, No. 11, pp. 2269-2279, DOI:10.1182/blood-2012-05-430470, ISSN 00064971, XP055081172.
Hassan G., et al., "Isolation of Umbilical Cord Mesenchymal Stem Cells Using Human Blood Derivative Accompanied With Explant Method," Stem Cell Investigation, 2019, pp. 1-8.
Herrera L., et al., "Adult Peripheral Blood and Umbilical Cord Blood NK Cells are Good Sources for Effective CAR Therapy Against CD19 Positive Leukemic Cells," Scientific Reports, Dec. 2019, vol. 9, Article. 18729, 2 Pages.
Huang Q., et al., "An Efficient Protocol to Generate Placental Chorionic Plate-derived Mesenchymal Stem Cells with Superior Proliferative and Immunomodulatory Properties," Stem Cell Research & Therapy, 2019, vol. 10(301), pp. 1-15.
International Preliminary Report on Patentability for International Application No. PCT/US2018/012998, mailed Jul. 18, 2019, 9 Pages.
International Preliminary Report on Patentability for International Application No. PCT/US2018/025733, mailed Oct. 17, 2019, 9 Pages.
International Preliminary Report on Patentability for International Application No. PCT/US2019/059828, mailed May 20, 2021, 10 Pages.
International Search Report and Written Opinion for International Application No. PCT/US2019/024410, mailed Jul. 22, 2019, 10 Pages.
International Search Report and Written Opinion for International Application No. PCT/US2019/059828, mailed Feb. 14, 2020, 12 Pages.
International Search Report and Written Opinion for International Application No. PCT/US2021/020721, mailed Jul. 21, 2021, 10 Pages.
International Preliminary Report on Patentability for International Application No. PCT/US2017/013399, mailed Jul. 26, 2018, 10 Pages.
International Preliminary Report on Patentability for International Application No. PCT/US2017/021639, mailed Sep. 20, 2018, 9 Pages.
International Preliminary Report on Patentability for International Application No. PCT/US2018/037924, mailed Dec. 26, 2019, 13 Pages.
International Search Report and Written Opinion for International Application No. PCT/US2022/013422, mailed May 13, 2022, 19 Pages.
International Search Report for International Application No. PCT/US2016/036519, mailed Nov. 7, 2016, 4 Pages.
International Search Report for International Application No. PCT/US2016/041456, mailed Oct. 19, 2016, 4 Pages.
International Search Report for International Application No. PCT/US2016/066185, mailed Jun. 9, 2017, 12 Pages.
International Search Report for International Application No. PCT/US2017/013019, mailed Jul. 17, 2017, 5 Pages.
International Search Report for International Application No. PCT/US2017/013024, mailed Jul. 14, 2017, 3 Pages.
International Search Report for International Application No. PCT/US2017/013399, mailed May 26, 2017, 4 Pages.
International Search Report for International Application No. PCT/US2017/021639, mailed Aug. 25, 2017, 5 Pages.
International Search Report for International Application No. PCT/US2017/036433, mailed Dec. 15, 2017, 5 Pages.
International Search Report for International Application No. PCT/US2017/041168, mailed Nov. 8, 2017, 4 Pages.
International Search Report for International Application No. PCT/US2017/043157, mailed Dec. 26, 2017, 7 Pages.
International Search Report for International Application No. PCT/US2018/012998, mailed May 29, 2018, 4 Pages.
International Search Report for International Application No. PCT/US2018/025733, mailed Sep. 24, 2018, 6 Pages.
International Search Report for International Application No. PCT/US2018/037924, mailed Nov. 9, 2018, 7 Pages.
International Search Report for International Application No. PCT/US2018/053919, mailed Apr. 12, 2019, 6 Pages.
Invitation to Pay Additional Fees and, Where Applicable, Protest Fee for International Application No. PCT/US2018/025733, mailed Jul. 17, 2018, 2 Pages.
Invitation to Pay Additional Fees and, where Applicable, Protest Fee for International Application No. PCT/US2018/037924, mailed Sep. 11, 2018, 3 Pages.
Invitation to Pay Additional Fees and, Where Applicable, Protest Fee for International Application No. PCT/US2018/053919, mailed Feb. 22, 2019, 3 Pages.
Jaalouk D.E., et al., "A Self-inactivating Retrovector Incorporating The IL-2 Promoter fOr Activation-Induced Transgene Expression Engineered T-cells," Virology, 2006, vol. 3, No. 97, 12 Pages.
Jakobsson J., et al., "Lentiviral Vectors for Use in the Central Nervous System," Molecular Therapy : The Journal of the American Society of Gene Therapy, Cell Press, US, Mar. 1, 2006, vol. 13, No. 3, pp. 484-493, DOI: 10.1016/J.YMTHE.2005.11.012, ISSN: 1525-0016, XP005326761.
Jiang X., et al., "A Novel EST-derived RNAi Screen Reveals a Critical Role For Farnesyl Diphosphate Synthase in Beta 2-adrenergic Receptor Internalization and Down-regulation," The FASEB Journal, Published Online on Jan. 27, 2012, vol. 26(5), pp. 1995-2007.
Journal of Cellular and Molecular Medicine, 2008, vol. 12, No. 3, pp. 928-941, ISSN 0004294202.
Kagdi H., et al., "Switching and Loss of Cellular Cytokine Producing Capacity Characterize In Vivo Viral Infection and Malignant Transformation in Human T-lymphotropic Virus Type 1 Infection," PLoS Pathogens, Feb. 14, 2018, vol. 14, No. 2, 25 Pages, e1006861.
Kagdi H.H., et al., "Risk Stratification of Adult T-Cell Leukemia/Lymphoma Using Immunophenotyping," Cancer Medicine, 2017, vol. 06, No. 01, pp. 298-309.
Kam T-I., et al., "Poly (ADP-ribose) Derived Pathologic [alpha]—Synuclein Neurodegeneration in Parkinson's disease," Science, US,

(56) References Cited

OTHER PUBLICATIONS

Nov. 2, 2018, vol. 362, No. 6414, eaat8407, 12 pages, ISSN: 00368075, DOI: 10.1126/science.aat8407, XP55672116.

Kaufman S., "A Model of Human Phenylalanine Metabolism in Normal Subjects and in Phenylketonuric Patients," Proceedings of the National Academy of Sciences, USA, Mar. 1999, vol. 96(6), pp. 3160-3164.

Kaufman S., et al., "Phenylalanine Hydroxylase Activity in Liver Biopsies from Hyperphenylalaninemia Heterozygotes: Deviation from Proportionality with Gene Dosage," Pediatric Research, 1975, vol. 9(8), pp. 632-634.

Kavanagh D.G., et al., "Expansion of HIV-specific CD4+ and CD8+ T Cells by Dendritic Cells Transfected with mRNA Encoding Cytoplasm- or lysosome-targeted Nef," Blood, American Society of Hematology, US, Mar. 2006, Oct. 25, 2005, vol. 107, No. 5, DOI: 10.1182/BLOOD-2005-04-1513, ISSN 0006-4971, XP008141565.

Kim H.Y., et al., "Farnesyl Diphosphate Synthase is Important for The Maintenance of Glioblastoma Stemness," Experimental & Molecular Medicine, Published Online on Oct. 17, 2018, vol. 50, No. 10, 12 pages, DOI: 10.1038/s12276-018-0166-2, XP055605154.

Krajinovic M., et al., "Sequencing Data on The Long Control Region of Human Papillomavirus Type 16," Journal of General Virology, 1991, vol. 72, pp. 2573-2576.

Lam S., et al., "T-cell Therapies for HIV," Immunotherapy, Future Medicine, London, Apr. 1, 2013, vol. 5, No. 4, pp. 407-414, DOI:10.2217/IMT.13.23, ISSN 1750-7448, XP009182920.

Ledley F.D., et al., "Molecular Biology of Phenylalanine Hydroxylase and Phenylketonuria," Trends in Genetics, Elsevier Science Publishers, B.V. Amsterdam, NL, Nov. 1985, vol. 1, pp. 309-313, DOI:10.1016/0168-9525(85)90121-0, ISSN 0168-9525, XP025943064.

Ledley F.D., et al., "Retroviral-Mediated Gene Transfer of Human Phenylalanine Hydroxylase Into NIH-3T3 and Hepatoma Cells," Proceedings of The National Academy of Sciences, National Academy of Sciences, Jan. 1986, vol. 83, No. 2, pp. 409-413, DOI:10.1073/PNAS.83.2.409, ISSN 0027-8424, XP002583115.

Lee S-K., et al., "Lentiviral Delivery of Short Hairpin RNAs Protects CD4 Cells from Multiple Clades and Primary Isolates of HIV," Blood, Aug. 1, 2005, vol. 106, No. 3, pp. 818-826.

Lee Y., et al., "Poly (ADP-ribose) in the Pathogenesis of Parkinson's Disease," BMB Reports, Korean Society for Biochemistry and Molecular Biology, KR, Aug. 31, 2014, vol. 47, No. 8, pp. 424-432, DOI:10.5483/BMBRep.2014.47.8.119, ISSN: 1976-6696, XP055671927.

Li J., et al., "Reduced Expression of the Mevalonate Pathway Enzyme Farnesyl Pyrophosphate Synthase Unveils Recognition of Tumor Cells by V[gamma]9V[delta]2 T Cells," The Journal of Immunology, US, (Jun. 3, 2009), Jun. 2009, vol. 182, No. 12, pp. 8118-8124, doi:10.4049/jimmunol.0900101, ISSN 0022-1767, XP055605150.

Li Z., et al., "Inhibition of Farnesyl Pyrophosphate Synthase Prevents Angiotensin II-induced Cardiac Fibrosis In Vitro," Clinical & Experimental Immunology, 2014, vol. 176, pp. 429-437.

Li Z., et al., "Zoledronic Acid Stimulates in Vitro Expansion of γδT Cells in Healthy Human and Osteosarcoma PBMCs," Journal of Cellular and Molecular Immunology.

Lin, et al., "Clinical Effects of Intra-arterial Infusion Chemotherapy with Cisplatin, Mitomycin C, Leucovor and 5-Fluorouracil for Unresectable Advanced Hepatocellular Carcinoma", J. Chin. Med. Assoc., 2004, vol. 67, pp. 602-610.

Lin Y., et al., "Up-Regulation of Bcl-2 is Required for the Progression of Prostate Cancer Cells from an Androgen-Dependent to an Androgen-Independent Growth Stage," Cell Research, Apr. 3, 2007, vol. 17, pp. 531-536.

Longo N., et al., "Single-Dose, Subcutaneous Recombinant Phenylalanine Ammonia Lyase Conjugated with Polyethylene Glycol in Adult Patients with Phenylketonuria: An Open-Label, Multicenter, Phase 1 Dose-Escalation Trial," The Lancet, Jul. 5, 2014, vol. 384(9937), pp. 37-44.

Lu R., et al., "Simian Virus 40-Based Replication of Catalytically Inactive Human Immunodeficiency Virus Type 1 Integrase Mutants in Nonpermissive T Cells and Monocyte-Derived Macrophages," Journal of Virology, Jan. 2004, pp. 658-668. DOI: 10.1128/JVI.78.2658-668.2004.

Lu X., et al., "Anti-sense-Mediated Inhibition of Human Immunodeficiency Virus (HIV) Replication by Use of an HIV Type 1-Based Vector Results in Severely Attenuated Mutants Incapable of Developing Resistance," Journal of Virology, Jul. 2004, vol. 79, No. 13, pp. 7079-7088.

Lv X., et al., "A New Method to Expand γδT Cells in Vitro," Chinese Journal of Immunology.

Macnamara A., et al., "HLA Class I Binding of HBZ Determines Outcome in HTLV-1 Infection," PLoS Pathog, Sep. 2010, vol. 06, No. 09:e1001117, pp. 1-12.

Manel N., et al., "The Ubiquitous Glucose Transporter GLUT-1 is a Receptor for HTLV," Cell, Nov. 14, 2003, vol. 115, No. 04, pp. 449-459.

Martinez M.P., et al., "Comparative Virology of HTLV-1 and HTLV-2," Retrovirology, Aug. 7, 2019, vol. 16, Article. 21, No. 1, 12 Pages.

Mason R.D., et al., "Inactivated Simian Immunodeficiency Virus-Pulsed Autologous Fresh Blood Cells as an Immunotherapy Strategy," Journal of Virology, Feb. 2009, vol. 83, No. 3, pp. 1501-1510.

McBride A.A, "The Papillomavirus E2 Proteins," Virology, Oct. 2013, vol. 445, No. 1-2, pp. 57-79.

Mensali N., et al., "NK Cells Specifically TCR-dressed to Kill Cancer Cells", EBioMedicine, Jan. 2019, vol. 40, pp. 106-117.

Miettinen T.P., et al., "Mevalonate Pathway Regulates Cell Size Homeostasis and Proteostasis Through Autophagy," Cell Reports, Dec. 22, 2015, vol. 13(11), pp. 2610-2620.

Mochizuki M., et al., "HTLV-I Uveitis: A Distinct Clinical Entity Caused by HTLV-1," Japanese Journal of Cancer Research, Mar. 1992, vol. 83, No. 3, pp. 236-239.

Mochizuki S., et al., "Long-Term Correction of Hyperphenylalaninemia by AAV-Mediated Gene Transfer Leads to Behavioral Recovery in Phenylketonuria Mice," Gene Therapy, 2004, vol. 11 (13), pp. 1081-1086.

Moser B., et al., "γ T Cells: Novel Initiators of Adaptive Immunity," Immunological Reviews, Feb. 2, 2007, vol. 215, pp. 89-102.

Mosley A.J., et al., "Cell-Mediated Immune Response to Human T-Lymphotropic Virus Type I," Viral Immunology, 2005, vol. 18, No. 2, pp. 293-305.

Munoz N.M., et al., "Ex Vivo Expansion and Lentiviral Transduction of Macaca Nemestrina CD4 + T Cells," Journal of Medical Primatology, Dec. 2009, vol. 38, No. 6, pp. 438-443.

Myers E.W., et al., "Optimal Alignments in Linear Space," CABIOS, 1988, vol. 4, No. 1, pp. 11-17.

Nada M.H., et al., "Enhancing Adoptive Cancer Immunotherapy with Vγ2Vδ2 T Cells Through Pulse Zoledronate Stimulation," Journal for Immunotherapy of Cancer, Feb. 21, 2017, vol. 5, No. 1, pp. 1-23, DOI: 10.1186/S40425-017-0209-6, XP021242440.

Nagai M., et al., "Human T-Cell Lymphotropic Virus Type I and Neurological Diseases," Journal of NeuroVirology, Apr. 2003, vol. 9, No. 2, pp. 228-235.

Nault J-C., et al., "Adeno-Associated Virus Type 2 as an Oncogenic Virus in Human Hepatocellular Carcinoma," Molecular & Cellular Oncology, 2016, vol. 3, No. 2, 4 Pages, e1095271.

NCBI: "Human Prothrombin Gene Liver-specific Enhancer," Nucleotide, Database Accession No. M65141.1, Apr. 27, 1993, 01 page, XP055613203, [Retrieved on Mar. 31, 2019] Retrieved from URL: https://www.ncbi.ntm.nih.gov/nuccore/M65141.1.

Needleman S.B., et al., "A General Method Applicable to the Search for Similarities in the Amino Acid Sequence of Two Proteins," Journal of Molecular Biology, 1970, vol. 48, pp. 444-453.

Nishioka K., et al., "Chronic Inflammatory Arthropathy Associated With HTLV-1," The Lancet, Feb. 25, 1989, vol. 1, No. 8635, 1 Page.

Non-Final Office Action for U.S. Appl. No. 13/333,882, mailed Apr. 18, 2019, 11 Pages.

Non-Final Office Action for U.S. Appl. No. 13/333,882, mailed Feb. 22, 2018, 08 Pages.

Non-Final Office Action for U.S. Appl. No. 15/580,661, mailed Jan. 13, 2020, 11 Pages.

Non-Final Office Action for U.S. Appl. No. 15/580,661, mailed Feb. 19, 2021, 27 Pages.

(56) References Cited

OTHER PUBLICATIONS

Non-Final Office Action for U.S. Appl. No. 15/736,284, mailed Oct. 19, 2018, 26 Pages.
Non-Final Office Action for U.S. Appl. No. 15/736,284, mailed Oct. 29, 2020, 26 Pages.
Non-Final Office Action for U.S. Appl. No. 15/849,062, mailed Feb. 22, 2018, 05 Pages.
Non-Final Office Action for U.S. Appl. No. 15/850,937, mailed Feb. 22, 2018, 05 Pages.
Non-Final Office Action for U.S. Appl. No. 15/904,131, mailed Jun. 15, 2018, 07 Pages.
Non-Final Office Action for U.S. Appl. No. 16/008,991, mailed May 7, 2019, 07 Pages.
Non-Final Office Action for U.S. Appl. No. 16/011,550, mailed Sep. 17, 2018, 8 Pages.
Non-Final Office Action for U.S. Appl. No. 16/076,655, dated Feb. 21, 2020, 45 Pages.
Non-Final Office Action for U.S. Appl. No. 16/083,384, mailed Mar. 16, 2020, 9 Pages.
Non-Final Office Action for U.S. Appl. No. 16/132,247, mailed May 16, 2019, 06 Pages.
Non-Final Office Action for U.S. Appl. No. 16/182,443, mailed Dec. 31, 2018, 10 Pages.
Non-Final Office Action for U.S. Appl. No. 16/218,010, mailed May 24, 2019, 06 Pages.
Non-Final Office Action for U.S. Appl. No. 16/308,373, mailed Sep. 22, 2020, 32 Pages.
Non-Final Office Action for U.S. Appl. No. 16/312,056, mailed Jul. 6, 2020, 23 Pages.
Non-Final Office Action for U.S. Appl. No. 16/318,345, mailed Nov. 18, 2020, 12 Pages.
Non-Final Office Action for U.S. Appl. No. 16/530,908, mailed Jun. 1, 2020, 6 Pages.
Non-Final Office Action for U.S. Appl. No. 16/563,738, mailed Mar. 12, 2021, 11 Pages.
Non-Final Office Action for U.S. Appl. No. 16/614,682, mailed Feb. 28, 2022, 75 Pages.
Non-Final Office Action for U.S. Appl. No. 16/943,800, mailed Nov. 25, 2020, 08 Pages.
Non-Final Office Action for U.S. Appl. No. 17/198,017, mailed Jul. 20, 2021, 7 Pages.
Notice of Allowance for Chinese Application No. 201780017712.6, dated Aug. 25, 2022, 4 Pages. (with English translation).
Notice of Allowance for Japanese Patent Application No. 2018-547354, dated Dec. 17, 2021,6 Pages. (with English translation).
Notice of Allowance for U.S. Appl. No. 13/333,882, mailed Nov. 27, 2019, 3 Pages.
Notice of Allowance for U.S. Appl. No. 13/333,882, mailed Oct. 29, 2019, 8 Pages.
Notice of Allowance for U.S. Appl. No. 14/706,481, mailed Oct. 13, 2019, 05 Pages.
Notice of Allowance for U.S. Appl. No. 15/652,080, mailed Nov. 2, 2017, 05 Pages.
Notice of Allowance for U.S. Appl. No. 15/668,223, mailed Mar. 26, 2018, 07 Pages.
Notice of Allowance for U.S. Appl. No. 15/849,062, mailed Apr. 26, 2018, 05 Pages.
Notice of Allowance for U.S. Appl. No. 15/850,937, mailed Apr. 23, 2018, 05 Pages.
Notice of Allowance for U.S. Appl. No. 15/904,131, mailed Aug. 10, 2018, 05 Pages.
Notice of Allowance for U.S. Appl. No. 16/008,991, mailed Aug. 14, 2019, 5 Pages.
Notice of Allowance for U.S. Appl. No. 16/011,550, mailed Oct. 31, 2018, 5 Pages.
Notice of Allowance for U.S. Appl. No. 16/076,655 mailed Dec. 2, 2020, 3 Pages.
Notice of Allowance for U.S. Appl. No. 16/083,384, mailed May 18, 2020, 8 Pages.
Notice of Allowance for U.S. Appl. No. 16/132,247, mailed Jul. 19, 2019, 05 Pages.
Notice of Allowance for U.S. Appl. No. 16/182,443, mailed Jul. 3, 2019, 3 Pages.
Notice of Allowance for U.S. Appl. No. 16/182,443, mailed Jun. 18, 2019, 5 Pages.
Notice of Allowance for U.S. Appl. No. 16/218,010, mailed Sep. 25, 2019, 8 Pages.
Notice of Allowance for U.S. Appl. No. 16/530,908, mailed Jul. 10, 2020, 05 Pages.
Notice of Allowance for U.S. Appl. No. 16/593,882, dated Jan. 26, 2021, 8 Pages.
Notice of Allowance for U.S. Appl. No. 16/687,525, mailed Jan. 13, 2021, 8 Pages.
Notice of Allowance for U.S. Appl. No. 16/943,800, mailed Feb. 10, 2021, 7 Pages.
Notice of Allowance for U.S. Appl. No. 16/988,427, mailed Aug. 26, 2022, 5 pages.
Notice of Allowance for U.S. Appl. No. 17/198,017, mailed Nov. 3, 2021,6 Pages.
Notice of Allowance for U.S. Appl. No. 17/289,653, mailed Jan. 5, 2022, 9 Pages.
Notice of Final Rejection for Japanese Patent Application No. 2018-536892, dated Nov. 16, 2020, 8 Pages.
Notice of Reasons for Refusal for japanese Patent Application No. 2018-536892, dated Jul. 11, 2022, 21 Pages.
Notice of Reasons for Refusal for Japanese Patent Application No. 2021-045605, dated Apr. 1, 2022, 5 Pages. (with English translation).
Notice of Reasons for Rejection for Japanese Patent Application No. 2018-547354, mailed Feb. 16, 2021, 22 Pages.
Notice of Reasons for Rejection for Japanese Patent Application No. 2021-523916, mailed Jul. 12, 2022, 7 Pages.
Nowacki P., et al., "The PAH Mutation Analysis Consortium Database: Update 1996," Nucleic Acids Research, Jan. 1, 1997, vol. 25, No. 1, pp. 139-142, DOI: 10.1093/nar/25.1.139, XP055707752.
Nucleotide: "Human Papillomavirus Type 16 (HPV16), Complete Genome," GenBank: K02718.1, Publication [online], Mar. 18, 1994, 4 Pages, Retrieved from URL: https://www.ncbi.nlm.nih.gov/nucleotide/333031?report=genbank&log$=nucltop&blast_rank=22&RID=H3E1THFU014.
Nucleotide: "{Long Control Region} [Human Papillomavirus, type 16, Genomic, 660 nt]," Accession S60559, Publication (online), May 7, 1993 [Retrieved May 9, 2017], 1 Page, XP055455689, Retrieved from URL: https://www.ncbi.nlm.nih.gov/nucleotide/237343?report=genbank&log$=nucltop&blast_rank=I&RID=H3FCKA00014.
Office Action for Chinese Application No. 202010396594.8, mailed Jan. 15, 2021, 12 Pages.
Office Action for Chinese Patent Application No. 201780017712.6, dated Nov. 3, 2021, 16 Pages. (with English translation).
Office Action for European Patent Application No. 17739028.3, dated Mar. 18, 2022, 5 Pages.
Office Action for Japanese Application No. 2017-564550, mailed Mar. 18, 2020, 12 Pages.
Office Action for Japanese Application No. 2017-567175, mailed Jun. 15, 2020, 7 Pages.
Office Action for Japanese Application No. 2018-536892, mailed Jun. 26, 2020, 07 Pages.
Office Action for Japanese Application No. 2018-563892 mailed Oct. 14, 2020, 11 Pages.
Office Action for Japanese Application No. 2019-50047, mailed Jun. 12, 2020, 09 Pages.
Office Action in the EPO Application No. 16808223.8, mailed May 11, 2020, 5 Pages.
Office Action in the Japanese Application No. 2018-541270, mailed Jan. 8, 2021, 8 Pages.
Oh H-J., et al., "Reversal of Gene Expression Profile in the Phenylketonuria Mouse Model After Adeno-Associated Virus Vector-Mediated Gene Therapy," Molecular Genetics and Metabolism, 2005, vol. 86, Supplement. 1, pp. S124-S132.

(56) References Cited

OTHER PUBLICATIONS

Oh H-J., et al., "Long-Term Enzymatic and Phenotypic Correction in the Phenylketonuria Mouse Model by Adeno-Associated Virus Vector-Mediated Gene Transfer," Pediatric Research, 2004, vol. 56, No. 2, pp. 278-284.
Oh T., et al., "Lentiviral Vector Design Using Alternative RNA Export Elements," Retrovirology, Jun. 5, 2007, vol. 4:38, pp. 1-10.
Olsen A.L. et al., "PARP Inhibitors and Parkinson's Disease," Clinical Implications of Basic Research, Jan. 31, 2019, pp. 492-494, XP55672111, [Retrieved on Feb. 27, 2020], Retrieved from URL: https://mfprac.com/web2019/07literature/literature/Neurology/ParkinsonPARPI_Olsen.pdf, the whole document.
Osame M., et al., "HTLV-I Associated Myelopathy, A New Clinical Entity," The Lancet, May 3, 1986, vol. 1, No. 8488, pp. 1031-1032.
Ostertag D., et al., "Brain Tumor Eradication and Prolonged Survival from Intratumoral Conversion of 5-Fluorocytosine to 5-fluorouracil Using a Nonlytic Retroviral Replicating Vector," Neoro-Oncology, Feb. 2012, vol. 14(2), pp. 145-159.
Pallikkuth S., et al., "Human Immunodeficiency Virus (HIV) Gag Anti-Specific T-Helper and Granule-Dependent CD8 T-Cell Activities in Exposed but Uninfected Heterosexual Partners of HIV Type 1-Infected Individuals in North India," Clinical and Vaccine Immunology, Sep. 2007, vol. 14, No. 9, pp. 1196-1202.
Pan D., et al., "Biodistribution and Toxicity Studies of VSVG-Pseudotyped Lentiviral Vector After Intravenous Administration in Mice with the Observation of in Vivo Transduction of Bone Marrow," Molecular Therapy, Jul. 2002, vol. 6, No. 1, pp. 19-29.
Pauza C.D., et al., "γδ T cells in HIV Disease: Past, Present, and Future," Frontiers in Immunology, Jan. 30, 2015, vol. 5, No. 687, 12 Pages.
Pauza C.D., et al., "Evolution and Function of the TCR Vgamma9 Chain Repertoire: It's Good to be Public," Cell Immunology, Jul. 2015, vol. 296, No. 1, pp. 22-30.
Pauza, et al., Frontiers in Immunology, 2014, vol. 5, p. 687.
Pauzacairo, Cell Immunology, 2015, vol. 296, No. 1.
PCT Application No. PCT/CN2016/094828, filed Aug. 12, 2016, 85 Pages.
Pearson W.R., et al., "Improved Tools for Biological Sequence Comparison," Proceeding of the National Academy of Sciences, USA, Apr. 1988, vol. 85, pp. 2444-2448.
Pearson W.R., et al., "Improved Tools for Biological Sequence Comparison," Proceedings of the National Academy of Sciences of the United States of America, Apr. 1988, vol. 85(8), pp. 2444-2448.
Poiesz B. J., et al., "Detection and Isolation of Type C Retrovirus Particles From Fresh and Cultured Lymphocytes of A Patient With Cutaneous T-cell Lymphoma," Proceedings of the National Academy of Sciences of the United States of America, Dec. 1980, vol. 77, No. 12, pp. 7415-7419.
Poiesz B.J., "T-cell Lines Established From Human T-lymphocytic Neoplasias by Direct Response to T-cell Growth Factor," Proceedings of the National Academy of Sciences of the United States of America, Nov. 1980, vol. 77, No. 11, pp. 6815-6819.
Poonia B., et al., "Gamma Delta T Cells From HIV+ Donors can be Expanded In Vitro by Zoledronate/Interleukin-2 to Become Cytotoxic Effectors for Antibody-dependent Cellular Cytotoxicity," Cytotherapy, 2012, vol. 14, No. 2, pp. 173-181.
Porichis F., et al., "HIV-specific CD4 T Cells and Immune Control of Viral Replication," Current Opinion in HIV and Aids, US, May 2011, vol. 6, No. 3, pp. 174-180, DOI: 10.1097/COH.0b013e3283454058, ISSN 1746-630X, XP055527164.
Qiu J., "Zoledronic Acid Stimulates Human Peripheral Blood Mononuclear Cells to Expand γδT Cells in Vitro and its Role in Non-specific Immunity in Liver Cancer," Journal of Soochow University (Medical Edition).
Quan J-J., et al., "Parp3 Interacts with FoxM1 to Confer Glioblastoma Cell Radio Resistance," Tumor Biology, Karger, BaseL CH, Published online on Jun. 4, 2015, vol. 36, No. 11, pp. 8617-8624, ISSN: 1010-4283, DOI: 10.1007/SI3277-015-3554-4, XP036217799.
Requirement for Restriction for U.S. Appl. No. 15/736,284, mailed Jul. 12, 2018, 9 Pages.

Restriction Requirement for U.S. Appl. No. 15/580,661, mailed Oct. 22, 2019, 14 Pages.
Restriction Requirement for U.S. Appl. No. 15/668,223, mailed Oct. 23, 2017, 06 Pages.
Restriction Requirement for U.S. Appl. No. 16/011,550, mailed Aug. 3, 2018, 06 Pages.
Restriction Requirement for U.S. Appl. No. 16/076,655, mailed Nov. 4, 2019, 8 Pages.
Restriction Requirement for U.S. Appl. No. 16/083,384, mailed Nov. 7, 2019, 8 Pages.
Restriction Requirement for U.S. Appl. No. 16/308,373, mailed Jun. 15, 2020, 16 Pages.
Restriction Requirement for U.S. Appl. No. 16/312,056, mailed Jan. 29, 2020, 7 Pages.
Restriction Requirement for U.S. Appl. No. 16/318,345, mailed Jun. 26, 2020, 9 Pages.
Restriction Requirement for U.S. Appl. No. 16/563,738, mailed Dec. 8, 2020, 6 Pages.
Restriction Requirement for U.S. Appl. No. 16/593,882, mailed Nov. 19, 2020, 06 Pages.
Riano F., et al., "Vγ9Vδ2 TCR-activation by Phosphorylated Antigens Requires Butyrophilin 3 A1 (BTN3A1) and Additional Genes on Human Chromosome 6," European Journal of Immunology, 2014, vol. 44, pp. 2571-2576.
Roc L., et al., "Rapid Subacute Myelopathy Following Kidney Transplantation From Htlv-1 Donors: Role of Immunosuppresors and Failure of Antiretrovirals," Therapeutic Advances in Infectious Disease, Jan.-Dec. 2019, vol. 6, 11 Pages.
Roden C., et al., "Novel Determinants of Mammalian Primary microRNA Processing Revealed by Systematic Evaluation of Hairpin-Containing Transcripts and Human Genetic Variation," Cold Spring Harbor Laboratory Press, 2017, vol. 27, pp. 374-384, ISSN 1088-9051/17, Retrieved from URL: www.genome.org.
Rose R.D., et al., "Safety, Immunogenicity and Efficacy of Peptide-Pulsed Cellular Immunotherapy in Macaques," Journal of Medical Primatology, 2008, vol. 37(2), pp. 69-78.
Sambrook J., et al., "Molecular Cloning: A Laboratory Manual," 3rd edition, Cold Spring Harbor Laboratory Press, 2000, 2272 Pages.
Sandstorm A., et al., "The Intracellular B30.2 Domain of Butyrophilin 3A1 Binds Phosphoantigens to Mediate Activation of Hu," Immunity, 2014, vol. 40, No. 4, pp. 490-500, DOI: 10.1016/j.immuni.2014.03.003, ISSN 0004789818, XP055481379.
Sangro, et al., "A Phase I Clinic Trial of Thymidine Kinase-based Gene Therapy in Advanced Hepatocellular Carcinoma", Cancer Gene Ther., 2010, vol. 17, pp. 837-843.
Schiller C.B., et al., "CD19-Specific Triplebody SPM-1 Engages NK and γ T Cells for Rapid and Efficient Lysis of Malignant B-Lymphoid Cells," Oncotarget, 2016, vol. 7(50), pp. 83392-83408.
Schiller D.S., et al., "Parameters Influencing Measurement of the Gag Antigen-Specific T-Proliferative Response to HIV Type 1 Infection," AIDS Research and Human Retroviruses, US, 2000, vol. 16, No. 03, pp. 259-271, DOI: 10.1089/088922200309359, ISSN 0889-2229, XP055617438.
Second Office Action for Chinese Application No. 201780017712.6, dated Feb. 3, 2021, 10 Pages. (with English translation).
Seedorf et al., "Human Papillomavirus Type 16 DNA Sequence," Virology, Aug. 1985, vol. 145, pp. 181-185.
Selbach M., et al., "Widespread Changes in Protein Synthesis Induced by MicroRNAs," Nature, Sep. 4, 2008, vol. 455, pp. 58-63, DOI: 10.1038/nature07228.
Shalova I.N., et al., "CD16 Regulates TRIF-Dependent TLR4 Response in Human Monocytes and Their Subsets", The Journal of Immunology, 2012, vol. 188, pp. 3584-3593.
Shedlovsky A., et al., "Mouse Models of Human Phenylketonuria," Genetics, Aug. 1993, vol. 134, No. 4, pp. 1205-1210.
Smith P.L., et al., "Developments in HIV-1 Immunotherapy and Therapeutic Vaccination," F1000Prime Reports, Jun. 2, 2014, vol. 06, No. 43, 12 Pages.
Smith T.F., et al., "Comparison of Biosequences," Advances in Applied Mathematics, 1981, vol. 2, pp. 482-489.
Soker S., et al., "Neuropilin-1 is Expressed by Endothelial and Tumor Cells as an Isoform-Specific Receptor for Vascular Endothelial Growth Factor," Cell, Mar. 20, 1998, vol. 92, No. 06, pp. 735-745.

(56) References Cited

OTHER PUBLICATIONS

Spartevello F., et al., "Development of Lentiviral Vectors Simultaneously Expressing Multiple siRNAs Against CCR5, vif and tat/rev Genes for an HIV-1 Gene Therapy Approach," Molecular Therapy—Nucleic Acids, Apr. 19, 2016, vol. 5, pp. 1-12.
Stunkel W., et al., "The Chromatin Structure of the Long Control Region of Human Papillomavirus Type 16 Represses Viral Oncoprotein Expression," Journal of Virology, Mar. 1999, vol. 73, No. 3, pp. 1918-1930.
Sverdrup FM., et al., "Development of Human Papillomavirus Plasmids Capable of Episomal Replication in Human Cell Lines," Gene Therapy, Mar. 26, 1999, pp. 1317-1321, Retrieved from URL: http://www.stockton-pressco.uk/gt.
Tebas P., et al., "Antiviral Effects of Autologous CD4 T Cells Genetically Modified With a Conditionally Replicating Lentiviral Vector Expressing Long Antisense to HIV," Pre published on Dec. 20, 2012, Blood, Feb. 28, 2013, vol. 121, No. 9, pp. 1524-1533, XP055345565.
Tebas P., et al., "Gene Editing of CCR5 in Autologous CD4 T Cells of Persons Infected with HIV," The New England Journal of Medicine, Mar. 6, 2014, vol. 370, No. 10, pp. 901-910, DOI:10.1056/NEJMoa1300662, ISSN 0028-4793, XP055172314.
Third Office Action for Chinese Application No. 201780017712.6, dated May 14, 2021, 8 Pages. (with English translation).
Thompson K., et al., "Alkylamines Cause Vγ9Vδ2 T-cell Activation and Proliferation by Inhibiting the Mevalonate Pathway," Blood, Jan. 15, 2006, vol. 107, No. 2, pp. 651-654.
Tian Y., et al., "MicroRNA-30a Promotes Chondrogenic Differentiation of Mesenchymal Stem Cells Through Inhibiting Delta-like 4 Expression," Life Science, Mar. 1, 2016, vol. 148, 36 Pages, DOI:10.1016/J.LFS.2016.02.031, ISSN 0024-3205, XP029460066.
Tokuyama H., et al., "Vy9Vδ2 T Cell Cytotoxicity Against Tumor Cells is Enhanced by Monoclonal Antibody Drugs—Rituximab and Trastuzumab," International Journal of Cancer, 2008, vol. 122 (11), pp. 2526-2534.
Tolmachov O.E., et al., "Designing Lentiviral Gene Vectors," Viral Gene Therapy, 2011, 23 Pages, ISBN: 978-953-307-539-6, Retrieved from URL: http://www.intechopen.com/books/viral-gene-therapy/designing-lentiviral-gene-vectors.
Tracey A., "Human DNA Sequence from Clone RP1-288M22 on Chromosome 6q 12-13, Complete Sequence," National Center for Biotechnology, GenBank Entry, Jan. 24, 2013, pp. 1-34, Retrieved from URL: https://www.ncbi.nlm.nih.gov/nucleotide/AL035467.23?report=genbank&log$=nucltop&blast_rank=1&RID=UUD4GX2DO14.
Twitty C.G., et al., "Retroviral Replicating Vectors Deliver Cytosine Deaminase Leading to Targeted 5-Fluorouracil-Mediated Cytotoxicity in Multiple Human Cancer Types," Human Gene Therapy Methods, Feb. 1, 2016, vol. 27, No. 1, pp. 17-31.
Uchiyama T., et al., "Adult T-Cell Leukemia: Clinical and Hematologic Features of 16 Cases," Blood, Sep. 1977, vol. 50, No. 03, pp. 481-492.
Ueda M., et al., "CD47-Dependent Molecular Mechanisms of Blood Outgrowth Endothelial Cell Attachment on Cholesterol-Modified Polyurethane," Biomaterials, Elsevier, Amsterdam, NL, Sep. 1, 2010, vol. 31, No. 25, pp. 6394-6399, ISSN: 0142-9612, XP027102945.
Vargas J., Jr., et al., "Novel Integrase-defective Lentiviral Episomal Vectors for Gene Transfer", Human Gene Therapy, Liebert, US, Apr. 2004, vol. 15, No. 4, pp. 361-372, DOI: 10.1089/104303404322959515, ISSN 1043-0342, XP001205920.
Vargas Jr J., et al., "Conditionally Replicating Lentiviral-Hybrid Episomal Vectors for Suicide Gene Therapy," Antiviral Research, Elsevier BV, NL, Dec. 1, 2008, Jul. 21, 2008, vol. 80, No. 3, pp. 288-294, DOI: 10.1016/J.ANTIVIRAL.2008.06.015, ISSN 0166-3542, XP025684743.
Wang B., et al., "Kinesin Family Member 11 is a Potential Therapeutic Target and is Suppressed by MicroRNA-30a in Breast Cancer," Molecular Carcinogenesis, Aug. 2020, vol. 59, No. 8, pp. 908-922.
Wang H., et al., "Butyrophilin 3A1 Plays an Essential Role in Prenyl Pyrophosphate Stimulation of Human Vγ2Vδ2 T cell," The Journal of Immunology, (2013), vol. 191, No. 3, pp. 1029-1042, doi:10.4049/jimmunol.1300658, ISSN 0004789817, XP055557660.
Wang H., et al., "Indirect Stimulation of Human Vy2Vδ2 T Cells through Alterations in Isoprenoid Metabolism," Journal of Immunology, 2011, vol. 187, pp. 5099-5113.
Wang H-B., et al., "HIV Vaccine Research: The Challenge and the Way Forward," Journal of Immunology Research, 2015, vol. 2015, Article. 503978, 5 pages.
Wang Y., et al., "Intravenous Delivery of SIRNA Targeting CD47 Effectively Inhibits Melanoma TumorGrmYth and Lung Metastasis," Molecular Therapy, Oct. 2013, vol. 21, No. 10, pp. 1919-1929.
Wendelburg B.J., et al., "An Enhanced EBNA1 Variant With Reduced IR3 Domain for Long-term Episomal Maintenance and Transgene Expression of Orip-based Plasmids in Human Cells," Gene Therapy, Nature Publishing Group, GB, Oct. 6, 1998, vol. 5, pp. 1389-1399, DOI: 10.1038/SJ.GT.3300736, ISSN: 0969-7128, XP002931315.
Westerhout E.M., et al., "A Conditionally Replicating HIV-based Vector That Stably Expresses an Antiviral shRNA Against HIV-1 Replication," Molecular Therapy, The Journal of the American Society of Gene Therapy, Academic Press, Nature Publishing Group, US, May 11, 2006, vol. 14, No. 2, pp. 268-275, DOI: 10.1016/J.YMTHE.2006.03.018, ISSN 1525-0016, XP005524738.
Wilkin D.J., et al., "Isolation and Sequence of the Human Farnesyl Pyrophosphate Synthetase eDNA," The Journal of Biological Chemistry, Mar. 15, 1990, vol. 265. No. 8, pp. 4607-4614.
Written Opinion for International Application No. PCT/US2016/036519, mailed Nov. 7, 2016, 6 Pages.
Written Opinion for International Application No. PCT/US2016/041456, mailed Oct. 19, 2016, 6 Pages.
Written Opinion for International Application No. PCT/US2016/066185, mailed Jun. 9, 2017, 12 Pages.
Written Opinion for International Application No. PCT/US2017/013019, mailed Jul. 17, 2017, 5 Pages.
Written Opinion for International Application No. PCT/US2017/013024, mailed Jul. 14, 2017, 7 Pages.
Written Opinion for International Application No. PCT/US2017/013399, mailed May 26, 2017, 8 Pages.
Written Opinion for International Application No. PCT/US2017/021639, mailed Aug. 25, 2017, 7 Pages.
Written Opinion for International Application No. PCT/US2017/036433, mailed Dec. 15, 2017, 10 Pages.
Written Opinion for International Application No. PCT/US2017/041168, mailed Nov. 8, 2017, 8 Pages.
Written Opinion for International Application No. PCT/US2017/043157, mailed Dec. 26, 2017, 10 Pages.
Written Opinion for International Application No. PCT/US2018/012998, mailed May 29, 2018, 07 Pages.
Written Opinion for International Application No. PCT/US2018/025733, mailed Sep. 24, 2018, 07 Pages.
Written Opinion for International Application No. PCT/US2018/037924, mailed Nov. 9, 2018, 11 Pages.
Written Opinion for International Application No. PCT/US2018/053919, mailed Apr. 12, 2019, 8 Pages.
Yagi H., et al., "Complete Restoration of Phenylalanine Oxidation in Phenylketonuria Mouse by a Self-Complementary Adena-Associated Virus Vector," Journal of Gene Medicine, 2011, vol. 13(2), pp. 114-122.
Yamano Y., et al., "Clinical Pathophysiology of Human T-Lymphotropic Virus-Type 1-Associated Myelopathy/Tropical Spastic Paraparesis," Frontiers in Microbiology, Nov. 9, 2012, vol. 3, Article. 389, pp. 1-10.
Yang H.L., et al., "Construction of PARP-1 gene Silencing Cell Lines by Lentiviral-Mediated RNA Interference Technology," School of Public Health, Guangdong Medical College, 2006, 1 Page. (Abstract).
Yang J., et al., "Lentiviral-Mediated Silencing of Famelsy1 Pyrophosphate Synthase through RNA Interference in Mice," Biomed Research International, 2015, vol. 2015, Article ID. 914026, 07 pages.

(56) References Cited

OTHER PUBLICATIONS

Yang M., et al., "Construction of PARP-1 Gene Silencing Cell Lines by Lentiviral-mediated RNA Interference," School of Public Health, 2009, 1 Page.

Yano S., et al., "Evaluation of Tetrahydrobiopterin Therapy with Large Neutral Amino Acid Supplementation in Phenylketonuria: Effects on Potential Peripheral Biomarkers, Melatonin and Dopamine, for Brain Monoamine Neurotransmitters," PLoS One, Aug. 11, 2016, vol. 11(8), e0160892, 14 pages.

Ye Y., et al., "Knockdown of Farnesylpyrophosphate Synthase Prevents Angiotensin II-Medicated Cardiac Hypertrophy," The International Journal of Biochemistry & Cell Biology, 2010, vol. 42, pp. 2056-2064.

Yoo L., et al., "PARP-1 Regulates the Expression of Caspase-11," Biochemical and Biophysical Research Communications, Apr. 22, 2011, vol. 408, No. 3, pp. 489-493, DOI: 10.1016/ J. BBRC.20 11.04.070, ISSN: 0006-291X, XP028209824.

Zhang F., et al., "Research Progress on the Mechanism of Antitumor Action of Bisphosphonates," Chinese Journal of Hospital Pharmacy.

Zufferey R., et al., "Self-Inactivating Lentivirus Vector for Safe and Efficient In Vivo Gene Delivery," Journal of Virology, Dec. 1998, vol. 72(12), pp. 9873-9880.

IL Office Action issued in Application No. 271274 on Aug. 6, 2023, 11 pages.

JP Office Action in Japanese Application No. 2022-006999, dated Jan. 5, 2023, 20 pages (with English translation).

JP Office Action in Japanese Application No. 2021-045605, dated Nov. 2, 2022, 8 pages (with English translation).

AU; Examination Report issued in Application No. 2021203836 on Jan. 30, 2024.

EP; Search Report issued in Application No. 23199847.7 on Mar. 5, 2024.

JP; Office Action issued in Application No. 2022-006999 on Sep. 20, 2023.

USPTO; Examiner's Answer in U.S. Appl. No. 16/614,682, dated Sep. 27, 2023.

Brake et al., "Lentiviral Vector Design for Multiple shRNA Expression and Durable HIV-1 Inhibition," Molecular Therapy, 16(3), 557-564, 2008.

KR; Office Action issued Oct. 20, 2023 in Application No. 10-2020-7000631.

UAE; Office Action issued Oct. 20, 2023 in Application No. P6001801/2019.

JP; Office Action issued Oct. 19, 2023 in Application No. 2021-523916.

CN Office Action in Chinese Application No. 201880039828.4, dated Mar. 1, 2023, 19 pages (with English translation).

JP Notice of Allowance in Japanese Application No. 2018-536892, dated Mar. 29, 2023, 4 pages (with English translation).

JP Office Action in Japanese Application No. 2019-569226, dated Mar. 20, 2023, 5 pages (with English translation).

JP Office Action in Japanese Application No. 2021-523916, dated Apr. 18, 2023.

JP Office Action in Japanese Application No. 2021-045605, dated Apr. 19, 2023.

CA Office Action in Canadian Application No. 3,011,529, dated Feb. 21, 2023, 7 pages.

JP Office Action in Japanese Application No. 2018-536892, dated Jan. 30, 2023, 4 pages (with English translation).

* cited by examiner

METHODS AND COMPOSITIONS FOR THE ACTIVATION OF GAMMA-DELTA T-CELLS

CROSS-REFERENCE TO RELATED APPLICATIONS

This application is a continuation of U.S. patent application Ser. No. 16/563,738, filed on Sep. 6, 2019 entitled "Methods and Compositions for the Activation of Gamma-Delta T-cells," which is a continuation of U.S. patent application Ser. No. 16/182,443, filed on Nov. 6, 2018 entitled "Methods and Compositions for the Activation of Gamma-Delta T-cells," which is a continuation of U.S. patent application Ser. No. 16/008,991, filed on Jun. 14, 2018 entitled "Methods and Compositions for the Activation of Gamma-Delta T-cells," which is a continuation of U.S. patent application Ser. No. 15/850,937, filed on Dec. 21, 2017 entitled "Methods and Compositions for the Activation of Gamma-Delta T-cells," which is a continuation of U.S. patent application Ser. No. 15/652,080, filed on Jul. 17, 2017 entitled "Methods and Compositions for the Activation of Gamma-Delta T-cells" which is a continuation of International Application No. PCT/US17/13399 filed on Jan. 13, 2017, entitled "Methods and Compositions for the Activation of Gamma-Delta T-cells" which claims priority to U.S. Provisional Patent Application No. 62/279,474, filed on Jan. 15, 2016, and entitled "Methods and Compositions for the Activation of Gamma-Delta T-cells," the disclosures of which are incorporated herein by reference.

SEQUENCE LISTING

A Sequence Listing in compliance with 37 CFR 1.831-1.834 was submitted with the application filed on Nov. 1, 2022 and is incorporated by reference. The Sequence Listing in .xml format includes no new matter. The Sequence Listing is supported throughout the application as filed and all sequences are listed on pages 64-100. The name of the file is 436313000390 SL and the file size is 123 kb.

FIELD OF THE INVENTION

The present disclosure relates generally to the fields of gene therapy and immunotherapy, specifically in relation to increased activation of gamma delta ("GD") T cells.

BACKGROUND

Human T cells are distinguished on the basis of T cell receptor structure. The major populations, including CD4+ and CD8+ subsets, express a receptor composed of alpha and beta chains. A smaller subset expresses T cell receptor made from gamma and delta chains. Gamma delta ("GD") T cells make up 3-10% circulating lymphocytes, and Vδ2+ subset makes up 75% of GD T cells in blood. Vδ2+ cells recognize non-peptide epitopes and do not require antigen presentation by major histocompatibility complexes ("MHC") or human leukocyte antigen ("HLA"). The majority of Vδ2+ T cells also express a Vγ9 chain and are stimulated by exposure to 5-carbon pyrophosphate compounds that are intermediates in mevalonate and non-mevalonate sterol/isoprenoid synthesis pathways. The response to isopentenyl pyrophosphate (5-carbon) is universal among healthy human beings.

Another subset of GD T cells, Vδ1+, make up a much smaller percentage of the T cells circulating in the blood, but Vδ+1 cells are commonly found in the epithelial mucosa and the skin.

In general, GD T cells have several functions, including killing tumor cells and pathogen-infected cells. Stimulation through their unique T cell receptor ("TCRs") composed of two glycoprotein chains, γ and δ, improves the capacity for cellular cytotoxicity, cytokine secretion and other effector functions. The TCRs of GD T cells have unique specificities and the cells themselves occur in high clonal frequencies, thus allowing rapid innate-like responses to tumors and pathogens.

Aminobisphosphonate drugs ("ABPs") and other inhibitors of farnesyl diphosphate synthase ("FDPS"), which are downstream from isopentenyl pyrophosphate ("IPP") in the mevalonate pathway (see, for e.g., FIG. 1), have been used to treat various diseases, including cancers, specifically those involving bone metastasis. ABPs include trade names such as Zometa® (Novartis) and Fosamax® (Merck).

ABPs have also been used to stimulate GD T cells. This may be because when FDPS is inhibited in myeloid cells, IPP begins to accumulate and geranylgeranyl pyrophosphate ("GGPP"), a downstream product of FDPS that suppresses activation of the inflammasome pathway, is reduced. The reduction in GGPP removes an inhibitor of the caspase-dependent inflammasome pathway and allows secretion of mature cytokines including interleukin-beta and interleukin-18, the latter being especially important for gamma delta T cell activation.

Thus, when FDPS is blocked, the increased IPP and decreased GGPP combine to activate Vδ2+ T cells. Vδ2+ cells activated by IPP or ABPs will proliferate rapidly, express a number of cytokines and chemokines, and can function to cytotoxically destroy tumor cells or cells infected with pathogenic microorganisms.

However, ABPs are associated with inflammation and osteonecrosis, as well as having poor bioavailability due to their chemistry. Likewise, IPP has a very short half-life and is difficult to synthesize. Both types of compounds require systemic administration in an individual. Accordingly, both ABPs in general, and IPP specifically, leave a great deal to be desired for therapeutic purposes.

SUMMARY OF THE INVENTION

In one aspect, a method of activating a GD T cell is provided. The method includes infecting, in the presence of the GD T cell, a target cell with a viral delivery system that encodes at least one genetic element. In embodiments, the at least one genetic element includes a small RNA capable of inhibiting production of an enzyme involved in the mevalonate pathway. In embodiments, the enzyme is FDPS. In embodiments, when the enzyme is inhibited in the target cell, the target cell subsequently activates the GD T cell. In embodiments, the target cell is a cancer cell or a cell that has been infected with an infectious agent. In a preferred embodiment, the activation of the GD T cell results in the GD T cell killing the cancer cell or the cell infected with an infectious agent. In embodiments, the at least one encoded genetic element includes a microRNA or a shRNA. In further embodiments, the target cell is also contacted with an aminobisphosphonate drug. In embodiments, the aminobisphosphonate drug is zoledronic acid.

In another aspect, a method of treating cancer in a subject is provided. The method includes administering to the subject a therapeutically-effective amount of a viral delivery system that encodes at least one genetic element. In embodiments, the at least one genetic element includes a small RNA capable of inhibiting production of an enzyme involved in the mevalonate pathway. In further embodiments, when the enzyme is inhibited in a cancer cell in the presence of a GD T cell, the cancer cell activates the GD T cell, to thereby treat the cancer. In embodiments, the enzyme is FDPS. In embodiments, the at least one encoded genetic element includes a microRNA or a shRNA. In further embodiments, the target cell is also contacted with an aminobisphosphonate drug. In embodiments, the aminobisphosphonate drug is zoledronic acid.

In another aspect, a method of treating an infectious disease in a subject is provided. The method includes administering to the subject a therapeutically-effective amount of a viral delivery system that encodes at least one genetic element. In embodiments, the at least one genetic element includes a small RNA capable of inhibiting production of an enzyme involved in the mevalonate pathway. In further embodiments, when the enzyme is inhibited in a cell that is infected with an infectious agent in the presence of a GD T cell, the infected cell activates the GD T cell, to thereby treat the infected cell, and the infectious disease. In embodiments, the enzyme is FDPS. In embodiments, the at least one encoded genetic element includes a microRNA or a shRNA. In further embodiments, the target cell is also contacted with an aminobisphosphonate drug. In embodiments, the aminobisphosphonate drug is zoledronic acid.

In another aspect, the at least one encoded genetic element includes a shRNA having at least 80%, or at least 85%, or at least 90%, or at least 95% percent identity with GTCCTGGAGTACAATGCCATTCTCGAGAATGGCATTGTACTCCAGGACTTTTT (SEQ ID NO: 1); GCAGGATTTCGTTCAGCACTTCTCGAGAAGTGCTGAACGAA ATCCTGCTTTTT (SEQ ID NO: 2); GCCATGTACATGGCAGGAATTCTCGAGAA TTCCTGCCATGTACATGGCTTTTT (SEQ ID NO: 3); or GCAGAAGGAGGCTGA GAAAGTCTCGAGACTTTCTCAGCCTCCTTCTGCTTTTT (SEQ ID NO: 4). In a preferred embodiment, the shRNA includes GTCCTGGAGTACAATGCCATTCTCGAG AATGGCATTGTACTCCAGGACTTTTT (SEQ ID NO: 1); GCAGGATTTCGTTCA GCACTTCTCGAGAAGTGCTGAACGAAATCCTGCTTTTT (SEQ ID NO: 2); GCCA TGTACATGGCAGGAATTCTCGAGAATTCCTGCCATGTACATGGCTTTTT (SEQ ID NO: 3); or GCAGAAGGAGGCTGAGAAAGTCTCGAGACTTTCTCAGCCTCCTT CTGCTTTTT (SEQ ID NO: 4).

In another aspect, the at least one encoded genetic element includes a microRNA having at least 80%, or at least 85%, or at least 90%, or at least 95% percent identity with AGGTATATTGCTGTTGACAGTGAGCGACACTTTCTCAGCCTCCTTCTGCGTGAAGCC ACAGATGGCAGAAGGAGGCTGAGAAAGTGCTGCCTACTGCCTCGGACTTCAAGGGG CT (SEQ ID NO: 5); AAGGTATATTGCTGTTGACAGTGAGCGACACT TTCTCAGCCTCCTTCTGCGTGAAGCCACAGATGGCAGAAGGGCTGAGAAAGTGCTGC CTACTGCCTCGGACTTCAAGGGGCT (SEQ ID NO: 6); TGCTGTTGACAGTG AGCGACTTTCTCAGCCTCCTTCTGCGTGAAGCCACAGATGGCAGAAGGAGGCTGAG AAAGTTGCCTACTGCCTCGGA (SEQ ID NO: 7); CCTGGAGGCTTGCTGAAG GCTGTATGCTGACTTTCTCAGCCTCCTTCTGCTTTTGGCCACTGACTGAGCAGAAGGG CTGAGAAAGTCAGGACACAAGGCCTGTTACTAGCACTCA (SEQ ID NO: 8); CATCTCCATGGCTGTACCACCTTGTCGGGACTTTCTCAGCCTCCTTCTGCCTGTTGAA TCTCATGGCAGAAGGAGGCGAGAAAGTCTGACATTTTGGTATCTTTCATCTGACCA (SEQ ID NO: 9); or GGGCCTGGCTCGAGCAGGGGGCGAGGGATACTTTCT CAGCCTCCTTCTGCTGGTCCCCTCCCCGCAGAAGGAGGCTGAGAAAGTCCTTCCCTC CCAATGACCGCGTCTTCGTCG (SEQ ID NO: 10). In a preferred embodiment, the microRNA includes AAGGTATATTGCTGTTGACAGTGAGCGACACTTTCTCAGCCT CCTTCTGCGTGAAGCCACAGATGGCAGAAGGAGGCTGAGAAAGTGCTGCCTACTGC CTCGGACTTCAAGGGGCT (SEQ ID NO: 5); AAGGTATATTGCTGTTGACAGT GAGCGACACTTTCTCAGCCTCCTTCTGCGTGAAGCCACAGATGGCAGAAGGGCTGA GAAAGTGCTGCCTACTGCCTCGGACTTCAAGGGGCT (SEQ ID NO: 6); TGCTG TTGACAGTGAGCGACTTTCTCAGCCTCCTTCTGCGTGAAGCCACAGATGGCAGAAGG AGGCTGAGAAAGTTGCCTACTGCCTCGGA (SEQ ID NO: 7); CCTGGAGGCT TGCTGAAGGCTGTATGCTGACTTTCTCAGCCTCCTTCTGCTTTTGGCCACTGACTGAG CAGAAGGGCTGAGAAAGTCAGGACACAAGGCCTGTTACTAGCACTCA (SEQ ID NO: 8); CATCTCCATGGCTGTACCACCTTGTCGGGACTTTCTCAGCCTCCTT CTGCCTGTTGAATCTCATGGCAGAAGGAGGCGAGAAAGTCTGACATTTTGGTATCTT TCATCTGACCA (SEQ ID NO: 9); or GGGCCTGGCTCGAGCAGGGGCGAGGG ATACTTTCTCAGCCTCCTTCTGCTGGTCCCCTCCCCGCAGAAGGAGGCTGAGAAAGT CCTTCCCTCCCAATGACCGCGTCTTCGTCG (SEQ ID NO: 10).

In another aspect, a viral vector comprising at least one encoded genetic element is provided. The at least one encoded genetic element includes a small RNA capable of inhibiting production of an enzyme involved in the mevalonate pathway. In embodiments, the enzyme involved in the mevalonate pathway is farnesyl diphosphate synthase (FDPS). In embodiments, the at least one encoded genetic element includes a microRNA or a shRNA.

In another aspect, the at least one encoded genetic element includes a shRNA having at least 80%, or at least 85%, or at least 90%, or at least 95% percent identity with v In a preferred embodiment, the shRNA includes SEQ ID NO: 1; SEQ ID NO: 2; SEQ ID NO: 3; or SEQ ID NO: 4.

In another aspect, the at least one encoded genetic element includes a microRNA having at least 80%, or at least 85%, or at least 90%, or at least 95% percent identity with SEQ ID NO: 5; SEQ ID NO: 6; SEQ ID NO: 7; SEQ ID NO: 8; SEQ ID NO: 9; or SEQ ID NO: 10. In a preferred embodiment, the microRNA includes SEQ ID NO: 5; SEQ ID NO: 6; SEQ ID NO: 7; SEQ ID NO: 8; SEQ ID NO: 9; or SEQ ID NO: 10.

In embodiments, the viral vector is comprised of any vector that can effectively transduce the small RNA into a target cell. In embodiments, the viral vector is a lentiviral vector. In other embodiments, the viral vector is an adeno-associated virus vector.

In another aspect, the viral vector includes a second encoded genetic element. In embodiments, the second genetic element includes at least one cytokine or chemokine. In embodiments, the at least one cytokine is selected from the group consisting of: IL-18, TNF-α, interferon-γ, IL-1, IL-2, IL-15, IL-17, and IL-12. In embodiments, the at least one chemokine is a CC chemokine or a CXC chemokine. In further embodiments, the at least one chemokine is RANTES.

In another aspect, a lentiviral vector system for expressing a lentiviral particle is provided. The system includes a lentiviral vector, at least one envelope plasmid for expressing an envelope protein optimized for infecting a cell; and at least one helper plasmid for expressing gag, pol, and rev genes. When the lentiviral vector, the at least one envelope plasmid, and the at least one helper plasmid are transfected into a packaging cell, a lentiviral particle is produced by the packaging cell. In embodiments, the lentiviral particle is capable of infecting a targeting cell, and inhibiting an enzyme involved in the mevalonate pathway within the target cell. In embodiments, the enzyme involved in the mevalonate pathway is FDPS. In embodiments, the lentiviral vector system includes a first helper plasmid for expressing the gag and pol genes, and a second helper plasmid for expressing the rev gene. In embodiments, the envelope protein is preferably optimized for infecting a target cell. In embodiments, the target cell is a cancer cell. In other embodiments, the target cell is a cell that is infected with an infectious agent.

DETAILED DESCRIPTION

Overview of Disclosure

Figure 1:
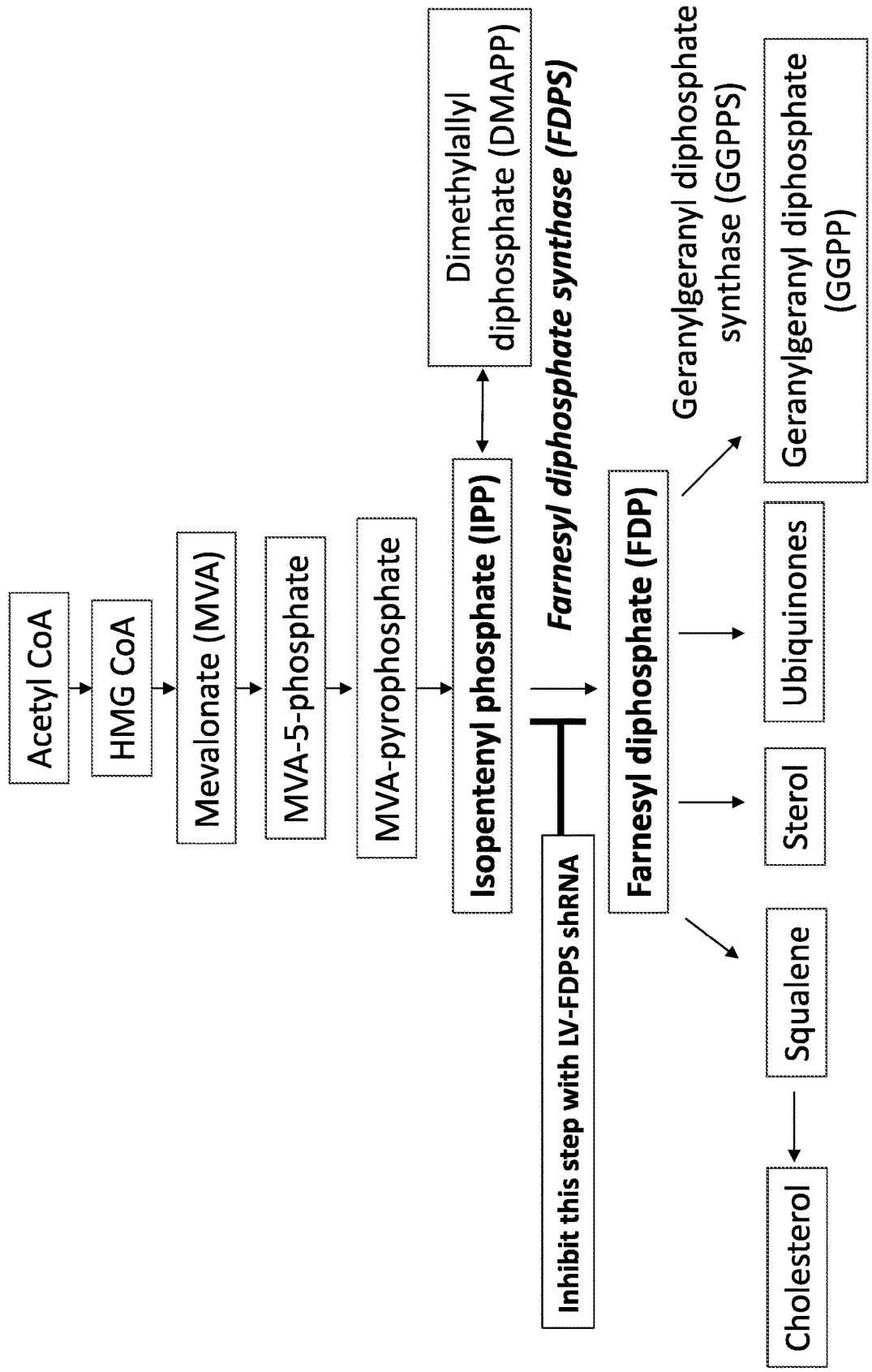
FIG. 1 depicts an overview of the major steps in the mevalonate pathway for biosynthesis of steroids and isoprenoids.

The present disclosure relates to gene therapy constructs and delivery of the same to cells, resulting in suppression of Farnesyl diphosphate synthase ("FDPS"), which is necessary to convert isopentenyl phosphate (IPP) to farnesyl diphosphate (FDP), as shown, for example, in FIG. 1. In embodiments, one or more viral vectors are provided with microRNAs or short homology RNAs (shRNA) that target FDPS, thereby reducing expression levels of this enzyme. The viral vectors include lentiviral vectors and AAV vectors. A consequence of modulating expression of FDPS is to increase the accumulation of IPP, which is a stimulator of GD T cell proliferation and differentiation. Accordingly, the constructs provided herein are used to activate GD T cells, and are used to treat cancers and infectious diseases.

Definitions and Interpretation

Unless otherwise defined herein, scientific and technical terms used in connection with the present disclosure shall have the meanings that are commonly understood by those of ordinary skill in the art. Further, unless otherwise required by context, singular terms shall include pluralities and plural terms shall include the singular. Generally, nomenclature used in connection with, and techniques of, cell and tissue culture, molecular biology, immunology, microbiology, genetics and protein and nucleic acid chemistry and hybridization described herein are those well-known and commonly used in the art. The methods and techniques of the present disclosure are generally performed according to conventional methods well-known in the art and as described in various general and more specific references that are cited and discussed throughout the present specification unless otherwise indicated. See, e.g.: Sambrook J. & Russell D. Molecular Cloning: A Laboratory Manual, 3rd ed., Cold Spring Harbor Laboratory Press, Cold Spring Harbor, N.Y. (2000); Ausubel et al., Short Protocols in Molecular Biology: A Compendium of Methods from Current Protocols in Molecular Biology, Wiley, John & Sons, Inc. (2002); Harlow and Lane Using Antibodies: A Laboratory Manual; Cold Spring Harbor Laboratory Press, Cold Spring Harbor, N.Y. (1998); and Coligan et al., Short Protocols in Protein Science, Wiley, John & Sons, Inc. (2003). Any enzymatic reactions or purification techniques are performed according to manufacturer's specifications, as commonly accomplished in the art or as described herein. The nomenclature used in connection with, and the laboratory procedures and techniques of, analytical chemistry, synthetic organic chemistry, and medicinal and pharmaceutical chemistry described herein are those well-known and commonly used in the art.

As used in the description and the appended claims, the singular forms "a", "an" and "the" are used interchangeably and intended to include the plural forms as well and fall within each meaning, unless the context clearly indicates otherwise. Also, as used herein, "and/or" refers to and encompasses any and all possible combinations of one or more of the listed items, as well as the lack of combinations when interpreted in the alternative ("or").

All numerical designations, e.g., pH, temperature, time, concentration, and molecular weight, including ranges, are approximations which are varied (+) or (−) by increments of 0.1. It is to be understood, although not always explicitly stated that all numerical designations are preceded by the term "about". The term "about" also includes the exact value "X" in addition to minor increments of "X" such as "X+0.1" or "X−0.1." It also is to be understood, although not always explicitly stated, that the reagents described herein are merely exemplary and that equivalents of such are known in the art.

As used herein, the term "about" will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term.

The terms "administration of" or "administering" an active agent should be understood to mean providing an active agent to the subject in need of treatment in a form that can be introduced into that individual's body in a therapeutically useful form and therapeutically effective amount.

As used herein, the term "comprising" is intended to mean that the compositions and methods include the recited elements, but not excluding others. "Consisting essentially of" when used to define compositions and methods, shall mean excluding other elements of any essential significance to the composition or method. "Consisting of" shall mean excluding more than trace elements of other ingredients for claimed compositions and substantial method steps. Embodiments defined by each of these transition terms are within the scope of this disclosure. Accordingly, it is intended that the methods and compositions can include additional steps and components (comprising) or alternatively including steps and compositions of no significance (consisting essentially of) or alternatively, intending only the stated method steps or compositions (consisting of).

As used herein, "expression," "expressed," or "encodes" refers to the process by which polynucleotides are transcribed into mRNA and/or the process by which the transcribed mRNA is subsequently being translated into peptides, polypeptides, or proteins. Expression may include splicing of the mRNA in a eukaryotic cell or other forms of post-transcriptional modification or post-translational modification.

The term "farnesyl diphosphate synthase" may also be referred to herein as FDPS, and may also be referred to herein as farnesyl pyrophosphate synthase or FPPS.

The term "gamma delta T cell" may also be referred to herein as a γδ T cell, or further as a GD T cell. The term "gamma delta T cell activation" refers to any measurable biological phenomenon associated with a gamma delta T cell that is representative of such T cell being activated. Non-limiting examples of such a biological phenomenon include an increase of cytokine production, changes in the qualitative or quantitative composition of cell surface proteins, an increase in T cell proliferation, and/or an increase in T cell effector function, such killing or a target cell or assisting another effector cell to kill a target cell.

The terms "individual," "subject," and "patient" are used interchangeably herein, and refer to any individual mammal subject, e.g., bovine, canine, feline, equine, or human.

The term "miRNA" refers to a microRNA, and also may be referred to herein as "miR".

The term "packaging cell line" refers to any cell line that can be used to express a lentiviral particle.

The term "percent identity," in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the "percent identity" can exist over a region of the sequence being compared, e.g., over a functional domain, or, alternatively, exist over the full length of the two sequences to be compared. For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information website.

The percent identity between two nucleotide sequences can be determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. The percent identity between two nucleotide or amino acid sequences can also be determined using the algorithm of E. Meyers and W. Miller (CABIOS, 4:11-17 (1989)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (I Mol. Biol. (48):444-453 (1970)) algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6.

The nucleic acid and protein sequences of the present disclosure can further be used as a "query sequence" to perform a search against public databases to, for example, identify related sequences. Such searches can be performed using the NBLAST and)(BLAST programs (version 2.0) of Altschul, et al. (1990) *J. Mol. Biol.* 215:403-10. BLAST nucleotide searches can be performed with the NBLAST program, score=100, word length=12 to obtain nucleotide sequences homologous to the nucleic acid molecules provided in the disclosure. BLAST protein searches can be performed with the)(BLAST program, score=50, word-length=3 to obtain amino acid sequences homologous to the protein molecules of the disclosure. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g., XBLAST and NBLAST) can be used. See http://www.ncbi.nlm.nih.gov.

As used herein, "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

As used herein, a "pharmaceutically acceptable carrier" refers to, and includes, any and all solvents, dispersion media, coatings, antibacterial and antifungal agents, isotonic and absorption delaying agents, and the like that are physiologically compatible. The compositions can include a pharmaceutically acceptable salt, e.g., an acid addition salt or a base addition salt (see, e.g., Berge et al. (1977) *J Pharm Sci* 66:1-19).

As used herein, the term "SEQ ID NO" is synonymous with the term "Sequence ID No."

As used herein, "small RNA" refers to non-coding RNA that are generally less than about 200 nucleotides or less in length and possess a silencing or interference function. In other embodiments, the small RNA is about 175 nucleotides or less, about 150 nucleotides or less, about 125 nucleotides or less, about 100 nucleotides or less, or about 75 nucleotides or less in length. Such RNAs include microRNA (miRNA), small interfering RNA (siRNA), double stranded RNA (dsRNA), and short hairpin RNA (shRNA). "Small RNA" of the disclosure should be capable of inhibiting or knocking-down gene expression of a target gene, generally through pathways that result in the destruction of the target gene mRNA.

The term "therapeutically effective amount" refers to a sufficient quantity of the active agents of the present disclosure, in a suitable composition, and in a suitable dosage form to treat or prevent the symptoms, progression, or onset of the complications seen in patients suffering from a given ailment, injury, disease, or condition. The therapeutically effective amount will vary depending on the state of the patient's condition or its severity, and the age, weight, etc., of the subject to be treated. A therapeutically effective amount can vary, depending on any of a number of factors, including, e.g., the route of administration, the condition of the subject, as well as other factors understood by those in the art.

As used herein, the term "therapeutic vector" includes, without limitation, reference to a lentiviral vector or an AAV vector.

"A treatment" is intended to target the disease state and combat it, i.e., ameliorate or prevent the disease state. The particular treatment thus will depend on the disease state to be targeted and the current or future state of medicinal therapies and therapeutic approaches. A treatment may have associated toxicities.

The term "treatment" or "treating" generally refers to an intervention in an attempt to alter the natural course of the subject being treated, and can be performed either for prophylaxis or during the course of clinical pathology. Desirable effects include, but are not limited to, preventing occurrence or recurrence of disease, alleviating symptoms, suppressing, diminishing or inhibiting any direct or indirect pathological consequences of the disease, ameliorating or palliating the disease state, and causing remission or improved prognosis.

Description of Aspects of the Disclosure

In one aspect, a method of activating a GDT cell is provided. The method includes infecting, in the presence of the GD T cell, a target cell with a viral delivery system encoding at least one genetic element. In embodiments, the at least one encoded genetic element includes a small RNA capable of inhibiting production of an enzyme involved in the mevalonate pathway. In embodiments, the enzyme is FDPS. In embodiments, when the enzyme is inhibited in the target cell, the target cell activates the GD T cell. In embodiments, the target cell is a cancer cell or a cell that has been infected with an infectious agent. In embodiments, the at least one encoded genetic element includes a microRNA or a shRNA.

In embodiments, the at least one encoded genetic element includes a shRNA having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95% or more percent identity with GTCCTGGAGTACAATGC-CATTCTCGAGAATGGCATTGTACTCCAGGACTTTTT (SEQ ID NO: 1); GCAGGAT-TTCGTTCAGCACTTCTCGAGAAGTGCTGAACGAA ATCCTGCTTTTT (SEQ ID NO: 2); GCCATGTA-CATGGCAGGAATTCTCGAGAA TTCCTGCCATGTA-CATGGCTTTTT (SEQ ID NO: 3); or GCAGAAGGAGGCTGA GAAAGTCTCGA-GACTTTCTCAGCCTCCTTCTGCTTTTT (SEQ ID NO: 4). In a preferred embodiment, the shRNA includes GTCCTGGAGTACAATGCCATTCTCGAG AATGGCAT-TGTACTCCAGGACTTTTT (SEQ ID NO: 1); GCAGGAT-TTCGTTCA GCACTTCTCGAGAAGTGCT-GAACGAAATCCTGCTTTTT (SEQ ID NO: 2); GCCA TGTACATGGCAGGAATTCTCGAGAATTCCTGC-CATGTACATGGCTTTTT (SEQ ID NO: 3); or GCAGAAGGAGGCTGAGAAAGTCTCGA-GACTTTCTCAGCCTCCTT CTGCTTTTT (SEQ ID NO: 4).

In another aspect, the at least one encoded genetic element includes a microRNA having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95% or more percent identity with AAGGTATAT-TGCTGTTGACAGT-GAGCGACACTTTCTCAGCCTCCTTCTGCGTGAAGC CACAGATGGCAGAAGGAGGCT-GAGAAAGTGCTGCCTACTGCCTCGGACTTCAAGGG GCT (SEQ ID NO: 5); AAGGTATATTGCTGTTGACAGT-GAGCGACACT TTCTCAGCCTCCTTCTGCGT-GAAGCCACAGATGGCAGAAGGGCT-GAGAAAGTGCTGC CTACTGCCTCGGACTTCAAGGGGCT (SEQ ID NO: 6); TGCTGTTGACAGTG AGCGACTTTCTCAGCCTCCTTCTGCGTGAAGC-CACAGATGGCAGAAGGAGGCTGAG AAAGTTGCC-TACTGCCTCGGA (SEQ ID NO: 7); CCTG-GAGGCTTGCTGAAG GCTGTATGCTGACTTTCTCAGCCTCCTTCTGCTT-TTGGCCACTGACTGAGCAGAAGGG CTGAGAAAGTCAGGACACAAGGCCTGT-TACTAGCACTCA (SEQ ID NO: 8); CATCTC-CATGGCTGTAC-CACCTTGTCGGGACTTTCTCAGCCTCCTTCTGC-CTGTTGAA TCT-CATGGCAGAAGGAGGCGAGAAAGTCTGACAT-TTTGGTATCTTTCATCTGACCA (SEQ ID NO: 9); or GGGCCTGGCTCGAGCAGGGGGCGAGGGA-TACTTTCT CAGCCTCCTTCTGCTGGTCCCCTCCCCGCAGA-AGGAGGCTGAGAAAGTCCTTCCCTC CCAATGACCGCGTCTTCGTCG (SEQ ID NO: 10). In a preferred embodiment, the microRNA includes AAGGTAT-ATTGCTGTTGACAGTGAGCGACACTTTCTCAGCCT CCTTCTGCGTGAAGCCACA-GATGGCAGAAGGAGGCTGAGAAAGTGCTGCC-TACTGC CTCGGACTTCAAGGGGCT (SEQ ID NO: 5); AAGGTATATTGCTGTTGACAGT GAGCGACACTTTCTCAGCCTCCTTCTGCGTGAAGC-CACAGATGGCAGAAGGGCTGA GAAAGTGCTGCC-TACTGCCTCGGACTTCAAGGGGCT (SEQ ID NO: 6); TGCTG TTGACAGT-GAGCGACTTTCTCAGCCTCCTTCTGCGTGAAGC-CACAGATGGCAGAAGG AGGCTGAGAAAGTTGCC-TACTGCCTCGGA (SEQ ID NO: 7); CCTGGAGGCT TGCT-GAAGGCTGTATGCTGACTTTCTCAGCCTCCTT-CTGCTTTTGGCCACTGACTGAG CAGAAGGGCT-GAGAAAGTCAGGACACAAGGCCTGT-TACTAGCACTCA (SEQ ID NO: 8); CATCTC-CATGGCTGTACCACCTTGTCGGGACTTTCTCAG-CCTCCTT CTGCCTGTTGAATCT-CATGGCAGAAGGAGGCGAGAAAGTCTGACAT-TTTGGTATCTT TCATCTGACCA (SEQ ID NO: 9); or GGGCCTGGCTCGAGCAGGGGGCGAGGG ATACTTTCTCAGCCTCCTTCTGCTGGTCCCCTCC-CCGCAGAAGGAGGCTGAGAAAGT CCTTCCCTCC-CAATGACCGCGTCTTCGTCG (SEQ ID NO: 10).

In another aspect, the target cell is also contacted with an aminobisphosphonate drug. In a preferred embodiment, the aminobisphosphonate drug is zoledronic acid.

In another aspect, a method of treating cancer in a subject is provided. The method includes administering to the subject a therapeutically-effective amount of a viral delivery system encoding at least one genetic element. In embodiments, the at least one encoded genetic element includes a small RNA capable of inhibiting production of an enzyme involved in the mevalonate pathway. In further embodiments, when the enzyme is inhibited in a cancer cell in the presence of a GD T cell, the cancer cell activates the GD T cell, to thereby treat the cancer. In embodiments, the enzyme is FDPS. In embodiments, the at least one encoded genetic element includes a microRNA or a shRNA.

In another aspect, a method of treating an infectious disease in a subject is provided. The method includes administering to the subject a therapeutically-effective amount of a viral delivery system encoding at least one genetic element. In embodiments, the at least one encoded genetic element includes a small RNA capable of inhibiting production of an enzyme involved in the mevalonate pathway. In further embodiments, when the enzyme is inhibited in a cell that is infected with an infectious agent and is in the presence of a GD T cell, the infected cell activates the GD T cell, to thereby treat the infected cell, and the infectious disease. In embodiments, the enzyme is FDPS. In embodiments, the at least one encoded genetic element includes a microRNA or a shRNA.

In embodiments, the at least one encoded genetic element includes a shRNA having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95% or more percent identity with SEQ ID NO: 1; SEQ ID NO: 2; SEQ ID NO: 3; or SEQ ID NO: 4. In a preferred embodiment, the shRNA includes SEQ ID NO: 1; SEQ ID NO: 2; SEQ ID NO: 3; or SEQ ID NO: 4.

In other embodiments, the at least one encoded genetic element includes a microRNA having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95% or more percent identity with SEQ ID NO: 5; SEQ ID NO: 6; SEQ ID NO: 7; SEQ ID NO: 8; SEQ ID NO: 9; or SEQ ID NO: 10. In a preferred embodiment, the microRNA includes SEQ ID NO: 5; SEQ ID NO: 6; SEQ ID NO: 7; SEQ ID NO: 8; SEQ ID NO: 9; or SEQ ID NO: 10.

In another aspect, a viral vector comprising at least one encoded genetic element is provided. The at least one encoded genetic element includes a small RNA capable of inhibiting production of an enzyme involved in the mevalonate pathway. In embodiments, the enzyme involved in the mevalonate pathway is farnesyl diphosphate synthase (FDPS). In embodiments, the at least one encoded genetic element includes a microRNA or a shRNA.

In another aspect, the at least one encoded genetic element includes a shRNA having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95% or more percent identity with SEQ ID NO: 1; SEQ ID NO: 2; SEQ ID NO: 3; or SEQ ID NO: 4. In a preferred embodiment, the shRNA includes SEQ ID NO: 1; SEQ ID NO: 2; SEQ ID NO: 3; or SEQ ID NO: 4.

In another aspect, the at least one encoded genetic element includes a microRNA having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95% or more percent identity with SEQ ID NO: 5; SEQ ID NO: 6; SEQ ID NO: 7; SEQ ID NO: 8; SEQ ID NO: 9; or SEQ ID NO: 10. In a preferred embodiment, the microRNA includes SEQ ID NO: 5; SEQ ID NO: 6; SEQ ID NO: 7; SEQ ID NO: 8; SEQ ID NO: 9; or SEQ ID NO: 10.

In embodiments, the viral vector includes any vector that can effectively transduce the small RNA. In embodiments, the viral vector is a lentiviral vector. In other embodiments, the viral vector is an adeno-associated virus (AAV) vector.

In another aspect, the viral vector includes a second encoded genetic element. In embodiments, the second genetic element includes at least one cytokine or chemokine. In embodiments, the at least one cytokine is selected from the group consisting of: IL-18, TNF-α, interferon-γ, IL-1, IL-2, IL-15, IL-17, and IL-12. In embodiments, the at least one chemokine is a CC chemokine, CXC chemokine, c CX3 chemokine or a XC chemokine. In a further embodiment, the at least one chemokine is the CC chemokine, RANTES.

In another aspect, a lentiviral vector system for expressing a lentiviral particle is provided. The system includes a lentiviral vector, at least one envelope plasmid for expressing an envelope protein optimized for infecting a cell; and at least one helper plasmid for expressing gag, pol, and rev genes. When the lentiviral vector, the at least one envelope plasmid, and the at least one helper plasmid are transfected into a packaging cell, a lentiviral particle is produced by the packaging cell. In embodiments, the lentiviral particle is capable of infecting a targeting cell, and inhibiting an enzyme involved in the mevalonate pathway within the target cell. In embodiments, the enzyme involved in the mevalonate pathway is FDPS. In embodiments, the lentiviral vector system includes a first helper plasmid for expressing the gag and pol genes, and a second helper plasmid for expressing the rev gene. In embodiments, the envelope protein is preferably optimized for infecting a target cell. In embodiments, the target cell is a cancer cell. In other embodiments, the target cell is a cell that is infected with an infectious disease.

Cancer

The compositions and methods provided herein are used to treat cancer. A cell, tissue, or target may be a cancer cell, a cancerous tissue, harbor cancerous tissue, or be a subject or patient diagnosed or at risk of developing a disease or condition. In certain aspects, a cell may be an epithelial, an endothelial, a mesothelial, a glial, a stromal, or a mucosal cell. The cancer cell population can include, but is not limited to a brain, a neuronal, a blood, an endometrial, a meninges, an esophageal, a lung, a cardiovascular, a liver, a lymphoid, a breast, a bone, a connective tissue, a fat, a retinal, a thyroid, a glandular, an adrenal, a pancreatic, a stomach, an intestinal, a kidney, a bladder, a colon, a prostate, a uterine, an ovarian, a cervical, a testicular, a splenic, a skin, a smooth muscle, a cardiac muscle, or a striated muscle cell, can also include a cancer cell population from any of the foregoing, and can be associated with one or more of carcinomas, sarcomas, myelomas, leukemias, lymphomas, mixed types or mixtures of the foregoing. In still a further aspect cancer includes, but is not limited to astrocytoma, acute myeloid leukemia, anaplastic large cell lymphoma, acute lymphoblastic leukemia, angiosarcoma, B-cell lymphoma, Burkitt's lymphoma, breast carcinoma, bladder carcinoma, carcinoma of the head and neck, cervical carcinoma, chronic lymphoblastic leukemia, chronic myeloid leukemia, colorectal carcinoma, endometrial carcinoma, esophageal squamous cell carcinoma, Ewing's sarcoma, fibrosarcoma, glioma, glioblastoma, gastrinoma, gastric carcinoma, hepatoblastoma, hepatocellular carcinoma, Kaposi's sarcoma, Hodgkin lymphoma, laryngeal squamous cell carcinoma, larynx carcinoma, leukemia, leiomyosarcoma, lipoma, liposarcoma, melanoma, mantle cell lymphoma, medulloblastoma, mesothelioma, myxofibrosarcoma, myeloid leukemia, mucosa-associated lymphoid tissue B cell lymphoma, multiple myeloma, high-risk myelodysplastic syndrome, nasopharyngeal carcinoma, neuroblastoma, neurofibroma, high-grade non-Hodgkin lymphoma, non-Hodgkin lymphoma, lung carcinoma, non-small cell lung carcinoma, ovarian carcinoma, oesophageal carcinoma, osteosarcoma, pancreatic carcinoma, pheochromocytoma, prostate carcinoma, renal cell carcinoma, retinoblastoma, rhabdomyosarcoma, salivary gland tumor, Schwanomma, small cell lung cancer, squamous cell carcinoma of the head and neck, testicular tumor, thyroid carcinoma, urothelial carcinoma, and Wilm's tumor.

The compositions and methods provided herein are also used to treat NSCLC (non-small cell lung cancer), pediatric malignancies, cervical and other tumors caused or promoted by human papilloma virus (HPV), melanoma, Barrett's esophagus (pre-malignant syndrome), adrenal and skin cancers and auto immune, neoplastic cutaneous diseases.

Infectious Diseases

The compositions and methods disclosed herein can be used to treat infectious diseases. The term "infectious disease" includes any disease that is caused by an infectious agent. An "infectious agent" includes any exogenous pathogen including, without limitation, bacteria, fungi, viruses, mycoplasma, and parasites. Infectious agents that may be treated with compositions provided for in this disclosure include any art-recognized infectious organisms that cause pathogenesis in an animal, including such organisms as bacteria that are gram-negative or gram-positive cocci or bacilli, DNA and RNA viruses, including, but not limited to, DNA viruses such as papilloma viruses, parvoviruses, adenoviruses, herpesviruses and vaccinia viruses, and RNA viruses, such as arenaviruses, coronaviruses, rhinoviruses, respiratory syncytial viruses, influenza viruses, picomaviruses, paramyxoviruses, reoviruses, retroviruses, and rhabdoviruses. Examples of fungi that may be treated with the compositions and methods of the disclosure include fungi that grow as molds or are yeastlike, including, for example, fungi that cause diseases such as ringworm, histoplasmosis, blastomycosis, aspergillosis, cryptococcosis, sporotrichosis, coccidioidomycosis, paracoccidio-idomycosis, and candidiasis. Compositions and methods provided for herein may be utilized to treat parasitic infections including, but not limited to, infections caused by somatic tapeworms, blood flukes, tissue roundworms, ameba, and *Plasmodium, Trypanosoma, Leishmania*, and *Toxoplasma* species.

Methods of GD T Cell Activation

Provided herein are compositions and methods for activating GD T cells in an individual, as well as methods for treating tumors and infectious diseases. For instance, in embodiments, the compositions and methods provided herein can be used in methods to treat all known cancers because activated GD T cells comprise a natural mechanism for immune surveillance of tumors (See for e.g.: Pauza et al. 2014 *Frontiers in Immunol.* 5:687). Likewise, in embodiments, the compositions and methods provided herein can be used to treat infectious diseases, including but not limited to flavivirus, influenza virus, human retrovirus, mycobacteria, plasmodia and a variety of other viral, fungal and bacterial infections. (See for e.g.: Pauza and Cairo, 2015 *Cell Immunol.* 296(1).

In general, a vector system is administered to an individual to transfect or transduce a target cell population with the disclosed constructs for decreasing expression of FDPS and, in other embodiments, increasing expression of chemokines or cytokines. Administration and transfection/transduction can occur in vivo or ex vivo, with the transfected cells later administered back into the subject in the latter scenario.

Administration of the disclosed vectors and transfection or transduction of the disclosed constructs into a subject's cells result in decreased expression of FDPS, increased expression of cytokines or chemokines, accumulation of IPP and in many cases, reduced growth rates for genetically modified tumor cells. All of these features work together to activate and co-localize GD T cells to the site of a tumor or infection.

The disclosed methods can also increase the capacity of NK cells to recognize and destroy tumor cells and/or infected cells. Crosstalk between GD T cells and NK cells is an important aspect of regulating the immune and inflammatory responses. Further, GD T cells are known to trigger dendritic cell maturation, recruit B cells and macrophages, and participate in a variety of cytolytic activities, such as secretion of interferon-γ and TNF-α.

In embodiments, the disclosed compositions and methods provided herein comprise a form of gene therapy for activating GD T cells at the site of tumor or infectious disease pathology. In an aspect, the compositions and methods provided herein activate GD T cells and support their proliferation, differentiation, and functional capacities by promoting the production of specific cytokines needed for cytolytic activity capable of killing cancer cells or treating infectious diseases.

In embodiments the gene therapy sequences (e.g., FDPS shRNAs) are carried by therapeutic vectors, including but not limited to viral vectors such as lentiviruses or adeno-associated viruses, although other viral vectors can also be suitable. Gene therapy constructs may also be delivered in the form of DNA or RNA, including but not limited to plasmid forms. In embodiments, the disclosed gene therapy constructs may also be delivered in the form of protein-nucleic acid complexes or lipid nucleic acid complexes and mixtures of these formulations. For instance, a protein-nucleic acid complex can comprise nucleic acids of interest in a complex with cationic peptides such as lysine and arginine. Lipid-nucleic acids complexes can comprise lipid emulsions, micelles, liposomes, and/or mixtures of neutral and cationic lipids such as DOTMA, DOSPA, DOTAP, and DMRIE.

In embodiments, therapeutic vectors may comprise a single construct or at least two, at least three, at least four, or at least five different constructs. When more than one construct is present in a vector the constructs may be identical, or they may be different. For instance, the constructs may vary in terms of their promoters, the presence or absence of an integrating elements, and/or their sequences. In some embodiments, a therapeutic vector will comprise at least one construct that encodes a small RNA capable of knocking down the expression of FDPS. In embodiments, the therapeutic vector will also encode a specific cytokine(s) and/or chemokine(s), including but not limited to TNF-α, interferon-γ, IL-1, IL-2, IL-15, IL-17, IL-18 or IL-12. In some embodiments, a single construct may encode both small RNAs capable of knocking down the expression of FDPS and specific cytokines or chemokines, including but not limited to TNF-α, interferon-γ, IL-1, IL-2, IL-15, IL-17, IL-18 or IL-12.

In embodiments, viral vectors may introduce nucleic acid constructs that become integrated into the host chromosome. Alternately, transient delivery vectors may be used to prevent chromosomal integration and limit the lifespan of gene therapy constructs.

In embodiments, the disclosed constructs and vectors comprise short homology region RNA ("shRNA"), micro RNA ("miRNA"), or siRNA capable of reducing or knocking down expression of FDPS and/or geranyl pyrophosphate synthase ("GPPS") and/or farnesyl transferase ("FT") genes. By down regulating these genes, which control steroid and isoprenoid synthesis, isopentenyl pyrophosphate ("IPP") levels are elevated. Elevation and accumulation of IPP is a known mechanism for increasing GD T cells activation. Further, down regulation of these pyrophosphate synthase genes removes an important negative regulator of inflammasome function that in turn results in increased expression of cytokines that are important for GD T cell activation and effector cell function.

In embodiments, the disclosed constructs are regulated by specific promoters that are capable of producing interleukin-2 and/or interleukin-15 to sustain GD T cell proliferation. In addition, the disclosed constructs may be regulated by specific promoters that are capable of producing interleukin-1 beta and/or interleukin-18 and/or interferon-gamma required for GD T cell differentiation and acquisition of all effector cell function. Desirable effector cell functions include the capacity for direct cytotoxic cell killing of tumors and/or infected cells, secretion of beneficial cytokines and/or chemokines, increased expression of NK receptors required to recognize cancerous or infected cells, and increased expression of Fc receptors needed to bind targeting antibodies in order to co-localize GD T cells with cancerous or infected cell targets.

In embodiments, the disclosed methods activate GD T cells, resulting in the indirect effect of increasing the capacity for NK cells to attack and destroy cancerous cells, tumors, or infected cells. The activation of NK cells requires GD T cells that are stimulated to proliferate and differentiate, and to express 4-1BBL costimulatory ligand needed to engage the 4-1BB costimulatory receptor on NK cells. This form of crosstalk is known as an important mechanism for activating NK cells and is achieved here through the action of the disclosed methods and compositions.

In another aspect, crosstalk between GD T cells and NK cells is an important mechanism for eliminating inflammatory dendritic cells that accumulate in diseased tissues. Alone, neither GD T cells nor NK cells are capable of destroying dendritic cells, but once the aforementioned crosstalk interactions have occurred, NK cells are altered to become cytotoxic against inflammatory dendritic cells. This immuno-regulatory mechanism depends on strong activation and proliferation of GD T cells.

In embodiments, the disclosed methods for activation of GD T cells further comprise a step of suppressing pathologic inflammatory responses that may include cellular proliferation leading to atherosclerosis, chronic immune activation that stimulates tumor growth, autoimmune diseases including psoriasis and other presentations in the epidermis, inflammatory diseases of the central nervous system, and arthritis and other diseases of unregulated immune responses.

In embodiments, therapeutic vectors are administered concurrently with aminobisphosphonate (ABP) drugs to achieve synergistic activation of gamma delta T cells. The synergism can allow alternate, modified or reduced doses of ABP and may decrease adverse reactions to ABP including acute inflammatory responses and chronic diseases.

Constructs for GD T Cell Activation

Inhibition of FDPS results in IPP accumulation, resulting in activation of Vδ2+GD T cells and expression of IL-18, which is also important in activating GD T cells. Inhibition of farnesyl transferase results in decreased prenylation of proteins. The disclosed constructs can be transfected or transduced into specific target cells, like tumor cells or infected cells, where they can express RNA sequences (i.e., siRNA, shRNA or microRNA) that will inhibit translation of FDPS as well as encode and express cytotoxic cytokines or chemokines.

Disclosed herein are constructs for decreasing expression of FDPS and/or FT, increasing expression of cytokines, and increasing expression of chemokines including RANTES.

For instance, in some embodiments the constructs may encode for interferon-gamma, IL-1, IL-2, IL-15, IL-17, IL-18 or IL-12.

Expression of cytokines and chemokines, like those listed above, will result in localized cytotoxic destruction of tumor cells or cells infected with pathogenic organisms. Accordingly, expression of such constructs by a tumor cell or an infected cell will result in the unwanted cells assisting in its own destruction.

Likewise, if the disclosed constructs are expressed in a tumor cell or infected cell, decreasing the expression of FDPS and FT will result in activation and recruitment of GD T cells to the tumor site of site of cell infection. Increasing expression of RANTES will further attract GD T cells to intended tissue location. Because GD T cells can kill a broad range of tumors of epithelial origin as well as many leukemias and lymphomas, and are further able to produce high levels of the anti-tumor cytokine, IFNγ, recruitment of GD T cells to the site of a tumor can be a particularly effective means of inducing anti-tumor immunity.

Decreased expression of FDPS can be achieved via shRNA, microRNA, siRNA, or other means known in the art. For instance, shRNAs according to SEQ ID NOS: 1, 2, 3, or 4, or variants thereof can be used in the disclosed constructs and methods, although this example is not limiting. The coding regions for RNAs to decrease expression of FDPS and FT and the coding regions of cytokine and chemokines may be in the same construct or on different constructs.

The classical approach for the production of recombinant polypeptides or gene regulatory molecules including small RNA is the use of stable expression constructs. These constructs are based upon chromosomal integration of a transduced expression plasmid (or at least a portion thereof) into the genome of the host cell, short-duration plasmid transfection, or non-integrating viral vectors also with limited half-life. The sites of gene integration are generally random, and the number and ratio of genes integrating at any particular site are often unpredictable; likewise, non-integrating plasmids or viral vectors also generate nuclear DNA but these species usually lack sequences required for DNA replication and continuous maintenance. Thus, constructs that rely on chromosomal integration result in permanent maintenance of the recombinant gene that may exceed the therapeutic interval.

An alternative to stable expression constructs for gene expression are transient expression constructs. The expression of the latter gene expression construct is based on non-integrated plasmids, and hence the expression is typically lost as the cell undergoes division or the plasmid vectors are destroyed by endogenous nucleases.

The disclosed constructs are preferably episomal constructs that are transiently expressed. Episomal constructs are degraded or diluted over time such that they do not make permanent changes to a subject's genome, nor are they incorporated into the chromosome of a target cell. The process of episomal replication typically incorporates both host cell replication machinery and viral trans-acting factors.

Avoiding chromosomal integration reduces certain barriers to in vivo gene delivery. However, even integration-defective constructs can have a background frequency of integration, and any DNA molecule can find rare homologies to recombine with host sequences; but these rates of integration are exceptionally rare and generally not clinically significant.

Thus, in some embodiments, the disclosed vectors support active gene and/or small RNA delivery over a period of about 1, about 2, about 3, about 4, about 5, about 6, about 7, about 8, about 9, about 10, about 11, or about 12 weeks. In some embodiments, the disclosed vectors support active gene and/or small RNA delivery over a period of about 1 month, 2 months, 3 months, 4 months, 5 months, 6 months, 7 months, 8 months, 9 months, 10 months, 11 months, 12 months, or longer. Any combination of these time periods can also be used in the methods of the invention, e.g., 1 month and 1 week, or 3 months and 2 weeks.

However, in some embodiments, the constructs comprise integrating elements that depend on a retroviral integrase gene, such that the construct becomes integrated into the subject's chromosome. Retrotransposition and transposition are additional examples of mechanisms whereby mobile genetic elements become integrated or inserted into the chromosome. Plasmids may become integrated into the chromosome by recombination, and gene editing technologies including CRISPR and TALEN utilize guide RNA sequences and alter chromosomal loci by gene conversion mechanisms.

Constructs may comprise specific promoters for expressing cytokines involved in the maintenance of GD T cells (i.e. IL-2, IL-7, IL-17, and IL-15). For example, promoters that may be incorporated into the disclosed constructs include but are not limited to TATA-box promoters, CpG-box promoters, CCAAT-box promoters, TTGACA-box promoters, BRE-box promoters, INR-box promoters, AT-based promoters, CG-based promoters, ATCG-compact promoters, ATCG-balanced promoters, ATCG-middle promoters, ATCG-less promoters, AT-less promoters, CG-less promoters, AT-spike promoters, and CG-spike promoters. See Gagniuc and Ionescu-Tirgoviste, *Eukaryotic genomes may exhibit up to* 10 *generic classes of gene promoters*, BMC GENOMICS 13:512 (2012).

Therapeutic Vectors

The construct can be delivered via known transfection and/or transduction vectors, including but not limited to lentiviral vectors, adeno-associated virus, poxvirus, herpesvirus vectors, protein and/or lipid complexes, liposomes, micelles, and the like.

Viral vectors can be preferentially targeted to cell types that are useful for the disclosed methods (i.e., tumor cells or myeloid cells). Viral vectors can be used to transduce genes into target cells owing to specific virus envelope-host cell receptor interactions and viral mechanisms for gene expression. As a result, viral vectors have been used as vehicles for the transfer of genes into many different cell types including whole embryos, fertilized eggs, isolated tissue samples, tissue targets in situ, and cultured cell lines. The ability to introduce and express foreign genes in a cell is useful for the study of gene expression, and the elucidation of cell lineages as well as providing the potential for therapeutic interventions such as gene therapy, somatic cell reprogramming of induced pluripotent stem cells, and various types of immunotherapy. Viral components from viruses like Papovaviridae (e.g. bovine papillomavirus or BPV) or Herpesviridae (e.g. Epstein Barr Virus or EBV) or Hepadnaviridae (e.g. Hepatitis B Virus or HBV) or pox vectors including vaccinia may be used in the disclosed vectors.

Lentiviral vectors are a preferred type of vector for the disclosed compositions and methods, although the disclosure is not specifically limited to lentiviral vectors. Lentivirus is a genus of viruses that can deliver a significant amount of viral nucleic acid into a host cell. Lentiviruses are characterized as having a unique ability to infect/transduce non-dividing cells, and following transduction, lentiviruses integrate their nucleic acid into the host cell's chromosomes.

Infectious lentiviruses have three main genes coding for the virulence proteins gag, pol, and env, and two regulatory genes including tat and rev. Depending on the specific serotype and virus, there may be additional accessory genes that code for proteins involved in regulation, synthesis, and/or processing viral nucleic acids and other replicative functions.

Moreover, lentiviruses contain long terminal repeat (LTR) regions, which may be approximately 600 nt long. LTRs may be segmented into U3, R, and U5 regions. LTRs can mediate integration of retroviral DNA into the host chromosome via the action of integrase. Alternatively, without functioning integrase, the LTRs may be used to circularize the viral nucleic acid.

Viral proteins involved in early stages of lentivirus replication include reverse transcriptase and integrase. Reverse transcriptase is the virally encoded, RNA-dependent DNA polymerase. The enzyme uses a viral RNA genome as a template for the synthesis of a complementary DNA copy. Reverse transcriptase also has RNaseH activity for destruction of the RNA-template. Integrase binds both the viral cDNA generated by reverse transcriptase and the host DNA. Integrase processes the LTR before inserting the viral genome into the host DNA. Tat acts as a trans-activator during transcription to enhance initiation and elongation. The rev responsive element acts post-transcriptionally, regulating mRNA splicing and transport to the cytoplasm.

Viral vectors, in general, comprise glycoproteins and the various glycoproteins may provide specific affinities. For instance, VSVG peptides can increase transfection into myeloid cells. Alternatively, viral vectors can also have targeting moieties, such as antibodies, attached to their shell peptides. Targeting antibodies can be specific for antigens that are overexpressed on a tumor, for instance, like HER-2, PSA, CEA, M2-PK, and CA19-9.

Other viral vector specificities are also known in the art and can be used to target particular populations of cells. For example, poxvirus vectors target to macrophages and dendritic cells.

Lentiviral Vector System

A lentiviral virion (particle) is expressed by a vector system encoding the necessary viral proteins to produce a virion (viral particle). There is at least one vector containing a nucleic acid sequence encoding the lentiviral pol proteins necessary for reverse transcription and integration, operably linked to a promoter. In another embodiment, the pol proteins are expressed by multiple vectors. There is also a vector containing a nucleic acid sequence encoding the lentiviral gag proteins necessary for forming a viral capsid operably linked to a promoter. In an embodiment, this gag nucleic acid sequence is on a separate vector than at least some of the pol nucleic acid sequence. In another embodiment, the gag nucleic acid is on a separate vector from all the pol nucleic acid sequences that encode poi proteins.

Numerous modifications can be made to the vectors, which are used to create the particles to further minimize the chance of obtaining wild type revertants. These include, but are not limited to deletions of the U3 region of the LTR, tat deletions and matrix (MA) deletions.

The gag, pol and env vector(s) do not contain nucleotides from the lentiviral genome that package lentiviral RNA, referred to as the lentiviral packaging sequence.

The vector(s) forming the particle preferably do not contain a nucleic acid sequence from the lentiviral genome that expresses an envelope protein. Preferably, a separate vector that contains a nucleic acid sequence encoding an envelope protein operably linked to a promoter is used. This env vector also does not contain a lentiviral packaging sequence. In one embodiment the env nucleic acid sequence encodes a lentiviral envelope protein.

In another embodiment the envelope protein is not from the lentivirus, but from a different virus. The resultant particle is referred to as a pseudotyped particle. By appropriate selection of envelopes one can "infect" virtually any cell. For example, one can use an env gene that encodes an envelope protein that targets an endocytic compartment such as that of the influenza virus, VSV-G, alpha viruses (Semliki forest virus, Sindbis virus), arenaviruses (lymphocytic choriomeningitis virus), flaviviruses (tick-borne encephalitis virus, Dengue virus, hepatitis C virus, GB virus), rhabdoviruses (vesicular stomatitis virus, rabies virus), paramyxoviruses (mumps or measles) and orthomyxoviruses (influenza virus). Other envelopes that can preferably be used include those from Moloney Leukemia Virus such as MLV-E, MLV-A and GALV. These latter envelopes are particularly preferred where the host cell is a primary cell. Other envelope proteins can be selected depending upon the desired host cell. For example, targeting specific receptors such as a dopamine receptor can be used for brain delivery. Another target can be vascular endothelium. These cells can be targeted using a filovirus envelope. For example, the GP of Ebola, which by post-transcriptional modification become the GP$_1$ and GP$_2$ glycoproteins. In another embodiment, one can use different lentiviral capsids with a pseudotyped envelope (for example, FIV or SHIV [U.S. Pat. No. 5,654,195]). A SHIV pseudotyped vector can readily be used in animal models such as monkeys.

As detailed herein, a lentiviral vector system typically includes at least one helper plasmid comprising at least one of a gag, pol, or rev gene. Each of the gag, pol and rev genes may be provided on individual plasmids, or one or more genes may be provided together on the same plasmid. In one embodiment, the gag, pol, and rev genes are provided on the same plasmid (e.g., FIG. 2). In another embodiment, the gag and pol genes are provided on a first plasmid and the rev gene is provided on a second plasmid (e.g., FIG. 3). Accordingly, both 3-vector and 4-vector systems can be used to produce a lentivirus as described in the Examples section and elsewhere herein. The therapeutic vector, the envelope plasmid and at least one helper plasmid are transfected into a packaging cell line. A non-limiting example of a packaging cell line is the 293T/17 HEK cell line. When the therapeutic vector, the envelope plasmid, and at least one helper plasmid are transfected into the packaging cell line, a lentiviral particle is ultimately produced.

In another aspect, a lentiviral vector system for expressing a lentiviral particle is disclosed. The system includes a lentiviral vector as described herein; an envelope plasmid for expressing an envelope protein optimized for infecting a cell; and at least one helper plasmid for expressing gag, pol, and rev genes, wherein when the lentiviral vector, the envelope plasmid, and the at least one helper plasmid are transfected into a packaging cell line, a lentiviral particle is produced by the packaging cell line, wherein the lentiviral particle is capable of inhibiting production of chemokine receptor CCR5 or targeting an HIV RNA sequence.

Figure 2:
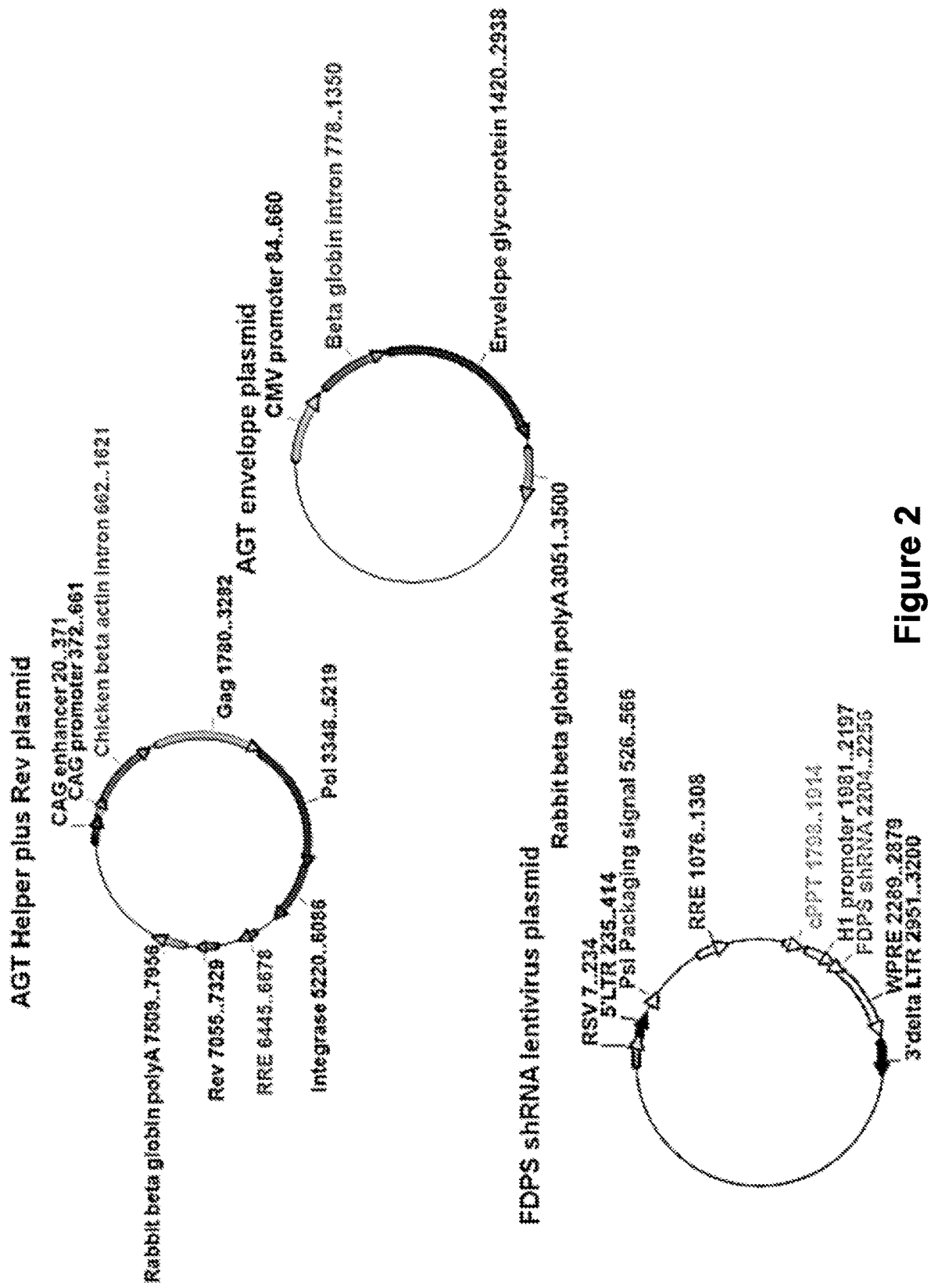
FIG. 2 depicts an exemplary 3-vector lentiviral vector system in a circularized form.

In another aspect, and as detailed in FIG. 2, the lentiviral vector, which is also referred to herein as a therapeutic vector, can include the following elements: hybrid 5' long terminal repeat (RSV/5' LTR) (SEQ ID NOS: 11-12), Psi sequence (RNA packaging site) (SEQ ID NO: 13), RRE (Rev-response element) (SEQ ID NO: 14), cPPT (polypurine tract) (SEQ ID NO: 15), H1 promoter (SEQ ID NO: 16), FDPS shRNA (SEQ ID NOS: 1, 2, 3, 4), Woodchuck Post-Transcriptional Regulatory Element (WPRE) (SEQ ID NO: 17), and 3' Delta LTR (SEQ ID NO: 18). In another aspect, sequence variation, by way of substitution, deletion, addition, or mutation can be used to modify the sequences references herein.

In another aspect, and as detailed herein, a helper plasmid has been designed to include the following elements: CAG promoter (SEQ ID NO: 19); HIV component gag (SEQ ID NO: 20); HIV component pol (SEQ ID NO: 21); HIV Int (SEQ ID NO: 22); HIV RRE (SEQ ID NO: 23); and HIV Rev (SEQ ID NO: 24). In another aspect, the helper plasmid may be modified to include a first helper plasmid for expressing the gag and pol genes, and a second and separate plasmid for expressing the rev gene. In another aspect, sequence variation, by way of substitution, deletion, addition, or mutation can be used to modify the sequences references herein.

In another aspect, and as detailed herein, an envelope plasmid has been designed to include the following elements being from left to right: RNA polymerase II promoter (CMV) (SEQ ID NO: 25) and vesicular stomatitis virus G glycoprotein (VSV-G) (SEQ ID NO: 26). In another aspect, sequence variation, by way of substitution, deletion, addition, or mutation can be used to modify the sequences references herein.

In another aspect, the plasmids used for lentiviral packaging can be modified with similar elements and the intron sequences could potentially be removed without loss of vector function. For example, the following elements can replace similar elements in the plasmids that comprise the packaging system: Elongation Factor-1 (EF-1), phosphoglycerate kinase (PGK), and ubiquitin C (UbC) promoters can replace the CMV or CAG promoter. SV40 poly A and bGH poly A can replace the rabbit beta globin poly A. The HIV sequences in the helper plasmid can be constructed from different HIV strains or clades. The VSV-G glycoprotein can be substituted with membrane glycoproteins from feline endogenous virus (RD114), gibbon ape leukemia virus (GALV), Rabies (FUG), lymphocytic choriomeningitis virus (LCMV), influenza A fowl plague virus (FPV), Ross River alphavirus (RRV), murine leukemia virus 10A1 (MLV), or Ebola virus (EboV).

Of note, lentiviral packaging systems can be acquired commercially (e.g., Lenti-vpak packaging kit from OriGene Technologies, Inc., Rockville, MD), and can also be designed as described herein. Moreover, it is within the skill of a person skilled in the art to substitute or modify aspects of a lentiviral packaging system to improve any number of relevant factors, including the production efficiency of a lentiviral particle.

Doses and Dosage Forms

The disclosed vectors allow for short, medium, or long-term expression of genes or sequences of interest and episomal maintenance of the disclosed vectors. Accordingly, dosing regimens may vary based upon the condition being treated and the method of administration.

In one embodiment, transduction vectors may be administered to a subject in need in varying doses. Specifically, a subject may be administered about $\geq 10^6$ infectious doses (where 1 dose is needed on average to transduce 1 target cell). More specifically, a subject may be administered about $\geq 10^7$, about $\geq 10^8$, about $\geq 10^9$, or about $\geq 10^{10}$ infectious doses, or any number of doses in-between these values. Upper limits of transduction vector dosing will be determined for each disease indication and will depend on toxicity/safety profiles for each individual product or product lot.

Additionally, a vector of the present disclosure may be administered periodically, such as once or twice a day, or any other suitable time period. For example, vectors may be administered to a subject in need once a week, once every other week, once every three weeks, once a month, every other month, every three months, every six months, every nine months, once a year, every eighteen months, every two years, every thirty months, or every three years.

In one embodiment, the disclosed vectors are administered as a pharmaceutical composition. In some embodiments, the pharmaceutical composition comprising the disclosed vectors can be formulated in a wide variety of dosage forms, including but not limited to nasal, pulmonary, oral, topical, or parenteral dosage forms for clinical application. Each of the dosage forms can comprise various solubilizing agents, disintegrating agents, surfactants, fillers, thickeners, binders, diluents such as wetting agents or other pharmaceutically acceptable excipients. The pharmaceutical composition comprising a vector can also be formulated for injection, insufflation, infusion, or intradermal exposure. For instance, an injectable formulation may comprise the disclosed vectors in an aqueous or non-aqueous solution at a suitable pH and tonicity.

The disclosed vectors may be administered to a subject via direct injection into a tumor site or at a site of infection. In some embodiments, the vectors can be administered systemically. In some embodiments, the vectors can be administered via guided cannulation to tissues immediately surrounding the sites of tumor or infection.

The disclosed vector compositions can be administered using any pharmaceutically acceptable method, such as intranasal, buccal, sublingual, oral, rectal, ocular, parenteral (intravenously, intradermally, intramuscularly, subcutaneously, intraperitoneally), pulmonary, intravaginal, locally administered, topically administered, topically administered after scarification, mucosally administered, via an aerosol, in semi-solid media such as agarose or gelatin, or via a buccal or nasal spray formulation.

Further, the disclosed vector compositions can be formulated into any pharmaceutically acceptable dosage form, such as a solid dosage form, tablet, pill, lozenge, capsule, liquid dispersion, gel, aerosol, pulmonary aerosol, nasal aerosol, ointment, cream, semi-solid dosage form, a solution, an emulsion, and a suspension. Further, the composition may be a controlled release formulation, sustained release formulation, immediate release formulation, or any combination thereof. Further, the composition may be a transdermal delivery system.

In some embodiments, the pharmaceutical composition comprising a vector can be formulated in a solid dosage form for oral administration, and the solid dosage form can be powders, granules, capsules, tablets or pills. In some embodiments, the solid dosage form can include one or more excipients such as calcium carbonate, starch, sucrose, lactose, microcrystalline cellulose or gelatin. In addition, the solid dosage form can include, in addition to the excipients, a lubricant such as talc or magnesium stearate. In some embodiments, the oral dosage form can be immediate release, or a modified release form. Modified release dosage forms include controlled or extended release, enteric release, and the like. The excipients used in the modified release dosage forms are commonly known to a person of ordinary skill in the art.

In a further embodiment, the pharmaceutical composition comprising a vector can be formulated as a sublingual or buccal dosage form. Such dosage forms comprise sublingual tablets or solution compositions that are administered under the tongue and buccal tablets that are placed between the cheek and gum.

In some embodiments, the pharmaceutical composition comprising a vector can be formulated as a nasal dosage form. Such dosage forms of the present invention comprise solution, suspension, and gel compositions for nasal delivery.

In some embodiments, the pharmaceutical composition comprising a vector can be formulated in a liquid dosage form for oral administration, such as suspensions, emulsions or syrups. In some embodiments, the liquid dosage form can include, in addition to commonly used simple diluents such as water and liquid paraffin, various excipients such as humectants, sweeteners, aromatics or preservatives. In particular embodiments, the composition comprising vectors can be formulated to be suitable for administration to a pediatric patient.

In some embodiment, the pharmaceutical composition can be formulated in a dosage form for parenteral administration, such as sterile aqueous solutions, suspensions, emulsions, non-aqueous solutions or suppositories. In some embodiments, the solutions or suspensions can include propyleneglycol, polyethyleneglycol, vegetable oils such as olive oil or injectable esters such as ethyl oleate.

The dosage of the pharmaceutical composition can vary depending on the patient's weight, age, gender, administration time and mode, excretion rate, and the severity of disease.

In some embodiments, the treatment of cancer is accomplished by guided direct injection of the disclosed vector constructs into tumors, using needle, or intravascular cannulation. In some embodiments, the disclosed vectors are administered into the cerebrospinal fluid, blood or lymphatic circulation by venous or arterial cannulation or injection, intradermal delivery, intramuscular delivery or injection into a draining organ near the site of disease.

The following examples are given to illustrate the present invention. It should be understood, however, that the invention is not to be limited to the specific conditions or details described in these examples. All printed publications referenced herein are specifically incorporated by reference.

EXAMPLES

Example 1: Development of a Lentiviral Vector System

Figure 4:
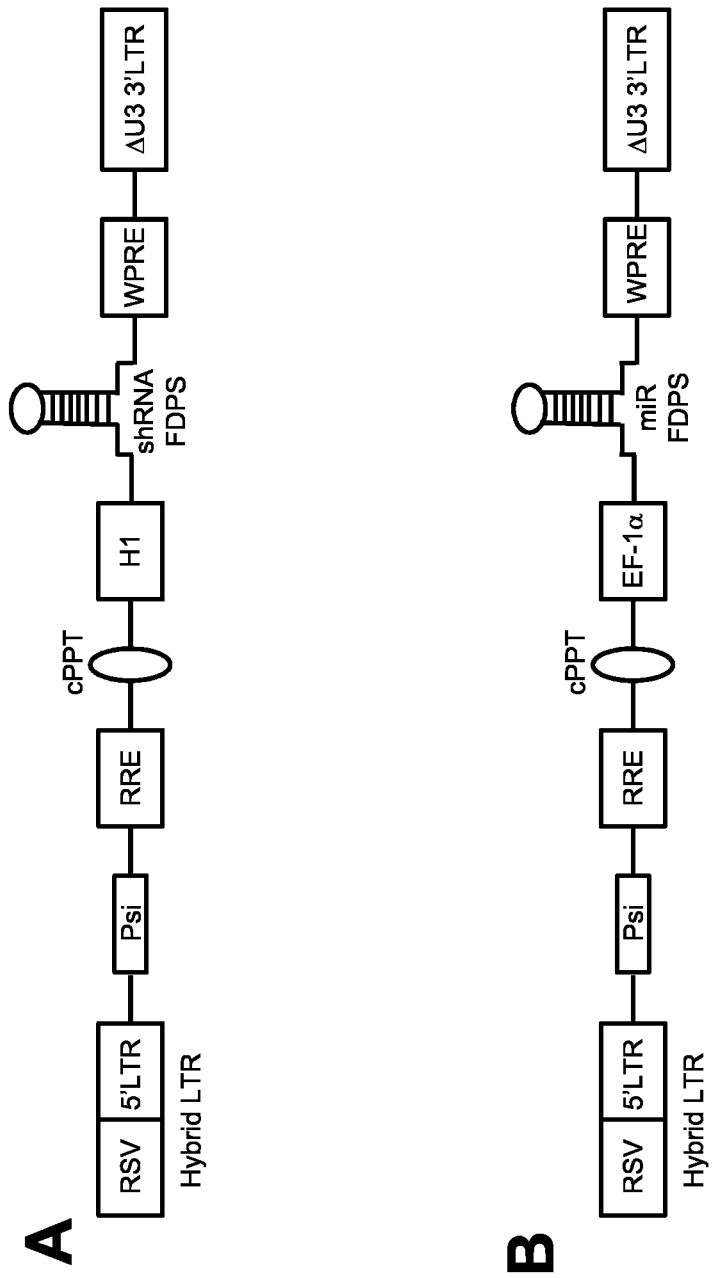
FIG. 4 depicts: (A) a linear map of a lentiviral vector expressing a FDPS shRNA targeting sequence; and (B) a linear map of a lentiviral vector expressing a synthetic microRNA with a FDPS targeting sequence.

A lentiviral vector system was developed as summarized in FIG. 4 (circularized form). Lentiviral particles were produced in 293T/17 HEK cells (purchased from American Type Culture Collection, Manassas, VA) following transfection with the therapeutic vector, the envelope plasmid, and the helper plasmid. The transfection of 293T/17 HEK cells, which produced functional viral particles, employed the reagent Poly(ethylenimine) (PEI) to increase the efficiency of plasmid DNA uptake. The plasmids and DNA were initially added separately in culture medium without serum in a ratio of 3:1 (mass ratio of PEI to DNA). After 2-3 days, cell medium was collected and lentiviral particles were purified by high-speed centrifugation and/or filtration followed by anion-exchange chromatography. The concentration of lentiviral particles can be expressed in terms of transducing units/ml (TU/ml). The determination of TU was accomplished by measuring HIV p24 levels in culture fluids (p24 protein is incorporated into lentiviral particles), measuring the number of viral DNA copies per cell by quantitative PCR, or by infecting cells and using light (if the vectors encode luciferase or fluorescent protein markers).

As mentioned above, a 3-vector system (i.e., a 2-vector lentiviral packaging system) was designed for the production of lentiviral particles. A schematic of the 3-vector system is shown in FIG. 2. Briefly, and with reference to FIG. 2, the top-most vector is a helper plasmid, which, in this case, includes Rev. The vector appearing in the middle of FIG. 2 is the envelope plasmid. The bottom-most vector is the therapeutic vector, as described herein.

Referring more specifically to FIG. 2, the Helper plus Rev plasmid includes a CAG enhancer (SEQ ID NO: 27); a CAG promoter (SEQ ID NO: 19); a chicken beta actin intron (SEQ ID NO: 28); a HIV gag (SEQ ID NO: 20); a HIV Pol (SEQ ID NO: 21); a HIV Int (SEQ ID NO: 22); a HIV RRE (SEQ ID NO: 23); a HIV Rev (SEQ ID NO: 24); and a rabbit beta globin poly A (SEQ ID NO: 29).

The Envelope plasmid includes a CMV promoter (SEQ ID NO: 25); a beta globin intron (SEQ ID NO: 30); a VSV-G (SEQ ID NO: 28); and a rabbit beta globin poly A (SEQ ID NO: 31).

Synthesis of a 2-Vector Lentiviral Packaging System Including Helper (Plus Rev) and Envelope Plasmids Materials and Methods Construction of the helper plasmid: The helper plasmid was constructed by initial PCR amplification of a DNA fragment from the pNL4-3 HIV plasmid (NIH Aids Reagent Program) containing Gag, Pol, and Integrase genes. Primers were designed to amplify the fragment with EcoRI and NotI restriction sites which could be used to insert at the same sites in the pCDNA3 plasmid (Invitrogen). The forward primer was (5'-TAAGCAGAATTC ATGAATTTGCCAG-GAAGAT-3') (SEQ ID NO: 32) and reverse primer was (5'-CCATACAAT-GAATGGACACTAGGCGGCCGCACGAAT-3') (SEQ ID NO: 33).

The sequence for the Gag, Pol, Integrase fragment was as follows:

```
                                    (SEQ ID NO: 34)
GAATTCATGAATTTGCCAGGAAGATGGAAACCAAAAATGA

TAGGGGGAATTGGAGGTTTTATCAAAGTAAGACAGTATGA

TCAGATACTCATAGAAATCTGCGGACATAAAGCTATAGGT

ACAGTATTAGTAGGACCTACACCTGTCAACATAATTGGAA

GAAATCTGTTGACTCAGATTGGCTGCACTTTAAATTTTCC

CATTAGTCCTATTGAGACTGTACCAGTAAAATTAAAGCCA

GGAATGGATGGCCCAAAAGTTAAACAATGGCCATTGACAG

AAGAAAAAATAAAAGCATTAGTAGAAATTTGTACAGAAAT

GGAAAAGGAAGGAAAAATTTCAAAAATTGGGCCTGAAAAT

CCATACAATACTCCAGTATTTGCCATAAAGAAAAAAGACA

GTACTAAATGGAGAAAATTAGTAGATTTCAGAGAACTTAA

TAAGAGAACTCAAGATTTCTGGGAAGTTCAATTAGGAATA

CCACATCCTGCAGGGTTAAAACAGAAAAAATCAGTAACAG
```

-continued
```
TACTGGATGTGGGCGATGCATATTTTTCAGTTCCCTTAGA
TAAAGACTTCAGGAAGTATACTGCATTTACCATACCTAGT
ATAAACAATGAGACACCAGGGATTAGATATCAGTACAATG
TGCTTCCACAGGGATGGAAAGGATCACCAGCAATATTCCA
GTGTAGCATGACAAAAATCTTAGAGCCTTTTAGAAAACAA
AATCCAGACATAGTCATCTATCAATACATGGATGATTTGT
ATGTAGGATCTGACTTAGAAATAGGGCAGCATAGAACAAA
AATAGAGGAACTGAGACAACATCTGTTGAGGTGGGGATTT
ACCACACCAGACAAAAAACATCAGAAAGAACCTCCATTCC
TTTGGATGGGTTATGAACTCCATCCTGATAAATGGACAGT
ACAGCCTATAGTGCTGCCAGAAAAGGACAGCTGGACTGTC
AATGACATACAGAAATTAGTGGGAAAATTGAATTGGGCAA
GTCAGATTTATGCAGGGATTAAAGTAAGGCAATTATGTAA
ACTTCTTAGGGGAACCAAAGCACTAACAGAAGTAGTACCA
CTAACAGAAGAAGCAGAGCTAGAACTGGCAGAAAACAGGG
AGATTCTAAAAGAACCGGTACATGGAGTGTATTATGACCC
ATCAAAAGACTTAATAGCAGAAATACAGAAGCAGGGGCAA
GGCCAATGGACATATCAAATTTATCAAGAGCCATTTAAAA
ATCTGAAAACAGGAAAGTATGCAAGAATGAAGGGTGCCCA
CACTAATGATGTGAAACAATTAACAGAGGCAGTACAAAAA
ATAGCCACAGAAAGCATAGTAATATGGGGAAAGACTCCTA
AATTTAAATTACCCATACAAAAGGAAACATGGGAAGCATG
GTGGACAGAGTATTGGCAAGCCACCTGGATTCCTGAGTGG
GAGTTTGTCAATACCCCTCCCTTAGTGAAGTTATGGTACC
AGTTAGAGAAAGAACCCATAATAGGAGCAGAAACTTTCTA
TGTAGATGGGGCAGCCAATAGGGAAACTAAATTAGGAAAA
GCAGGATATGTAACTGACAGAGGAAGACAAAAAGTTGTCC
CCCTAACGGACACAACAAATCAGAAGACTGAGTTACAAGC
AATTCATCTAGCTTTGCAGGATTCGGGATTAGAAGTAAAC
ATAGTGACAGACTCACAATATGCATTGGGAATCATTCAAG
CACAACCAGATAAGAGTGAATCAGAGTTAGTCAGTCAAAT
AATAGAGCAGTTAATAAAAAAGGAAAAAGTCTACCTGGCA
TGGGTACCAGCACACAAAGGAATTGGAGGAAATGAACAAG
TAGATAAATTGGTCAGTGCTGGAATCAGGAAAGTACTATT
TTTAGATGGAATAGATAAGGCCCAAGAAGAACATGAGAAA
TATCACAGTAATTGGAGAGCAATGGCTAGTGATTTTAACC
TACCACCTGTAGTAGCAAAAGAAATAGTAGCCAGCTGTGA
TAAATGTCAGCTAAAAGGGGAAGCCATGCATGGACAAGTA
GACTGTAGCCCAGGAATATGGCAGCTAGATTGTACACATT
TAGAAGGAAAAGTTATCTTGGTAGCAGTTCATGTAGCCAG
TGGATATATAGAAGCAGAAGTAATTCCAGCAGAGACAGGG
```
-continued
```
CAAGAAACAGCATACTTCCTCTTAAAATTAGCAGGAAGAT
GGCCAGTAAAAACAGTACATACAGACAATGGCAGCAATTT
CACCAGTACTACAGTTAAGGCCGCCTGTTGGTGGGCGGGG
ATCAAGCAGGAATTTGGCATTCCCTACAATCCCCAAAGTC
AAGGAGTAATAGAATCTATGAATAAAGAATTAAAGAAAAT
TATAGGACAGGTAAGAGATCAGGCTGAACATCTTAAGACA
GCAGTACAAATGGCAGTATTCATCCACAATTTTAAAAGAA
AAGGGGGGATTGGGGGGTACAGTGCAGGGGAAAGAATAGT
AGACATAATAGCAACAGACATACAAACTAAAGAATTACAA
AAACAAATTACAAAAATTCAAAATTTTCGGGTTTATTACA
GGGACAGCAGAGATCCAGTTTGGAAAGGACCAGCAAAGCT
CCTCTGGAAAGGTGAAGGGGCAGTAGTAATACAAGATAAT
AGTGACATAAAAGTAGTGCCAAGAAGAAAAGCAAAGATCA
TCAGGGATTATGGAAAACAGATGGCAGGTGATGATTGTGT
GGCAAGTAGACAGGATGAGGATTAA
```

Next, a DNA fragment containing the Rev, RRE, and rabbit beta globin poly A sequence with XbaI and XmaI flanking restriction sites was synthesized by MWG Operon. The DNA fragment was then inserted into the plasmid at the XbaI and XmaI restriction sites The DNA sequence was as follows:

(SEQ ID NO: 35)
```
TCTAGAATGGCAGGAAGAAGCGGAGACAGCGACGAAGAGC
TCATCAGAACAGTCAGACTCATCAAGCTTCTCTATCAAAG
CAACCCACCTCCCAATCCCGAGGGGACCCGACAGGCCCGA
AGGAATAGAAGAAGAAGGTGGAGAGAGAGACAGAGACAGA
TCCATTCGATTAGTGAACGGATCCTTGGCACTTATCTGGG
ACGATCTGCGGAGCCTGTGCCTCTTCAGCTACCACCGCTT
GAGAGACTTACTCTTGATTGTAACGAGGATTGTGGAACTT
CTGGGACGCAGGGGGTGGGAAGCCCTCAAATATTGGTGGA
ATCTCCTACAATATTGGAGTCAGGAGCTAAAGAATAGAGG
AGCTTTGTTCCTTGGGTTCTTGGGAGCAGCAGGAAGCACT
ATGGGCGCAGCGTCAATGACGCTGACGGTACAGGCCAGAC
AATTATTGTCTGGTATAGTGCAGCAGCAGAACAATTTGCT
GAGGGCTATTGAGGCGCAACAGCATCTGTTGCAACTCACA
GTCTGGGGCATCAAGCAGCTCCAGGCAAGAATCCTGGCTG
TGGAAAGATACCTAAAGGATCAACAGCTCCTAGATCTTTT
TCCCTCTGCCAAAAATTATGGGGACATCATGAAGCCCCTT
GAGCATCTGACTTCTGGCTAATAAAGGAAATTTATTTTCA
TTGCAATAGTGTGTTGGAATTTTTTGTGTCTCTCACTCGG
AAGGACATATGGGAGGGCAAATCATTTAAAACATCAGAAT
GAGTATTTGGTTTAGAGTTTGGCAACATATGCCATATGCT
```

-continued

GGCTGCCATGAACAAAGGTGGCTATAAAGAGGTCATCAGT

ATATGAAACAGCCCCCTGCTGTCCATTCCTTATTCCATAG

AAAAGCCTTGACTTGAGGTTAGATTTTTTTTATATTTTGT

TTTGTGTTATTTTTTTCTTTAACATCCCTAAAATTTTCCT

TACATGTTTTACTAGCCAGATTTTTCCTCCTCTCCTGACT

ACTCCCAGTCATAGCTGTCCCTCTTCTCTTATGAAGATCC

CTCGACCTGCAGCCCAAGCTTGGCGTAATCATGGTCATAG

CTGTTTCCTGTGTGAAATTGTTATCCGCTCACAATTCCAC

ACAACATACGAGCCGGAAGCATAAAGTGTAAAGCCTGGGG

TGCCTAATGAGTGAGCTAACTCACATTAATTGCGTTGCGC

TCACTGCCCGCTTTCCAGTCGGGAAACCTGTCGTGCCAGC

GGATCCGCATCTCAATTAGTCAGCAACCATAGTCCCGCCC

CTAACTCCGCCCATCCCGCCCCTAACTCCGCCCAGTTCCG

CCCATTCTCCGCCCCATGGCTGACTAATTTTTTTTATTTA

TGCAGAGGCCGAGGCCGCCTCGGCCTCTGAGCTATTCCAG

AAGTAGTGAGGAGGCTTTTTTGGAGGCCTAGGCTTTTGCA

AAAAGCTAACTTGTTTATTGCAGCTTATAATGGTTACAAA

TAAAGCAATAGCATCACAAATTTCACAAATAAAGCATTTT

TTTCACTGCATTCTAGTTGTGGTTTGTCCAAACTCATCAA

TGTATCTTATCAGCGGCCGCCCCGGG

Finally, the CMV promoter of pCDNA3.1 was replaced with the CAG enhancer/promoter plus a chicken beta actin intron sequence. A DNA fragment containing the CAG enhancer/promoter/intron sequence with MluI and EcoRI flanking restriction sites was synthesized by MWG Operon. The DNA fragment was then inserted into the plasmid at the MluI and EcoRI restriction sites. The DNA sequence was as follows:

(SEQ ID NO: 36)

ACGCGTTAGTTATTAATAGTAATCAATTACGGGGTCATTA

GTTCATAGCCCATATATGGAGTTCCGCGTTACATAACTTA

CGGTAAATGGCCCGCCTGGCTGACCGCCCAACGACCCCCG

CCCATTGACGTCAATAATGACGTATGTTCCCATAGTAACG

CCAATAGGGACTTTCCATTGACGTCAATGGGTGGACTATT

TACGGTAAACTGCCCACTTGGCAGTACATCAAGTGTATCA

TATGCCAAGTACGCCCCCTATTGACGTCAATGACGGTAAA

TGGCCCGCCTGGCATTATGCCCAGTACATGACCTTATGGG

ACTTTCCTACTTGGCAGTACATCTACGTATTAGTCATCGC

TATTACCATGGGTCGAGGTGAGCCCCACGTTCTGCTTCAC

TCTCCCCATCTCCCCCCCCTCCCCACCCCCAATTTTGTAT

TTATTTATTTTTTAATTATTTTGTGCAGCGATGGGGGCGG

GGGGGGGGGGGCGCGCGCCAGGCGGGGCGGGGCGGGGCG

AGGGGCGGGGCGGGGCGAGGCGGAGAGGTGCGGCGGCAGC

CAATCAGAGCGGCGCGCTCCGAAAGTTTCCTTTTATGGCG

AGGCGGCGGCGGCGGCGGCCCTATAAAAAGCGAAGCGCGC

GGCGGGCGGGAGTCGCTGCGTTGCCTTCGCCCCGTGCCCC

GCTCCGCGCCGCCTCGCGCCGCCCGCCCCGGCTCTGACTG

ACCGCGTTACTCCCACAGGTGAGCGGGCGGGACGGCCCTT

CTCCTCCGGGCTGTAATTAGCGCTTGGTTTAATGACGGCT

CGTTTCTTTTCTGTGGCTGCGTGAAAGCCTTAAAGGGCTC

CGGGAGGGCCCTTTGTGCGGGGGGGAGCGGCTCGGGGGGT

GCGTGCGTGTGTGTGTGCGTGGGGAGCGCCGCGTGCGGCC

CGCGCTGCCCGGCGGCTGTGAGCGCTGCGGGCGCGGCGCG

GGGCTTTGTGCGCTCCGCGTGTGCGCGAGGGGAGCGCGGC

CGGGGGCGGTGCCCCGCGGTGCGGGGGGGCTGCGAGGGGA

ACAAAGGCTGCGTGCGGGGTGTGTGCGTGGGGGGGTGAGC

AGGGGGTGTGGGCGCGGCGGTCGGGCTGTAACCCCCCCCT

GCACCCCCCTCCCCGAGTTGCTGAGCACGGCCCGGCTTCG

GGTGCGGGGCTCCGTGCGGGGCGTGGCGCGGGGCTCGCCG

TGCCGGGCGGGGGGTGGCGGCAGGTGGGGGTGCCGGGCGG

GGCGGGGCCGCCTCGGGCCGGGGAGGGCTCGGGGGAGGGG

CGCGGCGGCCCCGGAGCGCCGGCGGCTGTCGAGGCGCGGC

GAGCCGCAGCCATTGCCTTTTATGGTAATCGTGCGAGAGG

GCGCAGGGACTTCCTTTGTCCCAAATCTGGCGGAGCCGAA

ATCTGGGAGGCGCCGCCGCACCCCCTCTAGCGGGCGCGGG

CGAAGCGGTGCGGCGCCGGCAGGAAGGAAATGGGCGGGGA

GGGCCTTCGTGCGTCGCCGCGCCGCCGTCCCCTTCTCCAT

CTCCAGCCTCGGGGCTGCCGCAGGGGGACGGCTGCCTTCG

GGGGGGACGGGGCAGGGCGGGGTTCGGCTTCTGGCGTGTG

ACCGGCGGGAATTC

Construction of the VSV-G Envelope Plasmid:

The vesicular stomatitis Indiana virus glycoprotein (VSV-G) sequence was synthesized by MWG Operon with flanking EcoRI restriction sites. The DNA fragment was then inserted into the pCDNA3.1 plasmid (Invitrogen) at the EcoRI restriction site and the correct orientation was determined by sequencing using a CMV specific primer. The DNA sequence was as follows:

(SEQ ID NO: 37)

GAATTCATGAAGTGCCTTTTGTACTTAGCCTTTTTATTCA

TTGGGGTGAATTGCAAGTTCACCATAGTTTTTCCACACAA

CCAAAAAGGAAACTGGAAAAATGTTCCTTCTAATTACCAT

TATTGCCCGTCAAGCTCAGATTTAAATTGGCATAATGACT

TAATAGGCACAGCCTTACAAGTCAAAATGCCCAAGAGTCA

CAAGGCTATTCAAGCAGACGGTTGGATGTGTCATGCTTCC

AAATGGGTCACTACTTGTGATTTCCGCTGGTATGGACCGA

-continued

```
AGTATATAACACATTCCATCCGATCCTTCACTCCATCTGT

AGAACAATGCAAGGAAAGCATTGAACAAACGAAACAAGGA

ACTTGGCTGAATCCAGGCTTCCCTCCTCAAAGTTGTGGAT

ATGCAACTGTGACGGATGCCGAAGCAGTGATTGTCCAGGT

GACTCCTCACCATGTGCTGGTTGATGAATACACAGGAGAA

TGGGTTGATTCACAGTTCATCAACGGAAAATGCAGCAATT

ACATATGCCCCACTGTCCATAACTCTACAACCTGGCATTC

TGACTATAAGGTCAAAGGGCTATGTGATTCTAACCTCATT

TCCATGGACATCACCTTCTTCTCAGAGGACGGAGAGCTAT

CATCCCTGGGAAAGGAGGGCACAGGGTTCAGAAGTAACTA

CTTTGCTTATGAAACTGGAGGCAAGGCCTGCAAAATGCAA

TACTGCAAGCATTGGGGAGTCAGACTCCCATCAGGTGTCT

GGTTCGAGATGGCTGATAAGGATCTCTTTGCTGCAGCCAG

ATTCCCTGAATGCCCAGAAGGGTCAAGTATCTCTGCTCCA

TCTCAGACCTCAGTGGATGTAAGTCTAATTCAGGACGTTG

AGAGGATCTTGGATTATTCCCTCTGCCAAGAAACCTGGAG

CAAAATCAGAGCGGGTCTTCCAATCTCTCCAGTGGATCTC

AGCTATCTTGCTCCTAAAAACCCAGGAACCGGTCCTGCTT

TCACCATAATCAATGGTACCCTAAAATACTTTGAGACCAG

ATACATCAGAGTCGATATTGCTGCTCCAATCCTCTCAAGA

ATGGTCGGAATGATCAGTGGAACTACCACAGAAAGGGAAC

TGTGGGATGACTGGGCACCATATGAAGACGTGGAAATTGG

ACCCAATGGAGTTCTGAGGACCAGTTCAGGATATAAGTTT

CCTTTATACATGATTGGACATGGTATGTTGGACTCCGATC

TTCATCTTAGCTCAAAGGCTCAGGTGTTCGAACATCCTCA

CATTCAAGACGCTGCTTCGCAACTTCCTGATGATGAGAGT

TTATTTTTTGGTGATACTGGGCTATCCAAAAATCCAATCG

AGCTTGTAGAAGGTTGGTTCAGTAGTTGGAAAAGCTCTAT

TGCCTCTTTTTTCTTTATCATAGGGTTAATCATTGGACTA

TTCTTGGTTCTCCGAGTTGGTATCCATCTTTGCATTAAAT

TAAAGCACACCAAGAAAAGACAGATTTATACAGACATAGA

GATGAGAATTC
```

Figure 3:
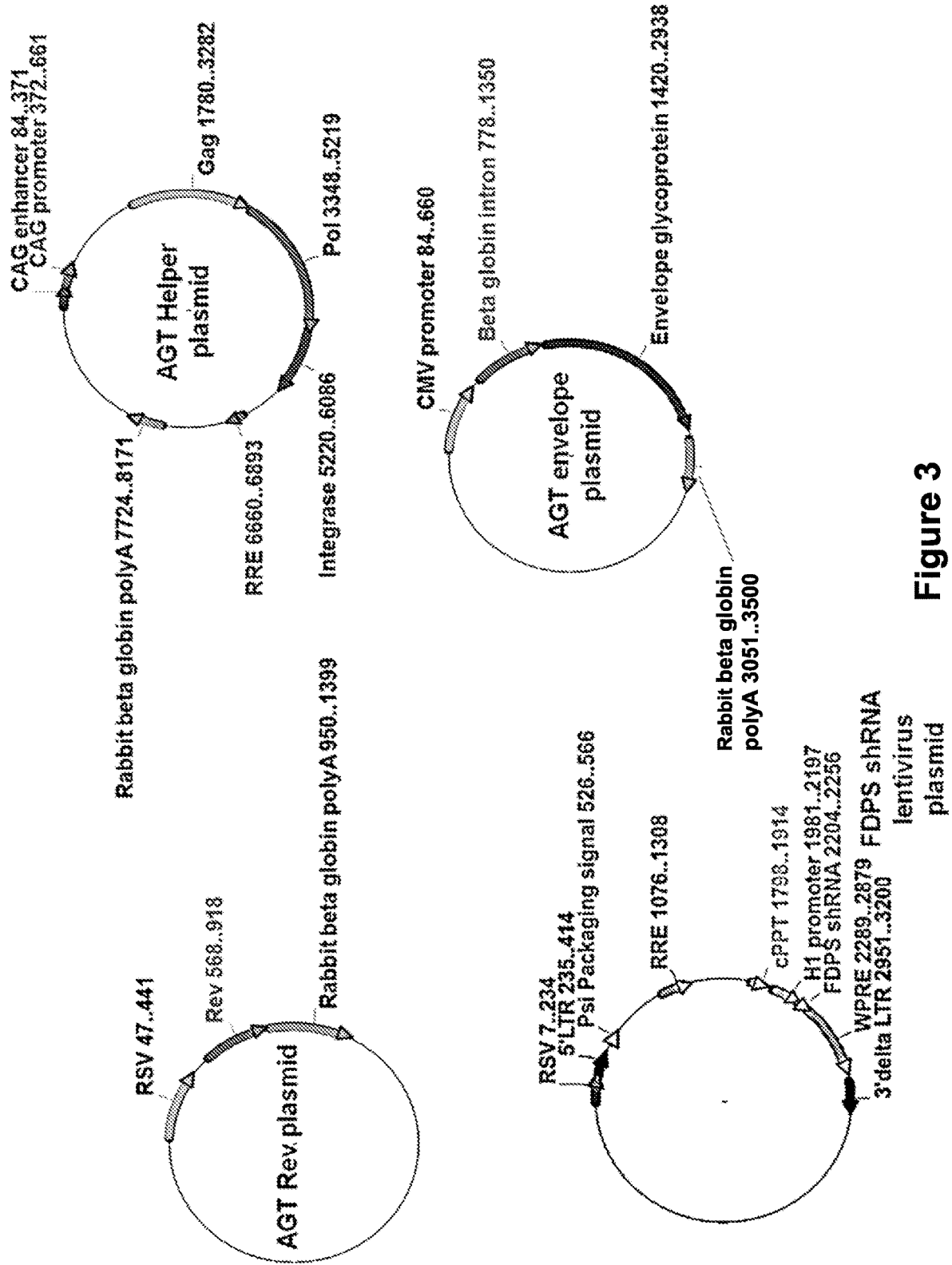
FIG. 3 depicts an exemplary 4-vector lentiviral vector system in a circularized form.

A 4-vector system (i.e., a 3-vector lentiviral packaging system) has also been designed and produced using the methods and materials described herein. A schematic of the 4-vector system is shown in FIG. 3. Briefly, and with reference to FIG. 3, the top-most vector is a helper plasmid, which, in this case, does not include Rev. The vector second from the top is a separate Rev plasmid. The vector second from the bottom is the envelope plasmid. The bottom-most vector is the previously described therapeutic vector.

Referring, in part, to FIG. 2, the Helper plasmid includes a CAG enhancer (SEQ ID NO: 27); a CAG promoter (SEQ ID NO: 19); a chicken beta actin intron (SEQ ID NO: 28); a HIV gag (SEQ ID NO: 20); a HIV Pol (SEQ ID NO: 21); a HIV Int (SEQ ID NO: 22); a HIV RRE (SEQ ID NO: 23); and a rabbit beta globin poly A (SEQ ID NO: 29).

The Rev plasmid includes a RSV promoter (SEQ ID NO: 38); a HIV Rev (SEQ ID NO: 39); and a rabbit beta globin poly A (SEQ ID NO: 29).

The Envelope plasmid includes a CMV promoter (SEQ ID NO: 25); a beta globin intron (SEQ ID NO: 30); a VSV-G (SEQ ID NO: 28); and a rabbit beta globin poly A (SEQ ID NO: 29).

Synthesis of a 3-Vector Lentiviral Packaging System Including Helper, Rev, and Envelope Plasmids Materials and Methods Construction of the Helper Plasmid without Rev:

The Helper plasmid without Rev was constructed by inserting a DNA fragment containing the RRE and rabbit beta globin poly A sequence. This sequence was synthesized by MWG Operon with flanking XbaI and XmaI restriction sites. The RRE/rabbit poly A beta globin sequence was then inserted into the Helper plasmid at the XbaI and XmaI restriction sites. The DNA sequence is as follows:

```
                                       (SEQ ID NO: 67)
TCTAGAAGGAGCTTTGTTCCTTGGGTTCTTGGGAGCAGCA

GGAAGCACTATGGGCGCAGCGTCAATGACGCTGACGGTAC

AGGCCAGACAATTATTGTCTGGTATAGTGCAGCAGCAGAA

CAATTTGCTGAGGGCTATTGAGGCGCAACAGCATCTGTTG

CAACTCACAGTCTGGGGCATCAAGCAGCTCCAGGCAAGAA

TCCTGGCTGTGGAAAGATACCTAAAGGATCAACAGCTCCT

AGATCTTTTTCCCTCTGCCAAAAATTATGGGGACATCATG

AAGCCCCTTGAGCATCTGACTTCTGGCTAATAAAGGAAAT

TTATTTTCATTGCAATAGTGTGTTGGAATTTTTTGTGTCT

CTCACTCGGAAGGACATATGGGAGGGCAAATCATTTAAAA

CATCAGAATGAGTATTTGGTTTAGAGTTTGGCAACATATG

CCATATGCTGGCTGCCATGAACAAAGGTGGCTATAAAGAG

GTCATCAGTATATGAAACAGCCCCCTGCTGTCCATTCCTT

ATTCCATAGAAAAGCCTTGACTTGAGGTTAGATTTTTTTT

ATATTTTGTTTTGTGTTATTTTTTCTTTAACATCCCTAA

AATTTTCCTTACATGTTTTACTAGCCAGATTTTTCCTCCT

CTCCTGACTACTCCCAGTCATAGCTGTCCCTCTTCTCTTA

TGAAGATCCCTCGACCTGCAGCCCAAGCTTGGCGTAATCA

TGGTCATAGCTGTTTCCTGTGTGAAATTGTTATCCGCTCA

CAATTCCACACAACATACGAGCCGGAAGCATAAAGTGTAA

AGCCTGGGGTGCCTAATGAGTGAGCTAACTCACATTAATT

GCGTTGCGCTCACTGCCCGCTTTCCAGTCGGGAAACCTGT

CGTGCCAGCGGATCCGCATCTCAATTAGTCAGCAACCATA

GTCCCGCCCCTAACTCCGCCCATCCCGCCCCTAACTCCGC

CCAGTTCCGCCCATTCTCCGCCCCATGGCTGACTAATTTT
```

-continued

```
TTTTATTTATGCAGAGGCCGAGGCCGCCTCGGCCTCTGAG

CTATTCCAGAAGTAGTGAGGAGGCTTTTTTGGAGGCCTAG

GCTTTTGCAAAAAGCTAACTTGTTTATTGCAGCTTATAAT

GGTTACAAATAAAGCAATAGCATCACAAATTTCACAAATA

AAGCATTTTTTCACTGCATTCTAGTTGTGGTTTGTCCAA

ACTCATCAATGTATCTTATCACCCGGG
```

Construction of the Rev Plasmid:

The RSV promoter and HIV Rev sequence was synthesized as a single DNA fragment by MWG Operon with flanking MfeI and XbaI restriction sites. The DNA fragment was then inserted into the pCDNA3.1 plasmid (Invitrogen) at the MfeI and XbaI restriction sites in which the CMV promoter is replaced with the RSV promoter. The DNA sequence was as follows:

```
                                        (SEQ ID NO: 40)
CAATTGCGATGTACGGGCCAGATATACGCGTATCTGAGGG

GACTAGGGTGTGTTTAGGCGAAAAGCGGGGCTTCGGTTGT

ACGCGGTTAGGAGTCCCCTCAGGATATAGTAGTTTCGCTT

TTGCATAGGGAGGGGGAAATGTAGTCTTATGCAATACACT

TGTAGTCTTGCAACATGGTAACGATGAGTTAGCAACATGC

CTTACAAGGAGAGAAAAAGCACCGTGCATGCCGATTGGTG

GAAGTAAGGTGGTACGATCGTGCCTTATTAGGAAGGCAAC

AGACAGGTCTGACATGGATTGGACGAACCACTGAATTCCG

CATTGCAGAGATAATTGTATTTAAGTGCCTAGCTCGATAC

AATAAACGCCATTTGACCATTCACCACATTGGTGTGCACC

TCCAAGCTCGAGCTCGTTTAGTGAACCGTCAGATCGCCTG

GAGACGCCATCCACGCTGTTTTGACCTCCATAGAAGACAC

CGGGACCGATCCAGCCTCCCCTCGAAGCTAGCGATTAGGC

ATCTCCTATGGCAGGAAGAAGCGGAGACAGCGACGAAGAA

CTCCTCAAGGCAGTCAGACTCATCAAGTTTCTCTATCAAA

GCAACCCACCTCCCAATCCCGAGGGGACCCGACAGGCCCG

AAGGAATAGAAGAAGAAGGTGGAGAGAGAGACAGAGACAG

ATCCATTCGATTAGTGAACGGATCCTTAGCACTTATCTGG

GACGATCTGCGGAGCCTGTGCCTCTTCAGCTACCACCGCT

TGAGAGACTTACTCTTGATTGTAACGAGGATTGTGGAACT

TCTGGGACGCAGGGGGTGGGAAGCCCTCAAATATTGGTGG

AATCTCCTACAATATTGGAGTCAGGAGCTAAAGAATAGTC

TAGA
```

The plasmids for the 2-vector and 3-vector packaging systems could be modified with similar elements and the intron sequences could potentially be removed without loss of vector function. For example, the following elements could replace similar elements in the 2-vector and 3-vector packaging system:

Promoters: Elongation Factor-1 (EF-1) (SEQ ID NO: 41), phosphoglycerate kinase (PGK) (SEQ ID NO: 42), and ubiquitin C (UbC) (SEQ ID NO: 43) can replace the CMV (SEQ ID NO: 25) or CAG promoter (SEQ ID NO: 19). These sequences can also be further varied by addition, substitution, deletion or mutation.

Poly A sequences: SV40 poly A (SEQ ID NO: 44) and bGH poly A (SEQ ID NO: 45) can replace the rabbit beta globin poly A (SEQ ID NO: 29). These sequences can also be further varied by addition, substitution, deletion or mutation.

HIV Gag, Pol, and Integrase sequences: The HIV sequences in the Helper plasmid can be constructed from different HIV strains or clades. For example, HIV Gag (SEQ ID NO: 20); HIV Pol (SEQ ID NO: 21); and HIV Int (SEQ ID NO: 22) from the Bal strain can be interchanged with the gag, pol, and int sequences contained in the helper/helper plus Rev plasmids as outlined herein. These sequences can also be further varied by addition, substitution, deletion or mutation.

Envelope: The VSV-G glycoprotein can be substituted with membrane glycoproteins from feline endogenous virus (RD114) (SEQ ID NO: 46), gibbon ape leukemia virus (GALV) (SEQ ID NO: 47), Rabies (FUG) (SEQ ID NO: 48), lymphocytic choriomeningitis virus (LCMV) (SEQ ID NO: 49), influenza A fowl plague virus (FPV) (SEQ ID NO: 50), Ross River alphavirus (RRV) (SEQ ID NO: 51), murine leukemia virus 10A1 (MLV) (SEQ ID NO: 52), or Ebola virus (EboV) (SEQ ID NO: 53). Sequences for these envelopes are identified in the sequence portion herein. Further, these sequences can also be further varied by addition, substitution, deletion or mutation.

In summary, the 3-vector versus 4-vector systems can be compared and contrasted, in part, as follows. The 3-vector lentiviral vector system contains: 1. Helper plasmid: HIV Gag, Pol, Integrase, and Rev/Tat; 2. Envelope plasmid: VSV-G/FUG envelope; and 3. Therapeutic vector: RSV 5'LTR, Psi Packaging Signal, Gag fragment, RRE, Env fragment, cPPT, WPRE, and 3'δ LTR. The 4-vector lentiviral vector system contains: 1. Helper plasmid: HIV Gag, Pol, and Integrase; 2. Rev plasmid: Rev; 3. Envelope plasmid: VSV-G/FUG envelope; and 4. Therapeutic vector: RSV 5'LTR, Psi Packaging Signal, Gag fragment, RRE, Env fragment, cPPT, WPRE, and 3' delta LTR. Sequences corresponding with the above elements are identified in the sequence listings portion herein.

Example 2: Development of a Lentiviral Vector that Expresses FDPS

The purpose of this Example was to develop an FDPS lentivirus vector.

Inhibitory RNA Design: The sequence of *Homo sapiens* Farnesyl diphosphate synthase (FDPS) (NM_002004.3) mRNA was used to search for potential siRNA or shRNA candidates to knockdown FDPS levels in human cells. Potential RNA interference sequences were chosen from candidates selected by siRNA or shRNA design programs such as from GPP Web Portal hosted by the Broad Institute (http://portals.broadinstitute.org/gpp/public/) or the BLOCK-iT RNAi Designer from Thermo Scientific (https://rnaidesigner.thermofisher.com/rnaiexpress/). Individual selected shRNA sequences were inserted into a lentiviral vector immediately 3 prime to a RNA polymerase III promoter such as H1 (SEQ ID NO: 16), U6 (SEQ ID NO: 54), or 7SK (SEQ ID NO: 55) to regulate shRNA expression. These lentivirus shRNA constructs were used to transduce cells and measure the change in specific mRNA levels. The shRNA most potent for reducing mRNA levels were embedded individually within a microRNA backbone to allow for expression by either the EF-1 alpha or CMV RNA polymerase II promoters. The microRNA backbone was selected from mirbase.org. RNA sequences were also synthesized as synthetic siRNA oligonucleotides and introduced directly into cells without using a lentiviral vector.

Vector Construction: For FDPS shRNA, oligonucleotide sequences containing BamHI and EcoRI restriction sites were synthesized by Eurofins MWG Operon. Overlapping sense and antisense oligonucleotide sequences were mixed and annealed during cooling from 70 degrees Celsius to room temperature. The lentiviral vector was digested with the restriction enzymes BamHI and EcoRI for one hour at 37 degrees Celsius. The digested lentiviral vector was purified by agarose gel electrophoresis and extracted from the gel using a DNA gel extraction kit from Thermo Scientific. The DNA concentrations were determined and vector to oligo (3:1 ratio) were mixed, allowed to anneal, and ligated. The ligation reaction was performed with T4 DNA ligase for 30 minutes at room temperature. 2.5 microliters of the ligation mix were added to 25 microliters of STBL3 competent bacterial cells. Transformation was achieved after heat-shock at 42 degrees Celsius. Bacterial cells were spread on agar plates containing ampicillin and drug-resistant colonies (indicating the presence of ampicillin-resistance plasmids) were recovered and expanded in LB broth. To check for insertion of the oligo sequences, plasmid DNA was extracted from harvested bacteria cultures with the Thermo Scientific DNA mini prep kit. Insertion of shRNA sequences in the lentiviral vector was verified by DNA sequencing using a specific primer for the promoter used to regulate shRNA expression. Using the following target sequences, exemplary shRNA sequences were determined to knock-down FDPS:

(FDPS target sequence #1; SEQ ID NO: 56)
GTCCTGGAGTACAATGCCATT;

(FDPS shRNA sequence #1; SEQ ID NO: 1)
GTCCTGGAGTACAATGCCATTCTCGAGAATGGCATTGTACTCCAGGACTT

TTT;

(FDPS target sequence #2; SEQ ID NO: 57)
GCAGGATTTCGTTCAGCACTT;

(FDPS shRNA sequence #2; SEQ ID NO: 2)
GCAGGATTTCGTTCAGCACTTCTCGAGAAGTGCTGAACGAAATCCTGCTT

TTT;

(FDPS target sequence #3; SEQ ID NO: 58)
GCCATGTACATGGCAGGAATT;

(FDPS shRNA sequence #3; SEQ ID NO: 3)
GCCATGTACATGGCAGGAATTCTCGAGAATTCCTGCCATGTACATGGCTT

TTT;

(FDPS target sequence #4; SEQ ID NO: 59)
GCAGAAGGAGGCTGAGAAAGT;
and (FDPS shRNA sequence #4; SEQ ID NO: 4)
GCAGAAGGAGGCTGAGAAAGTCTCGAGACTTTCTCAGCCTCCTTCTGCTT

TTT.

shRNA sequences were then assembled into a synthetic microRNA (miR) under control of the EF-1 alpha promoter. Briefly, a miR hairpin sequences, such as miR30, miR21, or miR185 as detailed below, was obtained from mirbase.org.

The 19-22mer shRNA target sequence was used to construct the synthetic miR sequence. The miR sequence was arranged as an anti-sense-target-sequence-hairpin loop sequence (specific for each microRNA)-sense target sequence.

The following miR sequences were developed:

(miR30 FDPS sequence #1; SEQ ID NO: 5)
AAGGTATATTGCTGTTGACAGTGAGCGACACTTTCTCAGCCTCCTTCTGC

GTGAAGCCACAGATGGCAGAAGGAGGCTGAGAAAGTGCTGCCTACTGCCT

CGGACTTCAAGGGGCT (miR30 FDPS sequence #2; SEQ ID NO: 6)
AAGGTATATTGCTGTTGACAGTGAGCGACACTTTCTCAGCCTCCTTCTGC

GTGAAGCCACAGATGGCAGAAGGGCTGAGAAAGTGCTGCCTACTGCCTCG

GACTTCAAGGGGCT (miR30 FDPS sequence #3; SEQ ID NO: 7)
TGCTGTTGACAGTGAGCGACTTTCTCAGCCTCCTTCTGCGTGAAGCCACA

GATGGCAGAAGGAGGCTGAGAAAGTTGCCTACTGCCTCGGA (miR155 FDPS sequence #1; SEQ ID NO: 8)
CCTGGAGGCTTGCTGAAGGCTGTATGCTGACTTTCTCAGCCTCCTTCTGC

TTTTGGCCACTGACTGAGCAGAAGGGCTGAGAAAGTCAGGACACAAGGCC

TGTTACTAGCACTCA (miR21 FDPS sequence #1; SEQ ID NO: 9)
CATCTCCATGGCTGTACCACCTTGTCGGGACTTTCTCAGCCTCCTTCTGC

CTGTTGAATCTCATGGCAGAAGGAGGCGAGAAAGTCTGACATTTTGGTAT

CTTTCATCTGACCA (miR185 FDPS sequence #1; SEQ ID NO: 10)
GGGCCTGGCTCGAGCAGGGGGCGAGGGATACTTTCTCAGCCTCCTTCTGC

TGGTCCCCTCCCCGCAGAAGGAGGCTGAGAAAGTCCTTCCCTCCCAATGA

CCGCGTCTTCGTCG

Example 3—Knock-Down of FDPS for 3 Days in THP1 Monocytic Leukemia by shRNA #4

Figure 5:
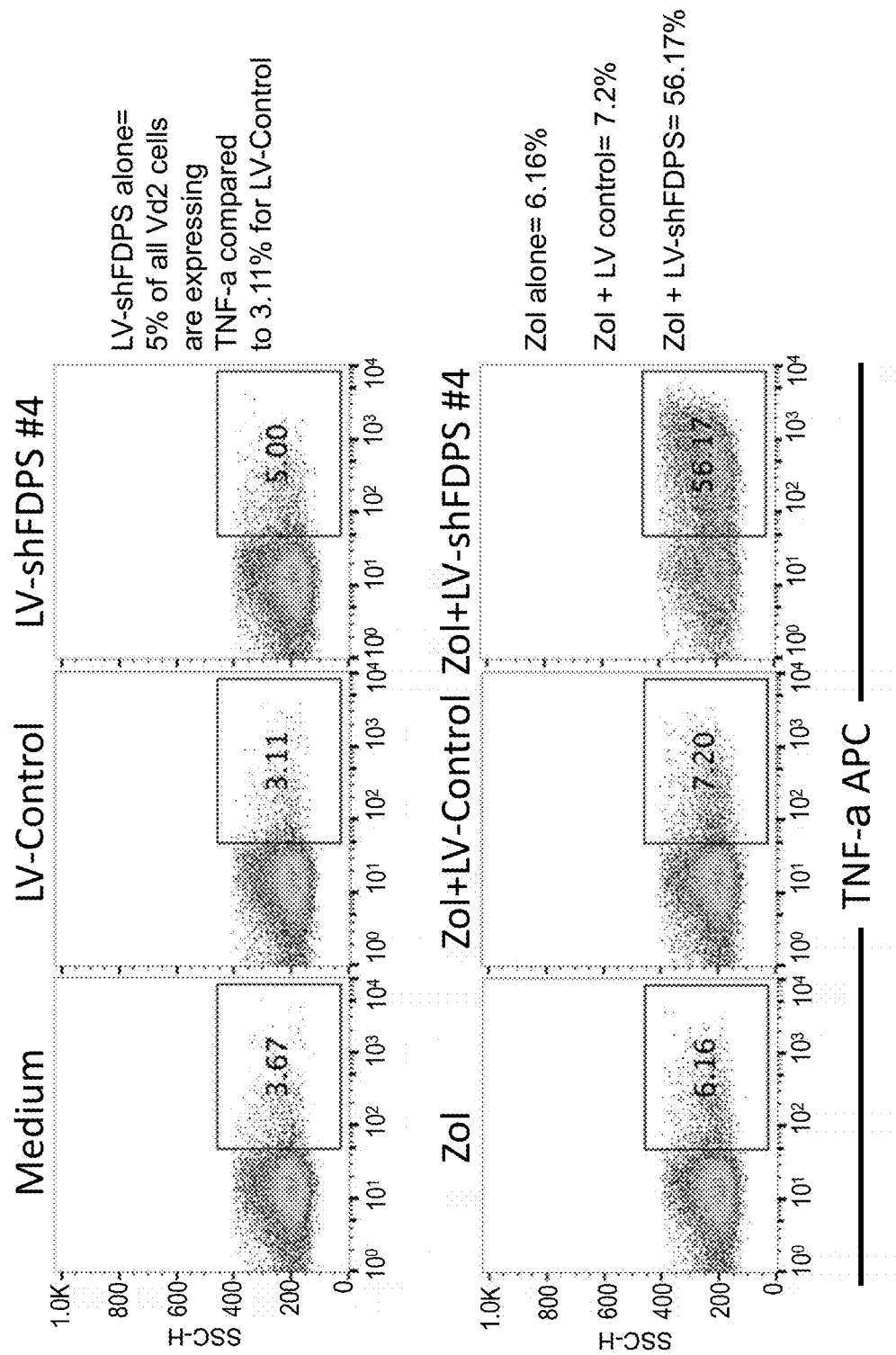
FIG. 5 depicts data demonstrating activation of Vδ2+ T cells THP-1 leukemia cells with a lentivirus expressing FDPS shRNA #4 (SEQ ID NO: 4), as described herein.

This Example illustrates that knock-down of FDPS in THP1 monocytic leukemia cells by lentiviral (LV)-expressing FDPS shRNA #4 stimulates TNF-α expression in gamma delta T cells, as shown in FIG. 5.

THP1 cells ($1 \times 10^5$ cells) were transduced with LV-control or LV-FDPS shRNA #4 for 3 days. Two days after transduction, cells were treated with or without 1 µM zoledronic acid. After 24 hours, the transduced THP-1 cells were co-cultured with $5 \times 10^5$ PBMC cells and IL-2 in a round bottom 96 well plate for 4 hours. The PBMC cells were pre-stimulated with zoledronic acid and IL-2 for 11 days to expand Vγ9Vδ2 T cells. After staining for Vγ9Vδ2 and TNF-α using fluorophore-conjugated anti TCR-Vδ2 and anti-TNF-α antibody, cells were analyzed via flow cytometry. Live cells were gated, and Vδ2+ and TNF-α+ cells were selected on a dot blot. The activated cytotoxic Vγ9Vδ2 T cells appeared in the upper right quadrant of flow cytograms. Without zoledronic acid, LV-control stimulated 3.1% of TNF-α expressing Vγ9Vδ2 T cells and LV-FDPS shRNA #4 stimulated 5%. With zoledronic acid treatment, LV-control stimulated 7.2% of TNF-α expressing Vγ9Vδ2 T cells and LV-FDPS shRNA #4 stimulated 56.2%.

Example 4—Knock-Down of FDPS for 14 Days in THP1 Leukemia Cells by shRNA #4

Figure 6:
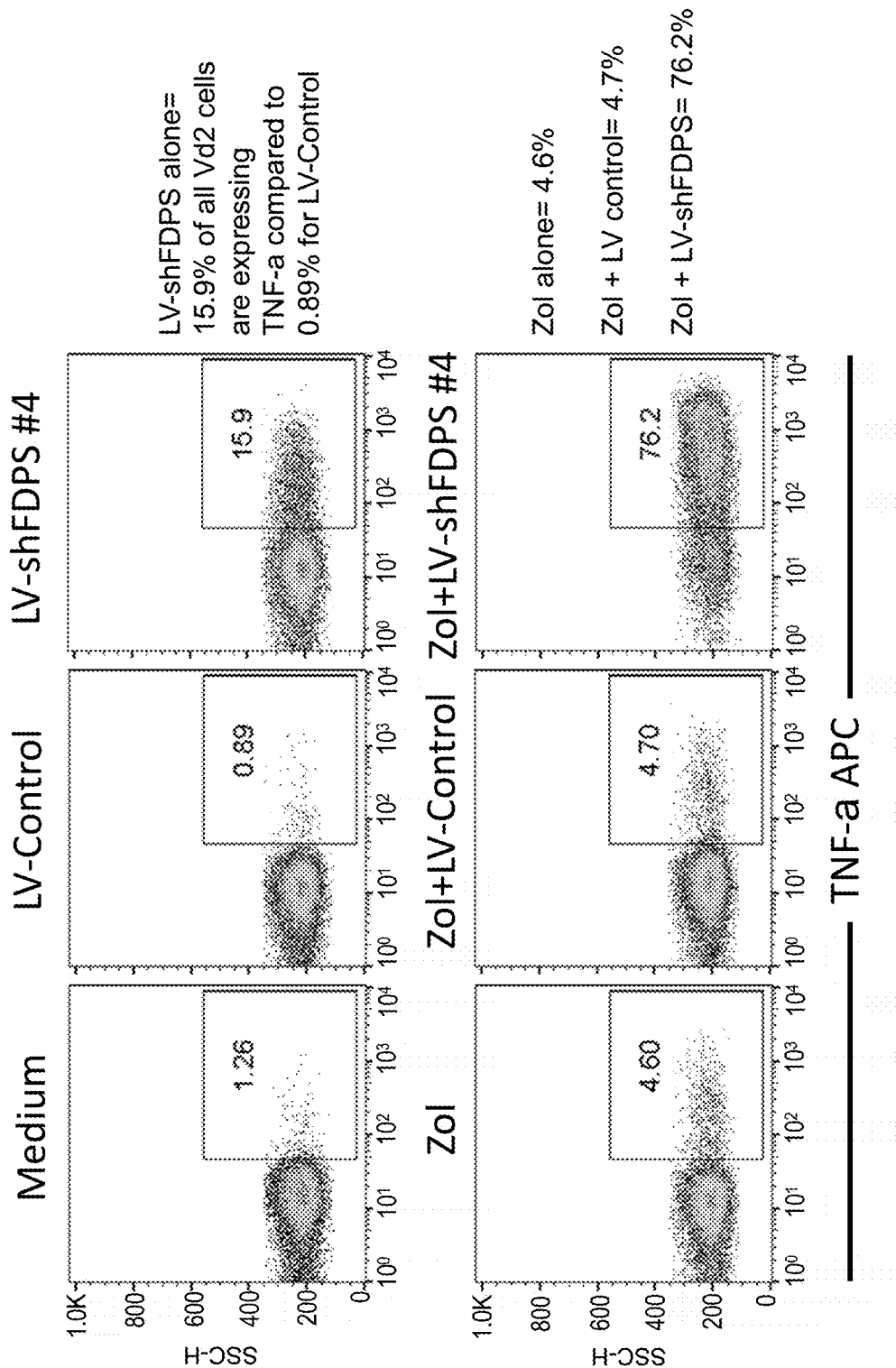
FIG. 6 depicts data demonstrating activation of Vδ2+ T cells by THP-1 leukemia cells with a lentivirus expressing FDPS shRNA #4 (SEQ ID NO: 4), as described herein.

This Example illustrates that Knock-down of FDPS for 14 days in THP1 leukemia cells by lentiviral (LV)-expressing FDPS shRNA #4 stimulates TNF-α expression in GD T cells, as shown in FIG. 6.

THP1 cells (1×10$^5$ cells) were transduced with LV-control or LV-FDPS shRNA #4 for 14 days. Two days after transduction, cells were treated with or without 1 uM zoledronic acid. After 24 hours, the transduced THP-1 cells were co-cultured with 5×10$^5$ PBMC cells and IL-2 in a round bottom 96 well plate for 4 hours. The PBMC cells were pre-stimulated with zoledronic acid and IL-2 for 11 days to expand Vγ9Vδ2 T cells. After staining for Vγ9Vδ2 and TNF-α using fluorophore-conjugated anti TCR-Vδ2 and anti-TNF-α antibody, cells were analyzed via flow cytometry. Live cells were gated, and Vδ2+ and TNF-α+ cells were selected on a dot blot. The activated cytotoxic Vγ9Vδ2 T cells appeared in the upper right quadrant of flow cytograms. Without zoledronic acid, LV-control stimulated 0.9% of TNF-α expressing Vγ9Vδ2 T cells and LV-FDPS shRNA #4 (SEQ ID NO: 4) stimulated 15.9%. With zoledronic acid treatment, LV-control stimulated 4.7% of TNF-α expressing Vγ9Vδ2 T cells and LV-FDPS shRNA #4 (SEQ ID NO: 4) stimulated 76.2%.

Example 5—Knock-Down of FDPS for 3 Days in PC3 Prostate Carcinoma Cells by shRNA #1

Figure 7:
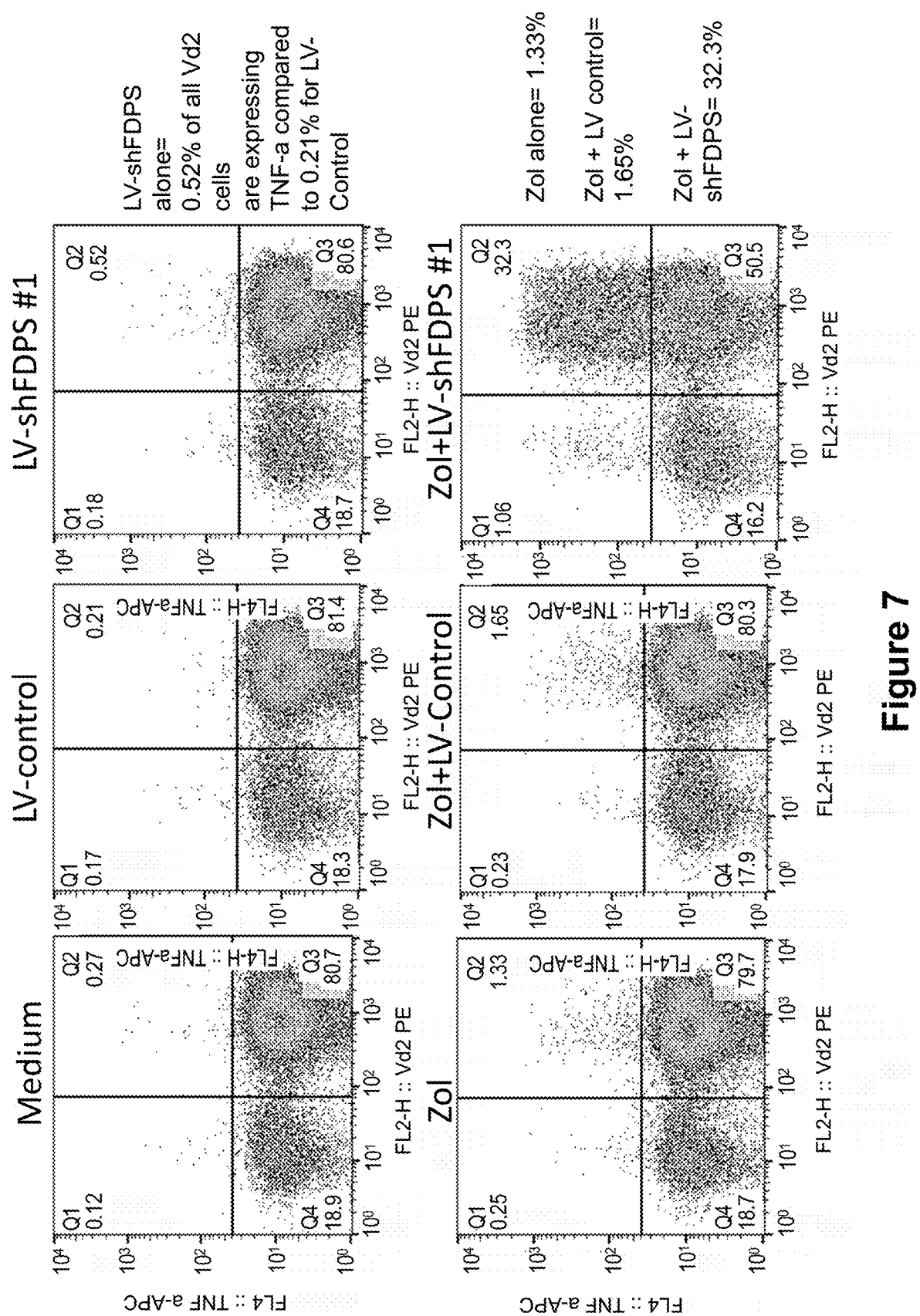
FIG. 7 depicts data demonstrating activation of Vδ2+ T cells by PC3 prostate carcinoma cells with a lentivirus expressing FDPS shRNA #1 (SEQ ID NO: 1), as described herein.

This Example illustrates that knock-down of FDPS for 3 days in PC3 prostate carcinoma cells by lentiviral (LV)-expressing FDPS shRNA #1 stimulates TNF-α expression in GD T cells, as shown in FIG. 7.

PC3 cells were transduced with LV-control or LV-FDPS shRNA #1 (SEQ ID NO: 1) for 3 days. Two days after transduction, cells were treated with or without luM zoledronic acid. After 24 hours, the transduced PC3 cells were co-cultured with 5×10$^5$ PBMC cells and IL-2 in a round bottom 96 well plate for 4 hours. The PBMC cells were pre-stimulated with zoledronic acid and IL-2 for 11 days to expand Vγ9Vδ2 T cells. After staining for Vγ9Vδ2 and TNF-α using fluorophore-conjugated anti TCR-Vδ2 and anti-TNF-α antibody, cells were analyzed via flow cytometry. Live cells were gated, and Vδ2+ and TNF-α+ cells were selected on a dot blot. The activated cytotoxic Vγ9Vδ2 T cells appeared in the upper right quadrant of flow cytograms. Without zoledronic acid, LV-control stimulated 0.2% of TNF-α expressing Vγ9Vδ2 T cells and LV-FDPS shRNA #1 stimulated 0.5%. With zoledronic acid treatment, LV-control stimulated 1.7% of TNF-α expressing Vγ9Vδ2 T cells and LV-FDPS shRNA #1 (SEQ ID NO: 1) stimulated 32.2%.

Example 6—Knock-Down of FDPS for 3 Days in PC3 Prostate Carcinoma Cells by shRNA #4

Figure 8:
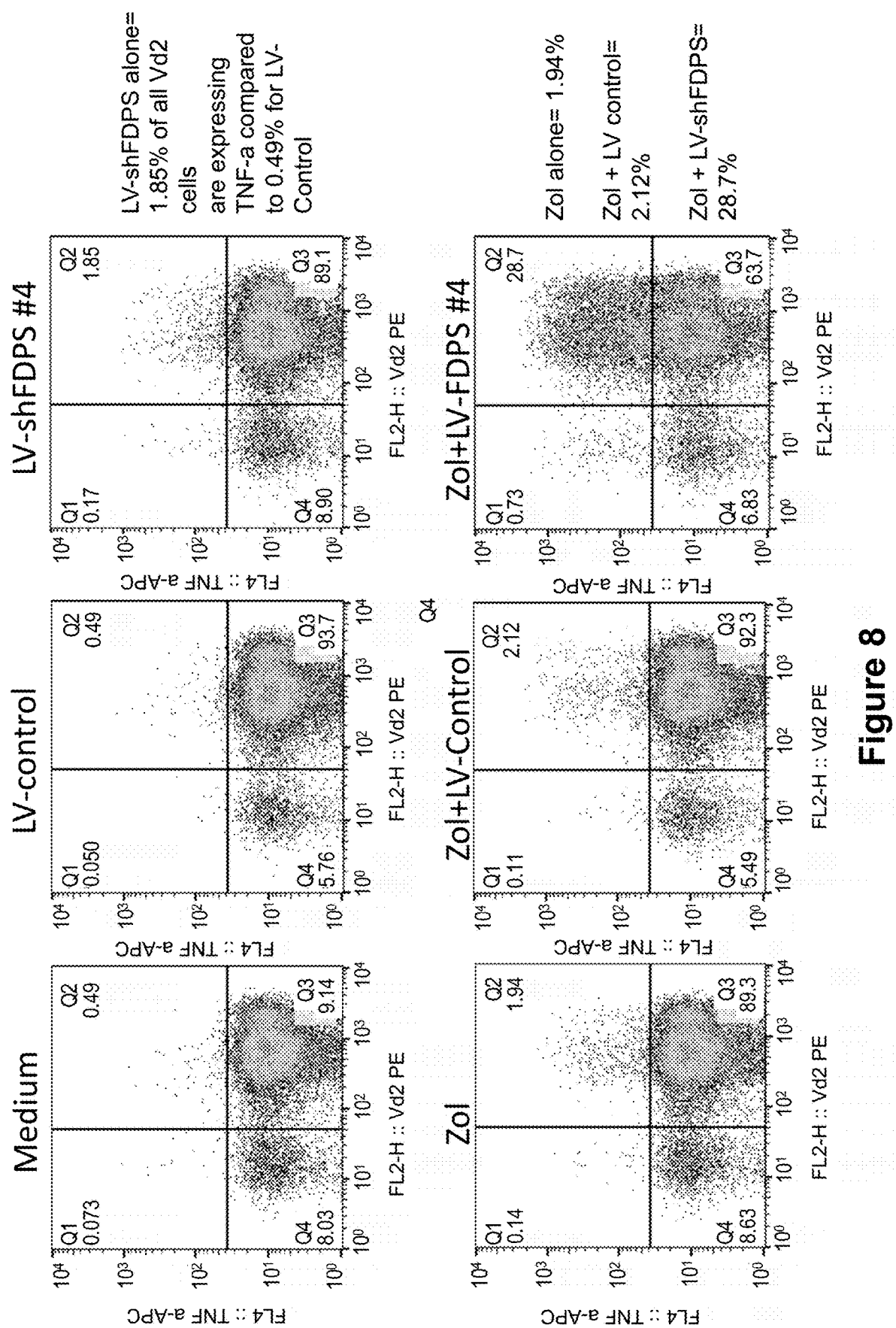
FIG. 8 depicts data demonstrating activation of Vδ2+ T cells by PC3 prostate carcinoma cells with a lentivirus expressing FDPS shRNA #4 (SEQ ID NO: 4), as described herein.

This Example illustrates that Knock-down of FDPS for 3 days in PC3 prostate carcinoma cells by lentiviral (LV)-expressing FDPS shRNA #4 stimulates TNF-α expression in GD T cells, as shown in FIG. 8.

PC3 cells were transduced with LV-control or LV-FDPS shRNA #4 (SEQ ID NO: 4) for 3 days. Two days after transduction, cells were treated with or without 1 uM zoledronic acid. After 24 hours, the transduced PC3 cells were co-cultured with 5×10$^5$ PBMC cells and IL-2 in a round bottom 96 well plate for 4 hours. The PBMC cells were pre-stimulated with zoledronic acid and IL-2 for 11 days to expand Vγ9Vδ2 T cells. After staining for Vγ9Vδ2 and TNF-α using fluorophore-conjugated anti TCR-Vδ2 and anti-TNF-α antibody, cells were analyzed via flow cytometry. Live cells were gated, and Vδ2+ and TNF-α+ cells were selected on a dot blot. The activated cytotoxic Vγ9Vδ2 T cells appeared in the upper right quadrant of flow cytograms. Without zoledronic acid, LV-control stimulated 0.5% of TNF-α expressing Vγ9Vδ2 T cells and LV-FDPS shRNA #4 (SEQ ID NO: 4) stimulated 1.9%. With zoledronic acid treatment, LV-control stimulated 2.1% of TNF-α expressing Vγ9Vδ2 T cells and LV-FDPS shRNA #4 stimulated 28.7%.

Example 7—Knock-Down of FDPS for 3 Days in HepG2 Liver Carcinoma Cells by shRNA #1 and #4

Figure 9:
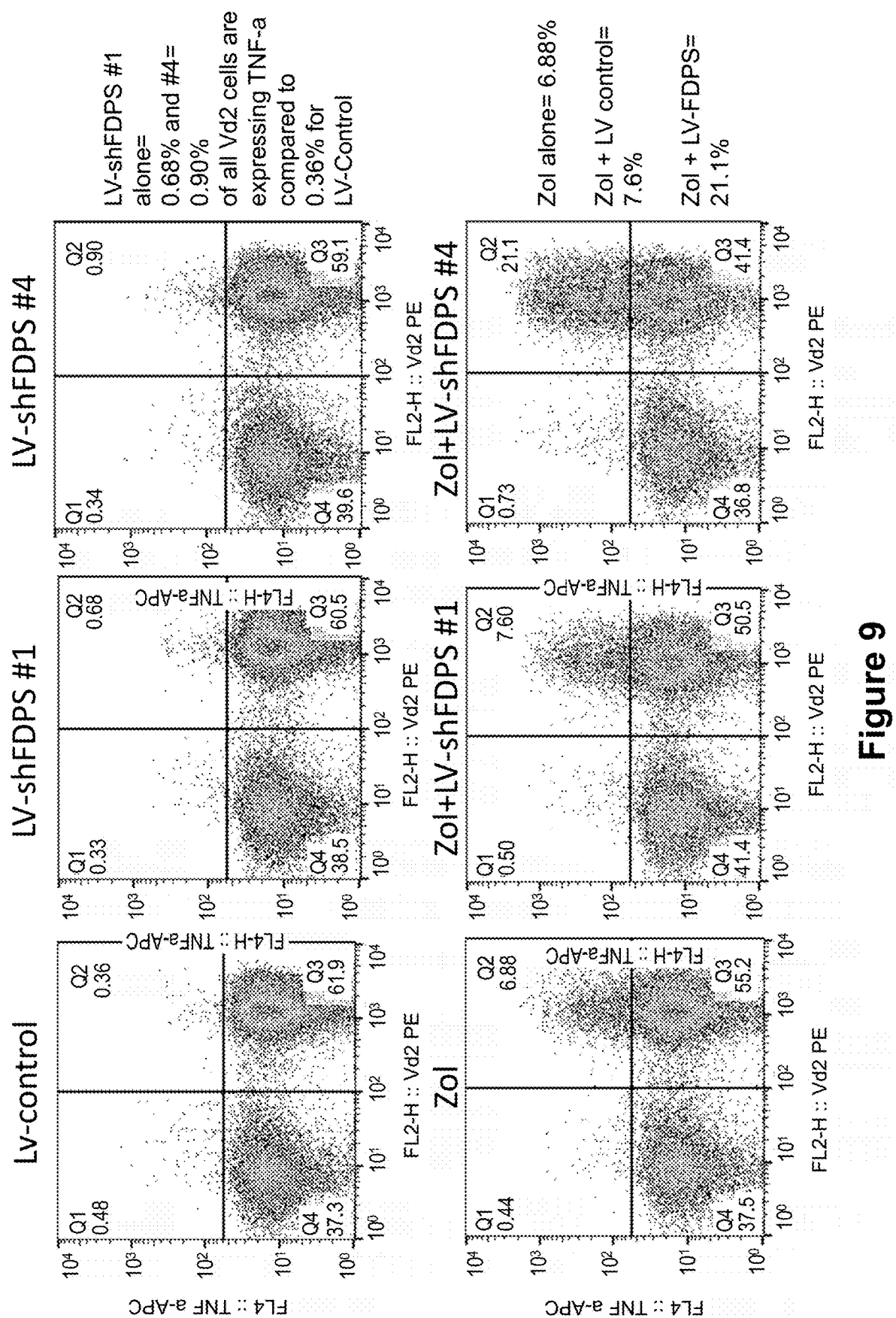
FIG. 9 depicts data demonstrating activation of Vδ2+ T cells by HepG2 carcinoma cells with a lentivirus expressing FDPS shRNA #1 (SEQ ID NO: 1) or FDPS shRNA #4 (SEQ ID NO: 4), as described herein.

This Example illustrates that Knock-down of FDPS for 3 days in HepG2 liver carcinoma cells by lentiviral (LV)-expressing FDPS shRNA #1 (SEQ ID NO: 1) and shRNA #4 (SEQ ID NO: 4) stimulates TNF-α expression in GD T cells, as shown in FIG. 9.

HepG2 cells were transduced with LV-control, LV-FDPS shRNA #1 (SEQ ID NO: 1), or LV-FDPS shRNA #4 (SEQ ID NO: 4) for 3 days. Two days after transduction, cells were treated with or without 1 uM zoledronic acid. After 24 hours, the transduced HepG2 cells were co-cultured with 5×10$^5$ PBMC cells and IL-2 in a round bottom 96 well plate for 4 hours. The PBMC cells were pre-stimulated with zoledronic acid and IL-2 for 11 days to expand Vγ9Vδ2 T cells. After staining for Vγ9Vδ2 and TNF-α using fluorophore-conjugated anti TCR-Vδ2 and anti-TNF-α antibody, cells were analyzed via flow cytometry. Live cells were gated, and Vδ2+ and TNF-α+ cells were selected on a dot blot. The activated cytotoxic Vγ9Vδ2 T cells appeared in the upper right quadrant of flow cytograms. Without zoledronic acid, LV-control stimulated 0.4% of TNF-α expressing Vγ9Vδ2 T cells and LV-FDPS shRNA #1 (SEQ ID NO: 1) and #4 (SEQ ID NO: 4) stimulated 0.7% and 0.9%, respectively. With zoledronic acid treatment, LV-control stimulated 6.9% of TNF-α expressing Vγ9Vδ2 T cells and LV-FDPS shRNA #1 and #4 stimulated 7.6% and 21.1%, respectively.

Example 8—Knock-Down of FDPS for 3 Days in THP1 Leukemia by microRNA-30

Figure 10:
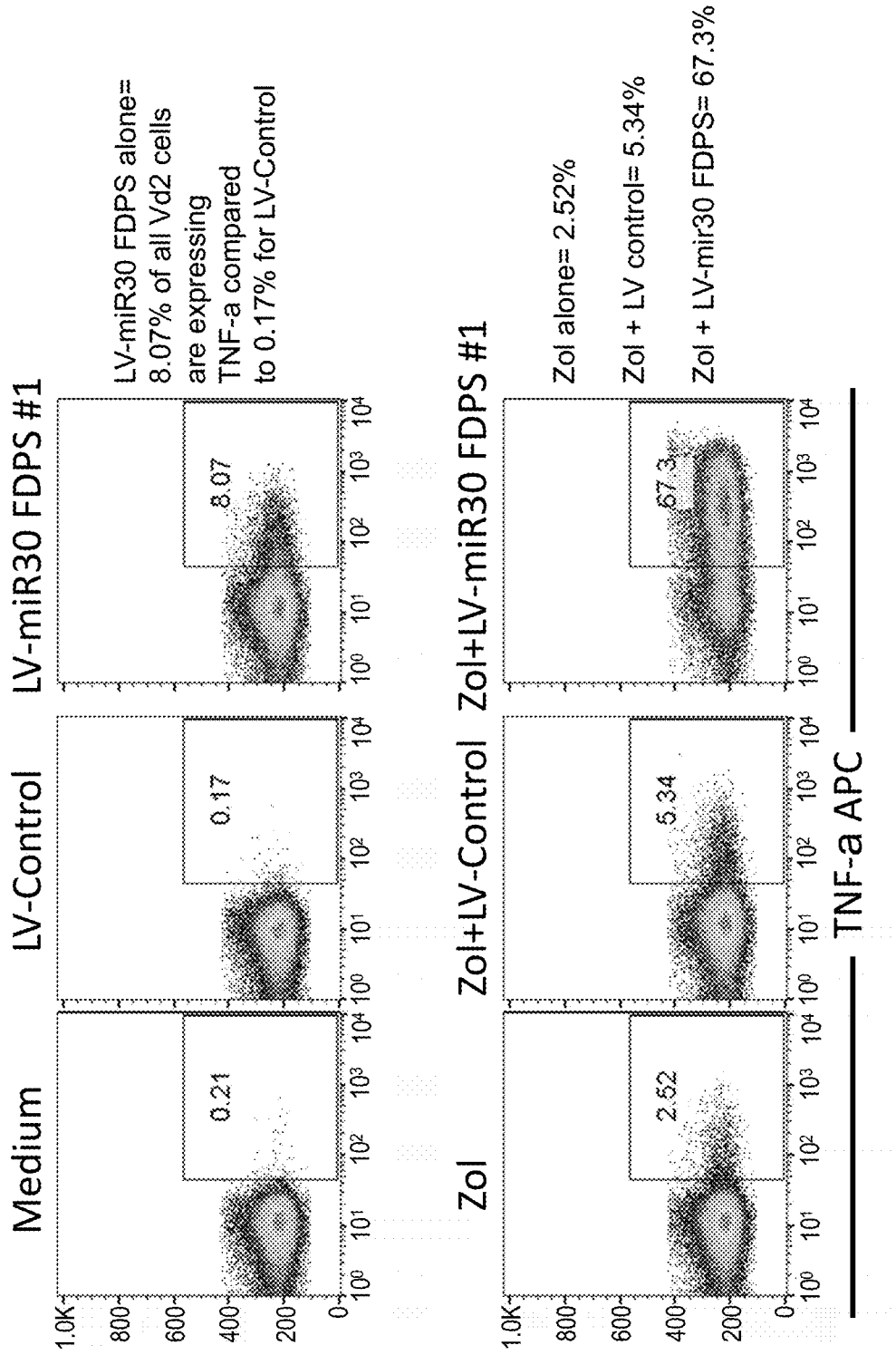
FIG. 10 depicts data demonstrating activation of Vδ2+ T cells by THP-1 leukemia cells with a lentivirus expressing miR30 FDPS #1 (SEQ ID NO: 5), as described herein.

This Example illustrates that Knock-down of FDPS for 3 days in THP1 leukemia cells by lentiviral (LV)-expressing FDPS-targeted synthetic microRNA-30 stimulates TNF-α expression in gamma delta T cells, as shown in FIG. 10.

THP1 cells (1×10$^5$ cells) were transduced with LV-control or LV-miR30 FDPS #1 (SEQ ID NO: 5) for 3 days. Two days after transduction, cells were treated with or without 1 uM zoledronic acid. After 24 hours, the transduced THP-1 cells were co-cultured with 5×10$^5$ PBMC cells and IL-2 in a round bottom 96 well plate for 4 hours. The PBMC cells were pre-stimulated with zoledronic acid and IL-2 for 11 days to expand Vγ9Vδ2 T cells. After staining for Vγ9Vδ2 and TNF-α using fluorophore-conjugated anti TCR-Vδ2 and anti-TNF-α antibody, cells were analyzed via flow cytometry. Live cells were gated, and Vδ2+ and TNF-α+ cells were selected on a dot blot. The activated cytotoxic Vγ9Vδ2 T cells appeared in the upper right quadrant of flow cytograms. Without zoledronic acid, LV-control stimulated 0.2% of TNF-α expressing Vγ9Vδ2 T cells and LV-miR30 FDPS stimulated 8.1%. With zoledronic acid treatment, LV-control stimulated 5.3% of TNF-α expressing Vγ9Vδ2 T cells and LV-miR30 FDPS #1 (SEQ ID NO: 5) stimulated 67.3%.

Example 9: E:T Ratios Resulting from Mixture of THP-1 Cells, Cultured Human GD T Cells, and/or Zometa (Zol)

Figure 11:
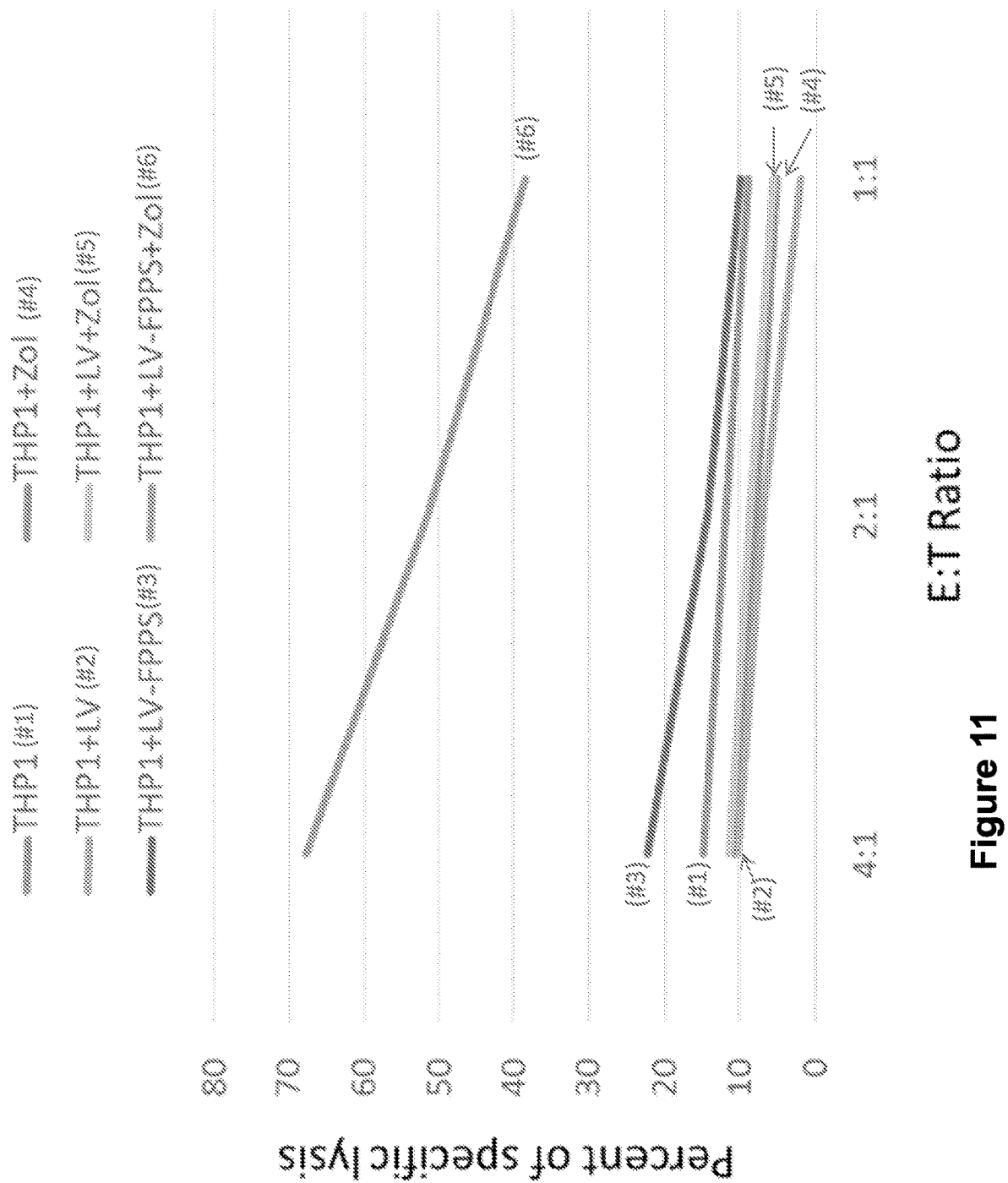
FIG. 11 depicts data demonstrating the percent of specific lysis versus an E:T ratio for a variety of experimental conditions, as described herein.

This Example demonstrates results from mixing treated THP-1 monocytoid tumor cells with cultured human GD T cells, as shown in FIG. 11.

The monocytoid cell line THP-1 was treated with control lentivirus vector (LV), LV suppressing farnesyl diphosphate synthase gene expression (LV-FDPS), zoledronic acid (Zol) or combinations. The legend, as shown in FIG. 11, was: lentiviral control vectors (LV-Control), lentiviral vectors expressing microRNA to down regulate FDPS (LV-FPPS), Zometa (Zol), Zometa plus lentiviral control (Zol+LV-Control), or Zometa plus lentiviral vectors expressing microRNA to down regulate FPPS (Zol+LV-FPPS).

Human GD T cells were cultured from an anonymous donor and added to treated THP-1 cells in 4:1. 2:1 or 1:1 ratios (GD T:THP-1) for 4 hours. Cell killing was measured by a fluorescence assay. When THP-1 cells were treated with a combination of LV-FDPS and Zol, cytotoxic T cell killing by GD T cells was increased greatly compared to either treatment alone. When LV-FDPS treatment alone was compared to Zol treatment alone, the LV-FDPS lead to greater killing but was >3-fold below tumor cell killing after combination treatment. The combined LV-FDPS plus Zol treatment caused nearly 70% tumor cell killing with 4:1 ratio; this was more than 3-fold higher than the second best treatment (LV-FDPS alone).

Figure 12:
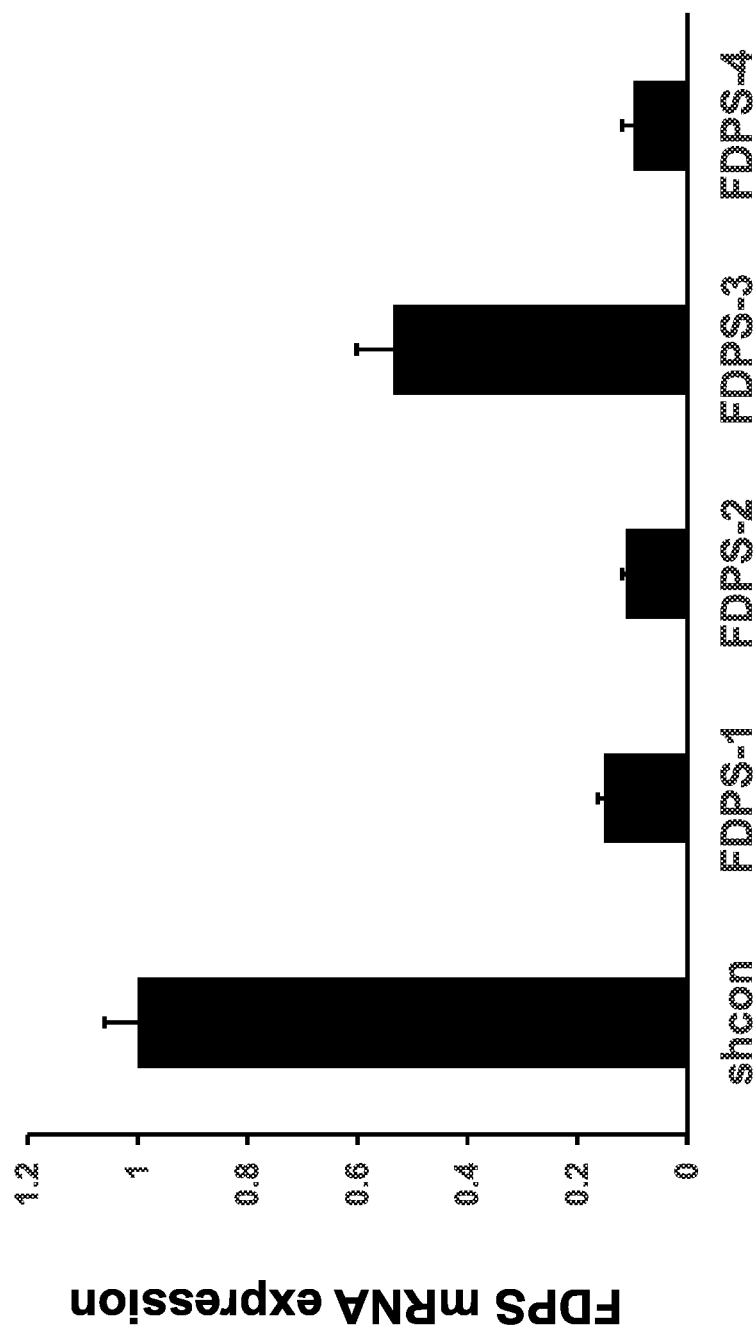
FIG. 12 depicts data demonstrating lentiviral-delivered shRNA-based RNA interference targeting the human FDPS gene.

Example 10—Lentiviral-Delivered shRNA-Based RNA Interference Targeting the Human Farnesyl Diphosphate Synthase (FDPS) Gene HepG2 human hepatocellular carcinoma cells were infected with lentiviral vectors containing the H1 promoter and either a non-targeting or four different FDPS shRNA sequences, as shown in FIG. 12. After 48 hours, RNA was extracted from the cells and converted to cDNA. Expression of FDPS cDNA was determined by quantitative PCR using SYBR Green and FDPS primers. FDPS expression was normalized to actin levels for each sample.

FDPS-targeting lentiviral vectors containing the H1 promoter and either a non-targeting sequence (5'-GCCGCTTTGTAGGATAGAGCTCGAGCTCTATCCTA-CAAAGCGGCTTTTT-3') (SEQ ID NO: 60) or one of four different FDPS shRNA sequences GTCCTGGAGTA-CAATGCCATTCTCGAGAATGGCAT-TGTACTCCAGGACTTTTT (FDPS shRNA sequence #1; SEQ ID NO: 1); GCAGGAT-TTCGTTCAGCACTTCTCGAGAAGTGCT-GAACGAAATCCTGCTTTTT (FDPS shRNA sequence #2; SEQ ID NO: 2); GCCATGTACATGGCAGGAAT-TCTCGAGAATTCCTGCCATGTACATGGCTTTTT (FDPS shRNA sequence #3; SEQ ID NO: 3; and GCAGAAGGAGGCTGAGAAAGTCTCGA-GACTTTCTCAGCCTCCTTCTGCTTTTT (FDPS shRNA sequence #4; SEQ ID NO: 4) were produced in 293 T cells.

HepG2 human hepatocellular carcinoma cells were then infected with lentiviral vectors to determine the efficacy of FDPS knock-down. After 48 hours, RNA was extracted from the cells using the RNeasy RNA isolation kit (Qiagen) and converted to cDNA with the SuperScript VILO cDNA synthesis kit (Thermo Scientific). Expression of FDPS cDNA was determined by quantitative PCR on an Applied Biosystems StepOne qPCR machine using a SYBR Green PCR mix (Thermo Scientific) and FDPS primers (Forward primer: 5'-AGGAATTGATGGCGAGAAGG-3' (SEQ ID NO: 61) and Reverse primer: 5'-CCCAAAGAGGT-CAAGGTAATCA-3' (SEQ ID NO: 62)). FDPS expression was normalized to actin levels for each sample using the actin primers (Forward primer: 5'-AGCGCGGCTA-CAGCTTCA-3' (SEQ ID NO: 63) and Reverse primer: 5'-GGCGACGTAGCACAGCTTCT-3') (SEQ ID NO: 64). The relative FDPS RNA expression of the shCon sample is set at 100%. There was an 85% (FDPS sequence #1), 89% (FDPS sequence #2), 46% (FDPS sequence #3), and 98% (FDPS sequence #4) decrease in FDPS expression.

Figure 13:
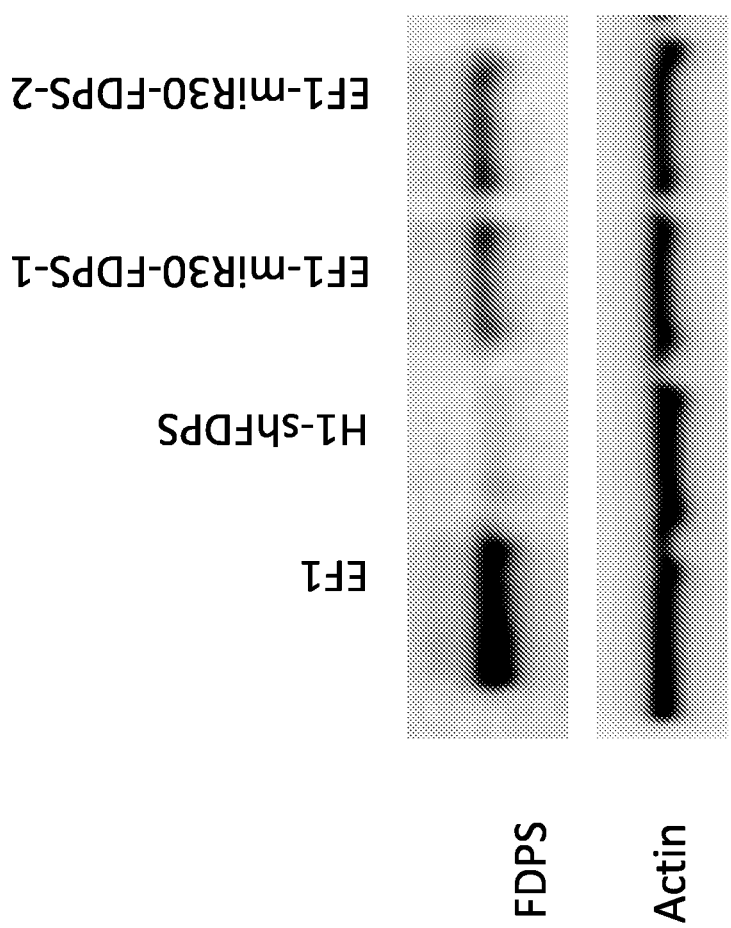
FIG. 13 depicts data demonstrating lentiviral-delivered miR-based RNA interference targeting the human FDPS gene.

Example 11—Lentiviral-Delivered miR-Based RNA Interference Targeting the Human Farnesyl Diphosphate Synthase (FDPS) Gene As shown in FIG. 13, HepG2 human hepatocellular carcinoma cells were infected with lentiviral vectors containing either the H1 promoter (SEQ ID NO: 16) the FDPS shRNA #4 (SEQ ID NO: 4) sequence or the EF-1α promoter (SEQ ID NO: 41) and miR30-based FDPS sequences. After 48 hours, cells were lysed and an immunoblot was performed using an anti-FDPS (Thermo Scientific) and an anti-actin (Sigma) antibody as a protein loading control.

More specifically, HepG2 human hepatocellular carcinoma cells were infected with lentiviral vectors containing either the H1 promoter (SEQ ID NO: 16) and the FDPS shRNA sequence GCAGAAGGAGGCT-GAGAAAGTCTCGA-GACTTTCTCAGCCTCCTTCTGCTTTTT (FDPS shRNA sequence #4; SEQ ID NO: 4) or the EF-1alpha promoter (SEQ ID NO: 41) and miR30-based FDPS sequences AAGGTATATTGCTGTTGACAGT-GAGCGACACTTTCTCAGCCTCCTTCTGCGTGAAGC CACAGATGGCAGAAGGAGGCT-GAGAAAGTGCTGCCTACTGCCTCGGACTTCAAGGG GCT (miR30 FDPS sequence #1; SEQ ID NO: 5) and AAGGTATATTGCTGTTGACAGT-GAGCGACACTTTCTCAGCCTCCTTCTGCGTGAAGC CACAGATGGCAGAAGGGCTGAGAAAGTGCTGCC-TACTGCCTCGGACTTCAAGGGGC T (miR30 FDPS sequence #2; SEQ ID NO: 6).

After 48 hours, cells were lysed with NP-40 lysis buffer and protein was quantified with the Bio-Rad protein assay reagent. Protein samples at 50 micrograms were electrophoresed on 4-12% Bis-Tris gels (Thermo Scientific and transferred to PVDF membranes (EMD Millipore). An immunoblot was performed using an anti-FDPS (Thermo Scientific) and an anti-actin (Sigma) antibody as a protein loading control. Antibodies were bound with HRP-conjugated secondary antibodies and detected with a Licor c-DiGit Blot scanner using the Immobilon Western ECL reagent (EMD Millipore). The densitometry of the immunoblot bands were quantified with the NIH image software. The LV control with the EF-1 promoter was set at 100%. There was a 68% (LV-shFDPS #4), 43% (LV-miR FDPS #1), and 38% (LV-miR FDPS #3) reduction of FDPS protein expression.

Example 12—Knock-Down of FDPS for 3 Days in HepG2 Liver Carcinoma Cells by Adeno-Associated Virus (AAV)-Expressing FDPS shRNA #4

Figure 14:
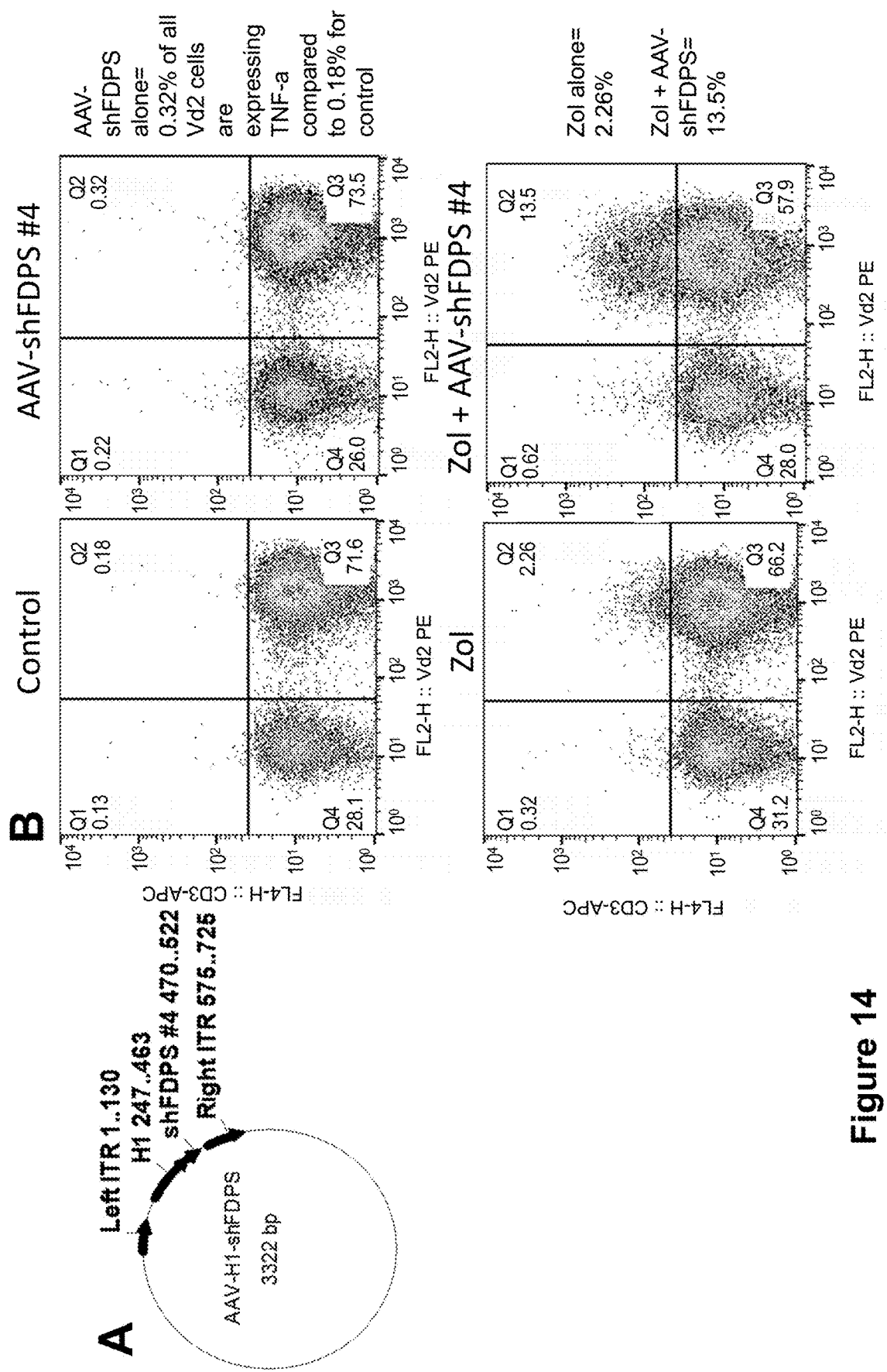
FIG. 14 depicts data demonstrating activation of Vδ2+ T cells by HepG2 carcinoma cells with an adeno-associated virus expressing FDPS shRNA #4 (SEQ ID NO: 4), as described herein.
Figure 15:
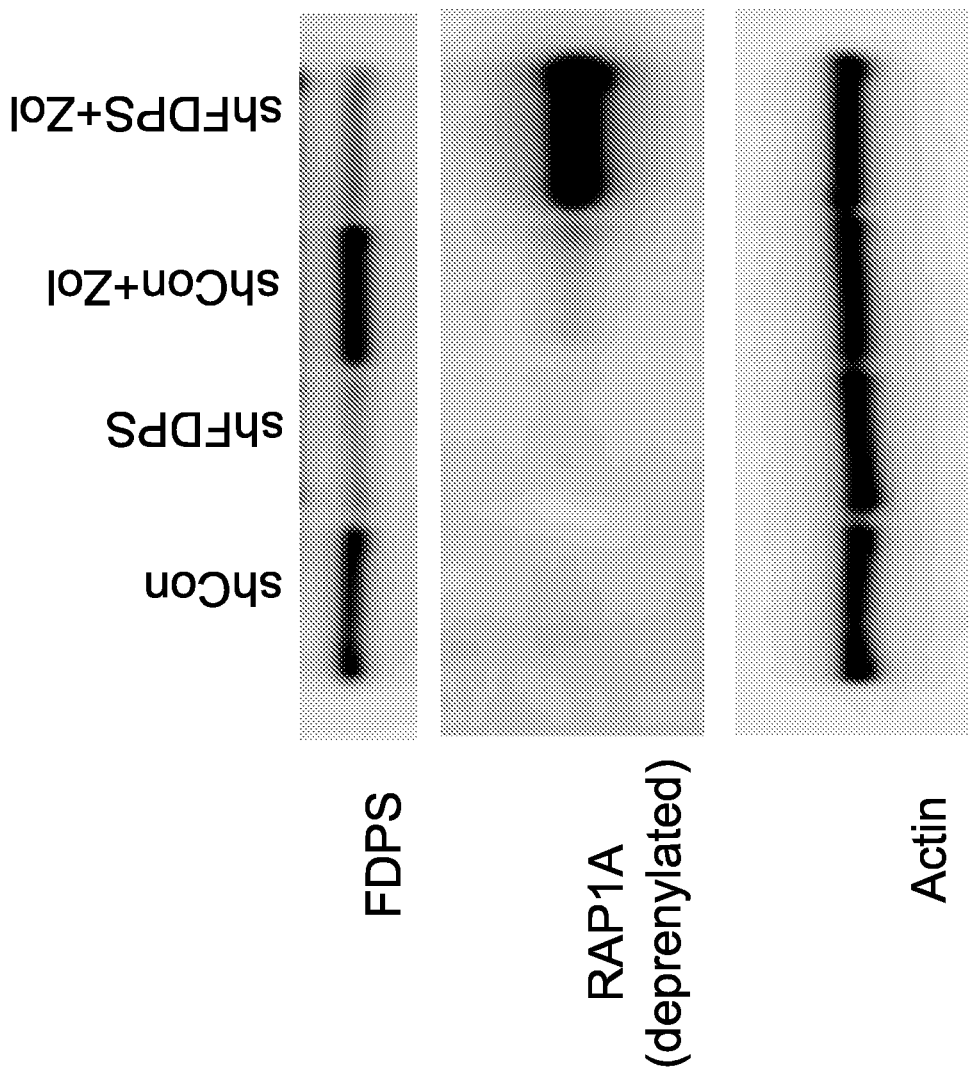
FIG. 15 depicts immunoblot data demonstrating lack of RAP1 prenylation in the cells transduced with LV-shFDPS and treated with zoledronic acid.

This Example illustrates that knock-down of FDPS for 3 days in HepG2 liver carcinoma cells by adeno-associated virus (AAV)-expressing FDPS shRNA #4 (SEQ ID NO: 4) stimulates TNF-α expression in GD T cells (FIG. 14, Panel B).

HepG2 cells were transduced with control or AAV-FDPS shRNA #4 (SEQ ID NO: 8) for 3 days. Two days after transduction, cells were treated with or without 1 uM zoledronic acid. After 24 hours, the transduced HepG2 cells were co-cultured with 5×10$^5$ PBMC cells and IL-2 in a round bottom 96 well plate for 4 hours. The PBMC cells were pre-stimulated with zoledronic acid and IL-2 for 11 days to expand Vγ9Vδ2 T cells. After staining for Vγ9Vδ2 and TNF-α using fluorophore-conjugated anti TCR-Vδ2 and anti-TNF-α antibody, cells were analyzed via flow cytometry. Live cells were gated, and Vδ2+ and TNF-α+ cells were selected on a dot blot. The activated cytotoxic Vγ9Vδ2 T cells appeared in the upper right quadrant of flow cytograms (FIG. 14, Panel B).

AAV Vector Construction. FDPS shRNA sequence #4 (SEQ ID NO: 4) was inserted into the pAAV plasmid (Cell Biolabs). FDPS oligonucleotide sequences containing BamHI and EcoRI restriction sites were synthesized by Eurofins MWG Operon. Overlapping sense and antisense oligonucleotide sequences were mixed and annealed during cooling from 70 degrees Celsius to room temperature. The pAAV was digested with the restriction enzymes BamHI and EcoRI for one hour at 37 degrees Celsius. The digested pAAV plasmid was purified by agarose gel electrophoresis and extracted from the gel using a DNA gel extraction kit from Thermo Scientific. The DNA concentrations were determined and vector to oligo (3:1 ratio) were mixed, allowed to anneal, and ligated. The ligation reaction was performed with T4 DNA ligase for 30 minutes at room temperature. 2.5 microliters of the ligation mix were added to 25 microliters of STBL3 competent bacterial cells. Transformation was achieved after heat-shock at 42 degrees Celsius. Bacterial cells were spread on agar plates containing ampicillin and drug-resistant colonies (indicating the presence of ampicillin-resistance plasmids) were recovered and expanded in LB broth. To check for insertion of the oligo sequences, plasmid DNA was extracted from harvested bacteria cultures with the Thermo Scientific DNA mini prep kit. Insertion of shRNA sequences in the pAAV plasmid was verified by DNA sequencing using a specific primer for the promoter used to regulate shRNA expression. An exemplary AAV vector with a H1 promoter (SEQ ID NO: 16), shFDPS sequence (e.g., SEQ ID NO: 4), Left Inverted Terminal Repeat (Left ITR; SEQ ID NO: 65), and Right Inverted Terminal Repeat (Right ITR; SEQ ID NO: 66) can be found in FIG. 14, Panel A.

Production of AAV particles. The AAV-FDPS shRNA plasmid was combined with the plasmids pAAV-RC2 (Cell Biolabs) and pHelper (Cell Biolabs). The pAAV-RC2 plasmid contains the Rep and AAV2 capsid genes and pHelper contains the adenovirus E2A, E4, and VA genes. To produce AAV particles, these plasmids were transfected in the ratio 1:1:1 (pAAV-shFDPS: pAAV-RC2: pHelper) into 293T cells. For transfection of cells in 150 mm dishes (BD Falcon), 10 micrograms of each plasmid were added together in 1 ml of DMEM. In another tube, 60 microliters of the transfection reagent PEI (1 microgram/ml) (Polysciences) was added to 1 ml of DMEM. The two tubes were mixed together and allowed to incubate for 15 minutes. Then the transfection mixture was added to cells and the cells were collected after 3 days. The cells were lysed by freeze/thaw lysis in dry ice/isopropanol. Benzonase nuclease (Sigma) was added to the cell lysate for 30 minutes at 37 degrees Celsius. Cell debris were then pelleted by centrifugation at 4 degrees Celsius for 15 minutes at 12,000 rpm. The supernatant was collected and then added to target cells.

Example 13—Decreased RAP1 Prenylation in the Cells Transduced with LV-shFDPS and Treated with Zoledronic Acid This Example illustrates that lentiviral-delivered shRNA targeting the human farnesyl diphosphate synthase (FDPS) gene and zoledronic acid synergize to inhibit farnesyl diphosphate production.

FDPS is an enzyme in the isoprenoid synthesis pathway that catalyzes the production of farnesyl diphosphate. Inhibiting the enzyme activity of FDPS by zoledronic acid or reduced protein expression by shRNA-mediated knockdown will result in reduced farnesyl diphosphate levels. Farnesylation of cellular proteins requires farnesyl diphosphate. RAP1A is a protein that is modified by farnesylation, which can be used as a biomarker for levels of cellular farnesyl diphosphate. An antibody that specifically recognizes reduced RAP1A farnesylation was used to measure FDPS activity after transduction with LV-shFDPS alone or in combination with zoledronic acid. HepG2 human hepatocellular carcinoma cells were infected with lentiviral vectors containing FDPS shRNA sequence #4. For the zoledronic acid treated cells, zoledronic acid (Sigma) was added for the last 24 hours. After 48 hours, cells were lysed with NP-40 lysis buffer and protein was quantified with the Bio-Rad protein assay reagent. Protein samples at 50 micrograms were electrophoresed on 4-12% Bis-Tris gels (Thermo Scientific and transferred to PVDF membranes (EMD Millipore). An immunoblot was performed using an anti-FDPS (Thermo Scientific), anti-RAP1A (Santa Cruz), and an anti-actin (Sigma) antibody as a protein loading control. Antibodies were bound with HRP-conjugated secondary antibodies and detected with a Licor c-DiGit Blot scanner using the Immobilon Western ECL reagent (EMD Millipore). An increase in the RAP1A band intensity correlates with reduced farnesylation. RAP1A defarnesylation occurred only in the cells transduced with LV-shFDPS and treated with zoledronic acid.

Example 14—Treatment of a Subject with Cancer

LV-FDPS is a Genetic Medicine Delivered by a Lentivirus Vector Via Local Administration to the Site of Late Stage, Non-Resectable Hepatocellular Carcinoma A Phase I clinical trial will test safety and feasibility of delivering LV-FDPS to the site of hepatocellular carcinoma (HCC) using ultrasound guided cannulation of the liver in patients without concomitant radiotherapy or chemotherapy. It is rationally predicted that this study will result in the successful treatment of HCC. The study is an open label, 4×3 dose escalation (4 dose ranges, up to 3 subjects per dose) to identify the maximum tolerable dose of LV-FDPS in patients 18 years or older with Stage III/IV non-resectable HCC.

LV-FDPS is a genetic therapy designed to reduce expression in tumor cells of the enzyme farnesyl diphosphate synthase. Experimental studies show that tumor cells modified by LV-FDPS induce the anti-tumor activity of human gamma delta T cells, including the capacity for tumor killing by cellular cytotoxicity.

Subjects with target lesions≥1 cm in longest diameter (measured by helical CT) and ≤4.9 cm maximum diameter and meeting inclusion and exclusion criteria detailed below, are enrolled into the next available dosing category. A maximum of 3 subjects are recruited for each dosage group. The dose is number of transducing units of LV-FDPS as described in the product release criteria, delivered via intrahepatic cannulation in a single bolus with volume not to exceed 25 mL. The minimum dose is $1\times10^9$ transducing units and escalation is 10-fold to a next dose of $1\times10^{10}$ transducing units, the next dose is $1\times10^{11}$ transducing units, and a maximum dose of $1\times10^{12}$ transducing units based on reported experience with recombinant adenovirus therapy for HCC (Sangro et al., A phase I clinic trial of thymidine kinase-based gene therapy in advanced hepatocellular carcinoma, 2010, *Cancer Gene Ther.* 17:837-43). Subjects are enrolled, treated and evaluated for 3 months. All safety evaluations are completed for each group prior to enrolling and treating subjects at the next higher dose level. Enrollment and dose escalation continue until a maximum tolerable dose is achieved or the study is terminated.

Cannulation is via the left subclavian artery until tip of catheter is at the proper hepatic artery junction. Cannulation is guided by ultrasonography as described (Lin et al., Clinical effects of intra-arterial infusion chemotherapy with cisplatin, mitomycin C, leucovor and 5-Fluorouracil for unresectable advanced hepatocellular carcinoma, 2004, *J. Chin. Med. Assoc.* 67:602-10).

Primary Outcome Measures

Safety: Systemic and locoregional adverse events are graded according to CTCAS and coded according to MedRA. The adverse events data for all subjects at a single dose range will be evaluated prior to dose escalation. The final safety assessment incorporates data from all dose ranges.

Secondary Outcome Measures
  Lesion distribution and retention of LV-FDPS following locoregional administration and subsequent biopsy or necropsy to obtain tissues.
  Objective response rate (ORR) in target and measurable non-local lesions (if present) by physical analysis, medical imaging or biopsy during 3 months after treatment.
  Levels of LV-FDPS in blood stream during 10 minutes, 30 minutes, 1 hour and 1 day after local injection.
  Changes in markers of hepatic function including ALP, ALT, ASAT, total bilirubin and GGT during 3 months after treatment.
  Disease free survival beyond historical control (no LV-FDPS) patients in ad hoc analysis.

Inclusion Criteria
  Greater than 18 years and including both males and females.
  Diagnosis confirmed by histology or cytology or based on currently accepted clinical standards of hepatocellular carcinoma of parenchyma cell origin that is not amenable, at the time of screening, to resection, transplant or other potentially curative therapies.
  Treating physician determines that the lesion is amenable to locoregional targeted delivery.
  Target lesion must represent measurable disease with a unidimensional longest diameter of $\geq 1.0$ cm by computed tomography; the maximum longest diameter is $\leq 5.0$ cm.
  Karnofsky performance score 60-80% of ECOG values.
  Life expectancy $\geq 12$ weeks.
  Hematopoietic function: WBC$\geq 2,500$/mm$^3$; ANC$\geq 1000$/mm$^3$; Hemoglobin$\geq 8$ g/dL; Platelet count$\geq 50,000$/mm$^3$; Coagulation INR$\leq 1.3$.
  AST and ALT<5 times ULN; ALPS<5 time ULN. Bilirubin$\leq 1.5$ times ULV; Creatine$\leq 1.5$ times ULN and eGFR$\geq 50$.
  Thyroid function: Total T3 or free T3, total T4 or free T4 and THC$\leq$CTCAE Grade 2 abnormality.
  Renal, cardiovascular and respiratory function adequate in the opinion of the attending physician.
  Immunological function: Circulating Vgamma9Vdelta2+ T cells$\geq 30$/mm$^3$; no immunodeficiency disease.
  Negative for HIV by serology and viral RNA test.
  Written informed consent.

Exclusion Criteria
  Target lesion contiguous with, encompasses or infiltrates blood vessel.
  Primary HCC amenable to resection, transplantation or other potentially curative therapies.
  Hepatic surgery or chemoembolization within the past 4 months.
  Hepatic radiation or whole body radiation therapy within past 4 months.
  Chemotherapy with 4 weeks or any use of nitrosourea, mitomycin C or cisplatin.
  Current or within past 4 weeks receipt of aminobisphosphonate therapy
  Investigational agents within 4 weeks or <5 drug half-lives.
  Impaired wound healing due to diabetes.
  Significant psychiatric illness, alcohol dependence or illicit drug use.
  Unwilling to comply with study protocols and reporting requirements.
  Aminobisphosphonate treatment within past 4 months.
  Presence of clinically significant cardiovascular, cerebrovascular (stroke), immunological (except hepatitis B or C virus infection, viral hepatitis or cirrhosis), endocrine or central nervous system disorders; current encephalopathy; variceal bleeding requiring hospitalization or transfusion within past 4 months.
  History of HIV or acquired immune deficiency syndrome.
  Current or prior treatment with antiretroviral medications.
  Pregnant, lactating or refusal to adopt barrier or chemical contraceptive use throughout trial and follow-up interval.

LV-FDPS is a Genetic Medicine Delivered by a Lentivirus Vector Via Local Administration to the Site of Late Stage, Non-Resectable Hepatocellular Carcinoma—Adjunct Administration of Aminobisphosphonate A Phase I clinical trial will test safety and feasibility of delivering LV-FDPS to the site of hepatocellular carcinoma (HCC) using ultrasound guided cannulation of the liver in patients with concomitant aminobisphosphonate chemotherapy. It is rationally predicted that this study will result in the successful treatment of HCC. The study is an open label, 4×3 dose escalation (4 dose ranges, up to 3 subjects per dose) to identify the maximum tolerable dose of LV-FDPS in patients 18 years or older with Stage III/IV non-resectable HCC.

LV-FDPS is a genetic therapy designed to reduce expression in tumor cells of the enzyme farnesyl diphosphate synthase. Experimental studies show that tumor cells modified by LV-FDPS induce the anti-tumor activity of human gamma delta T cells, including the capacity for tumor killing by cellular cytotoxicity. Prior experimental studies also showed the potential for positive interactions of LV-FDPS and specific aminobisphosphonate drugs that may be prescribed in primary or metastatic diseases. For this study, subjects will receive dose escalating amounts of LV-FDPS with continuous standard of care dosing with Aredia® (pamidronate), Zometa® (zoledronic acid) or Actonel® (risedronate) according to physician advice and subject preference.

Subjects with target lesions≥1 cm in longest diameter (measured by helical CT) and ≤4.9 cm maximum diameter and meeting inclusion and exclusion criteria detailed below, are enrolled and started on aminobisphonate therapy. 30 days later size of the target lesion is re-evaluated to ensure subjects still meet starting criteria for LV-FDPS. Subjects without objective clinical response on aminobisphosphonate are enrolled into the next available LV-FDPS dosing category. A maximum of 3 subjects are recruited for each dosage group and all continue on aminobisphonate fir the study duration unless otherwise advised by the attending physician. The LV-FDPS dose is a number of transducing units of LV-FDPS as described in the product release criteria, delivered via intrahepatic cannulation in a single bolus with volume not to exceed 25 mL. The minimum dose is $1 \times 10^9$ transducing units and escalation is 10-fold to a next dose of $1 \times 10^{10}$ transducing units, the next dose is $1 \times 10^{11}$ transducing units, and a maximum dose of $1 \times 10^{12}$ transducing units based on reported experience with recombinant adenovirus therapy for HCC (Sangro, et al., A phase I clinic trial of thymidine kinase-based gene therapy in advanced hepatocellular carcinoma, 2010, *Cancer Gene Ther.* 17:837-43). Subjects are enrolled, treated and evaluated for 3 months. All safety evaluations are completed for each group prior to enrolling and treating subjects at the next higher dose level. Enrollment and dose escalation continue until a maximum tolerable dose is achieved or the study is terminated.

Cannulation is via the left subclavian artery until tip of catheter is at the proper hepatic artery junction. Cannulation is guided by ultrasonography as described (Lin et al., Clinical effects of intra-arterial infusion chemotherapy with cisplatin, mitomycin C, leucovor and 5-Fluorouracil for unresectable advanced hepatocellular carcinoma, 2004, *J. Chin. Med. Assoc.* 67:602-10).

Primary Outcome Measures

Safety: Systemic and locoregional adverse events are graded according to CTCAS and coded according to MedRA. The adverse events data for all subjects at a single dose range will be evaluated prior to dose escalation. The final safety assessment incorporates data from all dose ranges.

Secondary Outcome Measures
- Lesion distribution and retention of LV-FDPS following locoregional administration and subsequent biopsy or necropsy to obtain tissues.
- Objective response rate (ORR) in target and measurable non-local lesions (if present) by physical analysis, medical imaging or biopsy during 3 months after treatment.
- Levels of LV-FDPS in blood stream during 10 minutes, 30 minutes, 1 hour and 1 day after local injection.
- Changes in markers of hepatic function including ALP, ALT, ASAT, total bilirubin and GGT during 3 months after treatment.
- Disease free survival beyond historical control (no LV-FDPS) patients in ad hoc analysis.

Inclusion Criteria
- Greater than 18 years and including both males and females.
- Diagnosis confirmed by histology or cytology or based on currently accepted clinical standards of hepatocellular carcinoma of parenchyma cell origin that is not amenable, at the time of screening, to resection, transplant or other potentially curative therapies.
- Treating physician determines that the lesion is amenable to locoregional targeted delivery.
- Target lesion must represent measurable disease with a unidimensional longest diameter of ≥1.0 cm by computed tomography; the maximum longest diameter is ≤5.0 cm.
- Karnofsky performance score 60-80% of ECOG values.
- Life expectancy≥12 weeks.
- Hematopoietic function: WBC≥2,500/mm$^3$; ANC≥1000/mm$^3$; Hemoglobin≥8 g/dL; Platelet count≥50,000/mm$^3$; Coagulation INR≤1.3.
- AST and ALT≤5 times ULN; ALPS≤5 time ULN. Bilirubin≤1.5 times ULV; Creatine≤1.5 times ULN and eGFR≥50.
- Thyroid function: Total T3 or free T3, total T4 or free T4 and THC≤CTCAE Grade 2 abnormality.
- Renal, cardiovascular and respiratory function adequate in the opinion of the attending physician.
- Immunological function: Circulating Vgamma9Vdelta2+ T cells≥30/mm$^3$; no immunodeficiency disease.
- Negative for HIV by serology and viral RNA test.
- Written informed consent.

Exclusion Criteria
- Intolerant to or unwilling to continue aminobisphosphonate adjunct therapy.
- Objective clinical response after aminobisphosphonate therapy.
- Target lesion contiguous with, encompasses or infiltrates blood vessel.
- Primary HCC amenable to resection, transplantation or other potentially curative therapies.
- Hepatic surgery or chemoembolization within the past 4 months.
- Hepatic radiation or whole body radiation therapy within past 4 months.
- Chemotherapy excluding aminobisphonate, within 4 weeks or any use of nitrosourea, mitomycin C or cisplatin.
- Investigational agents within 4 weeks or <5 drug half-lives.
- Impaired wound healing due to diabetes.
- Significant psychiatric illness, alcohol dependence or illicit drug use.
- Unwilling to comply with study protocols and reporting requirements.
- Presence of clinically significant cardiovascular, cerebrovascular (stroke), immunological (except hepatitis B or C virus infection, viral hepatitis or cirrhosis), endocrine or central nervous system disorders; current encephalopathy; variceal bleeding requiring hospitalization or transfusion within past 4 months.
- History of HIV or acquired immune deficiency syndrome.
- Current or prior treatment with antiretroviral medications.
- Pregnant, lactating or refusal to adopt barrier or chemical contraceptive use throughout trial and follow-up interval.

Example 15—Treatment of a Subject with Chronic Viral Disease(s) of the Liver

LV-FDPS is a Genetic Medicine Delivered by a Lentivirus Vector Via Local Administration to Liver for the Treatment of Hepatitis B Virus, Hepatitis C Virus, HIV or Other Viral Infection of the Liver A Phase I clinical trial will test safety and feasibility of delivering LV-FDPS to virally infected liver using ultrasound guided cannulation. It is rationally predicted that this study will result in the successful treatment of infections of the liver. The study is an open label, 4×3 dose escalation (4 dose ranges, up to 3 subjects per dose) to identify the maximum tolerable dose of LV-FDPS in patients 18 years or older with chronic viral disease of the liver that is resistant to chemotherapy.

LV-FDPS is a genetic therapy designed to reduce expression in tumor cells of the enzyme farnesyl diphosphate synthase. Experimental studies show that tumor cells modified by LV-FDPS induce human gamma delta T cells, including a capacity for cellular cytotoxicity against virally-infected cells.

Subjects with confirmed viral infection of the liver including hepatitis B virus, hepatitis C virus, HIV or other viruses are enrolled into the next available LV-FDPS dosing category. A maximum of 3 subjects are recruited for each dosage group. The LV-FDPS dose is a number of transducing units of LV-FDPS as described in the product release criteria, delivered via intrahepatic cannulation in a single bolus with volume not to exceed 25 mL. The minimum dose is $1\times10^9$ transducing units and escalation is 10-fold to a next dose of $1\times10^{10}$ transducing units, the next dose is $1\times10^{11}$ transducing units, and a maximum dose of $1\times10^{12}$ transducing units based on reported experience with recombinant adenovirus therapy for HCC (Sangro, et al., A phase I clinic trial of thymidine kinase-based gene therapy in advanced hepatocellular carcinoma, 2010, *Cancer Gene Ther.* 17:837-43). Subjects are enrolled, treated and evaluated for 3 months. All safety evaluations are completed for each group prior to enrolling and treating subjects at the next higher dose level. Enrollment and dose escalation continue until a maximum tolerable dose is achieved or the study is terminated.

Cannulation is via the left subclavian artery until tip of catheter is at the proper hepatic artery junction. Cannulation is guided by ultrasonography as described (Lin et al., Clinical effects of intra-arterial infusion chemotherapy with cisplatin, mitomycin C, leucovor and 5-Fluorouracil for unresectable advanced hepatocellular carcinoma, 2004, *J. Chin. Med. Assoc.* 67:602-10).

Primary Outcome Measures

Safety: Systemic and locoregional adverse events are graded according to CTCAS and coded according to MedRA. The adverse events data for all subjects at a single dose range will be evaluated prior to dose escalation. The final safety assessment incorporates data from all dose ranges.

Secondary Outcome Measures
- Lesion distribution and retention of LV-FDPS following locoregional administration and subsequent biopsy or necropsy to obtain tissues.
- Objective response rate (ORR) measured as a Sustained Viral Response (SVR) within the organ or systemically during 3 months after treatment.
- Levels of LV-FDPS in blood stream during 10 minutes, 30 minutes, 1 hour and 1 day after local injection.
- Changes in markers of hepatic function including ALP, ALT, ASAT, total bilirubin and GGT during 3 months after treatment.
- Disease free survival beyond historical control (no LV-FDPS) patients in ad hoc analysis.

Inclusion Criteria
- Greater than 18 years and including both males and females.
- Diagnosis confirmed by histology or cytology or based on currently accepted clinical standards of chronic viral infection of the liver that is not amenable, at the time of screening, to resection, transplant or other potentially curative therapies.
- Treating physician determines that the lesion is amenable to locoregional targeted delivery.
- Karnofsky performance score 60-80% of ECOG values.
- Life expectancy≥12 weeks.
- Hematopoietic function: WBC≥2,500/mm$^3$; ANC≥1000/mm$^3$; Hemoglobin≥8 g/dL; Platelet count≥50,000/mm$^3$; Coagulation INR≤1.3.
- AST and ALT≤5 times ULN; ALPS≤5 time ULN. Bilirubin≤1.5 times ULV; Creatine≤1.5 times ULN and eGFR≥50.
- Thyroid function: Total T3 or free T3, total T4 or free T4 and THC≤CTCAE Grade 2 abnormality.
- Renal, cardiovascular and respiratory function adequate in the opinion of the attending physician.
- Immunological function: Circulating Vgamma9Vdelta2+ T cells≥30/mm$^3$; no immunodeficiency disease.
- Negative for HIV by serology and viral RNA test.
- Written informed consent.

Exclusion Criteria
- Chronic viral disease amenable to resection, transplantation or other potentially curative therapies.
- Hepatic surgery or chemoembolization within the past 4 months.
- Hepatic radiation or whole body radiation therapy within past 4 months.
- Investigational agents within 4 weeks or <5 drug half-lives.
- Current (within past 4 weeks) or ongoing receipt of aminobisphosphonate therapy.
- Impaired wound healing due to diabetes.
- Significant psychiatric illness, alcohol dependence or illicit drug use.
- Unwilling to comply with study protocols and reporting requirements.
- Presence of clinically significant cardiovascular, cerebrovascular (stroke), immunological (except virus infection, viral hepatitis or cirrhosis), endocrine or central nervous system disorders; current encephalopathy; variceal bleeding requiring hospitalization or transfusion within past 4 months.
- Pregnant, lactating or refusal to adopt barrier or chemical contraceptive use throughout trial and follow-up interval.

LV-FDPS is a Genetic Medicine Delivered by a Lentivirus Vector Via Local Administration to Liver for the Treatment of Hepatitis B Virus, Hepatitis C Virus, HIV or Other Viral Infection of the Liver—Concomitant Adjunct Aminobisphosphonate Therapy A Phase I clinical trial will test safety and feasibility of delivering LV-FDPS to virally infected liver using ultrasound guided cannulation. It is rationally predicted that this study will result in the successful treatment of infections of the liver. The study is an open label, 4×3 dose escalation (4 dose ranges, up to 3 subjects per dose) to identify the maximum tolerable dose of LV-FDPS in patients 18 years or older with chronic viral disease of the liver that is resistant to chemotherapy.

LV-FDPS is a genetic therapy designed to reduce expression in tumor cells of the enzyme farnesyl diphosphate synthase. Experimental studies show that tumor cells modified by LV-FDPS induce human gamma delta T cells, including a capacity for cellular cytotoxicity against virally-infected cells. Prior experimental studies also showed the potential for positive interactions of LV-FDPS and specific aminobisphonate drugs that may be prescribed during infectious disease. For this study, subjects will receive dose escalating amounts of LV-FDPS with continuous standard of care dosing with Aredia® (pamidronate), Zometa® (zoledronic acid) or Actonel® (risedronate) according to physician advice and subject preference.

Subjects with confirmed viral infection of the liver including hepatitis B virus, hepatitis C virus, HIV or other viruses will initiate aminobisphonate therapy for 45 days before re-screening to meet enrollment criteria for LV-FDPS treatment of infectious disease. Eligible subjects are enrolled into the next available LV-FDPS dosing category. A maximum of 3 subjects are recruited for each dosage group. The LV-FDPS dose is a number of transducing units of LV-FDPS as described in the product release criteria, delivered via intrahepatic cannulation in a single bolus with volume not to exceed 25 mL. The minimum dose is $1 \times 10^9$ transducing units and escalation is 10-fold to a next dose of $1 \times 10^{10}$ transducing units, the next dose is $1 \times 10^{11}$ transducing units, and a maximum dose of $1 \times 10^{12}$ transducing units based on reported experience with recombinant adenovirus therapy for HCC (Sangro, et al., A phase I clinic trial of thymidine kinase-based gene therapy in advanced hepatocellular carcinoma, 2010, *Cancer Gene Ther.* 17:837-43). Subjects are enrolled, treated and evaluated for 3 months. All safety evaluations are completed for each group prior to enrolling and treating subjects at the next higher dose level. Enrollment and dose escalation continue until a maximum tolerable dose is achieved or the study is terminated.

Cannulation is via the left subclavian artery until tip of catheter is at the proper hepatic artery junction. Cannulation is guided by ultrasonography as described (Lin et al., Clinical effects of intra-arterial infusion chemotherapy with cisplatin, mitomycin C, leucovor and 5-Fluorouracil for unresectable advanced hepatocellular carcinoma, 2004, *J. Chin. Med. Assoc.* 67:602-10).

Primary Outcome Measures

Safety: Systemic and locoregional adverse events are graded according to CTCAS and coded according to MedRA. The adverse events data for all subjects at a single dose range will be evaluated prior to dose escalation. The final safety assessment incorporates data from all dose ranges.

Secondary Outcome Measures
- Lesion distribution and retention of LV-FDPS following locoregional administration and subsequent biopsy or necropsy to obtain tissues.
- Objective response rate (ORR) measured as a Sustained Viral Response (SVR) within the organ or systemically during 3 months after treatment.
- Levels of LV-FDPS in blood stream during 10 minutes, 30 minutes, 1 hour and 1 day after local injection.
- Changes in markers of hepatic function including ALP, ALT, ASAT, total bilirubin and GGT during 3 months after treatment.
- Disease free survival beyond historical control (no LV-FDPS) patients in ad hoc analysis.

Inclusion Criteria
- Greater than 18 years and including both males and females.
- Diagnosis confirmed by histology or cytology or based on currently accepted clinical standards of chronic viral infection of the liver that is not amenable, at the time of screening, to resection, transplant or other potentially curative therapies.
- Treating physician determines that the lesion is amenable to locoregional targeted delivery.
- Karnofsky performance score 60-80% of ECOG values.
- Life expectancy≥12 weeks.
- Hematopoietic function: WBC≥2,500/mm$^3$; ANC≥1000/mm$^3$; Hemoglobin≥8 g/dL;
- Platelet count≥50,000/mm$^3$; Coagulation INR≤1.3.
- AST and ALT≤5 times ULN; ALPS≤5 time ULN. Bilirubin≤1.5 times ULV; Creatine≤1.5 times ULN and eGFR≥50.
- Thyroid function: Total T3 or free T3, total T4 or free T4 and THC≤CTCAE Grade 2 abnormality.
- Renal, cardiovascular and respiratory function adequate in the opinion of the attending physician.
- Immunological function: Circulating Vgamma9Vdelta2+ T cells≥30/mm$^3$; no immunodeficiency disease.
- Negative for HIV by serology and viral RNA test.
- Written informed consent.

Exclusion Criteria
- Chronic viral disease amenable to resection, transplantation or other potentially curative therapies.
- Hepatic surgery or chemoembolization within the past 4 months.
- Hepatic radiation or whole body radiation therapy within past 4 months.
- Investigational agents within 4 weeks or <5 drug half-lives.
- Impaired wound healing due to diabetes.
- Significant psychiatric illness, alcohol dependence or illicit drug use.
- Unwilling to comply with study protocols and reporting requirements.
- Presence of clinically significant cardiovascular, cerebrovascular (stroke), immunological (except virus infection, viral hepatitis or cirrhosis), endocrine or central nervous system disorders; current encephalopathy; variceal bleeding requiring hospitalization or transfusion within past 4 months.
- Pregnant, lactating or refusal to adopt barrier or chemical contraceptive use
throughout trial and follow-up interval.

Sequences

The following sequences are referred to herein:

| SEQ ID NO: | Description | Sequence |
|---|---|---|
| 1 | FDPS shRNA sequence #1 | GTCCTGGAGTACAATGCCATTCTCGAGAAT GGCATTGTACTCCAGGACTTTTT |
| 2 | FDPS shRNA sequence #2 | GCAGGATTTCGTTCAGCACTTCTCGAGAAG TGCTGAACGAAATCCTGCTTTTT |
| 3 | FDPS shRNA sequence #3 | GCCATGTACATGGCAGGAATTCTCGAGAAT TCCTGCCATGTACATGGCTTTTT |
| 4 | FDPS shRNA sequence #4 | GCAGAAGGAGGCTGAGAAAGTCTCGAGACT TTCTCAGCCTCCTTCTGCTTTTT |
| 5 | miR30 FDPS sequence #1 | AAGGTATATTGCTGTTGACAGTGAGCGACA CTTTCTCAGCCTCCTTCTGCGTGAAGCCAC AGATGGCAGAAGGAGGCTGAGAAAGTGCTG CCTACTGCCTCGGACTTCAAGGGGCT |
| 6 | miR30 FDPS sequence #2 | AAGGTATATTGCTGTTGACAGTGAGCGACA CTTTCTCAGCCTCCTTCTGCGTGAAGCCAC |

| SEQ ID NO: | Description | Sequence |
|---|---|---|
| | | AGATGGCAGAAGGGCTGAGAAAGTGCTGCC TACTGCCTCGGACTTCAAGGGGCT |
| 7 | miR30 FDPS sequence #3 | TGCTGTTGACAGTGAGCGACTTTCTCAGCC TCCTTCTGCGTGAAGCCACAGATGGCAGAA GGAGGCTGAGAAAGTTGCCTACTGCCTCGG A |
| 8 | miR155 FDPS sequence #1 | CCTGGAGGCTTGCTGAAGGCTGTATGCTGA CTTTCTCAGCCTCCTTCTGCTTTTGGCCAC TGACTGAGCAGAAGGGCTGAGAAAGTCAGG ACACAAGGCCTGTTACTAGCACTCA |
| 9 | miR21 FDPS sequence #1 | CATCTCCATGGCTGTACCACCTTGTCGGGA CTTTCTCAGCCTCCTTCTGCCTGTTGAATC TCATGGCAGAAGGAGGCGAGAAAGTCTGAC ATTTTGGTATCTTTCATCTGACCA |
| 10 | miR185 FDPS sequence #1 | GGGCCTGGCTCGAGCAGGGGCGAGGGATA CTTTCTCAGCCTCCTTCTGCTGGTCCCCTC CCCGCAGAAGGAGGCTGAGAAAGTCCTTCC CTCCCAATGACCGCGTCTTCGTCG |
| 11 | Rous Sarcoma virus (RSV) promoter | GTAGTCTTATGCAATACTCTTGTAGTCTTG CAACATGGTAACGATGAGTTAGCAACATGC CTTACAAGGAGAGAAAAAGCACCGTGCATG CCGATTGGTGGAAGTAAGGTGGTACGATCG TGCCTTATTAGGAAGGCAACAGACGGGTCT GACATGGATTGGACGAACCACTGAATTGCC GCATTGCAGAGATATTGTATTTAAGTGCCT AGCTCGATACAATAAACG |
| 12 | 5' Long terminal repeat (LTR) | GGTCTCTCTGGTTAGACCAGATCTGAGCCT GGGAGCTCTCTGGCTAACTAGGGAACCCAC TGCTTAAGCCTCAATAAAGCTTGCCTTGAG TGCTTCAAGTAGTGTGTGCCCGTCTGTTGT GTGACTCTGGTAACTAGAGATCCCTCAGAC CCTTTTAGTCAGTGTGGAAAATCTCTAGCA |
| 13 | Psi Packaging signal | TACGCCAAAAATTTTGACTAGCGGAGGCTA GAAGGAGAGAG |
| 14 | Rev response element (RRE) | AGGAGCTTTGTTCCTTGGGTTCTTGGGAGC AGCAGGAAGCACTATGGGCGCAGCCTCAAT GACGCTGACGGTACAGGCCAGACAATTATT GTCTGGTATAGTGCAGCAGCAGAACAATTT GCTGAGGGCTATTGAGGCGCAACAGCATCT GTTGCAACTCACAGTCTGGGGCATCAAGCA GCTCCAGGCAAGAATCCTGGCTGTGGAAAG ATACCTAAAGGATCAACAGCTCC |
| 15 | Central polypurine tract (cPPT) | TTTTAAAAGAAAAGGGGGGATTGGGGGGTA CAGTGCAGGGGAAAGAATAGTAGACATAAT AGCAACAGACATACAAACTAAAGAATTACA AAAACAAATTACAAAAATTCAAAATTTTA |
| 16 | Polymerase III shRNA promoters; H1 promoter | GAACGCTGACGTCATCAACCCGCTCCAAGG AATCGCGGGCCCAGTGTCACTAGGCGGGAA CACCCAGCGCGCGTGCGCCCTGGCAGGAAG ATGGCTGTGAGGGACAGGGGAGTGGCGCCC TGCAATATTTGCATGTCGCTATGTGTTCTG GGAAATCACCATAAACGTGAAATGTCTTTG GATTTGGGAATCTTATAAGTTCTGTATGAG ACCACTT |
| 17 | Long WPRE sequence | AATCAACCTCTGATTACAAAATTTGTGAAA GATTGACTGGTATTCTTAACTATGTTGCTC CTTTTACGCTATGTGGATACGCTGCTTTAA TGCCTTTGTATCATGCTATTGCTTCCCGTA TGGCTTTCATTTTCTCCTCCTTGTATAAAT CCTGGTTGCTGTCTCTTTATGAGGAGTTGT GGCCCGTTGTCAGGCAACGTGGCGTGGTGT GCACTGTGTTTGCTGACGCAACCCCCACTG GTTGGGGCATTGCCACCACCTGTCAGCTCC TTTCCGGGACTTTCGCTTTCCCCCTCCCTA |
| | | TTGCCACGGCGGAACTCATCGCCGCCTGCC TTGCCCGCTGCTGGACAGGGGCTCGGCTGT TGGGCACTGACAATTCCGTGGTGTTGTCGG GGAAATCATCGTCCTTTCCTTGGCTGCTCG CCTGTGTTGCCACCTGGATTCTGCGCGGGA CGTCCTTCTGCTACGTCCCTTCGGCCCTCA ATCCAGCGGACCTTCCTTCCCGCGGCCTGC TGCCGGCTCTGCGGCCTCTTCCGCGTCTTC GCCTTCGCCCTCAGACGAGTCGGATCTCCC TTTGGGCCGCCTCCCCGCCT |
| 18 | 3' delta LTR | TGGAAGGGCTAATTCACTCCCAACGAAGAT AAGATCTGCTTTTTGCTTGTACTGGGTCTC TCTGGTTAGACCAGATCTGAGCCTGGGAGC TCTCTGGCTAACTAGGGAACCCACTGCTTA AGCCTCAATAAAGCTTGCCTTGAGTGCTTC AAGTAGTGTGTGCCCGTCTGTTGTGTGACT CTGGTAACTAGAGATCCCTCAGACCCTTTT AGTCAGTGTGGAAAATCTCTAGCAGTAGTA GTTCATGTCA |
| 19 | Helper/Rev; Chicken beta actin (CAG) promoter; Transcription | GCTATTACCATGGGTCGAGGTGAGCCCCAC GTTCTGCTTCACTCTCCCCATCTCCCCCCC CTCCCCACCCCCAATTTTGTATTTATTTAT TTTTTAATTATTTTGTGCAGCGATGGGGGC GGGGGGGGGGGGGCGCGCGCCAGGCGGGG CGGGGCGGGGCGAGGGGCGGGGCGGGGCGA GGCGGAGAGGTGCGGCGGCAGCCAATCAGA GCGGCGCGCTCCGAAAGTTTCCTTTTATGG CGAGGCGGCGGCGGCGGCGGCCCTATAAA AGCGAAGCGCGCGGCGGGCG |
| 20 | Helper/Rev; HIV Gag; Viral capsid | ATGGGTGCGAGAGCGTCAGTATTAAGCGGG GGAGAATTAGATCGATGGGAAAAAATTCGG TTAAGGCCAGGGGGAAAGAAAAAATATAAA TTAAAACATATAGTATGGGCAAGCAGGGAG CTAGAACGATTCGCAGTTAATCCTGGCCTG TTAGAAACATCAGAAGGCTGTAGACAAATA CTGGGACAGCTACAACCATCCCTTCAGACA GGATCAGAAGAACTTAGATCATTATATAAT ACAGTAGCAACCCTCTATTGTGTGCATCAA AGGATAGAGATAAAAGACACCAAGGAAGCT TTAGACAAGATAGAGGAAGAGCAAAACAAA AGTAAGAAAAAAGCACAGCAAGCAGCAGCT GACACAGGACACAGCAATCAGGTCAGCCAA AATTACCCTATAGTGCAGAACATCCAGGGG CAAATGGTACATCAGGCCATATCACCTAGA ACTTTAAATGCATGGGTAAAAGTAGTAGAA GAGAAGGCTTTCAGCCCAGAAGTGATACCC ATGTTTTCAGCATTATCAGAAGGAGCCACC CCACAAGATTTAAACACCATGCTAAACACA GTGGGGGGACATCAAGCAGCCATGCAAATG TTAAAAGAGACCATCAATGAGGAAGCTGCA GAATGGGATAGAGTGCATCCAGTGCATGCA GGGCCTATTGCACCAGGCCAGATGAGAGAA CCAAGGGGAAGTGACATAGCAGGAACTACT AGTACCCTTCAGGAACAAATAGGATGGATG ACACATAATCCACCTATCCCAGTAGGAGAA ATCTATAAAAGATGGATAATCCTGGGATTA AATAAAATAGTAAGAATGTATAGCCCTACC AGCATTCTGGACATAAGACAAGGACCAAAG GAACCCTTTAGAGACTATGTAGACCGATTC TATAAAACTCTAAGAGCCGAGCAAGCTTCA CAAGAGGTAAAAAATTGGATGACAGAAACC TTGTTGGTCCAAAATGCGAACCCAGATTGT AAGACTATTTTAAAAGCATTGGGACCAGGA GCGACACTAGAAGAAATGATGACAGCATGT CAGGGAGTGGGGGGACCCGGCCATAAAGCA AGAGTTTTGGCTGAAGCAATGAGCCAAGTA ACAAATCCAGCTACCATAATGATACAGAAA GGCAATTTTAGGAACCAAAGAAAGACTGTT AAGTGTTTCAATTGTGGCAAAGAAGGGCAC ATAGCCAAAAATTGCAGGGCCCCTAGGAAA AAGGGCTGTTGGAAATGTGGAAAGGAAGGA CACCAAATGAAAGATTGTACTGAGAGACAG |

| SEQ ID NO: | Description | Sequence |
|---|---|---|
| | | GCTAATTTTTTAGGGAAGATCTGGCCTTCC CACAAGGGAAGGCCAGGGAATTTTCTTCAG AGCAGACCAGAGCCAACAGCCCCACCAGAA GAGAGCTTCAGGTTTGGGGAAGAGACAACA ACTCCCTCTCAGAAGCAGGAGCCGATAGAC AAGGAACTGTATCCTTTAGCTTCCCTCAGA TCACTCTTTGGCAGCGACCCCTCGTCACAA TAA |
| 21 | Helper/Rev; HIV Pol; Protease and reverse transcriptase | ATGAATTTGCCAGGAAGATGGAAACCAAAA ATGATAGGGGGAATTGGAGGTTTTATCAAA GTAGGACAGTATGATCAGATACTCATAGAA ATCTGCGGACATAAAGCTATAGGTACAGTA TTAGTAGGACCTACACCTGTCAACATAATT GGAAGAAATCTGTTGACTCAGATTGGCTGC ACTTTAAATTTTCCCATTAGTCCTATTGAG ACTGTACCAGTAAAATTAAAGCCAGGAATG GATGGCCCAAAAGTTAAACAATGGCCATTG ACAGAAGAAAAAATAAAAGCATTAGTAGAA ATTTGTACAGAAATGGAAAGGAAGGAAAA ATTTCAAAAATTGGGCCTGAAAATCCATAC AATACTCCAGTATTTGCCATAAAGAAAAAA GACAGTACTAAATGGAGAAAATTAGTAGAT TTCAGAGAACTTAATAAGAGAACTCAAGAT TTCTGGGAAGTTCAATTAGGAATACCACAT CCTGCAGGGTTAAAACAGAAAAAATCAGTA ACAGTACTGGATGTGGGCGATGCATATTTT TCAGTTCCCTTAGATAAAGACTTCAGGAAG TATACTGCATTTACCATACCTAGTATAAAC AATGAGACACCAGGGATTAGATATCAGTAC AATGTGCTTCCACAGGGATGGAAAGGATCA CCAGCAATATTCCAGTGTAGCATGACAAAA ATCTTAGAGCCTTTTAGAAAACAAAATCCA GACATAGTCATCTATCAATACATGGATGAT TTGTATGTAGGATCTGACTTAGAAATAGGG CAGCATAGAACAAAAATAGAGGAACTGAGA CAACATCTGTTGAGGTGGGGATTTACCACA CCAGACAAAAAACATCAGAAAGAACCTCCA TTCCTTTGGATGGGTTATGAACTCCATCCT GATAAATGGACAGTACAGCCTATAGTGCTG CCAGAAAAGGACAGCTGGACTGTCAATGAC ATACAGAAATTAGTGGGAAAATTGAATTGG GCAAGTCAGATTTATGCAGGGATTAAAGTA AGGCAATTATGTAAACTTCTTAGGGGAACC AAAGCACTAACAGAAGTAGTACCACTAACA GAAGAAGCAGAGCTAGAACTGGCAGAAAAC AGGGAGATTCTAAAAGAACCGGTACATGGA GTGTATTATGACCCATCAAAAGACTTAATA GCAGAAATACAGAAGCAGGGGCAAGGCCAA TGGACATATCAAATTTATCAAGAGCCATTT AAAAATCTGAAAACAGGAAAATATGCAAGA ATGAAGGGTGCCCACACTAATGATGTGAAA CAATTAACAGAGGCAGTACAAAAAATAGCC ACAGAAAGCATAGTAATATGGGGAAAGACT CCTAAATTTAAATTACCCATACAAAAGGAA ACATGGGAAGCATGGTGGACAGAGTATTGG CAAGCCACCTGGATTCCTGAGTGGGAGTTT GTCAATACCCCTCCCTTAGTGAAGTTATGG TACCAGTTAGAGAAAGAACCCATAATAGGA GCAGAAACTTTCTATGTAGATGGGGCAGCC AATAGGGAAACTAAATTAGGAAAAGCAGGA TATGTAACTGACAGAGGAAGACAAAAAGTT GTCCCCCTAACGGACACAACAAATCAGAAG ACTGAGTTACAAGCAATTCATCTAGCTTTG CAGGATTCGGGATTAGAAGTAAACATAGTA ACAGACTCACAATATGCATTGGGAATCATT CAAGCACAACCAGATAAGAGTGAATCAGAG TTAGTCAGTCAAATAATAGAGCAGTTAATA AAAAGGAAAAGTCTACCTGGCATGGGTA CCAGCACACAAAGGAATTGGAGGAAATGAA CAAGTAGATGGGTTGGTCAGTGCTGGAATC AGGAAAGTACTA |
| 22 | Helper Rev; HIV Integrase; Integration of viral RNA | TTTTTAGATGGAATAGATAAGGCCCAAGAA GAACATGAGAAATATCACAGTAATTGGAGA GCAATGGCTAGTGATTTTAACCTACCACCT GTAGTAGCAAAAGAAATAGTAGCCAGCTGT GATAAATGTCAGCTAAAAGGGGAAGCCATG CATGGACAAGTAGACTGTAGCCCAGGAATA TGGCAGCTAGATTGTACACATTTAGAAGGA AAAGTTATCTTGGTAGCAGTTCATGTAGCC AGTGGATATATAGAAGCAGAAGTAATTCCA GCAGAGACAGGGCAAGAAACAGCATACTTC CTCTTAAAATTAGCAGGAAGATGGCCAGTA AAAACAGTACATACAGACAATGGCAGCAAT TTCACCAGTACTACAGTTAAGGCCGCCTGT TGGTGGGCGGGATCAAGCAGGAATTTGGC ATTCCCTACAATCCCCAAAGTCAAGGAGTA ATAGAATCTATGAATAAAGAATTAAAGAAA ATTATAGGACAGGTAAGAGATCAGGCTGAA CATCTTAAGACAGCAGTACAAATGGCAGTA TTCATCCACAATTTTAAAAGAAAAGGGGGG ATTGGGGGGTACAGTGCAGGGGAAAGAATA GTAGACATAATAGCAACAGACATACAAACT AAAGAATTACAAAAACAAATTACAAAAATT CAAAATTTTCGGGTTTATTACAGGGACAGC AGAGATCCAGTTTGGAAAGGACCAGCAAAG CTCCTCTGGAAAGGTGAAGGGGCAGTAGTA ATACAAGATAATAGTGACATAAAAGTAGTG CCAAGAAGAAAAGCAAAGATCATCAGGGAT TATGGAAAACAGATGGCAGGTGATGATTGT GTGGCAAGTAGACAGGATGAGGATTAA |
| 23 | Helper/Rev; HIV RRE; Binds Rev element | AGGGAGCTTTGTTCCTTGGGTTCTTGGGAGC AGCAGGAAGCACTATGGGCGCAGCGTCAAT GACGCTGACGGTACAGGCCAGACAATTATT GTCTGGTATAGTGCAGCAGCAGAACAATTT GCTGAGGGCTATTGAGGCGCAACAGCATCT GTTGCAACTCACAGTCTGGGGCATCAAGCA GCTCCAGGCAAGAATCCTGGCTGTGGAAAG ATACCTAAAGGATCAACAGCTCCT |
| 24 | Helper/Rev; HIV Rev; Nuclear export and stabilize viral mRNA | ATGGCAGGAAGAAGCGGAGACAGCGACGAA GAACTCCTCAAGGCAGTCAGACTCATCAAG TTTCTCTATCAAAGCAACCCACCTCCCAAT CCCGAGGGGACCCGACAGGCCCGAAGGAAT AGAAGAAGAAGGTGGAGAGAGAGACAGAGA CAGATCCATTCGATTAGTGAACGGATCCTT AGCACTTATCTGGGACGATCTGCGGAGCCT GTGCCTCTTCAGCTACCACCGCTTGAGAGA CTTACTCTTGATTGTAACGAGGATTGTGGA ACTTCTGGGACGCAGGGGGTGGGAAGCCCT CAAATATTGGTGGAATCTCCTACAATATTG GAGTCAGGAGCTAAAGAATAG |
| 25 | Envelope; CMV promoter; Transcription | ACATTGATTATTGACTAGTTATTAATAGTA ATCAATTACGGGGTCATTAGTTCATAGCCC ATATATGGAGTTCCGCGTTACATAACTTAC GGTAAATGGCCCGCCTGGCTGACCGCCCAA CGACCCCCGCCCATTGACGTCAATAATGAC GTATGTTCCCATAGTAACGCCAATAGGGAC TTTCCATTGACGTCAATGGGTGGAGTATTT ACGGTAAACTGCCCACTTGGCAGTACATCA AGTGTATCATATGCCAAGTACGCCCCCTAT TGACGTCAATGACGGTAAATGGCCCGCCTG GCATTATGCCCAGTACATGACCTTATGGGA CTTTCCTACTTGGCAGTACATCTACGTATT AGTCATCGCTATTACCATGGTGATGCGGTT TTGGCAGTACATCAATGGGCGTGGATAGCG GTTTGACTCACGGGGATTTCCAAGTCTCCA CCCCATTGACGTCAATGGGAGTTTGTTTTG GCACCAAAATCAACGGGACTTTCCAAAATG TCGTAACAACTCCGCCCCATTGACGCAAAT GGGCGGTAGGCGTGTACGGTGGGAGGTCTA TATAAGC |

| SEQ ID NO: | Description | Sequence |
|---|---|---|
| 26 | Envelope; VSV-G; Glycoprotein envelope-cell entry | ATGAAGTGCCTTTTGTACTTAGCCTTTTA TTCATTGGGGTGAATTGCAAGTTCACCATA GTTTTTCCACACAACCAAAAAGGAAACTGG AAAAATGTTCCTTCTAATTACCATTATTGC CCGTCAAGCTCAGATTTTAAATTGGCATAAT GACTTAATAGGCACAGCCTTACAAGTCAAA ATGCCCAAGAGTCACAAGGCTATTCAAGCA GACGGTTGGATGTGTCATGCTTCCAAATGG GTCACTACTTGTGATTTCCGCTGGTATGGA CCGAAGTATATAACACATTCCATCCGATCC TTCACTCCATCTGTAGAACAATGCAAGGAA AGCATTGAACAAACGAAACAAGGAACTTGG CTGAATCCAGGCTTCCCTCCTCAAAGTTGT GGATATGCAACTGTGACGGATGCCGAAGCA GTGATTGTCCAGGTGACTCCTCACCATGTG CTGGTTGATGAATACACAGGAGAATGGGTT GATTCACAGTTCATCAACGGAAAATGCAGC AATTACATATGCCCCACTGTCCATAACTCT ACAACCTGGCATTCTGACTATAAGGTCAAA GGGCTATGTGATTCTAACCTCATTTCCATG GACATCACCTTCTTCTCAGAGGACGGAGAG CTATCATCCCTGGGAAAGGAGGGCACAGGG TTCAGAAGTAACTACTTTGCTTATGAAACT GGAGGCAAGGCCTGCAAAATGCAATACTGC AAGCATTGGGGAGTCAGACTCCCATCAGGT GTCTGGTTCGAGATGGCTGATAAGGATCTC TTTGCTGCAGCCAGATTCCCTGAATGCCCA GAAGGGTCAAGTATCTCTGCTCCATCTCAG ACCTCAGTGGATGTAAGTCTAATTCAGGAC GTTGAGAGGATCTTGGATTATTCCCTCTGC CAAGAAACCTGGAGCAAAATCAGAGCGGGT CTTCCAATCTCTCCAGTGGATCTCAGCTAT CTTGCTCCTAAAAACCCAGGAACCGGTCCT GCTTTCACCATAATCAATGATCAGATCCCTAAAA TACTTTGAGACCAGATACATCAGAGTCGAT ATTGCTGCTCCAATCCTCTCAAGAATGGTC GGAATGATCAGTGGAACTACCACAGAAAGG GAACTGTGGGATGACTGGGCACCATATGAA GACGTGGAAATTGGACCCAATGGAGTTCTG AGGACCAGTTCAGGATATAAGTTTCCTTTA TACATGATTGGACATGGTATGTTGGACTCC GATCTTCATCTTAGCTCAAAGGCTCAGGTG TTCAACATCCTCACATTCAAGACGCTGCT TCGCAACTTCCTGATGATGAGAGTTTATTT TTTTGGTGATACTGGGCTATCCAAAAATCCA ATCGAGCTTGTAGAAGGTTGGTTCAGTAGT TGGAAAAGCTCTATTGCCTCTTTTTTCTTT ATCATAGGGTTAATCATTGGACTATTCTTG GTTCTCCGAGTTGGTATCCATCTTTGCATT AAAATTAAAGCACACCAAGAAAAGACAGATT TATACAGACATAGAGATGA |
| 27 | Helper/Rev; CMV early (CAG) enhancer; Enhance Transcription | TAGTTATTAATAGTAATCAATTACGGGGTC ATTAGTTCATAGCCCATATATGGAGTTCCG CGTTACATAACTTACGGTAAATGGCCCGCC TGGCTGACCGCCCAACGACCCCCGCCCATT GACGTCAATAATGACGTATGTTCCCATAGT AACGCCAATAGGGACTTTCCATTGACGTCA ATGGGTGGACTATTTACGGTAAACTGCCCA CTTGGCAGTACATCAAGTGTATCATATGCC AAGTACGCCCCCTATTGACGTCAATGACGG TAAATGGCCCGCCTGGCATTATGCCCAGTA CATGACCTTATGGGACTTTCCTACTTGGCA GTACATCTACGTATTAGTCATC |
| 28 | Helper/Rev; Chicken beta actin intron; Enhance gene expression | GGAGTCGCTGCGTTGCCTTCGCCCCGTGCC CCGCTCCGCGCCGCCTCGCGCCGCCCGCC CGGCTCTGACTGACCGCGTTACTCCCACAG GTGAGCGGGCGGGACGGCCCTTCTCCTCCG GGCTGTAATTAGCGCTTGGTTTAATGACGG CTCGTTTCTTTTCTGTGGCTGCGTGAAAGC CTTAAAGGGCTCCGGGAGGGCCCTTTGTGC GGGGGGGAGCGGCTCGGGGGGTGCGTGCGT GTGTGTGTGCGTGGGGAGCGCCGCGTGCGG CCCGCGCTGCCCGGCGGCTGTGAGCGCTGC GGGCGCGGCGCGGGGCTTTGTGCGCTCCGC GTGTGCGCGAGGGGAGCGCGGCCGGGGGCG GTGCCCCGCGGTGCGGGGGGCTGCGAGGG GAACAAAGGCTGCGTGCGGGGTGTGTGCGT GGGGGGGTGAGCAGGGGGTGTGGGCGCGGC GGTCGGGCTGTAACCCCCCCCTGCACCCCC CTCCCCGAGTTGCTGAGCACGGCCCGGCTT CGGGTGCGGGCTCCGTGCGGGCGTGGCG CGGGGCTCGCCGTGCCGGGCGGGGGTGGC GGCAGGTGGGGTGCCGGGCGGGGCGGGGC CGCCTCGGGCCGGGGAGGGCTCGGGGGAGG GGCGCGGCGGCCCCGGAGCGCCGGCGGCTG TCGAGGCGCGGCGAGCCGCAGCCATTGCCT TTTATGGTAATCGTGCGAGAGGGCGCAGGG ACTTCCTTTGTCCCAAATCTGGCGGAGCCG AAATCTGGGAGGCGCCGCCGCACCCCCTCT AGCGGGCGCGGGCGAAGCGGTGCGGCGCCG GCAGGAAGGAAATGGGCGGGAGGGGCCTTC GTGCGTCGCCGCGCCGCCGTCCCCTTCTCC ATCTCCAGCCTCGGGGCTGCCGCAGGGGGA CGGCTGCCTTCGGGGGGACGGGGCAGGGC GGGGTTCGGCTTCTGGCGTGTGACCGGCGG |
| 29 | Helper/Rev; Rabbit beta globin poly A; RNA stability | AGATCTTTTTCCCTCTGCCAAAAATTATGG GGACATCATGAAGCCCCTTGAGCATCTGAC TTCTGGCTAATAAAGGAAATTTATTTTCAT TGCAATAGTGTGTTGGAATTTTTTGTGTCT CTCACTCGGAAGGACATATGGGAGGGCAAA TCATTTAAAACATCAGAATGAGTATTTGGT TTAGAGTTTGGCAACATATGCCCATATGCTG GCTGCCATGAACAAAGGTGGCTATAAAGAG GTCATCAGTATATGAAACAGCCCCCTGCTG TCCATTCCTTATTCCATAGAAAAGCCTTGA CTTGAGGTTAGATTTTTTTATATTTTGTT TTGTGTTATTTTTTCTTTAACATCCCTAA AATTTTCCTTACATGTTTTACTAGCCAGAT TTTTCCTCCTCTCCTGACTACTCCCAGTCA TAGCTGTCCCTCTTCTCTTATGAAGATC |
| 30 | Envelope; Beta globin intron; Enhance gene expression | GTGAGTTTGGGGACCCTTGATTGTTCTTTC TTTTTCGCTATTGTAAAATTCATGTTATAT GGAGGGGGCAAAGTTTTCAGGGTGTTGTTT AGAATGGGAAGATGTCCCTTGTATCACCAT GGACCCTCATGATAATTTTGTTCTTTCAC TTTCTACTCTGTTGACAACCATTGTCTCCT CTTATTTTCTTTTCATTTTCTGTAACTTTT TCGTTAAACTTTAGCTTGCATTTGTAACGA ATTTTTAAATTCACTTTTGTTTATTTGTCA GATTGTAAGTACTTTCTCTAATCACTTTTT TTTCAAGGCAATCAGGGTATATTATATTGT ACTTCAGCACAGTTTTAGAGAACAATTGTT ATAATTAAATGATAAGGTAGAATATTTCTG CATATAAATTCTGGCTGGCGTGGAAATATT CTTATTGGTAGAAACAACTACACCCTGGTC ATCATCCTGCCTTTCTCTTTATGGTTACAA TGATATACACTGTTTGAGATGAGGATAAAA TACTCTGAGTCCAAACCGGGCCCCTCTGCT AACCATGTTCATGCCTTCTTCTCTTTCCTA CAG |
| 31 | Envelope; Rabbit beta globin poly A; RNA stability | AGATCTTTTTCCCTCTGCCAAAAATTATGG GGACATCATGAAGCCCCTTGAGCATCTGAC TTCTGGCTAATAAAGGAAATTTATTTTCAT TGCAATAGTGTGTTGGAATTTTTTGTGTCT CTCACTCGGAAGGACATATGGGAGGGCAAA TCATTTAAAACATCAGAATGAGTATTTGGT TTAGAGTTTGGCAACATATGCCCATATGCT GGCTGCCATGAACAAAGGTTGGCTATAAAG AGGTCATCAGTATATGAAACAGCCCCCTGC TGTCCATTCCTTATTCCATAGAAAAGCCTT GACTTGAGGTTAGATTTTTTTTATATTTTG TTTTGTGTTATTTTTTCTTTAACATCCCT AAAATTTTCCTTACATGTTTTACTAGCCAG ATTTTTCCTCCTCTCCTGACTACTCCCAGT CATAGCTGTCCCTCTTCTCTTATGGAGATC |

| SEQ ID NO: | Description | Sequence |
|---|---|---|
| 32 | Primer | TAAGCAGAATTCATGAATTTGCCAGGAAGAT |
| 33 | Primer | CCATACAATGAATGGACACTAGGCGGCCGCACGAAT |
| 34 | Gag, Pol, Integrase fragment | GAATTCATGAATTTGCCAGGAAGATGGAAACCAAAAATGATAGGGGGAATTGGAGGTTTTATCAAAGTAAGACAGTATGATCAGATACTCATAGAAATCTGCGGACATAAAGCTATAGGTACAGTATTAGTAGGACCTACACCTGTCAACATAATTGGAAGAAATCTGTTGACTCAGATTGGCTGCACTTTAAATTTTCCCATTAGTCCTATTGAGACTGTACCAGTAAAATTAAAGCCAGGAATGGATGGCCCAAAAGTTAAACAATGGCCATTGACAGAAGAAAAAATAAAAGCATTAGTAGAAATTTGTACAGAAATGGAAAAGGAAGGAAAAATTTCAAAAATTGGGCCTGAAAATCCATACAATACTCCAGTATTTGCCATAAAGAAAAAAGACAGTACTAAATGGAGAAAATTAGTAGATTTCAGAGAACTTAATAAGAGAACTCAAGATTTCTGGGAAGTTCAATTAGGAATACCACATCCTGCAGGGTTAAAACAGAAAAAATCAGTAACAGTACTGGATGTGGGCGATGCATATTTTTCAGTTCCCTTAGATAAAGACTTCAGGAAGTATACTGCATTTACCATACCTAGTATAAACAATGAGACACCAGGGATTAGATATCAGTACAATGTGCTTCCACAGGGATGGAAAGGATCACCAGCAATATTCCAGTGTAGCATGACAAAAATCTTAGAGCCTTTTAGAAAACAAAATCCAGACATAGTCATCTATCAATACATGGATGATTTGTATGTAGGATCTGACTTAGAAATAGGGCAGCATAGAACAAAAATAGAGGAACTGAGACAACATCTGTTGAGGTGGGGATTTACCACACCAGACAAAAAACATCAGAAAGAACCTCCATTCCTTTGGATGGGTTATGAACTCCATCCTGATAAATGGACAGTACAGCCTATAGTGCTGCCAGAAAAAGACAGCTGGACTGTCAATGACATACAGAAATTAGTGGGAAAATTGAATTGGGCAAGTCAGATTTATGCAGGGATTAAAGTAAGGCAATTATGTAAACTTCTTAGGGGAACCAAAGCACTAACAGAAGTAGTACCACTAACAGAAGAAGCAGAGCTAGAACTGGCAGAAAACAGGGAGATTCTAAAAGAACCGGTACATGGAGTGTATTATGACCCATCAAAAGACTTAATAGCAGAAATACAGAAGCAGGGGCAAGGCCAATGGACATATCAAATTTATCAAGAGCCATTTAAAAATCTGAAAACAGGAAAGTATGCAAGAATGAAGGGTGCCCACACTAATGATGTGAAACAATTAACAGAGGCAGTGCAAAAAATAGCCACAGAAAGCATAGTAATATGGGGAAAGACTCCTAAATTTAAATTACCCATACAAAAGGAAACATGGGAAGCATGGTGGACAGAGTATTGGCAAGCCACCTGGATTCCTGAGTGGGAGTTTGTCAATACCCCTCCCTTAGTGAAGTTATGGTACCAGTTAGAGAAAGAACCCATAATAGGAGCAGAAACTTTCTATGTAGATGGGGCAGCCAATAGGGAAACTAAATTAGGAAAAGCAGGATATGTAACTGACAGAGGAAGACAAAAAGTTGTCCCCCTAACGGACACAACAAATCAGAAGACTGAGTTACAAGCAATTCATCTAGCTTTGCAGGATTCGGGATTAGAAGTAAACATAGTGACAGACTCACAATATGCATTGGGAATCATTCAAGCACAACCAGATAAGAGTGAATCAGAGTTAGTCAGTCAAATAATAGAGCAGTTAATAAAAAGGAAAAGGTCTACCTGGCATGGGTACCAGCACACAAAGGAATTGGAGGAAATGAACAAGTAGATAAATTGGTCAGTGCTGGAATCAGGAAAGTACTATTTTTAGATGGAATAGATAAGGCCCAAGAAGAACATGAGAAATATCACAGTAATTGGAGAGCAATGGCTAGTGATTTTAACCTACCACCTGTAGTAGCAAAAGAAATAGTAGCCAGCTGTGATAAATGTCAGCTAAAAGGGGAAGCCATGCATGGACAAGTAGACTGTAGCCCAGGAATATGGCAGCTAGATTGTACACATTTAGAAGGAAAAGTTATCTTGGTAGCAGTTCATGTAGCCAGTGGATATATAGAAGCAGAAGTAATTCCAGCAGAGACAGGGCAAGAAACAGCATACTTCCTCTTAAAATTAGCAGGAAGATGGCCAGTAAAAACAGTACATACAGACAATGGCAGCAATTTCACCAGTACTACAGTTAAGGCCGCCTGTTGGTGGGCGGGGATCAAGCAGGAATTTGGCATTCCCTACAATCCCCAAAGTCAAGGAGTAATAGAATCTATGAATAAAGAATTAAAGAAAATTATAGGACAGGTAAGAGATCAGGCTGAACATCTTAAGACAGCAGTACAAATGGCAGTATTCATCCACAATTTTAAAAGAAAAGGGGGGATTGGGGGGTACAGTGCAGGGGAAAGAATAGTAGACATAATAGCAACAGACATACAAACTAAAGAATTACAAAAACAAATTACAAAAATTCAAAATTTTCGGGTTTATTACAGGGACAGCAGAGATCCAGTTTGGAAAGGACCAGCAAAGCTCCTCTGGAAAGGTGAAGGGGCAGTAGTAATACAAGATAATAGTGACATAAAAGTAGTGCCAAGAAGAAAAGCAAAGATCATCAGGGATTATGGAAAACAGATGGCAGGTGATGATTGTGTGGCAAGTAGACAGGATGAGGATTAA |
| 35 | DNA Fragment containing Rev, RRE and rabbit beta globin poly A | TCTAGAATGGCAGGAAGAAGCGGAGACAGCGACGAAGAGCTCATCAGAACAGTCAGACTCATCAAGCTTCTCTATCAAAGCAACCCACCTCCCAATCCCGAGGGGACCCGACAGGCCCGAAGGAATAGAAGAAGAAGGTGGAGAAGAGACAGAGACAGATCCATTCGATTAGTGAACGGATCCTTGGCACTTATCTGGGACGATCTGCGGAGCCTGTGCCTCTTCAGCTACCACCGCTTGAGAGACTTACTCTTGATTGTAACGAGGATTGTGGAACTTCTGGGACGCAGGGGGTGGGAAGCCCTCAAATATTGGTGGAATCTCCTACAATATTGGAGTCAGGAGCTAAAGAATAGAGGAGCTTTGTTCCTTGGGTTCTTGGGAGCAGCAGGAAGCACTATGGGCGCAGCGTCAATGACGCTGACGGTACAGGCCAGACAATTATTGTCTGGTATAGTGCAGCAGCAGAACAATTTGCTGAGGGCTATTGAGGCGCAACAGCATCTGTTGCAACTCACAGTCTGGGGCATCAAGCAGCTCCAGGCAAGAATCCTGGCTGTGGAAAGATACCTAAAGGATCAACAGCTCCTAGATCTTTTTCCCTCTGCCAAAAATTATGGGGACATCATGAAGCCCCTTGAGCATCTGACTTCTGGCTAATAAAGGAAATTTATTTTCATTGCAATAGTGTGTTGGAATTTTTTGTGTCTCTCACTCGGAAGGACATATGGGAGGGCAAATCATTTAAACATCAGAATGAGTATTTGGTTTAGAGTTTGGCAACATATGCCATATGCTGGCTGCCATGAACAAAGGTGGCTATAAAGAGGTCATCAGTATATGAAACAGCCCCCTGCTGTCCATTCCTTATTCCATAGAAAAGCCTTGACTTGAGGTTAGATTTTTTTTATATTTTGTTTTGTGTTATTTTTTTCTTTAACATCCCTAAAATTTTCCTTACATGTTTTACTAGCCAGATTTTTCCTCCTCTCCTGACTACTCCCAGTCATAGCTGTCCCTCTTCTCTTATGAAGATCCCTCGACCTGCAGCCCAAGCTTGGCGTAATCATGGTCATAGCTGTTTCCTGTGTGAAATTGTTATCCGCTCACAATTCCACACAACATACGAGCCGGAAGCATAAAGTGTAAAGCCTGGGGTGCCTAATGAGTGAGCTAACTCACATTAATTGCGTTGCGCTCACTGCCCGCTTTCCAGTCGGGAAACCTGTCGTGCCAGCGGATCCGCATCTCAATTAGTCAGCAACCATAGTCCCGCCCCTAACTCCGCCCATCCCGCCCCTAACTCCGCCCAGTTCCGCCCATTCTCCGCCCCATGGCTGACTAATTTTTTTATTTATGCAGAGGCCGAGGCCGCCTCGGCCTCTGAGCTATTCCAGAAGTAGTGAGGAGGCTTTTTTGGAGGCCTAGGCTTTTGCAAAAAGCTAACTTGTTTATTGCAGCTTATAATGGTTACAAATAAAGCAATAGCATCACAAA |

| SEQ ID NO: | Description | Sequence |
|---|---|---|
| | | TTTCACAAATAAAGCATTTTTTTCACTGCA TTCTAGTTGTGGTTTGTCCAAACTCATCAA TGTATCTTATCAGCGGCCGCCCCGGG |
| 36 | DNA fragment containing the CAG enhancer/ promoter/ intron sequence | ACGCGTTAGTTATTAATAGTAATCAATTAC GGGGTCATTAGTTCATAGCCCATATATGGA GTTCCGCGTTACATAACTTACGGTAAATGG CCCGCCTGGCTGACCGCCCAACGACCCCCG CCCATTGACGTCAATAATGACGTATGTTCC CATAGTAACGCCAATAGGGACTTTCCATTG ACGTCAATGGGTGGACTATTTACGGTAAAC TGCCCACTTGGCAGTACATCAAGTGTATCA TATGCCAAGTACGCCCCCTATTGACGTCAA TGACGGTAAATGGCCCGCCTGGCATTATGC CCAGTACATGACCTTATGGGACTTTCCTAC TTGGCAGTACATCTACGTATTAGTCATCGC TATTACCATGGTCGAGGTGAGCCCCACGT TCTGCTTCACTCTCCCCATCTCCCCCCCCT CCCCACCCCCAATTTTGTATTTATTTATTT TTTAATTATTTTGTGCAGCGATGGGGGCGG GGGGGGGGGGGCGCGCGCCAGGCGGGGCG GGGCGGGGCGAGGGGCGGGGCGGGGCGAGG CGGAGAGGTGCGGCGGCAGCCAATCAGAGC GGCGCGCTCCGAAAGTTTCCTTTTATGGCG AGGCGGCGGCGGCGGCGGCCCTATAAAAAG CGAAGCGCGCGGCGGGCGGGAGCTGCTGCG TTGCCTTCGCCCCGTGCCCCGCTCCGCGCC GCCTCGCGCCGCCCGCCCCGGCTCTGACTG ACCGCGTTACTCCCACAGGTGAGCGGGCGG GACGGCCCTTCTCCTCCGGGCTGTAATTAG CGCTTGGTTTAATGACGGCTCGTTTCTTTT CTGTGGCTGCGTGAAAGCCTTAAAGGGCTC CGGGAGGGCCCTTTGTGCGGGGGGGAGCGG CTCGGGGGGTGCGTGCGTGTGTGTGTGCGT GGGGAGCGCCGCGTGCGGCCCGCGCTGCCC GGCGGCTGTGAGCGCTGCGGGCGCGGCGCG GGGCTTTGTGCGCTCCGCGTGTGCGCGAGG GGAGCGCGGCCGGGCGGGTGCCCGCGCGT GCGGGGGGCTGCGAGGGGAACAAAGGCTG CGTGCGGGGTGTGTGCGTGGGGGGGTGAGC AGGGGGTGTGGGCGCGGCGGTCGGGCTGTA ACCCCCCCCTGCACCCCCCTCCCCGAGTTG CTGAGCACGGCCCGGCTTCGGGTGCGGGGC TCCGTGCGGGGCGTGGCGCGGGGCTCGCCG TGCCGGGCGGGGGTGGCGGCAGGTGGGGG TGCCGGGCGGGGCGGGGCCGCCTCGGGCCG GGGAGGGCTCGGGGGAGGGGCGCGGCGGCC CCGGAGCGCCGGCGGCTGTCGAGGCGCGGC GAGCCGCAGCCATTGCCTTTTATGGTAATC GTGCGAGAGGGCGCAGGGACTTCCTTTGTC CCAAATCTGGCGGAGCCGAAATCTGGGAGG CGCCGCCGCACCCCCTCTAGCGGGCGCGGG CGAAGCGGTGCGGCGCCGGCAGGAAGGAAA TGGGCGGGAGGGCCTTCGTGCGTCGCCGC GCCGCCGTCCCCTTCTCCGCCGCCTCCAGCCTC GGGGCTGCCGCAGGGGACGGCTGCCTTCG GGGGGGACGGGCAGGGCGGGGTTCGGCTT CTGGCGTGTGACCGGCGGGAATTC |
| 37 | DNA fragment containing VSV-G | GAATTCATGAAGTGCCTTTTGTACTTAGCC TTTTTATTCATTGGGGTGAATTGCAAGTTC ACCATAGTTTTTCCACACAACCAAAAAGGA AACTGGAAAATGTTCCTTCTAATTACCAT TATTGCCGTCAAGCTCAGATTTAAATTGG CATAATGACTTAATAGGCACAGCCTTACAA GTCAAAATGCCCAAGAGTCACAAGGCTATT CAAGCAGACGGTTGGATGTGTCATGCTTCC AAATGGGTCACTACTTGTGATTTCCGCTGG TATGGACCGAAGTATATAACACATTCCATC CGATCCTTCACTCCATCTGTAGAACAATGC AAGGAAAGCATTGAACAAACGAAACAAGGA ACTTGGCTGAATCCAGGCTTCCCTCCTCAA AGTTGTGGATATGCAACTGTGACGGATGCC GAAGCAGTGATTGTCCAGGTGACTCCTCAC CATGTGCTGGTTGATGAATACACAGGAGAA TGGGTTGATTCACAGTTCATCAACGGAAAA TGCAGCAATTACATATGCCCCACTGTCCAT AACTCTACAACCTGGCATTCTGACTATAAG GTCAAAGGGCTATGTGATTCTAACCTCATT TCCATGGACATCACCTTCTTCTCAGAGGAC GGAGAGCTATCATCCCTGGGAAAGGAGGGC ACAGGGTTCAGAAGTAACTACTTTGCTTAT GAAACTGGAGGCAAGGCCTGCAAAATGCAA TACTGCAAGCATTGGGGAGTCAGACTCCCA TCAGGTGTCTGGTTCGAGATGGCTGATAAG GATCTCTTTGCTGCAGCCAGATTCCCTGAA TGCCCAGAAGGGTCAAGTATCTCTGCTCCA TCTCAGACCTCAGTGGATGTAAGTCTAATT CAGGACGTTGAGAGGATCTTGGATTATTCC CTCTGCCAAGAAACCTGGAGCAAAATCAGA GCGGGTCTTCCAATCTCTCCAGTGGATCTC AGCTATCTTGCTCCTAAAAACCCAGGAACC GGTCCTGCTTTCACCATAATCAATGGTACC CTAAAATACTTTGAGACCAGATACATCAGA GTCGATATTGCTGCTCCAATCCTCTCAAGA ATGGTCGGAATGATCAGTGGAACTACCACA GAAAGGGAACTGTGGGATGACTGGGCACCA TATGAAGACGTGGAAATTGGACCCAATGGA GTTCTGAGGACCAGTTCAGGATATAAGTTT CCTTTATACATGATTGGACATGGTATGTTG GACTCCGATCTTCATCTTAGCTCAAAGGCT CAGGTGTTCGAACATCCTCACATTCAAGAC GCTGCTTCGCAACTTCCTGATGATGAGAGT TTATTTTTTGGTGATACTGGGCTATCCAAA AATCCAATCGAGCTTGTAGAAGGTTGGTTC AGTAGTTGGAAAAGCTCTATTGCCTCTTTT TTCTTTATCATAGGGTTAATCATTGGACTA TTCTTGGTTCTCCGAGTTGGTATCCATCTT TGCATTAAATTAAAGCACACCAAGAAAGA CAGATTTATACAGACATAGAGATGAGAATT C |
| 38 | Rev; RSV promoter; Transcription | ATGGCAGGAAGAAGCGGAGACAGCGACGAA GAACTCCTCAAGGCAGTCAGACTCATCAAG TTTCTCTATCAAAGCAACCCACCTCCCAAT CCCGAGGGGACCCGACAGGCCCGAAGGAAT AGAAGAAGAAGGTGGAGAGAGAGACAGAGA CAGATCCATTCGATTAGTGAACGGATCCTT AGCACTTATCTGGGACGATCTGCGGAGCCT GTGCCTCTTCAGCTACCACCGCTTGAGAGA CTTACTCTTGATTGTAACGAGGATTGTGGA ACTTCTGGGACGCAGGGGGTGGGAAGCCCT CAAATATTGTGGAATCTCCTACAATATTG GAGTCAGGAGCTAAGAATAG |
| 39 | Rev; HIV Rev; Nuclear export and stabilize viral mRNA | ATGGCAGGAAGAAGCGGAGACAGCGACGAA GAACTCCTCAAGGCAGTCAGACTCATCAAG TTTCTCTATCAAAGCAACCCACCTCCCAAT CCCGAGGGGACCCGACAGGCCCGAAGGAAT AGAAGAAGAAGGTGGAGAGAGAGACAGAGA CAGATCCATTCGATTAGTGAACGGATCCTT AGCACTTATCTGGGACGATCTGCGGAGCCT GTGCCTCTTCAGCTACCACCGCTTGAGAGA CTTACTCTTGATTGTAACGAGGATTGTGGA ACTTCTGGGACGCAGGGGGTGGGAAGCCCT CAAATATTGTGGAATCTCCTACAATATTG GAGTCAGGAGCTAAGAATAG |
| 40 | RSV promoter and HIV Rev | CAATTGCGATGTACGGGCCAGATATACGCG TATCTGAGGGGACTAGGGTGTGTTTAGGCG AAAAGCGGGGCTTCGGTTGTACGCGGTTAG GAGTCCCCTCAGGATATAGTAGTTTCGCTT TTGCATAGGGAGGGGGAAATGTAGTCTTAT GCAATACACTTGTAGTCTTGCAACATGGTA ACGATGAGTTAGCAACATGCCTTACAAGGA GAGAAAAAGCACCGTGCATGCCGATTGGTG GAAGTAAGGTGGTACGATCGTGCCTTATTA GGAAGGCAACAGACAGGTCTGACATGGATT GGACGAACCACTGAATTCCGCATTGCAGAG ATAATTGTATTTAAGTGCCTAGCTCGATAC |

| SEQ ID NO: | Description | Sequence |
|---|---|---|
| | | AATAAACGCCATTTGACCATTCACCACATT GGTGTGCACCTCCAAGCTCGAGCTCGTTTA GTGAACCGTCAGATCGCCTGGAGACGCCAT CCACGCTGTTTTGACCTCCATAGAAGACAC CGGGACCGATCCAGCCTCCCCTCGAAGCTA GCGATTAGGCATCTCCTATGGCAGGAAGAA GCGGAGACAGCGACGAAGAACTCCTCAAGG CAGTCAGACTCATCAAGTTTCTCTATCAAA GCAACCCACCTCCCAATCCCGAGGGGACCC GACAGGCCCGAAGGAATAGAAGAAGAAGGT GGAGAGAGAGACAGAGACAGATCCATTCGA TTAGTGAACGGATCCTTAGCACTTATCTGG GACGATCTGCGGAGCCTGTGCCTCTTCAGC TACCACCGCTTGAGAGACTTACTCTTGATT GTAACGAGGATTGTGGAACTTCTGGGACGC AGGGGGTGGGAAGCCCTCAAATATTGGTGG AATCTCCTACAATATTGGAGTCAGGAGCTA AGAATAGTCTAGA |
| 41 | Elongation Factor-1 alpha (EF1-alpha) promoter | CCGGTGCCTAGAGAAGGTGGCGCGGGGTAA ACTGGGAAAGTGATGTCGTGTACTGGCTCC GCCTTTTTCCCGAGGGTGGGGGAGAACCGT ATATAAGTGCAGTAGTCGCCGTGAACGTTC TTTTTTCGCAACGGGTTTGCCGCCAGAACAC AGGTAAGTGCCGTGTGTGGTTCCCGCGGGC CTGGCCTCTTTACGGGTTATGGCCCTTGCG TGCCTTGAATTACTTCCACGCCCCTGGCTG CAGTACGTGATTCTTGATCCCGAGCTTCGG GTTGGAAGTGGGTGGGAGAGTTCGAGGCCT TGCGCTTAAGGAGCCCCTTCGCCTCGTGCT TGAGTTGAGGCCTGGCCTGGGCGCTGGGGC CGCCGCGTGCGAATCTGGTGGCACCTTCGC GCCTGTCTCGCTGCTTTCGATAAGTCTCTA GCCATTTAAAATTTTTGATGACCTGCTGCG ACGCTTTTTTTCTGGCAAGATAGTCTTGTA AATGCGGGCCAAGATCTGCACACTGGTATT TCGGTTTTTGGGGCCGCGGGCGGCGACGGG GCCCGTGCGTCCCAGCGCACATGTTCGGCG AGGCGGGGCCTGCGAGCGCGCGCCACCGAGA ATCGGACGGGGGTAGTCTCAAGCTGGCCGG CCTGCTCTGGTGCCTGGCCTCGCGCCGCCG TGTATCGCCCCGCCCTGGGCGGCAAGGCTG GCCCGGTCGGCACCAGTTGCGTGAGCGGAA AGATGGCCGCTTCCCGGCCCTGCTGCAGGG AGCTCAAAATGGAGGACGCGGCGCTCGGGA GAGCGGGCGGGTGAGTCACCCACACAAAGG AAAAGGGCTTTCCGTCCTCAGCCGTCGCT TCATGTGACTCCACGGAGTACCGGGCGCCG TCCAGGCACCTCGATTAGTTCTCGAGCTTT TGGAGTACGTCGTCTTTAGGTTGGGGGGAG GGGTTTTATGCGATGGAGTTTCCCCACACT GAGTGGGTGGAGACTGAAGTTAGGCCAGCT TGGCACTTGATGTAATTCTCCTTGGAATTT GCCCTTTTTGAGTTTGGATCTTGGTTCATT CTCAAGCCTCAGACAGTGGTTCAAAGTTTT TTTCTTCCATTTCAGGTGTCGTGA |
| 42 | Promoter; PGK | GGGGTTGGGGTTGCGCCTTTTCCAAGGCAG CCCTGGGTTTGCGCAGGGACGCGGCTGCTC TGGGCGTGGTTCCGGGAAACGCAGCGGCGC CGACCCTGGGTCTCGCACATTCTTCACGTC CGTTCGCAGCGTCACCCGGATCTTCGCCGC TACCCTTGTGGGCCCCCCGGCGACGCTTCC TGCTCCGCCCCTAAGTCGGGAAGGTTCCTT GCGGTTCGCGGCGTGCCGGACGTGACAAAC GGAAGCCGCACGTCTCACTAGTACCCTCGC AGACGGACAGCGCCAGGGAGCAATGGCAGC GCGCCGACCGCGATGGGCTGTGGCCAATAG CGGCTGCTCAGCAGGGCGCGCCGAGAGCAG CGGCCGGGAAGGGGCGGTGCGGGAGGCGGG GTGTGGGCGGTAGTGTGGGCCCTGTTCCT GCCCGCGCGGTGTTCCGCATTCTGCAAGCC TCCGGAGCGCACGTCGGCAGTCGGCTCCCT CGTTGACCGAATCACCGACCTCTCTCCCCA G |
| 43 | Promoter; UbC | GCGCCGGGTTTTGGCGCCTCCCGCGGGCGC CCCCCTCCTCACGGCGAGCGCTGCCACGTC AGACGAAGGGCGCAGGAGCGTTCCTGATCC TTCCGCCCGGACGCTCAGGACAGCGGCCCG CTGCTCATAAGACTCGGCCTTAGAACCCCA GTATCAGCAGAAGGACATTTTAGGACGGGA CTTGGGTGACTCTAGGGCACTGGTTTTCTT TCCAGAGAGCGGAACAGGCGAGGAAAAGTA GTCCCTTCTCGGCGATTCTGCGGAGGGATC TCCGTGGGGCGGTGAACGCCGATGATTATA TAAGGACGCGCCGGGTGTGGCACAGCTAGT TCCGTCGCAGCCGGGATTTGGGTCGCGGTT CTTGTTTGTGGATCGCTGTGATCGTCACTT GGTGAGTTGCGGGCTGCTGGGCTGGCCGGG GCTTTCGTGGCCGCCGGGCGCTCGGTGGG ACGGAAGCGTGTGGAGAGACCGCCAAGGGC TGTAGTCTGGGTCCGCGAGCAAGGTTGCCC TGAACTGGGGGTTGGGGGAGCGCACAAAA TGGCGGCTGTTCCCGAGTCTTGAATGGAAG ACGCTTGTAAGGCGGGCTGTGAGGTCGTTG AAACAAGGTGGGGGCGCGGTGGGCGGCAA GAACCCAAGGTCTTGAGGCCTTCGCTAATG CGGGAAAGCTCTTATTCGGGTGAGATGGGC TGGGGCACCATCTGGGGACCCTGACGTGAA GTTTGTCACTGACTGGAGAACTCGGGTTTG TCGTCTGGTTGCGGGGCGGCAGTTATGCG GTGCCGTTGGGCAGTGCACCCGTACCTTTG GGAGCGCGCGCCTCGTCGTGTCGTGACGTC ACCCGTTCTGTTGCTTATAATGCAGGGTG GGGCCACCTGCCGGTAGGTGTGCGGTAGGC TTTTTCTCCGTCGCAGGACGCAGGGTTCGG CCTAGGGTAGGCTCTCCTGAATCGACAGGC GCCGGACCTCTGGTGAGGGGAGGGATAAGT GAGGCGTCAGTTTCTTTGGTCGGTTTTATG TACCTATCTTCTTAAGTAGCTGAAGCTCCG GTTTTGAACTATGCGCTCGGGGTTGGCGAG TGTGTTTTGTGAAGTTTTTTAGGCACCTTT TGAAATGTAATCATTTGGGTCAATATGTAA TTTTCAGTGTTAGACTAGTAAA |
| 44 | Poly A; SV40 | GTTTATTGCAGCTTATAATGGTTACAAATA AAGCAATAGCATCACAAATTTCACAAATAA AGCATTTTTTTCACTGCATTCTAGTTGTGG TTTGTCCAAACTCATCAATGTATCTTATCA |
| 45 | Poly A, bGH | GACTGTGCCTTCTAGTTGCCAGCCATCTGT TGTTTGCCCCTCCCCCGTGCCTTCCTTGAC CCTGGAAGGTGCCACTCCCACTGTCCTTTC CTAATAAAATGAGGAAATTGCATCGCATTG TCTGAGTAGGTGTCATTCTATTCTGGGGGG TGGGGTGGGGCAGGACAGCAAGGGGGAGGA TTGGGAAGACAATAGCAGGCATGCTGGGGA TGCGGTGGGCTCTATGG |
| 46 | Envelope; RD114 | ATGAAACTCCCAACAGGAATGGTCATTTTA TGTAGCCTAATAATAGTTCGGGCAGGGTTT GACGACCCCGCAAGGCTATCGCATTAGTA CAAAAACAACATGGTAAACCATGCGAATGC AGCGGAGGGCAGGTATCCGAGGCCCCACCC AACTCCATCCAACAGGTAACTTGCCCAGGC AAGACGCCTACTTAATGACCAACCAAAAA TGGAAATGCAGAGTCACTCCAAAAAATCTC ACCCCTAGCGGGGGAGAACTCCAGAACTGC CCCTGTAACACTTTCCAGGACTCGATGCAC AGTTCTTGTTATACTGAATACCGGCAATGC AGGGCGAATAATAAGACATACTACACGGCC ACCTTGCTTAAAATACGGTCTGGGAGCCTC AACGAGGTACAGATATTACAAAACCCCAAT CAGCTCCTACAGTCCCCTTGTAGGGGCTCT ATAAATCAGCCCGTTTGCTGGAGTGCCACA GCCCCATCCATATCTCCGATGGTGGAGGA CCCCTCGATACTAAGAGAGTGTGGACAGTC CAAAAAAGGCTAGAACAAATTCATAAGGCT ATGCATCCTGAACTTCAATACCACCCCTTA |

| SEQ ID NO: | Description | Sequence |
|---|---|---|
| | | GCCCTGCCCAAAGTCAGAGATGACCTTAGC CTTGATGCACGGACTTTTGATATCCTGAAT ACCACTTTTAGGTTACTCCAGATGTCCAAT TTTTAGCCTTGCCCAAGATTGTTGGCTCTGT TTAAAACTAGGTACCCCTACCCCTCTTGCG ATACCCACTCCCTCTTTAACCTACTCCCTA GCAGACTCCCTAGCGAATGCCTCCTGTCAG ATTATACCTCCCCTCTTGGTTCAACCGATG CAGTTCTCCAACTCGTCCTGTTTATCTTCC CCTTTCATTAACGATACGGAACAAATAGAC TTAGGTGCAGTCACCTTTACTAACTGCACC TCTGTAGCCAATGTCAGTAGTCCTTTATGT GCCCTAAACGGGTCAGTCTTCCTCTGTGGA AATAACATGGCATACACCTATTTACCCCAA AACTGGACAGGACTTTGCGTCCAAGCCTCC CTCCTCCCCGACATTGACATCATCCCGGGG GATGAGCCAGTCCCCATTCCTGCCATTGAT CATTATATACATAGACCTAAACGAGCTGTA CAGTTCATCCCTTTACTAGCTGGACTGGGA ATCACCGCAGCATTCACCACCGGAGCTACA GGCCTAGGTGTCTCCGTCACCCAGTATACA AAATTATCCCATCAGTTAATATCTGATGTC CAAGTCTTATCCGGTACCATACAAGATTTA CAAGACCAGGTAGACTCGTTAGCTGAAGTA GTTCTCCAAAATAGGAGGGGACTGGACCTA CTAACGGCAGAACAAGGAGGAATTTGTTTA GCCTTACAAGAAAATGCTGTTTTTATGCT AACAAGTCAGGAATTGTGAGAAACAAAATA AGAACCCTACAAGAAGAATTACAAAAACGC AGGGAAAGCCTGGCATCCAACCCTCTCTGG ACCGGGCTGCAGGGCTTTCTTCCGTACCTC CTACCTCTCCTGGGACCCCTACTCACCCTC CTACTCATACTAACCATTGGGCCATGCGTT TTCAATCGATTGGTCCAATTTGTTAAAGAC AGGATCTCAGTGGTCCAGGCTCTGGTTTTG ACTCAGCAATATCACCAGCTAAAACCCATA GAGTACGAGCCATGA |
| 47 | Envelope; GALV | ATGCTTCTCACCTCAAGCCCGCACCACCTT CGGCACCAGATGAGTCCTGGGAGCTGGAAA AGACTGATCATCCTCTTAAGCTGCGTATTC GGAGACGGCAAAACGAGTCTGCAGAATAAG AACCCCCACCAGCCTGACCCCTCACCTGG CAGGTACTGTCCCAAACTGGGGACGTTGTC TGGGACAAAAAGGCAGTCCAGCCCCTTTGG ACTTGGTGGCCCTCTCTTACACCTGATGTA TGTGCCCTGGCGGCCGGCCTTGAGTCCTGG GATATCCCGGGATCCGATGTATCGTCCTCT AAAAAGAGTTAGACCTCCTGATTCAGACTAT ACTGCCGCTTATAAGCAAATCACCTGGGGA GCCATAGGGTGCAGCTACCCTCGGGCTAGG ACCAGGATGGCAAATTCCCCCTTCTACGTG TGTCCCCGAGCTGGCCGAACCCATTCAGAA GCTAGGAGGTGTGGGGGGCTAGAATCCCTA TACTGTAAAGAATGGAGTTGTGAGACCACG GGTACCGTTTATTGGCAACCCAAGTCCTCA TGGGACCTCATAACTGTAAAATGGGACCAA AATGTGAAATGGGAGCAAAAATTTCAAAAG TGTGAACAAACCGGCTGGTGTAACCCCCTC AAGATAGACTTCACAGAAAAGGAAACTC TCCAGAGATTGGATAACGGAAAAAACCTGG GAATTAAGGTTCTATGTATATGGACACCCA GGCATACAGTTGACTATCCGCTTAGAGGTC ACTAACATGCCGGTTGTGGCAGTGGGCCCA GACCCTGTCCTTGCGGAACAGGGACCTCCT AGCAAGCCCCTCACTCTCCCTCTCTCCCCA CGGAAAGCGCCGCCCACCCCTCTACCCCCG GCGGCTAGTGAGCAAACCCCTGCGGTGCAT GGAGAAACTGTTACCCTAAACTCTCCGCCT CCCACCAGTGGCGACCGACTCTTTGGCCTT GTGCAGGGGCCTTCCTAACCTTGAATGCT ACCAACCCAGGGGCACTAAGTCTTGCTGG CTCTGTTTGGGCATGAGCCCCCCTTATTAT GAAGGGATAGCCTCTTCAGGAGAGGTCGCT TATACCTCCAACCATACCCGATGCCACTGG |
| 48 | Envelope; FUG | GGGGCCCAAGGAAAGCTTACCCTCACTGAG GTCTCCGGACTCGGGTCATGCATAGGGAAG GTGCCTCTTACCCATCAACATCTTTGCAAC CAGACCTTACCCATCAATTCCTCTAAAAAC CATCAGTATCTGCTCCCCTCAAACCATAGC TGGTGGGCCTGCAGCACTGGCCTCACCCCC TGCCTCTCCACCTCAGTTTTTAATCAGTCT AAAGACTTCTGTGTCCAGGTCCAGCTGATC CCCCGCATCTATTACCATTCTGAAGAAACC TTGTTACAAGCCTATGACAAATCACCCCCC AGGTTTAAAAGAGAGCCTGCCTCACTTACC CTAGCTGTCTTCCTGGGGTTAGGGATTGCG GCAGGTATAGGTACTGGCTCAACCGCCCTA ATTAAAGGGCCCATAGACCTCCAGCAAGGC CTAACCAGCCTCCAAATCGCCATTGACGCT GACCTCCGGGCCCTTCAGGACTCAATCAGC AAGCTAGAGGACTCACTGACTTCCCTATCT GAGGTAGTACTCCAAAATAGGAGAGGCCTT GACTTACTATTCCTTAAAGAAGGAGGCCTC TGCGCGGCCCTAAAAGAAGAGTGCTGTTTT TATGTAGACCACTCAGGTGCAGTACGAGAC TCCATGAAAAAACTTAAAGAAAGACTAGAT AAAAGACAGTTAGAGCGCCAGAAAAACCAA AACTGGTATGAAGGGTGGTTCAATAACTCC CCTTGGTTTACTACCCTACTATCAACCATC GCTGGGCCCCTATTGCTCCTCCTTTTGTTA CTCACTCTTGGGCCCTGCATCATCAATAAA TTAATCCAATTCATCAATGATAGGATAAGT GCAGTCAAAATTTTAGTCCTTAGACAGAAA TATCAGACCCTAGATAACGAGGAAAACCTT TAA ATGGTTCCGCAGGTTCTTTTGTTTGTACTC CTTCTGGGTTTTTCGTTGTGTTTCGGGAAG TTCCCCATTTACACATACCAGACGAACTT GGTCCCTGGAGCCCTATTGACATACACCAT CTCAGCTGTCCAAATAACCTGGTTGTGGAG GATGAAGGATGTACCAACCTGTCCGAGTTC TCCTACATGGAACTCAAAGTGGGATACATC TCAGCCATCAAAGTGAACGGGTTCACTTGC ACAGGTGTTGTGACAGAGGCAGAGACCTAC ACCAACTTTGTTGGTTATGTCACAACCACA TTCAAGAGAAAGCATTTCCGCCCGCACCCA GACGCATGTAGAGCCGCGTATAACTGGAAG ATGGCCGGTGACCCCAGATATGAAGAGTCC CTACACAATCCATACCCCGACTACCACTGG CTTCGAACTGTAAGAACCACCAAAGAGTCC CTCATTATCATATCCCCAAGTGTGACAGAT TTGGACCCATATGACAAATCCCTTCACTCA AGGGTCTTCCCTGGCGGAAAGTGCTCAGGA ATAACGGTGTCCTCTACCTACTGCTCAACT AACCATGATTACACCATTTGGATGCCCGAG AATCCGAGACCAAGGACACCTTGTGACATT TTTACCAATAGCAGAGGGAAGAGAGCATCC AACGGGAACAAGACTTGCGGCTTTGTGGAT GAAAGAGGCCTGTATAAGTCTCTAAAAG GAGCATGCAGGCTCAAGTTATGTGGAGTTC TTGGACTTAGACTTATGGATGGAACATGGG TCGCGATGCAAACATCAGATGAGACCAAT GGTGCCCTCCAGATCAGTTGGTGAATTTGC ACGACTTTCGCTCAGACGAGATCGAGCATC TCGTTGTGGAGGAGTTAGTAAGAAAAGAG AGGAATGTCTGGATGCATTAGAGTCCATCA TGACCACCAAGTCAGTAAGTTTCAGACGTC TCAGTCACCTGAGAAAACTTGTCCCAGGGT TTGGAAAAGCATATACCATATTCAACAAAA CCTTGATGGAGGCTGATGCTCACTACAAGT CAGTCCGGACCTGGAATGAGATCATCCCCT CAAAAGGTGTTTGAAAGTTGGAGGAAGGT GCCATCCTCATGTGAACGGGGTGTTTTTCA ATGGTATAATATTAGGGCCTGACGACCATG TCCTAATCCCAGAGATGCAATCATCCCTCC TCCAGCAACATATGGAGTTGTTGGAATCTT CAGTTATCCCCCTGATGCACCCCCTGGCAG ACCCTTCTACAGTTTTCAAAGAAGGTGATG |

-continued

| SEQ ID NO: | Description | Sequence |
|---|---|---|
| | | AGGCTGAGGATTTTGTTGAAGTTCACCTCC<br>CCGATGTGTACAAACAGATCTCAGGGGTTG<br>ACCTGGGTCTCCCGAACTGGGGAAAGTATG<br>TATTGATGACTGCAGGGGCCATGATTGGCC<br>TGGTGTTGATATTTTCCCTAATGACATGGT<br>GCAGAGTTGGTATCCATCTTTGCATTAAAT<br>TAAAGCACACCAAGAAAAGACAGATTTATA<br>CAGACATAGAGATGAACCGACTTGGAAAGT<br>AA |
| 49 | Envelope; LCMV | ATGGGTCAGATTGTGACAATGTTTGAGGCT<br>CTGCCTCACATCATCGATGAGGTGATCAAC<br>ATTGTCATTATTGTGCTTATCGTGATCACG<br>GGTATCAAGGCTGTCTACAATTTTGCCACC<br>TGTGGGATATTCGCATTGATCAGTTTCCTA<br>CTTCTGGCTGGCAGGTCCTGTGGCATGTAC<br>GGTCTTAAGGGACCCGACATTTACAAAGGA<br>GTTTACCAATTTAAGTCAGTGGAGTTTGAT<br>ATGTCACATCTGAACCTGACCATGCCCAAC<br>GCATGTTCAGCCAACAACTCCCACCATTAC<br>ATCAGTATGGGGACTTCTGGACTAGAATTG<br>ACCTTCACCAATGATTCCATCATCAGTCAC<br>AACTTTTGCAATCTGACCTCTGCCTTCAAC<br>AAAAAGACCTTTGACCACACACTCATGAGT<br>ATAGTTTCGAGCCTACACCTCAGTATCAGA<br>GGGAACTCCAACTATAAGGCAGTATCCTGC<br>GACTTCAACAATGGCATAACCATCCAATAC<br>AACTTGACATTCTCAGATCGACAAAGTGCT<br>CAGAGCCAGTGTAGAACCTTCAGAGGTAGA<br>GTCCTAGATATGTTTAGAACTGCCTTCGGG<br>GGGAAATACATGAGGAGTGGCTGGGGCTGG<br>ACAGGCTCAGATGGCAAGACCACCTGGTGT<br>AGCCAGACGAGTTACCAATACCTGATTATA<br>CAAAATAGAACCTGGGAAAACCACTGCACA<br>TATGCAGGTCCTTTTGGGATGTCCAGGATT<br>CTCCTTTCCCAAGAGAAGACTAAGTTCTTC<br>ACTAGGAGACTAGCGGGCACATTCACCTGG<br>ACTTTGTCAGACTCTTCAGGGGTGGAGAAT<br>CCAGGTGGTTATTGCCTGACCAAATGGATG<br>ATTCTTGCTGCAGAGCTTAAGTGTTTCGGG<br>AACACAGCAGTTGCGAAATGCAATGTAAAT<br>CATGATGCCGAATTCTGTGACATGCTGCGA<br>CTAATTGACTACAACAAGGCTGCTTTGAGT<br>AAGTTCAAAGAGGACGTAGAATCTGCCTTG<br>CACTTATTCAAAACAACAGTGAATTCTTTG<br>ATTTCAGATCAACTACTGATGAGGAACCAC<br>TTGAGAGATCTGATGGGGGTGCCATATTGC<br>AATTACTCAAAGTTTTGGTACCTAGAACAT<br>GCAAAGACCGGCGAAACTAGTGTCCCCAAG<br>TGCTGGCTTGTCACCAATGGTTCTTACTTA<br>AATGAGACCCACTTCAGTGATCAAATCGAA<br>CAGGAAGCCGATAACATGATTACAGAGATG<br>TTGAGGAAGGATTACATAAAGAGGCAGGGG<br>AGTACCCCCCTAGCATTGATGGACCTTCTG<br>ATGTTTTCCACATCTGCATATCTAGTCAGC<br>ATCTTCCTGCACCTTGTCAAAATACCAACA<br>CACAGGCACATAAAAGGTGGCTCATGTCCA<br>AAGCCACACCGATTAACCAACAAAGGAATT<br>TGTAGTTGTGGTGCATTTAAGGTGCCTGGT<br>GTAAAAACCGTCTGGAAAAGACGCTGA |
| 50 | Envelope; FPV | ATGAACACTCAAATCCTGGTTTTCGCCCTT<br>GTGGCAGTCATCCCCACAAATGCAGACAAA<br>ATTTGTCTTGGACATCATGCTGTATCAAAT<br>GGCACCAAAGTAAACACACTCACTGAGAGA<br>GGAGTAGAAGTTGTCAATGCAACGGAAACA<br>GTGGAGCGGACAAACATCCCCAAAATTTGC<br>TCAAAAGGGAAAAGAACCACTGATCTTGGC<br>CAATGCGGACTGTTAGGGACCATTACCGGA<br>CCACCTCAATGCGACCAATTTCTAGAATTT<br>TCAGCTGATCTAATAATCGAGAGACGAGAA<br>GGAAATGATGTTTGTTACCCGGGGAAGTTT<br>GTTAATGAAGAGGCATTGCGACAAATCCTC<br>AGAGGATCAGGTGGGATTGACAAAGAAACA<br>ATGGGATTCACATATAGTGGAATAAGGACC<br>AACGGAACAACTAGTGCATGTAGAAGATCA<br>GGGTCTTCATTCTATGCAGAAATGGAGTGG<br>CTCCTGTCAAATACAGACAATGCTGCTTTC<br>CCACAAATGACAAAATCATACAAAAACACA<br>AGGAGAGAATCAGCTCTGATAGTCTGGGGA<br>ATCCACCATTCAGGATCAACCACCGAACAG<br>ACCAAACTATATGGGAGTGGAAATAAACTG<br>ATAACAGTCGGGAGTTCCAAATATCATCAA<br>TCTTTTGTGCCGAGTCCAGGAACACGACCG<br>CAGATAAATGGCCAGTCCGGACGGATTGAT<br>TTTCATTGGTTGATCTTGGATCCCAATGAT<br>ACAGTTACTTTTAGTTTCAATGGGGCTTTC<br>ATAGCTCCAAATCGTGCCAGCTTCTTGAGG<br>GGAAAGTCCATGGGGATCCAGAGCGATGTG<br>CAGGTTGATGCCAATTGCGAAGGGGAATGC<br>TACCACAGTGGAGGGACTATAACAAGCAGA<br>TTGCCTTTTCAAAACATCAATAGCAGAGCA<br>GTTGGCAAATGCCCAAGATATGTAAAACAG<br>GAAAGTTTATTATTGGCAACTGGGATGAAG<br>AACGTTCCCGAACCTTCCAAAAAAAGGAAA<br>AAAAGAGGCCTGTTTGGCGCTATAGCAGGG<br>TTTATTGAAAATGGTTGGGAAGGTCTGGTC<br>GACGGGTGGTACGGTTTCAGGCATCAGAAT<br>GCACAAGGAGAAGGAACTGCAGCAGACTAC<br>AAAAGCACCCAATCGGCAATTGATCAGATA<br>ACCGGAAAGTTAAATAGACTCATTGAGAAA<br>ACCAACCAGCAATTTGAGCTAATAGATAAT<br>GAATTCACTGAGGTGGAAAAGCAGATTGGC<br>AATTTAATTAACTGGACCAAAGACTCCATC<br>ACAGAAGTATGGTCTTACAATGCTGAACTT<br>CTTGTGGCAATGGAAAACCAGCACACTATT<br>GATTTGGCTGATTCAGAGATGAACAAGCTG<br>TATGAGCGAGTGAGGAAACAATTAAGGGAA<br>AATGCTGAAGAGGATGGCACTGGTTGCTTT<br>GAAATTTTTCATAAATGTGACGATGATTGT<br>ATGGCTAGTATAAGGAACAATACTTATGAT<br>CACAGCAAATACAGAGAAGAAGCGATGCAA<br>AATAGAATACAAATTGACCCAGTCAAATTG<br>AGTAGTGGCTACAAAGATGTGATACTTTGG<br>TTTAGCTTCGGGGCATCATGCTTTTTGCTT<br>CTTGCCATTGCAATGGGCCTTGTTTTCATA<br>TGTGTGAAGAACGGAAACATGCGGTGCACT<br>ATTTGTATATAA |
| 51 | Envelope; RRV | AGTGTAACAGAGCACTTTAATGTGTATAAG<br>GCTACTAGACCATACCTAGCACATTGCGCC<br>GATTGCGGGGACGGGTACTTCTGCTATAGC<br>CCAGTTGCTATCGAGGAGATCCGAGATGAG<br>GCGTCTGATGGCATGCTTAAGATCCAAGTC<br>TCCGCCCAAATAGGTCTGGACAAGGCAGGC<br>ACCCACGCCCACACGAAGCTCCGATATATG<br>GCTGGTCATGATGTTCAGGAATCTAAGAGA<br>GATTCCTTGAGGGTGTACACGTCCGCAGCG<br>TGCTCCATACATGGGACGATGGGACACTTC<br>ATCGTCGCACACTGTCCACCAGGCGACTAC<br>CTCAAGGTTTCGTTCGAGGACGCAGATTCG<br>CACGTGAAGGCATGTAAGGTCCAATACAAG<br>CACAATCCATTGCCGGTGGGTAGAGAGAAG<br>TTCGTGGTTAGACCACACTTTGGCGTAGAG<br>CTGCCATGCACCTCATACCAGCTGACAACG<br>GCTCCCACCGACGAGGAGATTGACATGCAT<br>ACACCGCCAGATATACCGGATCGCACCCTG<br>CTATCACAGACGGCGGGCAACGTCAAAATA<br>ACAGCAGGCGGCAGGACTATCAGGTACAAC<br>TGTACCTGCGGCCGTGACAACGTAGGCACT<br>ACCAGTACTGACAAGACCATCAACACATGC<br>AAGATTGACCAATGCCATGCTGCCGTCACC<br>AGCCATGACAAATGGCAATTTACCTCTCCA<br>TTTGTTCCCAGGGCTGATCAGACAGCTAGG<br>AAAGGCAAGGTACACGTTCCGTTCCCTCTG<br>ACTAACGTCACCTGCCGAGTGCCGTTGGCT<br>CGAGCGCCGGATGCCACCTATGGTAAGAAG<br>GAGGTGACCCTGAGATTACACCCAGATCAT<br>CCGACGCTCTTCTCCTATAGGAGTTTAGGA<br>GCCGAACCGCACCCGTACGAGGAATGGGTT |

| SEQ ID NO: | Description | Sequence |
|---|---|---|
|  |  | GACAAGTTCTCTGAGCGCATCATCCCAGTG ACGGAAGAAGGGATTGAGTACCAGTGGGGC AACAACCCGCCGGTCTGCCTGTGGGCGCAA CTGACGACCGAGGGCAAACCCCATGGCTGG CCACATGAAATCATTCAGTACTATTATGGA CTATACCCCGCCGCCACTATTGCCGCAGTA TCCGGGGCGAGTCTGATGGCCCTCCTAACT CTGGCGGCCACATGCTGCATGCTGGCCACC GCGAGGAGAAAGTGCCTAACACCGTACGCC CTGACGCCAGGAGCGGTGGTACCGTTGACA CTGGGGCTGCTTTGCTGCGCACCGAGGGCG AATGCA |
| 52 | Envelope; MLV 10A1 | AGTGTAACAGAGCACTTTAATGTGTATAAG GCTACTAGACCATACCTAGCACATTGCGCC GATTGCGGGGACGGGTACTTCTGCTATAGC CCAGTTGCTATCGAGGAGATCCGAGATGAG GCGTCTGATGGCATGCTTAAGATCCAAGTC TCCGCCCAAATAGGTCTGGACAAGGCAGGC ACCCACGCCCACACGAAGCTCCGATATATG GCTGGTCATGATGTTCAGGAATCTAAGAGA GATTCCTTGAGGGTGTACGTCCGCAGCG TGCTCCATACATGGGACGATGGGACACTTC ATCGTCGCACACTGTCCACCAGGCGACTAC CTCAAGGTTTCGTTCGAGGACGCAGATTCG CACGTGAAGGCATGTAAGGTCCAATACAAG CACAATCCATTGCCGGTGGGTAGAGAGAAG TTCGTGGTTAGACCACACTTTGGCGTAGAG CTGCCATGCACCTCATACCAGCTGACAACG GCTCCCACCGACGAGGAGATTGACATGCAT ACACCGCCAGATATACCGGATCGCACCCTG CTATCACAGACGGCGGGCAACGTCAAAATA ACAGCAGGCGGCAGGACTATCAGGTACAAC TGTACCTGCGCGCCAACGTAGGCACT ACCAGTACTGACAAGACCATCAACACATGC AAGATTGACCAATGCCATGCTGCCGTCACC AGCCATGACAAATGGCAATTTACCTCTCCA TTTGTTCCCAGGGCTGATCAGACAGCTAGG AAAGGCAAGGTACAGTTCCGTTCCCTCTG ACTAACGTCACCTGCCGAGTGCCGTTGGCT CGAGCGCCGGATGCCACCTATGGTAAGAAG GAGGTGACCCTGAGATTACACCCAGATCAT CCGACGCTCTTTCTCCTATAGAGTTTAGGA GCCGAACCGCACCCGTACGAGGAATGGGTT GACAAGTTCTCTGAGCGCATCATCCCAGTG ACGGAAGAAGGGATTGAGTACCAGTGGGGC AACAACCCGCCGGTCTGCCTGTGGGCGCAA CTGACGACCGAGGGCAAACCCCATGGCTGG CCACATGAAATCATTCAGTACTATTATGGA CTATACCCCGCCGCCACTATTGCCGCAGTA TCCGGGGCGAGTCTGATGGCCCTCCTAACT CTGGCGGCCACATGCTGCATGCTGGCCACC GCGAGGAGAAAGTGCCTAACACCGTACGCC CTGACGCCAGGAGCGGTGGTACCGTTGACA CTGGGGCTGCTTTGCTGCGCACCGAGGGCG AATGCA |
| 53 | Envelope; Ebola | ATGGGTGTTACAGG

| SEQ ID NO: | Description | Sequence |
|---|---|---|
| 58 | FDPS target sequence #3 | GCCATGTACATGGCAGGAATT |
| 59 | FDPS target sequence #4 | GCAGAAGGAGGCTGAGAAAGT |
| 60 | Non-targeting sequence | GCCGCTTTGTAGGATAGAGCTCGAGCTCTA TCCTACAAAGCGGCTTTTT |
| 61 | Forward primer | AGGAATTGATGGCGAGAAGG |
| 62 | Reverse primer | CCCAAAGAGGTCAAGGTAATCA |
| 63 | Forward primer | AGCGCGGCTACAGCTTCA |
| 64 | Reverse primer | GGCGACGTAGCACAGCTTCT |
| 65 | Left Inverted Terminal Repeat (Left ITR) | CCTGCAGGCAGCTGCGCGCTCGCTCGCTCA CTGAGGCCGCCCGGGCGTCGGGCGACCTTT GGTCGCCCGGCCTCAGTGAGCGAGCGAGCG CGCAGAGAGGGAGTGGCCAACTCCATCACT AGGGGTTCCT |
| 66 | Right Inverted Terminal Repeat (Right ITR) | GAGCGGCCGCAGGAACCCCTAGTGATGGAG TTGGCCACTCCCTCTCTGCGCGCTCGCTCG CTCACTGAGGCCGGGCGACCAAAGGTCGCC CGACGCCCGGGCTTTGCCCGGGCGGCCTCA GTGAGCGAGCGAGCGCGCAGCTGCCTGCAG G |

While certain of the preferred embodiments of the present invention have been described and specifically exemplified above, it is not intended that the invention be limited to such embodiments. Various modifications may be made thereto without departing from the scope and spirit of the present invention.

What is claimed is:

1. A viral vector comprising:
an EF-1 alpha promoter and
at least one encoded shRNA or microRNA that, when expressed, inhibits production of farnesyl diphosphate synthase (FDPS),
wherein the at least one encoded shRNA or microRNA comprises a sequence having at least 80 percent identity with SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, or SEQ ID NO: 10.

2. The viral vector of claim 1, wherein the at least one encoded shRNA or microRNA activates a gamma delta T cell (GD T cell).

3. An immunotherapy-based system comprising:
(a) at least one helper plasmid comprising DNA sequences for expressing a functional protein derived from each of a gag, pol, and rev gene;
(b) an envelope plasmid comprising a DNA sequence for expressing an envelope protein capable of infecting a target cell; and
(c) a therapeutic vector comprising:
an EF-1 alpha promoter and
at least one encoded shRNA or microRNA that, when expressed, inhibits production of farnesyl diphosphate synthase (FDPS),
wherein the at least one encoded shRNA or microRNA comprises a sequence having at least 80 percent identity with SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, or SEQ ID NO: 10.

4. The immunotherapy-based system of claim 3, wherein the target cell is a cancer cell.

5. The immunotherapy-based system of claim 4, wherein the at least one encoded shRNA or microRNA activates a GD T cell.

6. A method of treating a condition associated with the mevalonate pathway in a subject in patients in need thereof, the method comprising administering or having administered a therapeutically-effective amount of an immunotherapy-based composition comprising:
(a) at least one helper plasmid comprising DNA sequences for expressing a functional protein derived from each of a gag, pol, and rev gene;
(b) an envelope plasmid comprising a DNA sequence for expressing an envelope protein capable of infecting a target cell; and
(c) a therapeutic vector comprising:
an EF-1 alpha promoter and
at least one encoded shRNA or microRNA that, when expressed, inhibits production of farnesyl diphosphate synthase (FDPS),
wherein the at least one encoded shRNA or microRNA comprises a sequence having at least 80 percent identity with SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, or SEQ ID NO: 10.

7. The method of claim 6, wherein the at least one encoded shRNA or microRNA activates a GD T cell.

8. The method of claim 6, wherein the condition associated with the mevalonate pathway is a cancer, and wherein the target cell is a cancer cell.

9. The method of claim 8, wherein the at least one encoded shRNA or microRNA activates a GD T cell.

10. A method of treating a condition associated with the mevalonate pathway in a subject in patients in need thereof, the method comprising administering or having administered a therapeutically-effective amount of a viral vector comprising:
an EF-1 alpha promoter and
at least one encoded shRNA or microRNA that, when expressed, inhibits production of farnesyl diphosphate synthase (FDPS),
wherein the at least one encoded shRNA or microRNA comprises a sequence having at least 80 percent identity with SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, or SEQ ID NO: 10.

11. The method of claim 10, wherein the condition associated with the mevalonate pathway is a cancer.

12. A method of treating a condition associated with the mevalonate pathway in a subject in patients in need thereof, the method comprising administering or having administered a therapeutically-effective amount of a viral vector comprising at least one encoded shRNA or microRNA that, when expressed, inhibits production of farnesyl diphosphate synthase (FDPS) and activates a GD T cell, wherein the at least one encoded shRNA or microRNA comprises a sequence having at least 80 percent identity with SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, or SEQ ID NO: 10.

13. The method of claim 12, wherein the condition associated with the mevalonate pathway is a cancer.

* * * * *

```
                         SEQUENCE LISTING

Sequence total quantity: 67
SEQ ID NO: 1            moltype = DNA  length = 53
FEATURE                 Location/Qualifiers
misc_feature            1..53
                        note = FDPS shRNA sequence #1
source                  1..53
                        mol_type = other DNA
                        organism = synthetic construct
SEQUENCE: 1
gtcctggagt acaatgccat tctcgagaat ggcattgtac tccaggactt ttt          53

SEQ ID NO: 2            moltype = DNA  length = 53
FEATURE                 Location/Qualifiers
misc_feature            1..53
                        note = FDPS shRNA sequence #2
source                  1..53
                        mol_type = other DNA
                        organism = synthetic construct
SEQUENCE: 2
gcaggatttc gttcagcact tctcgagaag tgctgaacga aatcctgctt ttt          53

SEQ ID NO: 3            moltype = DNA  length = 53
FEATURE                 Location/Qualifiers
misc_feature            1..53
                        note = FDPS shRNA sequence #3
source                  1..53
                        mol_type = other DNA
                        organism = synthetic construct
SEQUENCE: 3
gccatgtaca tggcaggaat tctcgagaat tcctgccatg tacatggctt ttt          53

SEQ ID NO: 4            moltype = DNA  length = 53
FEATURE                 Location/Qualifiers
misc_feature            1..53
                        note = FDPS shRNA sequence #4
source                  1..53
                        mol_type = other DNA
                        organism = synthetic construct
SEQUENCE: 4
gcagaaggag gctgagaaag tctcgagact ttctcagcct ccttctgctt ttt          53

SEQ ID NO: 5            moltype = DNA  length = 116
FEATURE                 Location/Qualifiers
misc_feature            1..116
                        note = miR30 FDPS sequence #1
source                  1..116
                        mol_type = other DNA
                        organism = synthetic construct
SEQUENCE: 5
aaggtatatt gctgttgaca gtgagcgaca ctttctcagc ctccttctgc gtgaagccac   60
```

```
agatggcaga aggaggctga gaaagtgctg cctactgcct cggacttcaa ggggct       116

SEQ ID NO: 6           moltype = DNA  length = 114
FEATURE                Location/Qualifiers
misc_feature           1..114
                       note = miR30 FDPS sequence #2
source                 1..114
                       mol_type = other DNA
                       organism = synthetic construct
SEQUENCE: 6
aaggtatatt gctgttgaca gtgagcgaca ctttctcagc ctccttctgc gtgaagccac   60
agatggcaga agggctgaga aagtgctgcc tactgcctcg gacttcaagg ggct         114

SEQ ID NO: 7           moltype = DNA  length = 91
FEATURE                Location/Qualifiers
misc_feature           1..91
                       note = miR30 FDPS sequence #3
source                 1..91
                       mol_type = other DNA
                       organism = synthetic construct
SEQUENCE: 7
tgctgttgac agtgagcgac tttctcagcc tccttctgcg tgaagccaca gatggcagaa   60
ggaggctgag aaagttgcct actgcctcgg a                                  91

SEQ ID NO: 8           moltype = DNA  length = 115
FEATURE                Location/Qualifiers
misc_feature           1..115
                       note = miR155 FDPS sequence #1
source                 1..115
                       mol_type = other DNA
                       organism = synthetic construct
SEQUENCE: 8
cctggaggct tgctgaaggc tgtatgctga ctttctcagc ctccttctgc ttttggccac   60
tgactgagca gaagggctga gaaagtcagg acacaaggcc tgttactagc actca        115

SEQ ID NO: 9           moltype = DNA  length = 114
FEATURE                Location/Qualifiers
misc_feature           1..114
                       note = miR21 FDPS sequence #1
source                 1..114
                       mol_type = other DNA
                       organism = synthetic construct
SEQUENCE: 9
catctccatg gctgtaccac cttgtcggga ctttctcagc ctccttctgc ctgttgaatc   60
tcatggcaga aggaggcgag aaagtctgac attttggtat ctttcatctg acca         114

SEQ ID NO: 10          moltype = DNA  length = 114
FEATURE                Location/Qualifiers
misc_feature           1..114
                       note = miR185 FDPS sequence #1
source                 1..114
                       mol_type = other DNA
                       organism = synthetic construct
SEQUENCE: 10
gggcctggct cgagcagggg gcgagggata ctttctcagc ctccttctgc tggtcccctc   60
cccgcagaag gaggctgaga aagtccttcc ctcccaatga ccgcgtcttc gtcg         114

SEQ ID NO: 11          moltype = DNA  length = 228
FEATURE                Location/Qualifiers
misc_feature           1..228
                       note = Rous Sarcoma virus (RSV) promoter
source                 1..228
                       mol_type = other DNA
                       organism = synthetic construct
SEQUENCE: 11
gtagtcttat gcaatactct tgtagtcttg caacatggta acgatgagtt agcaacatgc   60
cttacaagga gagaaaaagc accgtgcatg ccgattggtg gaagtaaggt ggtacgatcg   120
tgccttatta ggaaggcaac agacgggtct gacatggatt ggacgaacca ctgaattgcc   180
gcattgcaga gatattgtat ttaagtgcct agctcgatac aataaacg                228

SEQ ID NO: 12          moltype = DNA  length = 180
FEATURE                Location/Qualifiers
misc_feature           1..180
                       note = 5 Long terminal repeat (LTR)
source                 1..180
                       mol_type = other DNA
                       organism = synthetic construct
SEQUENCE: 12
ggtctctctg gttagaccag atctgagcct gggagctctc tggctaacta gggaacccac   60
```

```
tgcttaagcc tcaataaagc ttgccttgag tgcttcaagt agtgtgtgcc cgtctgttgt    120
gtgactctgg taactagaga tccctcagac ccttttagtc agtgtggaaa atctctagca    180

SEQ ID NO: 13          moltype = DNA  length = 41
FEATURE                Location/Qualifiers
misc_feature           1..41
                       note = Psi Packaging signal
source                 1..41
                       mol_type = other DNA
                       organism = synthetic construct
SEQUENCE: 13
tacgccaaaa attttgacta gcggaggcta aaggagaga g                         41

SEQ ID NO: 14          moltype = DNA  length = 233
FEATURE                Location/Qualifiers
misc_feature           1..233
                       note = Rev response element (RRE)
source                 1..233
                       mol_type = other DNA
                       organism = synthetic construct
SEQUENCE: 14
aggagctttg ttccttgggt tcttgggagc agcaggaagc actatgggcg cagcctcaat    60
gacgctgacg gtacaggcca gacaattatt gtctggtata gtgcagcagc agaacaattt    120
gctgagggct attgaggcgc aacagcatct gttgcaactc acagtctggg gcatcaagca    180
gctccaggca agaatcctgg ctgtggaaag atacctaaag gatcaacagc tcc           233

SEQ ID NO: 15          moltype = DNA  length = 118
FEATURE                Location/Qualifiers
misc_feature           1..118
                       note = Central polypurine tract (cPPT)
source                 1..118
                       mol_type = other DNA
                       organism = synthetic construct
SEQUENCE: 15
ttttaaaaga aaaggggggga ttggggggta cagtgcaggg gaaagaatag tagacataat   60
agcaacagac atacaaacta aagaattaca aaaacaaatt acaaaattca aaatttta     118

SEQ ID NO: 16          moltype = DNA  length = 217
FEATURE                Location/Qualifiers
misc_feature           1..217
                       note = Polymerase III shRNA promoters- H1 promoter
source                 1..217
                       mol_type = other DNA
                       organism = synthetic construct
SEQUENCE: 16
gaacgctgac gtcatcaacc cgctccaagg aatcgcgggc ccagtgtcac taggcgggaa    60
cacccagcgc gcgtgcgccc tggcaggaag atggctgtga gggacagggg agtggcgccc    120
tgcaatattt gcatgtcgct atgtgttctg ggaaatcacc ataaacgtga aatgtctttg    180
gatttgggaa tcttataagt tctgtatgag accactt                             217

SEQ ID NO: 17          moltype = DNA  length = 590
FEATURE                Location/Qualifiers
misc_feature           1..590
                       note = Long WPRE sequence
source                 1..590
                       mol_type = other DNA
                       organism = synthetic construct
SEQUENCE: 17
aatcaacctc tgattacaaa atttgtgaaa gattgactgg tattcttaac tatgttgctc    60
cttttacgct atgtggatac gctgctttaa tgcctttgta tcatgctatt gcttcccgta    120
tggctttcat tttctcctcc ttgtataaat cctggttgct gtctctttat gaggagttgt    180
ggcccgttgt caggcaacgt ggcgtggtgt gcactgtgtt tgctgacgca accccccactg   240
gttggggcat tgccaccacc tgtcagctcc tttccgggac tttcgctttc ccctcccta    300
tgccacggc ggaactcatc gccgcctgcc ttgcccgctg ctggacaggg gctcggctgt    360
tgggcactga caattccgtg tgttgtcgg ggaaatcatc gtcctttcct ggctgctcg    420
cctgtgttgc cacctggatt ctgcgcggga cgtcctcctg ctacgtccct tcggccctca    480
atccagcgga ccttccttcc cgcggcctgc tgccggctct gcggcctctt ccgcgtcttc    540
gccttcgccc tcagacgagt cggatctccc tttgggccgc ctccccgcct                590

SEQ ID NO: 18          moltype = DNA  length = 250
FEATURE                Location/Qualifiers
misc_feature           1..250
                       note = 3 delta LTR
source                 1..250
                       mol_type = other DNA
                       organism = synthetic construct
SEQUENCE: 18
tggaagggct aattcactcc caacgaagat aagatctgct tttgcttgt actgggtctc     60
tctggttaga ccagatctga gcctgggagc tctctggcta actagggaac ccactgctta    120
```

```
agcctcaata aagcttgcct tgagtgcttc aagtagtgtg tgcccgtctg ttgtgtgact    180
ctggtaacta gagatccctc agacccttttt agtcagtgtg gaaaatctct agcagtagta   240
gttcatgtca                                                          250
```

| SEQ ID NO: 19 | moltype = DNA  length = 290 |
|---|---|
| FEATURE | Location/Qualifiers |
| misc_feature | 1..290 |
| | note = Helper/Rev- Chicken beta actin (CAG) promoter-Transcription |
| source | 1..290 |
| | mol_type = other DNA |
| | organism = synthetic construct |

```
SEQUENCE: 19
gctattacca tgggtcgagg tgagccccac gttctgcttc actctcccca tctcccccc    60
ctccccaccc ccaattttgt atttatttat tttttaatta ttttgtgcag cgatgggggc   120
ggggggggg gggcgcgcg ccaggcgggg cgggcgggg cgaggggcgg ggcggggcga     180
ggcggagagg tgcggcggca gccaatcaga gcggcgcgct ccgaaagttt ccttttatgg   240
cgaggcggcg gcggcggcgg ccctataaaa agcgaagcgc gcggcgggcg             290
```

| SEQ ID NO: 20 | moltype = DNA  length = 1503 |
|---|---|
| FEATURE | Location/Qualifiers |
| misc_feature | 1..1503 |
| | note = Helper/Rev- HIV Gag- Viral capsid |
| source | 1..1503 |
| | mol_type = other DNA |
| | organism = synthetic construct |

```
SEQUENCE: 20
atgggtgcga gagcgtcagt attaagcggg ggagaattag atcgatggga aaaaattcgg   60
ttaaggccag ggggaaagaa aaaatataaa ttaaaacata tagtatgggc aagcagggag   120
ctagaacgat tcgcagttaa tcctggcctg ttagaaacat caggaaggctg tagacaaata   180
ctgggacagc tacaaccatc ccttcagaca ggatcagaag aacttagatc attatataat   240
acagtagcaa ccctctattg tgtgcatcaa aggatagaga taaaagacac caaggaagct   300
ttagacaaga tagaggaaga gcaaaacaaa agtaagaaaa agcacagca agcagcagct   360
gacacaggac acagcaatca ggtcagccaa aattacccta gtgtgcagaa catccaggggg   420
caaatggtac atcaggccat atcacctaga actttaaatg catgggtaaa agtagtagaa   480
gagaaggctt tcagcccaga agtgataccc atgttttcag cattatcaga aggagccacc   540
ccacaagatt taaacaccat gctaaacaca gtgggggga tcaagcagc catgcaaatg   600
ttaaaagaga ccatcaatga ggaagctgca gaatgggata gagtgcatcc agtgcatgca   660
gggcctattg caccaggcca gatgagagaa ccaaggggaa gtgacatagc aggaactact   720
agtacccttc aggaacaaat aggatggatg acacataatc cacctatccc agtaggagaa   780
atctataaaa gatggataat cctgggatta aataaaatag taagaatgta tagccctacc   840
agcattctgg acataagaca aggaccaaag gaacccttta gagactatgt agaccgattc   900
tataaaactc taagagccga gcaagcttca caagaggtaa aaaattggat gacagaaacc   960
ttgttggtcc aaaatgcgaa cccagattgt aagactattt taaaagcatt gggaccagga  1020
gcgacactag aagaaatgat gacagcatgt caggagtgg ggggaccggg ccataaagca   1080
agagtttttg ctgaagcaat gagccaagta acaaatccag ctaccataat gatacagaaa   1140
ggcaattttta ggaaccaaag aaaagttgtt aagtgtttca attgtggcaa agaagggcac  1200
atagccaaaa attgcagggc ccctaggaaa aaggggctgtt ggaaatgtgg aaggaagga   1260
caccaaatga aagattgtac tgagagacag gctaatttttt tagggaagat ctggccttcc  1320
cacaagggaa ggccagggaa ttttcttcag agcagaccag agccaacagc cccaccagaa   1380
gagagcttca ggtttgggga agagacaaca actccctctc agaagcagga gccgatagac  1440
aaggaactgt atcctttagc ttccctcaga tcactctttg gcagcgaccc ctcgtcacaa   1500
taa                                                                1503
```

| SEQ ID NO: 21 | moltype = DNA  length = 1872 |
|---|---|
| FEATURE | Location/Qualifiers |
| misc_feature | 1..1872 |
| | note = Helper/Rev- HIV Pol- Protease and reverse transcriptase |
| source | 1..1872 |
| | mol_type = other DNA |
| | organism = synthetic construct |

```
SEQUENCE: 21
atgaatttgc caggaagatg gaaaccaaaa atgataggg gaattggagg ttttatcaaa    60
gtaggacagt atgatcagat actcatagaa atctgcggac ataaagctat aggtacagta   120
ttagtaggac ctacacctgt caacataatt ggaagaaatc tgttgactca gattggctgc   180
actttaaatt ttcccattag tcctattgag actgtaccag taaaattaaa gccaggaatg   240
gatggcccaa aagttaaaca atggccattg acagaagaaa aaataaaagc attagtagaa   300
atttgtacag aaatggaaaa ggaaggaaaa atttcaaaaa ttgggcctga aaatccatac   360
aatactccag tatttgccat aaagaaaaaa gacagtacta aatggagaaa attagtagat   420
ttcagagaac ttaataagag aactcaagat ttctgggaag ttcaattagg aataccacat   480
cctgcagggt taaaacagaa aaaatcagta acagtactgg atgtgggcga tgcatatttt   540
tcagttccct tagataaaga cttcaggaag tatactgcat ttaccatacc tagtataaac   600
aatgagacac caggggattag atatcagtac aatgtgctca cagggatga aaggatca    660
ccagcaatat tccagtgtag catgacaaaa atcttagagc cttttagaaa acaaaatcca   720
gacatagtca tctatcaata catggatgat ttgtatgtag gatctgactt agaaataggg   780
cagcatagaa caaaaataga ggaactgaga caacatctgt tgaggtgggg atttaccaca   840
ccagacaaaa aacatcagaa agaacctcca ttcctttgga tgggttatga actccatcct   900
gataaatgga cagtacagcc tatagtgctg ccagaaaagg acagctggac tgtcaatgac   960
```

```
atacagaaat tagtgggaaa attgaattgg gcaagtcaga tttatgcagg gattaaagta    1020
aggcaattat gtaaacttct taggggaacc aaagcactaa cagaagtagt accactaaca    1080
gaagaagcag agctagaact ggcagaaaac agggagattc taaaagaacc ggtacatgga    1140
gtgtattatg acccatcaaa agacttaata gcagaaatac agaagcaggg gcaaggccaa    1200
tggacatatc aaatttatca agagccattt aaaaatctga aaacaggaaa atatgcaaga    1260
atgaaggggtg cccacactaa tgatgtgaaa caattaacag aggcagtaca aaaaatagcc    1320
acagaaagca tagtaatatg gggaaagact cctaaattta aattacccat acaaaaggaa    1380
acatgggaag catggtggac agagtattgg caagccacct ggattcctga gtgggagttt    1440
gtcaataccc ctcccttagt gaagttatgg taccagttag agaaagaacc cataatagga    1500
gcagaaactt tctatgtaga tggggcagcc aataggaaaa ctaaattagg aaaagcagga    1560
tatgtaactg acagaggaag acaaaaagtt gtcccoctaa cggacacaac aaatcagaag    1620
actgagttac aagcaattca tctagctttg caggattcgg gattagaagt aaacatagtg    1680
acagactcac aatatgcatt gggaatcatt caagcacaac cagataagag tgaatcagag    1740
ttagtcagtc aaataataga gcagttaata aaaaaggaaa aagtctacct ggcatgggta    1800
ccagcacaca aaggaattgg aggaaatgaa caagtagatg ggttggtcag tgctggaatc    1860
aggaaagtac ta                                                        1872

SEQ ID NO: 22           moltype = DNA  length = 867
FEATURE                 Location/Qualifiers
misc_feature            1..867
                        note = Helper Rev- HIV Integrase- Integration of viral RNA
source                  1..867
                        mol_type = other DNA
                        organism = synthetic construct
SEQUENCE: 22
tttttagatg gaatagataa ggcccaagaa gaacatgaga aatatcacag taattggaga    60
gcaatggcta gtgattttaa cctaccacct gtagtagcaa aagaaatagt agccagctgt    120
gataaatgtc agctaaaagg ggaagccatg catggacaag tagactgtag cccaggaata    180
tggcagctag attgtacaca tttagaagga aaagttatct tggtagcagt tcatgtagcc    240
agtggatata tagaagcaga agtaattcca gcagagacag ggcaagaaac agcatactttc    300
ctcttaaaat tagcaggaag atggccagta aaaacagtac atacagacaa tggcagcaat    360
ttcaccagta ctacagttaa ggccgcctgt tggtgggcgg ggatcaagca ggaatttggc    420
attccctaca atccccaaag tcaaggagta atagaatcta tgaataaaga attaagaaa    480
attataggac aggtaagaga tcaggctgaa catcttaaga cagcagtaca aatggcagta    540
ttcatccaca attttaaaag aaaagggggg attgggggggt acagtgcagg ggaaagagta    600
gtagacataa tagcaacaga catacaaact aaagaattac aaaaacaaat tacaaaaatt    660
caaaattttc gggtttatta cagggacagc agagatccag tttggaaagg accagcaaag    720
ctcctctgga aaggtgaagg ggcagtagta atacaagata atagtgacat aaaagtagtg    780
ccaagaagaa aagcaaagat catcagggat tatggaaaac agatggcagg tgatgattgt    840
gtggcaagta gacaggatga ggattaa                                        867

SEQ ID NO: 23           moltype = DNA  length = 234
FEATURE                 Location/Qualifiers
misc_feature            1..234
                        note = Helper/Rev- HIV RRE- Binds Rev element
source                  1..234
                        mol_type = other DNA
                        organism = synthetic construct
SEQUENCE: 23
aggagctttg ttccttgggt tcttgggagc agcaggaagc actatgggcg cagcgtcaat    60
gacgctgacg gtacaggcca gacaattatt gtctggtata gtgcagcagc agaacaattt    120
gctgagggct attgaggcgc aacagcatct gttgcaactc acagtctggg gcatcaagca    180
gctccaggca agaatcctgg ctgtggaaag atacctaaag gatcaacagc tcct           234

SEQ ID NO: 24           moltype = DNA  length = 351
FEATURE                 Location/Qualifiers
misc_feature            1..351
                        note = Helper/Rev- HIV Rev- Nuclear export and stabilize
                         viral mRNA
source                  1..351
                        mol_type = other DNA
                        organism = synthetic construct
SEQUENCE: 24
atggcaggaa gaagcggaga cagcgacgaa gaactcctca aggcagtcag actcatcaag    60
tttctctatc aaagcaaccc acctcccaat cccgagggga cccgacaggc ccgaaggaat    120
agaagaagaa ggtggagaga gagacagaga cagatccatt cgattagtga acggatcctt    180
agcacttatc tgggacgatc tgcggagcct gtgcctcttc agctaccacc gcttgagaga    240
cttactcttg attgtaacga ggattgtgga acttctggga cgcagggggt gggaagccct    300
caaatattgg tggaatctcc tacaatattg gagtcaggag ctaaagaata g              351

SEQ ID NO: 25           moltype = DNA  length = 577
FEATURE                 Location/Qualifiers
misc_feature            1..577
                        note = Envelope- CMV promoter- Transcription
source                  1..577
                        mol_type = other DNA
                        organism = synthetic construct
SEQUENCE: 25
acattgatta ttgactagtt attaatagta atcaattacg gggtcattag ttcatagccc    60
```

```
atatatggag ttccgcgtta cataacttac ggtaaatggc ccgcctggct gaccgcccaa  120
cgacccccgc ccattgacgt caataatgac gtatgttccc atagtaacgc caatagggac  180
tttccattga cgtcaatggg tggagtattt acggtaaact gcccacttgg cagtacatca  240
agtgtatcat atgccaagta cgccccctat tgacgtcaat gacggtaaat ggcccgcctg  300
gcattatgcc cagtacatga ccttatggga ctttcctact tggcagtaca tctacgtatt  360
agtcatcgct attaccatgg tgatgcggtt ttggcagtac atcaatgggc gtggatagcg  420
gtttgactca cggggatttc caagtctcca ccccattgac gtcaatggga gtttgttttg  480
gcaccaaaat caacgggact ttccaaaatg tcgtaacaac tccgccccat tgacgcaaat  540
gggcggtagg cgtgtacggt gggaggtcta tataagc                           577

SEQ ID NO: 26           moltype = DNA   length = 1519
FEATURE                 Location/Qualifiers
misc_feature            1..1519
                        note = Envelope- VSV-G- Glycoprotein envelope-cell entry
source                  1..1519
                        mol_type = other DNA
                        organism = synthetic construct
SEQUENCE: 26
atgaagtgcc ttttgtactt agcctttta ttcattgggg tgaattgcaa gttcaccata   60
gttttttccac acaaccaaaa aggaaactgg aaaaatgttc cttctaatta ccattattgc  120
ccgtcaagct cagatttaaa ttggcataat gacttaatag gcacagcctt acaagtcaaa  180
atgccaaaga gtcacaaggc tattcaagca acgggttgaa tgtgtcatgc ttccaaatgg  240
gtcactactt tgtgatttcc ctggtatgga ccgaagtata taacacattc atccgatcc  300
ttcactccat ctgtagaaca atgcaaggaa agcattgaac aaacgaaaca aggaacttgg  360
ctgaatccag gcttccctcc tcaaagttgt ggatatgcaa ctgtgacgga tgccgaagca  420
gtgattgtcc aggtgactcc tcaccatgtg ctggttgatg aatacacagg agaatgggtt  480
gattcacagt tcatcaacgg aaaatgcagc aattacatat gccccactgt ccataactct  540
acaacctggc attctgacta taaggtcaaa gggctatgtg attctaacct catttccatg  600
gacatccacct tcttctcaga ggacggagag ctatcatccc tgggaaagga gggcacaggg  660
ttcagaagta actactttgc ttatgaaact ggaggcaagg cctgcaaaat gcaatactgc  720
aagcattggg gagtcagact cccatcaggt gtctggttcg agatggctga taaggatctc  780
tttgctgcag ccagattccc tgaatgccca aagggtcaa gtatctctgc tccatctcag  840
acctcagtga atgtaagtct aattcaggac gttgagagga tcttggatta ttccctctgc  900
caagaaacct ggagcaaaat cagagcgggt cttccaatct ctccagtgga tctcagctat  960
cttgctccta aaaacccagg aaccggtcct gcttttcacca taatgagt taccctaaaa  1020
tactttgaga ccagatacat cagagtcgat attgctgctc caatcctctc aagaatggtc  1080
ggaatgatca gtgaactac cacagaaagg gaactgtgg atgactgggc accatatgaa  1140
gacgtggaa ttggacccaa tggagttctg aggaccagtt caggatataa gtttcctta  1200
tacatgattg gacatggtat gttggactcc gatcttcatc ttagctcaaa ggctcaggtg  1260
ttcgaacatc ctcacattca agacgctgct tcgcaacttc ctgatgatga gagtttattt  1320
tttggtgata ctgggctatc caaaaatcca atcgagcttg tagaaggttg gttcagtagt  1380
tggaaaagct ctattgcctc ttttttcttt atcataggt taatcattgg actattcttg  1440
gttctccgag ttggtatcca tctttgcatt aaattaaagc acaccaagaa aagacagatt  1500
tatacagaca tagagatga                                               1519

SEQ ID NO: 27           moltype = DNA   length = 352
FEATURE                 Location/Qualifiers
misc_feature            1..352
                        note = Helper/Rev- CMV early (CAG) enhancer-
                        EnhanceTranscription
source                  1..352
                        mol_type = other DNA
                        organism = synthetic construct
SEQUENCE: 27
tagttattaa tagtaatcaa ttacggggtc attagttcat agcccatata tggagttccg   60
cgttacataa cttacggtaa atggcccgcc tggctgaccg cccaacgacc cccgcccatt  120
gacgtcaata atgacgtatg ttcccatagt aacgccaata gggactttcc attgacgtca  180
atgggtggac tatttacggt aaactgccca cttggcagta catcaagtgt atcatatgcc  240
aagtacgccc cctattgacg tcaatgacgg taaatggccc gctggcatt atgcccagta  300
catgacctta tgggactttc ctacttggca gtacatctac gtattagtca tc          352

SEQ ID NO: 28           moltype = DNA   length = 960
FEATURE                 Location/Qualifiers
misc_feature            1..960
                        note = Helper/Rev- Chicken beta actin intron- Enhance gene
                        expression
source                  1..960
                        mol_type = other DNA
                        organism = synthetic construct
SEQUENCE: 28
ggagtcgctg cgttgccttc gccccgtgcc ccgctccgcg ccgcctcgcg ccgcccgccc   60
cggctctgac tgaccgcgtt actcccacag gtgagcgggc gggacggccc ttctcctccg  120
ggctgtaatt agcgcttggt ttaatgacgg ctcgtttctt ttctgtggct gcgtgaaagc  180
cttaaagggc tccgggaggg ccctttgtgc ggggggagcg gctcggggg gtgcgtgcgt  240
gtgtgtgtgc gtggggagcg ccgcgtgcgg cccgcgctgc ccggcggctg tgagcgctgc  300
gggcgcggcg cggggctttg tgcgctccgc gtgtgcgcga ggagagcgcg gccggggcg  360
gtgccccgcg gtgcggggg gctgcgaggg gaacaaaggc tgcgtgcggg gtgtgtgcgt  420
ggggggtga gcaggggtg tgggcgcggc ggtcgggctg taacccccc ctgcacccc  480
ctccccgagt tgctgagcac ggcccggctt cgggtgcggg gctccgtgcg gggcgtggcg  540
```

```
cggggctcgc cgtgccgggc gggggtggc ggcaggtggg ggtgccgggc ggggcggggc   600
cgcctcgggc cggggagggc tcggggagg ggcgcggcgg ccccggagcg ccggcggctg   660
tcgaggcgcg gcgagccgca gccattgcct tttatggtaa tcgtgcgaga gggcgcaggg   720
acttcctttg tcccaaatct ggcggagccg aaatctggga ggcgccgccg cacccctctc   780
agccggcgcg ggcgaagcgg tgcggcgccg gcaggaagga aatgggcggg gagggccttc   840
gtgcgtcgcc gcgccgccgt ccccttctcc atctccagcc tcggggctgc cgcaggggga   900
cggctgcctt cggggggac ggggcagggc ggggttcggc ttctggcgtg tgaccggcgg   960
```

```
SEQ ID NO: 29           moltype = DNA   length = 448
FEATURE                 Location/Qualifiers
misc_feature            1..448
                        note = Helper/Rev- Rabbit beta globin poly A- RNA stability
source                  1..448
                        mol_type = other DNA
                        organism = synthetic construct
SEQUENCE: 29
agatctttt ccctctgcca aaaattatgg ggacatcatg aagccccttg agcatctgac   60
ttctggctaa taaaggaaat ttattttcat tgcaatagtg tgttggaatt ttttgtgtct   120
ctcactcgga aggacatatg ggagggcaaa tcatttaaaa catcagaatg agtatttggt   180
ttagagtttg gcaacatatg ccatatgctg gctgccatga acaaaggtgg ctataaagag   240
gtcatcagta tatgaaacag ccccctgctg tccattcctt attccataga aaagccttga   300
cttgaggtta gattttttt atattttgtt tgtgttatt ttttctctta acatccctaa   360
aattttcctt acatgtttta ctagccagat ttttcctcct ctcctgacta ctcccagtca   420
tagctgtccc tcttctctta tgaagatc                                     448
```

```
SEQ ID NO: 30           moltype = DNA   length = 573
FEATURE                 Location/Qualifiers
misc_feature            1..573
                        note = Envelope- Beta globin intron- Enhance gene expression
source                  1..573
                        mol_type = other DNA
                        organism = synthetic construct
SEQUENCE: 30
gtgagtttgg ggacccttga ttgttcttc ttttttcgcta ttgtaaaatt catgttatat   60
ggaggggca aagttttcag ggtgttgttt agaatgggaa gatgtccctt gtatcaccat   120
ggaccctcat gataatttg tttctttcac tttctactct gttgacaacc attgtctcct   180
cttatttttct tttcatttc tgtaacttttt tcgttaaact ttagcttgca tttgtaacga   240
attttttaaat tcacttttgt ttattttgtca gattgtaagt acttctcta atcactttttt   300
tttcaaggca atcagggtat attatattgt acttcagcac agttttagag aacaattgtt   360
ataattaaat gataaggtag aatatttctg catataaatt ctggctggcg tggaaaatt   420
cttattggta gaaacaacta cacccctggtc atcatcctgc ctttctcttt atggttacaa   480
tgatatacac tgtttgagat gaggataaaa tactctgagt ccaaaccggg cccctctgct   540
aaccatgttc atgccttctt ctctttccta cag                               573
```

```
SEQ ID NO: 31           moltype = DNA   length = 450
FEATURE                 Location/Qualifiers
misc_feature            1..450
                        note = Envelope- Rabbit beta globin poly A- RNA stability
source                  1..450
                        mol_type = other DNA
                        organism = synthetic construct
SEQUENCE: 31
agatctttt ccctctgcca aaaattatgg ggacatcatg aagccccttg agcatctgac   60
ttctggctaa taaaggaaat ttattttcat tgcaatagtg tgttggaatt ttttgtgtct   120
ctcactcgga aggacatatg ggagggcaaa tcatttaaaa catcagaatg agtatttggt   180
ttagagtttg gcaacatatg cccatatgct ggctgccatg aacaaaggtt ggctataaag   240
aggtcatcag tatatgaaac agccccctgc tgtccattcc ttattccata gaaaagcctt   300
gacttgaggt tagattttt ttatattttg ttttgtgtta ttttttctt taacatccct   360
aaaattttcc ttacatgttt tactagccag attttcctc ctctcctgac tactcccagt   420
catagctgtc cctcttctct tatggagatc                                   450
```

```
SEQ ID NO: 32           moltype = DNA   length = 31
FEATURE                 Location/Qualifiers
misc_feature            1..31
                        note = Primer
source                  1..31
                        mol_type = other DNA
                        organism = synthetic construct
SEQUENCE: 32
taagcagaat tcatgaattt gccaggaaga t                                 31
```

```
SEQ ID NO: 33           moltype = DNA   length = 36
FEATURE                 Location/Qualifiers
misc_feature            1..36
                        note = Primer
source                  1..36
                        mol_type = other DNA
                        organism = synthetic construct
SEQUENCE: 33
```
ccatacaatg aatggacact aggcggccgc acgaat 36

SEQ ID NO: 34                  moltype = DNA   length = 2745
FEATURE                        Location/Qualifiers
misc_feature                   1..2745
                               note = Gag, Pol, Integrase fragment
source                         1..2745
                               mol_type = other DNA
                               organism = synthetic construct
SEQUENCE: 34
gaattcatga atttgccagg aagatggaaa ccaaaaatga taggggaat tggaggtttt    60
atcaaagtaa gacagtatga tcagatactc atagaaatct gcggacataa agctataggt   120
acagtattag taggacctac acctgtcaac ataattggaa gaaatctgtt gactcagatt   180
ggctgcactt taaattttcc cattagtcct attgagactg taccagtaaa attaaagcca   240
ggaatggatg gcccaaaagt taaacaatgg ccattgacag aagaaaaaat aaaagcatta   300
gtagaaattt gtacagaaat ggaaaaggaa ggaaaaattt caaaaattgg gcctgaaaat   360
ccatacaata ctccagtatt tgccataaag aaaaaagaca gtactaaatg gagaaaatta   420
gtagatttca gagaacttaa taagagaact caagatttct gggaagttca attaggaata   480
ccacatcctg cagggttaaa acagaaaaaa tcagtaacag tactggatgt gggcgatgca   540
tatttttcag ttcccttaga taaagacttc aggaagtata ctgcatttac catacctagt   600
ataaacaatg agacaccagg gattagatat cagtacaatg tgcttccaca gggatggaaa   660
ggatcaccag caatattcca gtgtagcatg acaaaaatct tagagccttt tagaaaacaa   720
aatccagaca tagtcatcta tcaatacatg gatgatttgt atgtaggatc tgacttagaa   780
atagggcagc atagaacaaa aatagaggaa ctgagacaac atctgttgag gtggggattt   840
accacaccag acaaaaaaca tcagaaagaa cctccattcc tttggatggg ttatgaactc   900
catcctgata aatggacagt aaagcctata gtgctgccag aaaaggacag ctggactgtc   960
aatgacatac agaaattagt gggaaaattg aattgggcaa gtcagattta tgcagggatt  1020
aaagtaaggc aattatgtaa acttcttagg ggaaccaaag cactaacaga agtagtacca  1080
ctaacagaag aagcagagct agaactggca gaaaacaggg agattctaaa agaaccggta  1140
catggagtgt attatgaccc atcaaaagac ttaatagcag aaatacagaa gcaggggcaa  1200
ggccaatgga catatcaaat ttatcaagag ccatttaaaa atctgaaaac aggaaagtat  1260
gcaagaatga agggtgccca cactaatgat gtgaaacaat taacagaggc agtacaaaaa  1320
atagccacag aaagcatagt aatatgggga aagactccta aatttaaatt acccatacaa  1380
aaggaaacat gggaagcatg gtggacagag tattggcaag ccacctggat tcctgagtgg  1440
gagtttgtca ataccccctcc cttagtgaag ttatggtacc agttagagaa agaacccata  1500
ataggagcag aaactttcta tgtagatggg gcagccaata gggaaactaa attaggaaaa  1560
gcaggatatg taactgacag aggaagacaa aaagttgtcc ccctaacgga cacaacaaat  1620
cagaagactg agttacaagc aattcatcta gctttgcagg attcgggatt agaagtaaac  1680
atagtaacag actcacaata tgcattggga atcattcaag caacaccaga taagagtgaa  1740
tcagagttag tcagtcaaat aatagagcag ttaataaaaa aggaaaaagt ctacctggca  1800
tgggtaccag cacacaaagg aattggagga aatgaacaag tagataaatt ggtcagtgct  1860
ggaatcagga agtactattt ttagatgga atagataagg cccaagaaga acatgagaaa  1920
tatcacagta atttggagagc aatggctagt gattttaacc taccacctgt agtagcaaaa  1980
gaaatagtag ccagctgtga taatgtcag ctaaaagggg aagccatgca tggacaagta  2040
gactgtagcc caggaatatg gcagctagat tgtacacatt tagaaggaaa agttatcttg  2100
gtagcagttc atgtagccag tggatatata gaagcagaag taattccagc agagacaggg  2160
caagaaacag catacttcct cttaaaatta gcaggaagat ggccagtaaa aacagtacat  2220
acagacaatg gcagcaattt caccagtact acagttaagg ccgcctgttg gtgggcgggg  2280
atcaagcagg aatttggcat tccctacaat ccccaaagtc aaggagtaat agaatctatg  2340
aataaagaat taaagaaaat tataggacag gtaagagatc aggctgaaca tcttaagaca  2400
gcagtacaaa tggcagtatt catccacaat tttaaaagaa aaggggggat tgggggtac  2460
agtgcagggg aaagaatagt agacataata gcaacagaca tacaaactaa agaattacaa  2520
aaacaaatta caaaaattca aaattttcgg gtttattaca gggacagcag agatccagtt  2580
tggaaaggac cagcaaagct cctctggaaa ggtgaagggg cagtagtaat acaagataat  2640
agtgacataa aagtagtgcc aagaagaaaa gcaaagatca tcagggatta tggaaaacag  2700
atggcaggtg atgattgtgt ggcaagtaga caggatgagg attaa              2745

SEQ ID NO: 35                  moltype = DNA   length = 1586
FEATURE                        Location/Qualifiers
misc_feature                   1..1586
                               note = DNA Fragment containing Rev, RRE and rabbit beta
                                globin poly A
source                         1..1586
                               mol_type = other DNA
                               organism = synthetic construct
SEQUENCE: 35
tctagaatgg caggaagaag cggagacagc gacgaagagc tcatcagaac agtcagactc    60
atcaagcttc tctatcaaag caacccacct cccaatcccg aggggaccccg acaggcccga   120
aggaatagaa gaagaaggtg gagagagaca gagacagatcc cattcgat tagtgaacgg   180
atccttggca cttatctggg acgatctgcg gagcctgtgc ctcttcagct accaccgctt   240
gagagactta ctcttgattg taacgaggat tgtggaactt ctgggacgca ggggtgggaa   300
agccctcaaa tattggtgga atctcctaca atattggagt caggagctaa agaatagagg   360
agctttgttc cttgggttct tgggagcagc aggaagcact atgggcgcag cgtcaatgac   420
gctgacggta caggccagac aattattgtc tggtatagtg cagcagaa caaatttgct   480
gagggctatt gaggcgcaac agcatctgtt gcaactcaca gtctgggggca tcaagcagct   540
ccaggcaaga atcctggctg tggaaagata cctaaaggat caacagctcc tagatctttt   600
tccctctgcc aaaaattatg gggacatcat gaagcccctt gagcatctga cttctggcta   660
ataaaggaaa tttattttca ttgcaatagt gtgttggaat tttttgtgtc tctcactcgg   720
aaggacatat gggagggcaa atcatttaaa acatcagaat gagtatttgg tttagagttt   780

```
ggcaacatat gccatatgct ggctgccatg aacaaaggtg gctataaaga ggtcatcagt    840
atatgaaaca gccccctgct gtccattcct tattccatag aaaagccttg acttgaggtt    900
agattttttt tatattttgt tttgtgttat ttttttcttt aacatcccta aaattttcct    960
tacatgtttt actagccaga ttttcctcc tctcctgact actcccagtc atagctgtcc   1020
ctcttctctt atgaagatcc ctcgacctgc agcccaagct tggcgtaatc atggtcatag   1080
ctgtttcctg tgtgaaattg ttatccgctc acaattccac acaacatacg agccggaagc   1140
ataaagtgta aagcctgggg tgcctaatga gtgagctaac tcacattaat tgcgttgcgc   1200
tcactgcccg ctttccagtc gggaaacctg tcgtgccagc ggatccgcat ctcaattagt   1260
cagcaaccat agtcccgccc ctaactccgc ccatccgcc ctaactccg cccagttccg   1320
cccattctcc gccccatggc tgactaattt tttttattta tgcagaggcc gaggccgcct   1380
cggcctctga gctattccag aagtagtgag gaggcttttt tggaggccta ggcttttgca   1440
aaaagctaac ttgtttattg cagcttataa tggttacaaa taaagcaata gcatcacaaa   1500
tttcacaaat aaagcatttt tttcactgca ttctagttgt ggtttgtcca aactcatcaa   1560
tgtatcttat cagcggccgc cccggg                                        1586
```

```
SEQ ID NO: 36           moltype = DNA   length = 1614
FEATURE                 Location/Qualifiers
misc_feature            1..1614
                        note = DNA fragment containing the CAG
                        enhancer/promoter/intron sequence
source                  1..1614
                        mol_type = other DNA
                        organism = synthetic construct
SEQUENCE: 36
acgcgttagt tattaatagt aatcaattac ggggtcatta gttcatagcc catatatgga    60
gttccgcgtt acataactta cggtaaatgg cccgcctggc tgaccgccca acgacccccg   120
cccattgacg tcaataatga cgtatgttcc catagtaacg ccaataggga ctttccattg   180
acgtcaatgg gtggactatt tacggtaaac tgcccacttg gcagtacatc aagtgtatca   240
tatgccaagt acgcccccta ttgacgtcaa tgacggtaaa tggcccgcct ggcattatgc   300
ccagtacata accttatggg actttcctac ttggcagtac atctacgtat tagtcatcgc   360
tattaccatg gtcgaggtg agccccacgt tctgcttcac tctccccatc tcccccccct   420
ccccaccccc aattttgtat ttatttattt tttaattatt ttgtgcagcg atggggggcgg   480
ggggggggg ggcgcgcgcc aggcggggcg gggcggggcg aggggcgggg cggggcgagg   540
cggagaggtg cggcggcagc caatcagagc ggcgcgctcc gaaagtttcc ttttatggcg   600
aggcggcggc ggcggcggcc ctataaaaag cgaagcgcgc ggcgggcggg agtcgctgcg   660
ttgccttcgc cccgtgcccc gctccgcgcc gcctcgcgcc gcccgccccg gctctgactg   720
accgcgttac tcccacaggt gagcgggcgg gacggccctt ctcctccggg ctgtaattag   780
cgcttggttt aatgacggct cgtttctttt ctgtggctgc gtgaaagcct taaagggctc   840
cgggagggcc ctttgtgcgg gggggagcgg tctggggtgcgtgcgt gtgtgtgcgt    900
ggggagcgcg gcgtgcggcc cgcgctgccc ggcggctgtg agcgctgcgg gcgcggcgcg   960
gggctttgtg cgctccgcgt gtgcgcgagg ggagcgcggc cgggggcggt gccccgcggt  1020
gcggggggc tgcgagggga acaaaggctg cgtgcgggt gtgtgcgtgg gggggtgagc   1080
aggggtgtg ggcgcggcgg tcgggctgta acccccccct gcacccccct ccccgagttg  1140
ctgagcacgg cccggcttcg ggtgcgggc tccgtgcggg gcgtggccgc gggctcgccg   1200
tgccgggcgg ggggtggcgg caggtggggg tgccgggcgg ggcggggccg cctcgggccg   1260
gggagggctc ggggagggg gcgcggcggcc ccggagcgcc ggcggctgtc gaggcgcggc   1320
gagccgcagc cattgccttt tatggtaatc gtgcgagagg ttccttgtc   1380
ccaaatctgg cggagccgaa atctgggagg cgccgccgca ccccctctag cgggcgcggg  1440
cgaagcggtg cggcgccggc aggaaggaaa tgggcgggga gggccttcgt gcgtcgccgc  1500
gccgccgtcc ccttctccat ctccagcctc ggggctgccg caggggacg gctgccttcg  1560
gggggacgg ggcagggcgg ggttcggctt ctggcgtgtg accggcggga attc          1614
```

```
SEQ ID NO: 37           moltype = DNA   length = 1531
FEATURE                 Location/Qualifiers
misc_feature            1..1531
                        note = DNA fragment containing VSV-G
source                  1..1531
                        mol_type = other DNA
                        organism = synthetic construct
SEQUENCE: 37
gaattcatga agtgcctttt gtacttagcc ttttattca ttggggtgaa ttgcaagttc    60
accatagttt ttccacacaa ccaaaaagga aactggaaaa atgttccttc taattaccat   120
tattgcccgt caagctcaga tttaaattgg cataatgact taataggcac agccttacaa   180
gtcaaaatgc ccaagagtca caagctattt caagcagacg gttgatgtg tcatgcttcc   240
aaatgggtca ctacttgtga tttccgctgg tatggaccga agtatataac acattccatc   300
cgatccttca ctccatctgt agaacaatgc aaggaaagca ttgaacaaac gaaacaagga   360
acttggctga atcccaggctt ccctcctcaa agttgtggat atgcaactgt gacggatgcc   420
gaagcagtga ttgtccaggt gactcctcac catgtgctgg ttgataataa cacaggagaa   480
tggggttgatt cacagttcat caacggaaaa tgcagcagga acatatgccc cactgtccat   540
aactctacaa cctggcattc tgactataag gtcaaaggc tatgtgattc taacctcatt   600
tccatggaca tcaccttctt ctcagaggac ggagagctat catccctggg aaaggagggc   660
acagggttca gaagtaacta ctttgcttat gaaactggag gcaaggcctg caaaatgcaa   720
tactgcaagc attgggagt cagactccca tcaggtgtct ggttcgagat ggctgataag   780
gatctctttg ctgcagaag atccctgaa tgcccagtaa tgtcaagtat ctcgctcca   840
tctcagacct cagtggatgt aagtctaatt caggacgttg agaggatctt ggattattcc   900
ctctgccaag aaacctggag caaaatcaga gcgggtctcc aatctctcc agtggatctc   960
agctatcttg ctcctaaaaa cccaggaacc ggtcctgctt tcaccataat caatggtacc  1020
ctaaaatact tgagaccag atacatcaga gtcgatattg ctgctccaat cctctcaaga  1080
atggtcgaa tgatcagtgg aactaccaca gaaagggaac tgtgggatga ctgggcacca  1140
```

```
tatgaagacg tggaaattgg acccaatgga gttctgagga ccagttcagg atataagttt    1200
cctttataca tgattggaca tggtatgttg gactccgatc ttcatcttag ctcaaaggct    1260
caggtgttcg aacatcctca cattcaagac gctgcttcgc aacttcctga tgatgagagt    1320
ttatttttg tgatactgg gctatccaaa aatccaatcg agcttgtaga aggttggttc      1380
agtagttgga aaagctctat tgcctctttt ttctttatca tagggttaat cattggacta    1440
ttcttggttc tccgagttgg tatccatctt tgcattaaat taaagcacac caagaaaaga    1500
cagatttata cagacataga gatgagaatt c                                   1531

SEQ ID NO: 38              moltype = DNA   length = 351
FEATURE                    Location/Qualifiers
misc_feature               1..351
                           note = Rev- RSV promoter- Transcription
source                     1..351
                           mol_type = other DNA
                           organism = synthetic construct
SEQUENCE: 38
atggcaggaa gaagcggaga cagcgacgaa gaactcctca aggcagtcag actcatcaag     60
tttctctatc aaagcaaccc acctcccaat cccgagggga cccgacaggc ccgaaggaat    120
agaagaagaa ggtggagaga gagacagaga cagatccatt cgattagtga acggatcctt    180
agcacttatc tgggacgatc tgcggagcct gtgcctcttc agctaccacc gcttgagaga    240
cttactcttg attgtaacga ggattgtgga acttctggga cgcaggggt gggaagccct     300
caaatattgg tggaatctcc tacaatattg gagtcaggag ctaaagaata g             351

SEQ ID NO: 39              moltype = DNA   length = 351
FEATURE                    Location/Qualifiers
misc_feature               1..351
                           note = Rev- HIV Rev- Nuclear export and stabilize viral mRNA
source                     1..351
                           mol_type = other DNA
                           organism = synthetic construct
SEQUENCE: 39
atggcaggaa gaagcggaga cagcgacgaa gaactcctca aggcagtcag actcatcaag     60
tttctctatc aaagcaaccc acctcccaat cccgagggga cccgacaggc ccgaaggaat    120
agaagaagaa ggtggagaga gagacagaga cagatccatt cgattagtga acggatcctt    180
agcacttatc tgggacgatc tgcggagcct gtgcctcttc agctaccacc gcttgagaga    240
cttactcttg attgtaacga ggattgtgga acttctggga cgcaggggt gggaagccct     300
caaatattgg tggaatctcc tacaatattg gagtcaggag ctaaagaata g             351

SEQ ID NO: 40              moltype = DNA   length = 884
FEATURE                    Location/Qualifiers
misc_feature               1..884
                           note = RSV promoter and HIV Rev
source                     1..884
                           mol_type = other DNA
                           organism = synthetic construct
SEQUENCE: 40
caattgcgat gtacgggcca gatatacgcg tatctgaggg gactaggtg tgtttaggcg      60
aaaagcgggg cttcggttgt acgcggttag gagtccctc aggatatagt agtttcgctt    120
ttgcataggg aggggaaat gtagtcttat gcaatacact tgtagtcttg aacatggta     180
acgatgagtt agcaacatgc cttacaagga gagaaaagc accgtgcatg ccgattggtg    240
gaagtaaggt ggtacgatcg tgccttatta ggaaggcaac agacaggtct gacatggatt    300
ggacgaacca ctgaattccg cattgcagag ataattgtat ttaagtgcct agctcgatac    360
aataaacgcc atttgaccat tcaccacatt ggtgtgcacc tccaagctcg agctcgttta    420
gtgaaccgtc agatcgcctg agacgccat ccacgctgtt tgacctcca tagaagacac     480
cgggaccgat ccagcctccc ctcgaagcta gcgattagc atctcctatg gcaggaagaa    540
gcggagacag cgacgaagaa ctcctcaagg cagtcagact catcaagttt ctctatcaaa    600
gcaacccacc tcccaatccc gaggggaccc gacaggcccg aaggaataga agaagaaggt    660
ggagagagag acagagacag atccattcga ttagtgaacg gatccttagc acttatctgg    720
gacgatctgc ggagcctgtg cctcttcagc taccaccgct tgagagactt actcttgatt    780
gtaacgagga ttgtggaact tctgggacgc aggggtggg aagccctcaa atattggtgg     840
aatctcctac aatattggag tcaggagcta aagaatagtc taga                     884

SEQ ID NO: 41              moltype = DNA   length = 1104
FEATURE                    Location/Qualifiers
misc_feature               1..1104
                           note = Elongation Factor-1 alpha (EF1-alpha) promoter
source                     1..1104
                           mol_type = other DNA
                           organism = synthetic construct
SEQUENCE: 41
ccggtgccta gagaaggtgg cgcggggtaa actgggaaag tgatgtcgtg tactggctcc     60
gcctttttcc cgagggtggg ggagaaccgt atataagtgc agtagtcgcc gtgaacgttc    120
tttttcgcaa cgggtttgcc gccagaacac aggtaagtgc cgtgtgtggt tcccgcgggc    180
ctggcctctt tacgggttat ggcccttgcg tgccttgaat tacttccacg ccctggctg     240
cagtacgtga ttcttgatcc cgagcttcgg gttggaagtg gtgggagag ttcgaggcct     300
tgcgcttaag gagccccttc gcctcgtgct tgagttgagg cctggcctgg gcgctgggcc    360
cgccgcgtgc gaatctggtg gcaccttcgc gcctgtctcg ctgctttcga taagtctcta    420
gccatttaaa atttttgatg acctgctgcg acgctttttt tctggcaaga tagtcttgta    480
aatgcgggcc aagatctgca cactggtatt tcggtttttg gggccgcggg cggcgacggg    540
```

```
gcccgtgcgt cccagcgcac atgttcggcg aggcggggcc tgcgagcgcg gccaccgaga    600
atcggacggg ggtagtctca agctggccgg cctgctctgg tgcctggcct cgcgccgccg    660
tgtatcgccc cgccctgggc ggcaaggctg gcccggtcgg caccagttgc gtgagcggaa    720
agatggccgc ttcccggccc tgctgcaggg agctcaaaat ggaggacgcg gcgctcggga    780
gagcgggcgg gtgagtcacc cacacaaagg aaaagggcct ttccgtcctc agccgtcgct    840
tcatgtgact ccacggagta ccgggcgccg tccaggcacc tcgattagtt ctcgagcttt    900
tggagtacgt cgtctttagg ttggggggag ggttttatg cgatggagtt tccccacact    960
gagtgggtgg agactgaagt taggccagct tggcacttga tgtaattctc cttgaatttt   1020
gccctttttg agtttggatc ttggttcatt ctcaagcctc agacagtggt tcaaagtttt   1080
tttcttccat ttcaggtgtc gtga                                          1104

SEQ ID NO: 42         moltype = DNA   length = 511
FEATURE               Location/Qualifiers
misc_feature          1..511
                      note = Promoter- PGK
source                1..511
                      mol_type = other DNA
                      organism = synthetic construct
SEQUENCE: 42
gggggttgggg ttgcgccttt tccaaggcag ccctgggttt gcgcagggac gcggctgctc     60
tgggcgtggt tccgggaaac gcagcggcgc cgacctggg tctcgcacat tcttcacgtc     120
cgttcgcagc gtcacccgga tcttcgccgc taccctgcg ccccccgg cgacgcttcc       180
tgctccgccc ctaagtcggg aaggttcctt gcggttcgcg gcgtgccgga cgtgacaaac    240
ggaagccgca cgtctcacta gtaccctcgc agacggacag cgccaggag caatggcagc    300
gcgccgaccg cgatgggctg tggccaatag cggctgctca gcaggcgcg ccgagagcag    360
cggccgggaa ggggcggtgc gggaggcggg gtgtggggcg gtagtgtggg ccctgttcct    420
gcccgcgcgg tgttccgcat tctgcaagcc tccggagcgc acgtcggcag tcggctccct    480
cgttgaccga atcaccgacc tctctccccca g                                  511

SEQ ID NO: 43         moltype = DNA   length = 1162
FEATURE               Location/Qualifiers
misc_feature          1..1162
                      note = Promoter- UbC
source                1..1162
                      mol_type = other DNA
                      organism = synthetic construct
SEQUENCE: 43
gcgccgggtt ttggcgcctc ccgcgggcgc cccctcctc acggcgagcg ctgccacgtc      60
agacgaaggg cgcaggagcg ttcctgatcc ttccgcccgg acgctcagga cagcggcccg    120
ctgctcataa gactcggcct tagaacccca gtatcagcag aaggacattt taggacggga    180
cttgggtgac tctagggcac tggttttctt tccagagagc ggaacaggcg aggaaaagta    240
gtcccttctc ggcgattctg cggagggatc tccgtggggc ggtgaacgcc gatgattata    300
taaggacgcg ccgggtgtgg cacagctagt tccgtcgcag ccgggatttg gtcgcggtt    360
cttgtttgtg gatcgctgtg atcgtcactt ggtgagttgc gggctgctgg gctggccggg    420
gctttcgtgg ccgccgggcc gctcggtggg acgaagcgt gtggagagac cgccaagggc    480
tgtagtctgt gtccgcgagc aaggttgccc tgaactgggg gttgggggga gcgcacaaaa    540
tggcggctgt tcccgagtct tgaatggaag acgcttgtaa cgcttggctgt gaggtcgttg    600
aaacaaggtg gggggcatgt tgggcggcaa gaacccaagg tcttgaggcc ttcgctaatg    660
cgggaaagct cttattcggg tgagatgggc tggggcacca tctggggacc ctgacgtgaa    720
gtttgtcact gactggagaa ctcgggtttg tcgtctggtt gcggggcgg cagttatgcg    780
gtgccgttgg gcagtgcacc cgtacctttg ggagcgcgcc cctcgtcgtg tcgtgacgtc    840
acccgttctg ttggcttata atgcaggggt gggccacctg ccggtaggtg tgcggtaggc    900
tttttctccgt cgcaggacgc agggttcggg cctagggtag gctctcctga atcgacaggc    960
gccgacctc tggtgagggg agggataagt gaggcgtcag tttctttggt cggttttatg   1020
tacctatctt cttaagtagc tgaagctccg gttttgaact atgcgctcgg ggttggcgag   1080
tgtgttttgt gaagtttttt aggcaccttt tgaaatgtaa tcatttgggt caatatgtaa   1140
ttttcagtgt tagactagta aa                                             1162

SEQ ID NO: 44         moltype = DNA   length = 120
FEATURE               Location/Qualifiers
misc_feature          1..120
                      note = Poly A- SV40
source                1..120
                      mol_type = other DNA
                      organism = synthetic construct
SEQUENCE: 44
gtttattgca gcttataatg gttacaaata aagcaatagc atcacaaatt tcacaaataa      60
agcatttttt tcactgcatt ctagttgtgg tttgtccaaa ctcatcaatg tatcttatca    120

SEQ ID NO: 45         moltype = DNA   length = 227
FEATURE               Location/Qualifiers
misc_feature          1..227
                      note = Poly A- bGH
source                1..227
                      mol_type = other DNA
                      organism = synthetic construct
SEQUENCE: 45
gactgtgcct tctagttgcc agccatctgt tgtttgcccc tcccccgtgc cttccttgac     60
cctggaaggt gccactccca ctgtcctttc ctaataaaat gaggaaattg catcgcattg    120
```

```
tctgagtagg tgtcattcta ttctgggggg tggggtgggg caggacagca aggggggagga    180
ttgggaagac aatagcaggc atgctgggga tgcggtgggc tctatgg                  227
```

| SEQ ID NO: 46 | moltype = DNA length = 1695 |
|---|---|
| FEATURE | Location/Qualifiers |
| misc_feature | 1..1695 |
| | note = Envelope- RD114 |
| source | 1..1695 |
| | mol_type = other DNA |
| | organism = synthetic construct |

SEQUENCE: 46
```
atgaaactcc caacaggaat ggtcatttta tgtagcctaa taatagttcg ggcagggttt     60
gacgacccccc gcaaggctat cgcattagta caaaaacaac atggtaaaacc atgcgaatgc  120
agcggagggc aggtatccga ggccccaccg aactccatcc aacaggtaac ttgcccaggc    180
aagacggcct acttaatgac caaccaaaaa tggaaatgca gagtcactcc aaaaaatctc    240
acccctagcg ggggagaact ccagaactgc cctgtaaca cttttccagga ctcgatgcac    300
agttcttgtt atactgaata ccggcaatgc agggcgaata taagacata ctacacggcc     360
accttgctta aaatacgtc tgggagcctc aacgaggtac agtattaca aaaccccaat      420
cagctcctac agtcccttg taggggctct ataaatcagc ccgtttgctg gagtgccaca     480
gcccccatcc atatctccga tggtggagga ccccctcgata ctaagagagt gtggacagtc   540
caaaaaaggc tagaacaaat tcataaggct atgcatcctg aacttcaata ccacccctta   600
gccctgccca aagtcagaga tgaccttagc cttgatgcac ggactttttga tatcctgaat  660
accacttttta ggttactcca gatgtccaat tttagccttg cccaagattg ttggctctgt  720
ttaaaactag gtaccctac ccctcttgcg atacccactc cctctttaac ctactcccta    780
gcagactccc tagcgaatgc ctcctgtcag attataacctc ccctcttggt tcaaccgatg  840
cagttctcca actcgtcctg ttttatcttcc cctttcatta acgatacgga acaaatagac  900
ttaggtgcag tcacctttac taactgcacc tctgtagcca atgtcagtag tcctttatgt   960
gccctaaacg ggtcagtctt cctctgtgga ataacatgg catacaccta tttaccccaa   1020
aactggacag actttgcgt ccaagcctcc ctcctcccg acattgacat catcccgggg    1080
gatgagccag tccccattcc tgccattgat cattatatac atagacctaa acgagctgta  1140
cagttcatcc ctttactagc tggactggga atcaccgcag cattcaccac cggagctaca  1200
ggcctaggtg tctccgtcac ccagtataca aaattatccc atcagttaat atctgatgtc  1260
caagtcttat ccggtaccat acaagattta caagaccagg tagactcgtt agctgaagta  1320
gttctccaaa ataggaggg actggaccta ctaaggcag aacaaggag aatttgttta    1380
gccttacaag aaaaatgctg tttttatgct aacaagtcag gaattgtgag aaacaaaata  1440
agaacccctac aagaagaatt acaaaaacgc agggaaagcc tggcatccaa ccctctctgg  1500
accgggctgc agggctttct tccgtacctc ctacctctcc tgggacccct actcacccctc 1560
ctactcatac taaccattgg gccatgcgtt ttcaatcgat tggtccaatt tgttaaagac  1620
aggatctcag tggtccaggc tctggttttg actcagcaat atcaccagct aaaacccata  1680
gagtacgagc catga                                                    1695
```

| SEQ ID NO: 47 | moltype = DNA length = 2013 |
|---|---|
| FEATURE | Location/Qualifiers |
| misc_feature | 1..2013 |
| | note = Envelope- GALV |
| source | 1..2013 |
| | mol_type = other DNA |
| | organism = synthetic construct |

SEQUENCE: 47
```
atgcttctca cctcaagccc gcaccacctt cggcaccaga tgagtcctgg gagctggaaa    60
agactgatca tcctcttaag ctgcgtattc ggagacgaca aaacgagtcc gcagaataag  120
aacccccacc agcctgtgac cctcacctgg caggtactgt cccaaactgg ggacgttgtc   180
tgggacaaaa aggcagtcca gcccctttgg acttggtggc cctctcttac acctgatgta   240
tgtgccctgg cggccggtct tgagtcctgg gatatcccgg gatccgatgt atcgtcctct   300
aaaagagtta gacctcctga ttcagactat actgccgtct ataagcaaat cacctgggga    360
gccataggt gcagctaccc tcgggctagg accaggatgg caaattcccc cttctacgtg    420
tgtccccgag ctgccgaac ccattcagaa gctaggaggt gtgggggct agaatcccta     480
tactgtaaag aatggagttg tgagaccacg ggtaccgttt attggcaacc caagtcctca    540
tgggacctca taactgtaaa atgggaccaa aatgtgaaat gggagcaaaa attttcaaaag  600
tgtgaacaaa ccggctggtg taaccccctc aagatagact tcacagaaaaa aggaaaactc  660
tccagagatt ggataacgga aaaacctgg gaattaaggt tctatgtata tggacaccca  720
ggcatacagt tgactatccg cttagaggtc actaacatgc cggttgtggc agtgggcca    780
gaccctgtcc ttgcggaaca gggacctcct agcaagccc tcactctccc tctctctccca   840
cggaaagcc cgcccacccc tctaccccg gcggctagtg agcaaacccc tgccgtgtgca   900
ggagaaactg ttaccctaaa ctctccgcct cccaccagtg cgaccgact ctttggcctt   960
gtgcaggggg ccttcctaac cttgaatgct accaacccag ggccactaa gtcttgctgg  1020
ctctgtttgg gcatgagccc ccttattat gaagggatag cctcttcagg agaggtcgct 1080
tatacctcca accatacccg atgcctctgg gggccccaag gaaagcttac ccctcactgag 1140
gtctccggac tcgggtcatg cataggggaag gtgcctcta cctcaacaa tctttgcaac   1200
cagaccttac ccatcaattc ctctaaaaac catcagtatc tgctcccctc aaaccatagc  1260
tggtgggcct gcagcactgg cctcacccccc tgcctctcca cctcagtttt taatcagtct   1320
aaagacttct gtgtccaggt ccagctgatc ccccgcatct attaccatc tgaagaaacc   1380
ttgttacaag cctatgacaa atcaccccccc aggtttaaaa gagagcctgc ctcacttacc  1440
ctgtctgtct tcctgggtt agggattgcg gcaggatagtc gtactggctc aaccgcctgcat 1500
attaaagggc catagacct ccagcaaggc ctaaccagcc tccaaatcgc cattgacgct   1560
gacctccggg cccttcagga ctcaatcagc aagctagagg actcactgac ttccctatct   1620
gaggtagtac tccaaaatag gagaggcctt gacttactat tccttaaaga aggaggcctc   1680
tgcgcggccc taaaagaaga gtgctgtttt tatgtagacc actcaggtgc agtacgagac   1740
tccatgaaaa aacttaagga aagactagat aaaagacagt tagagcgcca gaaaaaccaa   1800
```

```
aactggtatg aagggtggtt caataactcc ccttggttta ctaccctact atcaaccatc   1860
gctgggcccc tattgctcct ccttttgtta ctcactcttg ggccctgcat catcaataaa   1920
ttaatccaat tcatcaatga taggataagt gcagtcaaaa ttttagtcct tagacagaaa   1980
tatcagaccc tagataacga ggaaaacctt taa                                2013

SEQ ID NO: 48          moltype = DNA   length = 1530
FEATURE                Location/Qualifiers
misc_feature           1..1530
                       note = Envelope- FUG
source                 1..1530
                       mol_type = other DNA
                       organism = synthetic construct
SEQUENCE: 48
atggttccgc aggttctttt gtttgtactc cttctgggtt tttcgttgtg tttcggaag    60
ttccccattt acacgatacc agacgaactt ggtccctgga gcctattga catacaccat    120
ctcagctgtc caaataacct ggtgtggag gatgaaggat gtaccaacct gtccgagttc    180
tcctacatgg aactcaaagt gggatacatc tcagccatca aagtgaacgg gttcacttgc    240
acaggtgttg tgacagaggc agagacctac accaacttgt tggttatgt cacaaccaca    300
ttcaagagaa agcatttccg ccccacccca gacgcatgta gagccgcgta taactggaag    360
atggccggtg accccagata tgaagagtcc ctacacaatc cataccccga ctaccactgg    420
cttcgaactg taagaaccac caaagagtcc ctcattatca tatccccaag tgtgacagat    480
tggacccat atgacaaatc ccttcactca agggtcttcc tcggcggaaa gtgctcagga    540
ataacggtgt cctctaccta ctgctcaact aaccatgatt acaccatttg gatgcccgag    600
aatccgagac aaggacacc ttgtgacatt tttaccaata gcagaggaa gagagcatcc    660
aacgggaaca agacttgcgg cttgtgggat gaaagaggcc tgtataagtc tctaaaagga    720
gcatgcaggc tcaagttatg tggagttctt ggacttgaca ttatggatgg aacatgggtc    780
gcgatgcaaa catcagatga gaccaaatgg tgccctccag atcagttggt gaatttgcac    840
gactttcgct cagacgagat cgagcatctc gttgtgagg agttagttaa gaaaagagag    900
gaatgtctgg atgcattaga gtccatcatg accaccaagt cagtaagttt cagacgtctc    960
agtcacctga gaaacttgt cccagggttt ggaaaagcat ataccatatt caacaaaacc    1020
ttgatggagg ctgatgctca ctacaagtca gtccggaccc ggaatgagat catcccctca    1080
aaagggtgtt tgaaagttgg aggaaggtgc atcctcatg tgaacggggt gtttttcaat    1140
ggtataaat tagggcctga cgaccatgtc ctaatcccag agatgcaatc atccctcctc    1200
cagcaacata tggagttgtt ggaatcttca gttatccccc tgtgcaccc cctggcagac    1260
ccttctacag ttttcaaaga aggtgatgag gctgaggatt ttgttgaagt tcacctcccc    1320
gatgtgtaca acagatctc aggggttgac ctgggtctcc cgaactgggg aaagtatgta    1380
ttgatgactc aggggccat gattggcctg tgttgatat tttccctaat gacatggtgc    1440
agagttggta tccatctttg cattaaaatta agcaccacca gaaaagaca gatttataca    1500
gacatagaga tgaaccgact tggaaagtaa                                   1530

SEQ ID NO: 49          moltype = DNA   length = 1497
FEATURE                Location/Qualifiers
misc_feature           1..1497
                       note = Envelope- LCMV
source                 1..1497
                       mol_type = other DNA
                       organism = synthetic construct
SEQUENCE: 49
atgggtcaga ttgtgacaat gtttgaggct ctgcctcaca tcatcgatga ggtgatcaac   60
attgtcatta ttgtgcttat cgtgatcacg ggtatcaagg ctgtctacaa ttttgccacc   120
tgtgggatat tcgcattgat cagtttccta ctttctgctg gcaggtcctg tggcatgtac   180
ggtcttaagg gacccgacat ttacaaagga gtttaccaat ttaagtcagt ggagtttgat   240
atgtcacatc tgaacctgac catgcccaac gcatgttcag ccaacaactc ccaccattac   300
atcagtatgg gacttctgg actagaattg accttcacca tgattccat catcagtcac   360
aactttttgca atctgacctc tgccttcaac aaaaagactt tgaccacac actcatgagt   420
atagtttcga gcctacacct cagtatcaga gggaactcca actataaggc agtatcctgc   480
gacttcaaca atgcataac catccaatac aacttgacat tctcagatcg acaaagtgct   540
cagagccagt gtagaacctt cagaggtaga gtcctagata tgtttagaac tgccttcggg   600
gggaaataca tgaggagtgg ctgggctgg acaggctcag atggcaagac cacctggtg    660
agccagacga gttaccaata cctgattata caaatagaa cctgggaaaa ccactgcaca   720
tatgcaggtc ctttggggat gtccaggatt ctccttttccc aagagaagac taagttcttc   780
actaggagac tagcgggcac attcacctgg actttgtcag actcttcagg ggtggagaat   840
ccaggtggtt attgcctgac caaatggatg attcttgctg cagagcttaa gtgtttcggg   900
aacacagcag ttgcgaaatg caatgtaaat catgatgcga aattctgctga catgctgcga   960
ctaattgact acaacaaggc tgctttgagt aagttcaaag aggacgtaga atctgccttg   1020
cacttattca aaaacaacagt gaattctttg atttcagatc aactactgat gaggaaccac   1080
ttgagagatc tgatggggt gccatattgc aattactcaa agttttggta cctagaacat   1140
gcaaagaccg gcgaaactag tgtccccaag tgctggcttg tcaccaatgg ttcttactta   1200
aatgagacca cttcagtga tcaaatcgaa caggaagccg ataacatgat tacagagatg   1260
ttgaggaagg attacataaa gaggcagggg agtaccccccc tagcattgat ggaccttctg   1320
atgttttcca catctgcata tctagtcagc atcttcctgc accttgtcaa ataccaaca   1380
cacaggcaca taaaaggtgg ctcatgtcca aagccacacc gattaaccaa caaggaatt   1440
tgtagttgtg gtgcatttaa ggtgcctggt gtaaaaccg tctggaaaag acgctga      1497

SEQ ID NO: 50          moltype = DNA   length = 1692
FEATURE                Location/Qualifiers
misc_feature           1..1692
                       note = Envelope- FPV
source                 1..1692
```

```
                        mol_type = other DNA
                        organism = synthetic construct
SEQUENCE: 50
atgaacactc aaatcctggt tttcgccctt gtggcagtca tccccacaaa tgcagacaaa    60
atttgtcttg gacatcatgc tgtatcaaat ggcaccaaag taaacacact cactgagaga   120
ggagtagaag ttgtcaatgc aacgaaaaca gtggagcgga caaacatccc caaaatttgc   180
tcaaaaggga aaagaaccac tgatcttggc caatgcggac tgttagggac cattaccgga   240
ccacctcaat gcgaccaatt tctagaattt tcagctgatc taataatcga gagacgaaaa   300
ggaaatgatg tttgttaccc ggggaagttt gttaatgaag aggcattgcg acaaatcctc   360
agaggatcag gtgggattga caaagaaaca atgggattca catatagtgg aataaggacc   420
aacggaacaa ctagtgcatg tagaagatca gggtcttcat tctatgcaga aatggagtgg   480
ctcctgtcaa atacagacaa tgctgctttc ccacaaatga caaatcata caaaaacaca   540
aggagagaat cagctctgat agtctgggga atccaccatt caggatcaac caccgaacag   600
accaaactat atggagtgg aaataaactg ataacagtcg ggagttccaa atatcatcaa   660
tcttttgtgc cgagtccagg aacacgaccg cagataaatg gccagtccgg acggattgat   720
tttcattggt tgatccttga tcccaatgat acagttactt ttagtttcaa tggggctttc   780
atagctccaa atcgtgccag cttcttgagg ggaaagtcca tggggatcca gagcgatgtg   840
caggttgatg ccaattgcga aggggaatgc taccacagtg gagggactat aacaagcaga   900
ttgccttttc aaaacatcaa tagcagagca gttggcaaat gcccaagata tgtaaaacag   960
gaaagtttat tattggcaac tgggatgaag aacgttcccg aaccttccaa aaaaaggaaa  1020
aaaagaggc tgtttggcgc tatagcaggg tttattgaaa atggttggga aggtctggtc  1080
gacggtggt acggtttcag gcatcagaat gcacaaggag aaggaactgc agcagactac  1140
aaaagcaccc aatcggcaat tgatcagata accggaaagt taaatagact cattgagaaa  1200
accaaccagc aatttgagct aatagataat gaattcactg aggtggaaaa gcagattggc  1260
aatttaatta actggaccaa agactccatc acagaagtat ggtcttacaa tgctgaactt  1320
cttgtggcaa tggaaaacca gcacactatt gatttggcta ttcagagat gaacaagctg  1380
tatgagcgag tgaggaaaca attaaggaaa aatgctgaag aggatggcac tggttgcttt  1440
gaaattttc ataaatgtga cgatgattgt atggctagta taaggaacaa tacttatgat  1500
cacagcaaat acagagaaga agcgatgcaa aatagaatac aaattgaccc agtcaaattg  1560
agtagtggct acaaagatgt gatactttgg tttagcttcg gggcatcatg cttttttgctt  1620
cttgccattg caatgggcct tgtttttcata tgtgtgaaga acgaaacat gcggtgcact  1680
atttgtatat aa                                                      1692

SEQ ID NO: 51           moltype = DNA  length = 1266
FEATURE                 Location/Qualifiers
misc_feature            1..1266
                        note = Envelope- RRV
source                  1..1266
                        mol_type = other DNA
                        organism = synthetic construct
SEQUENCE: 51
agtgtaacag agcactttaa tgtgtataag gctactagac catacctagc acattgcgcc    60
gattgcgggg acgggtactt ctgctatagc ccagttgcta tcgaggagat ccgagatgag   120
gcgtctgatg gcatgcttaa gatccaagtc tccgcccaaa taggtctgga caaggcaggc   180
acccacgccc acacgaagct ccgatatatg gctggtcatg atgttcagga atctaagaga   240
gattccttga gggtgtacac gtccgcagcg tgctccatac atgggacgat gggacacttc   300
atcgtcgcac actgtccacc aggcgactac ctcaaggttt cgttcgagga cgcagattcg   360
cacgtgaagg catgtaaggt ccaatacaag cacaatccat tgccggtggg tagagagaag   420
ttcgtggtta gaccacactt tggcgtagag ctgccatgca cctcatacca gctgacaacg   480
gctcccaccg acgaggagat tgacatgcat acaccgccag atataccgga tcgcaccctg   540
ctatcacaga cggcgggcaa cgtcaaaata acagcaggcg aggactat caggtacaac   600
tgtacctgcg gccgtgacaa cgtaggcact accagtactg acaagaccat caacacatgc   660
aagattgacc aatgccatgc tgccgtcacc agccatgaca aatggcaatt tacctctcca   720
tttgttccca gggctgatca gacagctagg aaaggcaagg tacacgttcc gttccctctg   780
actaacgtca cctgccgagt gccgttggct cgagcgccga atgccaccta tggtaagaag   840
gaggtgaccc tgagattaca cccagatcat ccgacgctct tctcctatag gagtttagga   900
gccgaaccgc acccgtacga ggaatgggtt gacaagttct ctgagcgcat catcccagtg   960
acggaagaag ggattgagta ccagtggggc aacaacccgc cggtctgcct gtgggcgcaa  1020
ctgacgaccg agggcaaacc ccatggctgg ccacatgaaa tcattcagta ctattatga  1080
ctatacccg ccgccactat tgccgcagta tccggggcga gtctgatggc cctcctaact  1140
ctggcggcca catgctgcat gctggccacc gcgaggagaa agtgcctaac accgtacgcc  1200
ctgacgccag gagcggtggt accgttgaca ctggggctgc tttgctgcgc accgagggcg  1260
aatgca                                                             1266

SEQ ID NO: 52           moltype = DNA  length = 1266
FEATURE                 Location/Qualifiers
misc_feature            1..1266
                        note = Envelope- MLV 10A1
source                  1..1266
                        mol_type = other DNA
                        organism = synthetic construct
SEQUENCE: 52
agtgtaacag agcactttaa tgtgtataag gctactagac catacctagc acattgcgcc    60
gattgcgggg acgggtactt ctgctatagc ccagttgcta tcgaggagat ccgagatgag   120
gcgtctgatg gcatgcttaa gatccaagtc tccgcccaaa taggtctgga caaggcaggc   180
acccacgccc acacgaagct ccgatatatg gctggtcatg atgttcagga atctaagaga   240
gattccttga gggtgtacac gtccgcagcg tgctccatac atgggacgat gggacacttc   300
atcgtcgcac actgtccacc aggcgactac ctcaaggttt cgttcgagga cgcagattcg   360
cacgtgaagg catgtaaggt ccaatacaag cacaatccat tgccggtggg tagagagaag   420
```

```
ttcgtggtta gaccacactt tggcgtagag ctgccatgca cctcatacca gctgacaacg    480
gctcccaccg acgaggagat tgacatgcat acaccgccag atataccgga tcgcaccctg    540
ctatcacaga cggcgggcaa cgtcaaaata acagcaggcg gcaggactat caggtacaac    600
tgtacctgcg gccgtgacaa cgtaggcact accagtactg acaagaccat caacacatgc    660
aagattgacc aatgccatgc tgccgtcacc agccatgaca aatggcaatt tacctctcca    720
tttgttccca gggctgatca gacagctagg aaaggcaagg tacacgttcc gttccctctg    780
actaacgtca cctgccgagt gccgttggct cgagcgccgg atgccaccta tggtaagaag    840
gaggtgaccc tgagattaca cccagatcat ccgacgctct tctcctatag gagtttagga    900
gccgaaccgc acccgtacga ggaatgggtt gacaagttct ctgagcgcat catcccagtg    960
acggaagaag ggattgagta ccagtggggc aacaacccgc cggtctgcct gtgggcgcaa   1020
ctgacgaccg agggcaaacc ccatggctgg ccacatgaaa tcattcagta ctattatgga   1080
ctataccccg ccgccactat tgccgcagta tccggggcga gtctgatggc cctcctaact   1140
ctggcggcca catgctgcat gctggccacc gcgaggagaa agtgcctaac accgtacgcc   1200
ctgacgccag gagcggtggt accgttgaca ctggggctgc tttgctgcgc accgagggcg   1260
aatgca                                                              1266

SEQ ID NO: 53           moltype = DNA   length = 2030
FEATURE                 Location/Qualifiers
misc_feature            1..2030
                        note = Envelope- Ebola
source                  1..2030
                        mol_type = other DNA
                        organism = synthetic construct
SEQUENCE: 53
atgggtgtta caggaatatt gcagttacct cgtgatcgat tcaagaggac atcattcttt     60
ctttgggtaa ttatccttt ccaaagaaca ttttccatcc cacttggagt catccacaat    120
agcacattac aggttagtga tgtcgacaaa ctggtttgcc gtgacaaact gtcatccaca    180
aatcaattga gatcagttgg actgaatctc gaagggaatg gagtggcaac tgacgtgcca    240
tctgcaacta aaagatgggg cttcaggtcc ggtgtcccac caaaggtggt caattatgaa    300
gctggtgaat gggctgaaaa ctgctacaat cttgaaatca aaaaacctga cgggagtgag    360
tgtctaccag cagcgccaga cgggattcgg ggcttccccc ggtgccggta tgtgcacaaa    420
gtatcaggaa cgggaccgtg tgccggagac ttttgccttc c acaaagaggg tgctttcttc    480
ctgtatgacc gacttgcttc cacagttatc taccgaggaa cgactttcgc tgaaggtgtc    540
gttgcatttc tgatactgcc ccaagctaag aaggacttct tcagctcaca ccccttgaga    600
gagccggtca atgcaacgga ggacccgtct agtggctact attctaccac aattagatat    660
caagctaccg gttttggaac caatgagaca gagtatttgt tcgaggttga aattttgacc    720
tacgtccaac ttgaatcaag attcacacca cagtttctgc tccagctgaa tgagacaata    780
tatacaagtg gaaaaggag caataccacg ggaaaactaa tttggaaggt caaccccgaa    840
attgatacaa caatcgggga gtgggccttc tgggaaacta aaaaaaccctc actagaaaaa    900
ttcgcagtga agagttgtct ttcacagctg tatcaaacag agccaaaaac atcagtggtc    960
agagtccggc gcgaacttct tccgacccag ggaccaacac aacaactgaa gaccacaaaa   1020
tcatggcttc agaaaattcc tctgcaatgg ttcaagtgca cagtcaagga agggaagctg   1080
cagtgtcgca tctgacaacc cttgccacaa tctccacgag tcctcaaccc cccacaacca   1140
aaccaggtcc ggacaacagc acccacaata caccccgtgta taaacttgac atctctgagg   1200
caactcaagt tgaacaacat caccgcagaa cagacaacga cagcacagcc tccgacactc   1260
cccccgccac gaccgcagcc ggaccctaa aagcagagaa caccaacacg agcaagggta   1320
ccgacctcct ggaccccgcc accacaacaa gtccccaaca ccacagcgag accgctggca   1380
acaacaacac tcatcaccaa gataccggag aagagagtgc cagcagcggg aagctaggct   1440
taattaccaa tactattgct ggagtcgcag gactgatcac aggcgggagg agagctcgaa   1500
gagaagcaat tgtcaatgct caacccaaat gcaaccctaa tttacattac tggactactc   1560
aggataaggg tgctgcaatc ggactggcct ggataccata tttcgggcca cagcgaccgg   1620
gaatttacat agaggggctg atgcacaatc aagatggttt aatctgtggg ttgagacagc   1680
tggccaacga gacgactcaa gctcttcaac tgttcctgag agccacaacc gagctacgca   1740
ccttttcaat cctcaaccgt aaggcaattg attcttgct gcagcgatgg ggcggacat    1800
gccacatttt gggaccggac tgctgtatcg aaccacatga ttggaccaag aacataacag   1860
acaaaattga tcagattatt catgattttg ttgataaaac ccttccggac caggggga ca   1920
atgacaattg tgtgacagga tggagacaat ggataccggc aggtattgga gttacaggcg   1980
ttataattgc agttatcgct ttattctgta tatgcaaatt tgtcttttag                 2030

SEQ ID NO: 54           moltype = DNA   length = 237
FEATURE                 Location/Qualifiers
misc_feature            1..237
                        note = Polymerase III shRNA promoters- U6 promoter
source                  1..237
                        mol_type = other DNA
                        organism = synthetic construct
SEQUENCE: 54
tttcccatga ttccttcata tttgcatata cgatacaagg ctgttagaga gataattgga     60
attaatttga ctgtaaacac aaagatatta gtacaaaata cgtgacgtag aaagtaataa    120
tttcttgggt agtttgcagt tttaaaatta tgttttaaaa tggactatca tatgcttacc    180
gtaacttgaa agtatttcga tttcttggct ttatatatct tgtggaaagg acgaaac       237

SEQ ID NO: 55           moltype = DNA   length = 243
FEATURE                 Location/Qualifiers
misc_feature            1..243
                        note = Polymerase III shRNA promoters- 7SK promoter
source                  1..243
                        mol_type = other DNA
                        organism = synthetic construct
```

```
SEQUENCE: 55
ctgcagtatt tagcatgccc cacccatctg caaggcattc tggatagtgt caaaacagcc    60
ggaaatcaag tccgtttatc tcaaacttta gcattttggg aataaatgat atttgctatg   120
ctggttaaat tagattttag ttaaatttcc tgctgaagct ctagtacgat aagcaacttg   180
acctaagtgt aaagttgaga tttccttcag gtttatatag cttgtgcgcc gcctggctac   240
ctc                                                                 243

SEQ ID NO: 56           moltype = DNA   length = 21
FEATURE                 Location/Qualifiers
misc_feature            1..21
                        note = FDPS target sequence #1
source                  1..21
                        mol_type = other DNA
                        organism = synthetic construct
SEQUENCE: 56
gtcctggagt acaatgccat t                                              21

SEQ ID NO: 57           moltype = DNA   length = 21
FEATURE                 Location/Qualifiers
misc_feature            1..21
                        note = FDPS target sequence #2
source                  1..21
                        mol_type = other DNA
                        organism = synthetic construct
SEQUENCE: 57
gcaggatttc gttcagcact t                                              21

SEQ ID NO: 58           moltype = DNA   length = 21
FEATURE                 Location/Qualifiers
misc_feature            1..21
                        note = FDPS target sequence #3
source                  1..21
                        mol_type = other DNA
                        organism = synthetic construct
SEQUENCE: 58
gccatgtaca tggcaggaat t                                              21

SEQ ID NO: 59           moltype = DNA   length = 21
FEATURE                 Location/Qualifiers
misc_feature            1..21
                        note = FDPS target sequence #4
source                  1..21
                        mol_type = other DNA
                        organism = synthetic construct
SEQUENCE: 59
gcagaaggag gctgagaaag t                                              21

SEQ ID NO: 60           moltype = DNA   length = 49
FEATURE                 Location/Qualifiers
misc_feature            1..49
                        note = Non-targeting sequence
source                  1..49
                        mol_type = other DNA
                        organism = synthetic construct
SEQUENCE: 60
gccgctttgt aggatagagc tcgagctcta tcctacaaag cggctttt                 49

SEQ ID NO: 61           moltype = DNA   length = 20
FEATURE                 Location/Qualifiers
misc_feature            1..20
                        note = Forward primer
source                  1..20
                        mol_type = other DNA
                        organism = synthetic construct
SEQUENCE: 61
aggaattgat ggcgagaagg                                                20

SEQ ID NO: 62           moltype = DNA   length = 22
FEATURE                 Location/Qualifiers
misc_feature            1..22
                        note = Reverse primer
source                  1..22
                        mol_type = other DNA
                        organism = synthetic construct
SEQUENCE: 62
cccaaagagg tcaaggtaat ca                                             22

SEQ ID NO: 63           moltype = DNA   length = 18
FEATURE                 Location/Qualifiers
```

```
misc_feature           1..18
                       note = Forward primer
source                 1..18
                       mol_type = other DNA
                       organism = synthetic construct
SEQUENCE: 63
agcgcggcta cagcttca                                                     18

SEQ ID NO: 64          moltype = DNA   length = 20
FEATURE                Location/Qualifiers
misc_feature           1..20
                       note = Reverse primer
source                 1..20
                       mol_type = other DNA
                       organism = synthetic construct
SEQUENCE: 64
ggcgacgtag cacagcttct                                                   20

SEQ ID NO: 65          moltype = DNA   length = 130
FEATURE                Location/Qualifiers
misc_feature           1..130
                       note = Left Inverted Terminal Repeat (Left ITR)
source                 1..130
                       mol_type = other DNA
                       organism = synthetic construct
SEQUENCE: 65
cctgcaggca gctgcgcgct cgctcgctca ctgaggccgc ccgggcgtcg ggcgaccttt        60
ggtcgcccgg cctcagtgag cgagcgagcg cgcagagagg gagtggccaa ctccatcact      120
aggggttcct                                                             130

SEQ ID NO: 66          moltype = DNA   length = 151
FEATURE                Location/Qualifiers
misc_feature           1..151
                       note = Right Inverted Terminal Repeat (Right ITR)
source                 1..151
                       mol_type = other DNA
                       organism = synthetic construct
SEQUENCE: 66
gagcggccgc aggaacccct agtgatggag ttggccactc cctctctgcg cgctcgctcg       60
ctcactgagg ccgggcgacc aaaggtcgcc cgacgcccgg gctttgcccg ggcggcctca      120
gtgagcgagc gagcgcgcag ctgcctgcag g                                     151

SEQ ID NO: 67          moltype = DNA   length = 1227
FEATURE                Location/Qualifiers
misc_feature           1..1227
                       note = Helper plasmid without REV
source                 1..1227
                       mol_type = other DNA
                       organism = synthetic construct
SEQUENCE: 67
tctagaagga gctttgttcc ttgggttctt gggagcagca ggaagcacta tgggcgcagc       60
gtcaatgacg ctgacggtac aggccagaca attattgtct ggtatagtgc agcagcagaa      120
caatttgctg agggctattg aggcgcaaca gcatctgttg caactcacag tctgggcat       180
caagcagctc caggcaagaa tcctggctgt ggaaagatac ctaaaggatc aacagctcct      240
agatcttttt ccctctgcca aaaattatgg ggacatcatg aagcccctg agcatctgac       300
ttctggctaa taaggaaat ttattttcat tgcaatagtg tgttggaatt ttttgtgtct      360
ctcactcgga aggacatatg ggagggcaaa tcatttaaaa catcagaatg agtatttggt      420
ttagagtttg gcaacatatg ccatatgctg gctgccatga acaaaggtgg ctataaagag      480
gtcatcagta tatgaaacag ccccctgctg tccattcctt attccataga aaagccttga      540
cttgaggtta gatttttttt atattttgtt ttgtgttatt tttttcttta acatccctaa      600
aatttttcctt acatgtttta ctagccagat ttttcctcct ctcctgacta ctcccagtca      660
tagctgtccc tcttctctta tgaagatccc tcgacctgca gcccaagctt ggcgtaatca      720
tggtcatagc tgtttcctgt gtgaaattgt tatccgctca caattccaca caacatacga      780
gccggaagca taaagtgtaa agcctggggt gcctaatgag tgagctaact cacattaatt      840
gcgttgcgct cactgcccgc tttccagtcg ggaaacctgt cgtgccagcg gatccgcatc      900
tcaattagtc agcaaccata gtcccgcccc taactccgcc catcccgccc ctaactccgc      960
ccagttccgc ccattctccg ccccatggct gactaatttt ttttatttat gcagaggccg     1020
aggccgcctc ggcctctgag ctattccaga agtagtgagg aggctttttt ggaggcctag     1080
gcttttgcaa aaagctaact tgtttattgc agcttataat ggttacaaat aaagcaatag     1140
catcacaaat ttcacaaata aagcattttt ttcactgcat tctagttgtg gtttgtccaa     1200
actcatcaat gtatcttatc acccggg                                         1227
```